US008894946B2

(12) United States Patent
Nielsen et al.

(10) Patent No.: US 8,894,946 B2
(45) Date of Patent: Nov. 25, 2014

(54) SAMPLE PREPARATION, PROCESSING AND ANALYSIS SYSTEMS

(71) Applicant: IntegenX Inc., Pleasanton, CA (US)

(72) Inventors: William D. Nielsen, San Jose, CA (US); Richard J. Belcinski, San Jose, CA (US); Gregory Bogdan, San Jose, CA (US); David Eberhart, Santa Clara, CA (US); Omar El-Sissi, Fremont, CA (US); Stevan B. Jovanovich, Livermore, CA (US); Michael Recknor, Oakland, CA (US); Ezra Van Gelder, Palo Alto, CA (US); David W. Wyrick, Livermore, CA (US)

(73) Assignee: IntegenX Inc., Pleasanton, CA (US)

( * ) Notice: Subject to any disclaimer, the term of this patent is extended or adjusted under 35 U.S.C. 154(b) by 0 days.

(21) Appl. No.: 13/656,503

(22) Filed: Oct. 19, 2012

(65) Prior Publication Data

US 2013/0115607 A1      May 9, 2013

Related U.S. Application Data

(60) Provisional application No. 61/703,194, filed on Sep. 19, 2012, provisional application No. 61/696,809, filed on Sep. 5, 2012, provisional application No. 61/691,242, filed on Aug. 20, 2012, provisional application No. 61/674,295, filed on Jul. 20, 2012, provisional application No. 61/671,592, filed on Jul. 13, 2012, provisional application No. 61/664,726, filed on Jun. 26, 2012, provisional application No. 61/654,749, filed on Jun. 1, 2012, provisional application No. 61/641,120, filed on May 1, 2012, provisional application No. 61/610,977, filed on Mar. 14, 2012, provisional application No. 61/605,169, filed on Feb. 29, 2012, provisional application No. 61/550,364, filed on Oct. 21, 2011.

(51) Int. Cl.
| | |
|---|---|
| *G01N 21/75* | (2006.01) |
| *C07H 21/00* | (2006.01) |
| *C12Q 1/68* | (2006.01) |
| *C12P 19/34* | (2006.01) |

(52) U.S. Cl.
USPC ........... 422/417; 422/131; 435/6.1; 435/6.12; 435/91.2; 536/25.3

(58) Field of Classification Search
USPC ................ 422/417, 131; 435/6.1, 6.12, 91.2; 536/25.3
See application file for complete search history.

(56) References Cited

U.S. PATENT DOCUMENTS

| | | | |
|---|---|---|---|
| 6,685,678 B2 * | 2/2004 | Evans et al. .................. 604/207 |
| 7,445,926 B2 | 11/2008 | Mathies et al. | |
| 7,998,708 B2 * | 8/2011 | Handique et al. ............ 435/91.2 |
| 2004/0209354 A1 | 10/2004 | Mathies et al. | |
| 2005/0161669 A1 | 7/2005 | Jovanovich et al. | |
| 2006/0073484 A1 | 4/2006 | Mathies et al. | |
| 2007/0248958 A1 | 10/2007 | Jovanovich et al. | |
| 2007/0263049 A1 | 11/2007 | Preckel et al. | |
| 2008/0014576 A1 | 1/2008 | Jovanovich et al. | |
| 2009/0253181 A1 | 10/2009 | Vangbo et al. | |
| 2010/0010472 A1 * | 1/2010 | Moore ......................... 604/520 |
| 2010/0165784 A1 | 7/2010 | Jovanovich et al. | |
| 2010/0303687 A1 | 12/2010 | Blaga et al. | |
| 2011/0005932 A1 | 1/2011 | Jovanovich et al. | |
| 2011/0126911 A1 | 6/2011 | Kobrin et al. | |
| 2011/0207140 A1 | 8/2011 | Handique et al. | |
| 2011/0240127 A1 | 10/2011 | Eberhart et al. | |
| 2011/0290648 A1 | 12/2011 | Majlof et al. | |
| 2012/0181460 A1 | 7/2012 | Eberhart et al. | |

FOREIGN PATENT DOCUMENTS

| | | | |
|---|---|---|---|
| WO | WO 01/01025 A2 | 1/2001 |
| WO | WO 01/01025 A3 | 7/2001 |
| WO | WO 02/43615 A2 | 6/2002 |
| WO | WO 02/43615 A3 | 3/2003 |
| WO | WO 2004/062804 A1 | 7/2004 |
| WO | WO 2005/072858 A1 | 8/2005 |
| WO | WO 2008/115626 A2 | 9/2008 |
| WO | WO 2008/115626 A3 | 11/2008 |
| WO | WO 2011/011172 A1 | 1/2011 |
| WO | WO 2012/024657 A1 | 2/2012 |

OTHER PUBLICATIONS

Unger, et al. Monolithic Microfabricated Valves and Pumps by Multilayer Soft Lithography. Science. 2000;288:113-116.
International search report and written opinion dated Mar. 8, 2013 for PCT/US2012/061223.

* cited by examiner

*Primary Examiner* — Ardin Marschel

(57) ABSTRACT

This disclosure provides an integrated and automated sample-to-answer system that, starting from a sample comprising biological material, generates a genetic profile in less than two hours. In certain embodiments, the biological material is DNA and the genetic profile involves determining alleles at one or a plurality of loci (e.g., genetic loci) of a subject, for example, an STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module; a detection and analysis module and a control module.

30 Claims, 46 Drawing Sheets

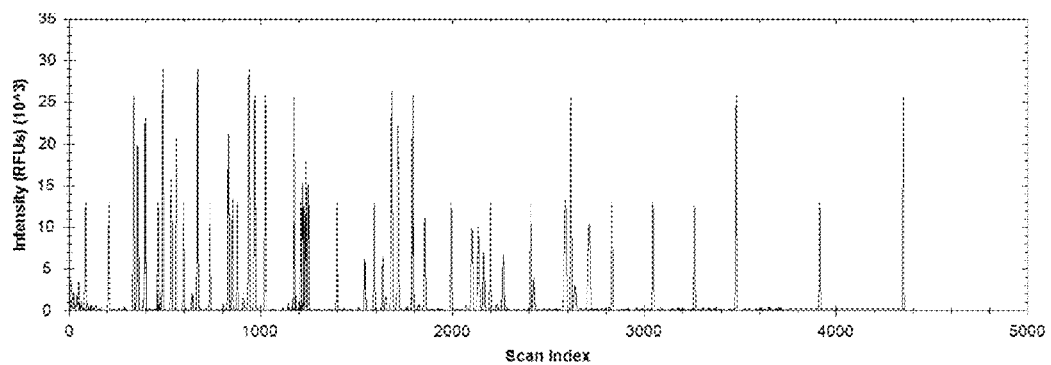
FIG. 51A. A typical electropherogram that can be generated from data collected

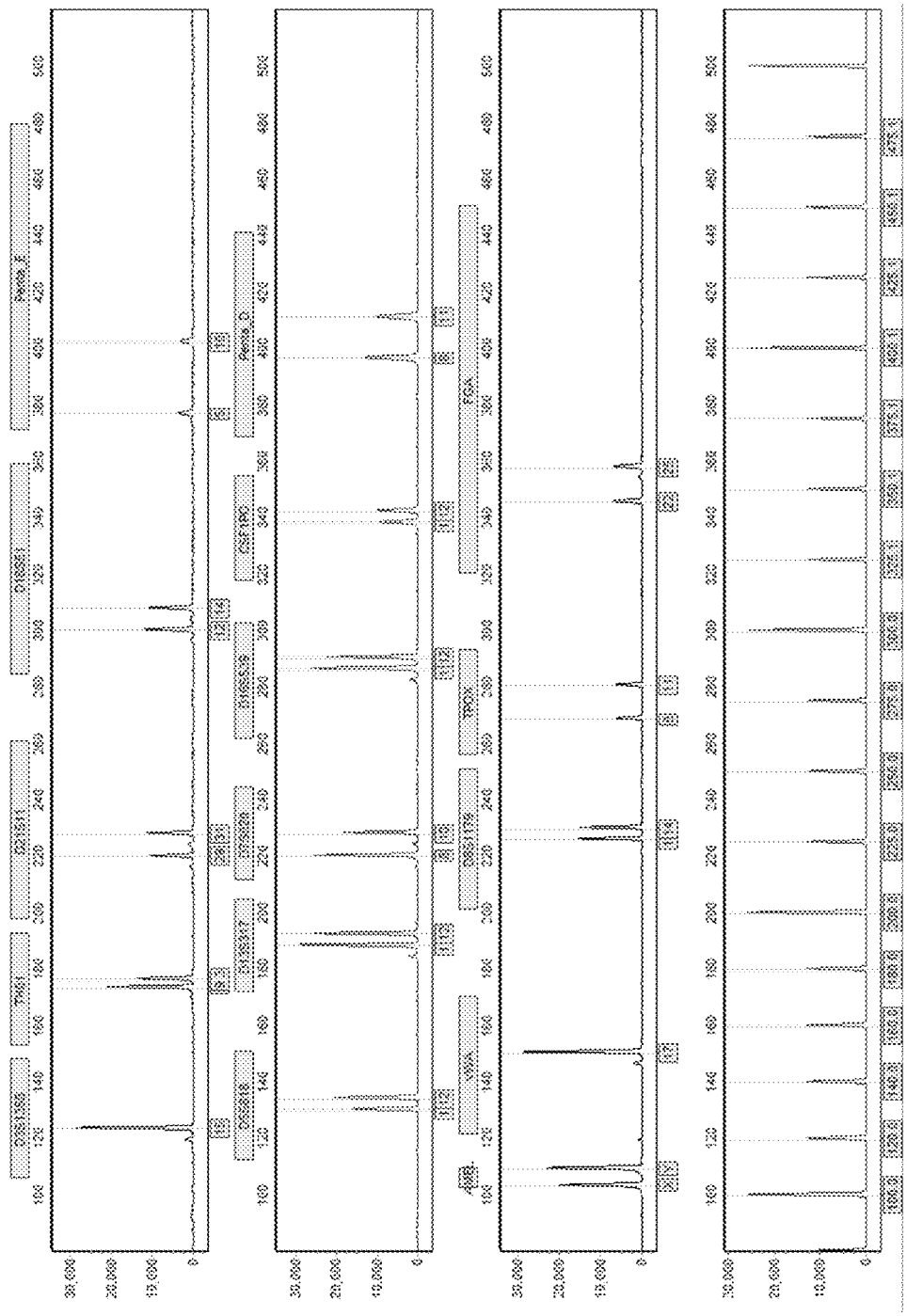
FIG. 51B. A typical plot of a nucleic acid profile that can be generated from data collected device for actuating premix delivery

SAMPLE PREPARATION, PROCESSING AND ANALYSIS SYSTEMS

CROSS-REFERENCE

This application claims the benefit of and priority to U.S. Provisional Patent Application Ser. No. 61/550,364, filed Oct. 21, 2011; U.S. Provisional Patent Application Ser. No. 61/605,169, filed Feb. 29, 2012; U.S. Provisional Patent Application Ser. No. 61/610,977, filed Mar. 14, 2012; U.S. Provisional Patent Application Ser. No. 61/641,120, filed May. 1, 2012; U.S. Provisional Patent Application Ser. No. 61/654,749, filed Jun. 1, 2012; U.S. Provisional Patent Application Ser. No. 61/664,726, filed Jun. 26, 2012; U.S. Provisional Patent Application Ser. No. 61/671,592, filed Jul. 13, 2012; U.S. Provisional Patent Application Ser. No. 61/674,295, filed Jul. 20, 2012; U.S. Provisional Patent Application Ser. No. 61/691,242, filed Aug. 20, 2012; U.S. Provisional Patent Application Ser. No. 61/696,809, filed Sep. 5, 2012; and U.S. Provisional Patent Application Ser. No. 61/703,194, filed Sep. 19, 2012, each of which is entirely incorporated herein by reference.

STATEMENT AS TO FEDERALLY SPONSORED RESEARCH

None.

BACKGROUND OF THE INVENTION

DNA profiling (also called DNA testing, DNA typing, or genetic fingerprinting) is a technique employed by forensic scientists to assist in the identification of individuals by their respective DNA profiles. DNA profiles may be encrypted sets of numbers that reflect a person's DNA makeup, which can also be used as the person's identifier.

DNA profiling, or genetic profiling, can be used to identify a suspect of a crime or verify the identity of a subject, such as to verify the identity of a victim of a crime. This can enable law enforcement personnel to accurately identify the perpetrator of a crime from a list of suspects, and minimize instances of misidentification. In a battlefield scenario, DNA profiling can identify the opposition in assymetric warfare, identify suspects in raids, identify suspected terrorists, link improvised explosive devices (IED's) to bomb makers, find captured soldiers (such as, e.g., by identifying their DNA from a tissue sample on a vehicle and tracking the vehicle), and unravel a combatant network, to name a few examples.

DNA profiling typically involves sample preparation, processing and analysis. This is ordinarily done in a laboratory setting. Sample preparation is a ubiquitous problem in biological analytical systems. The issue of providing sufficiently purified targets from diverse raw sample types to reliably perform downstream analytical assays is pervasive and covers cell biology, genomics, proteomics, metabolomics, food biology, molecular diagnostics, and many other biological and medical assays.

Methods and systems currently available for DNA profiling have various limitations. For instance, sample preparation and analysis systems for DNA profiling are typically bulky and difficult to transport without substantial effort. This makes the use of such systems in the field, such as on a battlefield, difficult and impractical. In addition, current systems and methods are expensive to use and maintain, and genetic profiles take a substantially large amount of time to prepare. In some cases, a genetic profile of a subject is provided in one to two days. This is unappealing in cases in which time is of the essence, such as cases in which law enforcement officials are in pursuit of a suspect or can detain a suspect for only a limited period of time.

SUMMARY OF THE INVENTION

Recognized herein is the need for improved systems and methods for genetic profiling. In particular, recognized is the need for systems that have a smaller footprint in relation to other systems and in a faster time. In addition, there is a need for systems and methods that enable genetic profiling at lower cost with less skilled operators.

This disclosure provides an integrated and automated sample-to-answer system that, starting from a sample comprising biological material, generates a genetic profile in less than two hours. In certain embodiments, the biological material is DNA and the genetic profile involves determining one or a plurality of alleles at one or a plurality of loci (e.g., genetic loci) of a subject, for example, an STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module; a detection and analysis module and a control module. These modules are shown in FIG. 48 and FIG. 49. (One or more computer systems can communicate with and control the operation of various components (e.g., the fluidics manifold and the pneumatic manifold) of the analyte preparation module in FIG. 48; such computer system(s) are not shown in FIG. 48.)

Systems provided herein may be fully integrated. Sample processing can be accomplished in a single system without having to remove a sample and transferring the sample to another system. Systems provided herein can be fully automated, enabling a user to process a sample without substantial input from the user. Systems provided herein can be dimensioned to minimize footprint, thereby enabling portability. This can advantageously enable system use in on-the-go situations, such as remote locations, situations in which transportation is not readily available or user mobility is desired, such as battlefield scenarios.

An analyte preparation module includes a cartridge module assembly configured to engage and operate one or more than one sample cartridge. A sample cartridge is configured to receive one or more samples and to perform nucleic acid extraction and isolation, and DNA amplification when the cartridge is engaged with a cartridge module assembly in the system. It can also include controls and standards for assisting in analysis.

The sample cartridge includes a sample receptacle for receiving the sample; compartments for DNA extraction and isolation; on-board reagents in fluidically isolated compartments for nucleic acid extraction, purification and amplification (e.g., process beads to concentrate the samples); assemblies for thermal cycling; fluidic channels (e.g., microfluidic channels) for routing fluids to different functional compartments within the cartridge and ports to engage sub-assemblies in the cartridge module assembly that operate valves, pumps and routers on the cartridge; provide pressure for moving liquids; and provide consumables not stored on the cartridge. In some examples, diaphragm valves, pumps and routers, e.g., MOVe pumps, valves and routers transport, process and enable analysis of samples. When the cartridge is engaged with a cartridge receptacle in the cartridge module assembly, fluidically isolated chambers are brought into fluidic connection with fluidic channels in the cartridge, allowing movement and routing of fluids and reagents to functional compartments in the cartridge and, subsequently, to the detection and analysis module.

The analyte preparation module can include a receptacle for receiving one or more cartridges, an engagement assembly to engage the cartridge; a fluidic manifold configured to engage ports in a cartridge and to deliver pressure and/or fluids to the cartridge through the ports; a delivery assembly configured to deliver reagents, such as amplification pre-mix, from a compartment in the sample cartridge to an amplification compartment; a pneumatic manifold configured to engage ports in a cartridge and to deliver positive or negative pressure to the cartridge through the ports for moving fluids and operating valves, pumps and routers in the cartridge; a pump configured to deliver pressure to the fluidic and pneumatic manifold. Consumable reagents can be carried in a module, e.g., a buffer module, that is removably engagable with the cartridge module. Reagents can be provided (e.g., stored) in an aqueous solution, or can be provided (e.g., stored) in a solid or dry (e.g., lyophilized) form and then placed into solution by addition of a liquid (e.g., an aqueous solution) as appropriate. Alternatively, reagents can be provided (e.g., stored) in a substantially water-free non-ionic organic solvent (e.g., an alcohol solvent) or in a substantially water-free ionic organic solvent (e.g., a deep eutectic solvent) and can be re-hydrated by addition of an aqueous solution as appropriate, as described in U.S. Provisional Patent Application No. 61/709,417, which is incorporated herein by reference in its entirety.

An analysis and detection module is configured to receive analyte from the analyte preparation module; perform capillary electrophoresis on the analyte; to detect analytes separated by electrophoresis and to analyze the detected analytes. It can include a capillary electrophoresis assembly, a detection assembly and an analysis assembly.

The capillary electrophoresis assembly can include an injection assembly, that can include a denature heater assembly, a positioning assembly for positioning an analyte for capillary injection; a cathode assembly; a capillary assembly; an anode assembly; a capillary filling assembly for filling a capillary with separation medium and a power source for applying a voltage between the anode and the cathode. A denature assembly can include a heater configured to denature double stranded DNA molecules. A cathode assembly can include a cathode. The cathode can be a forked cathode for stacking analyte for capillary injection. The capillary assembly can include a capillary configured to receive a separation medium and a temperature control unit for regulating temperature in the capillary. For example, the temperature control unit can have a circuit board material including heating traces connected to current source and to temperature sensors to regulate temperature in the capillary. The anode assembly can comprise an anode. The anode can be comprised in an anode cartridge that is removably insertable into the analysis and detection module. An anode cartridge can include separation medium and optionally a buffer supply, and an electrode. A capillary filling assembly can include a source of separation medium, e.g., separation gel comprised in an anode cartridge, and a pump for delivering separation medium into the capillary.

A detection assembly can comprise a laser configured to illuminate the capillaries and a detector. The laser can be configured to excite fluorescent dyes in the analyte. The detector can include a CCD array, for detecting light produced by excited dyes and for producing an output signal.

An analysis assembly can include a computer comprising memory and a processor for executing code (e.g., code on a tangible medium) for analyzing the output signal and producing a computer file containing an analysis of the signal. Such an analysis can include, for example, identification of alleles from various STR loci. The computer file can be in a format that is compatible with public databases. For example, the file can be in CODIS format which is compatible with the National DNA Index (NDIS) operated by the FBI. The analysis assembly can further comprise code that performs kinship analysis on a sample being tested and a reference sample. The analysis assembly can query databases that may be part of the system or remote databases to determine if a sample fully or partially matches a profile in the database. The results of the database query can be displayed to the user.

The system can be operated by a control module. The control module can include a user interface configured to receive instructions from and deliver information to a user. It can include software programmed to execute routines for performing the operations mentioned, above, and transmit and receive information, such as computer files, from remote locations, e.g., over the internet. The control module also can include sensors positioned in various parts of the instrument to detect and measure operation and to transmit such parameters to a computer for analysis by software configured to monitor operation of the instrument and alter operation of the instrument if measurements are not within selected parameters. Systems and methods of the invention are fully integrated and automated, which advantageously reduces processing times for sample processing while providing flexibility in processing and analyzing samples in various locations, including remote locations that may not be readily accessible.

For example, starting from the sample, the present invention can be applied to concentrate and separate components for further processing to detect and classify human and other organisms in matrices comprising aerosol samples, water, liquids, blood, stools, nasal, buccal and other swabs, bodily fluids, environmental samples with analysis by ELISA, PCR or other nucleic acid amplification techniques, single molecule detection, protein arrays, mass spectroscopy, and other analytical methods well known to one skilled in the art.

INCORPORATION BY REFERENCE

All publications, patents, and patent applications mentioned in this specification are incorporated herein by reference in their entirety to the same extent as if each individual publication, patent, or patent application was specifically and individually indicated to be incorporated herein by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 51A shows a typical electropherogram that can be generated from the data collected.

FIG. 51B shows a typical plot of the nucleic acid profile generated from the data collected.

FIG. 54A shows three electrodes opposite a capillary inside the lumen of tubing; the third electrode is not electrically connected, but is independently electrified. FIG. 54B shows three electrodes opposite a capillary inside the lumen of tubing; all the electrodes are electrically connected.

DETAILED DESCRIPTION OF THE INVENTION

Figure 1:
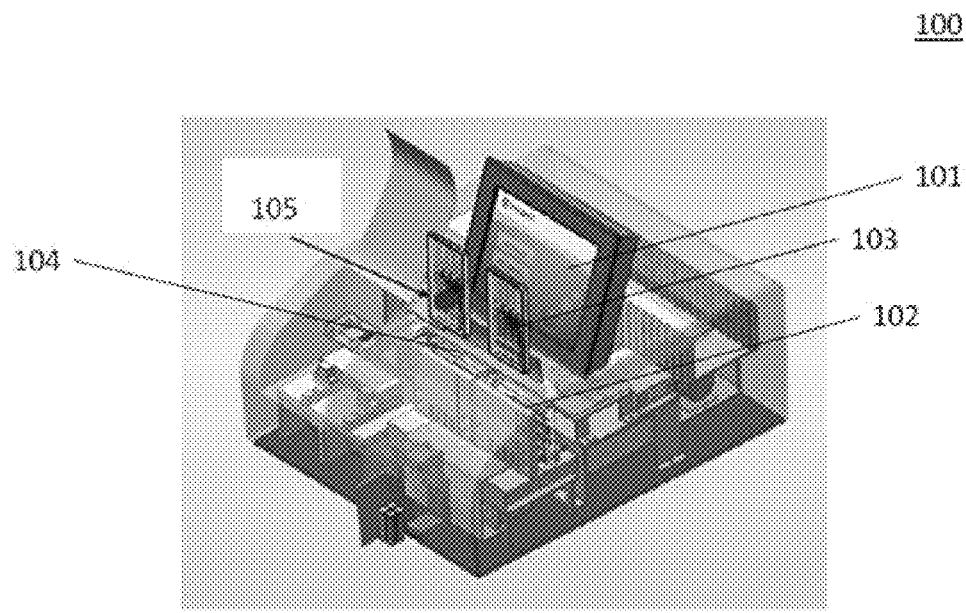
FIG. 1 shows a system for processing a sample, in accordance with an embodiment of the invention.

Every embodiment of the disclosure may optionally be combined with any one or more of the other embodiments described herein which are consistent with that embodiment.

Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values. In certain embodiments, the term "about" or "approximately" means within 10% or 5% of the specified value.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "sample", as used herein, refers to a sample containing biological material. A sample may be, e.g., a fluid sample (e.g., a blood sample) or a tissue sample (e.g., a cheek swab). A sample may be a portion of a larger sample. A sample can be a biological sample having a nucleic acid, such as deoxyribonucleic acid (DNA) or ribonucleic acid (RNA), or a protein. A sample can be a forensic sample or an environmental sample. A sample can be pre-processed before it is introduced to the system; the preprocessing can include extraction from a material that would not fit into the system, quantification of the amount of cells, DNA or other biopolymers or molecules, concentration of a sample, separation of cell types such as sperm from epithelial cells, concentration of DNA using an Aurora system (Boreal Genomics) or bead processing or other concentration methods or other manipulations of the sample. A sample can be carried in a carrier, such as a swab, a wipe, a sponge, a scraper, a piece punched out a material, a material on which a target analyte is splattered, a food sample, a liquid in which an analyte is dissolved, such as water, soda. A sample can be a direct biological sample such as a liquid such as blood, semen, saliva; or a solid such a solid tissue sample, flesh or bone.

The invention can also be applied to process and analyze a sample that has been previously preprocessed, for example, by extraction of DNA from large object such as a bed sheet or chair and other processing which may include quantification of DNA concentration, cell concentration, or other manipulations before input of the pre-processed sample into the sample cartridge.

The term "module", as used herein, refers to a device or component as part of a larger device, instrument or system.

The terms "cassette" and "cartridge" are used interchangeably herein unless expressly indicated otherwise.

Reference will now be made to the figures, wherein like numerals refer to like parts throughout. It will be appreciated that the figures are not necessarily drawn to scale.

I. Introduction

FIG. 1 shows a system 100 for sample processing and analysis. The system comprises a display 101 having a graphical user interface (GUI) for enabling a user to, for example, initiate sample processing and view the progress of sample processing and analysis or the results of an analysis. The system 100 includes a first port 102 for accepting and securing a sample cartridge 103 and a second port 104 for accepting and securing a second cartridge that can be a control cartridge 105. The first port 102 and second port 104 are configured to release the sample cartridges 103 and 104 following sample processing. The first port 102 and second port 104 are cartridge bays for mating with sample and/or control cartridges. As will be discussed in further detail below, various reagents for sample processing are included in the cartridges 103 and 105. The system 100 is used for sample preparation, processing and analysis.

Figure 2:
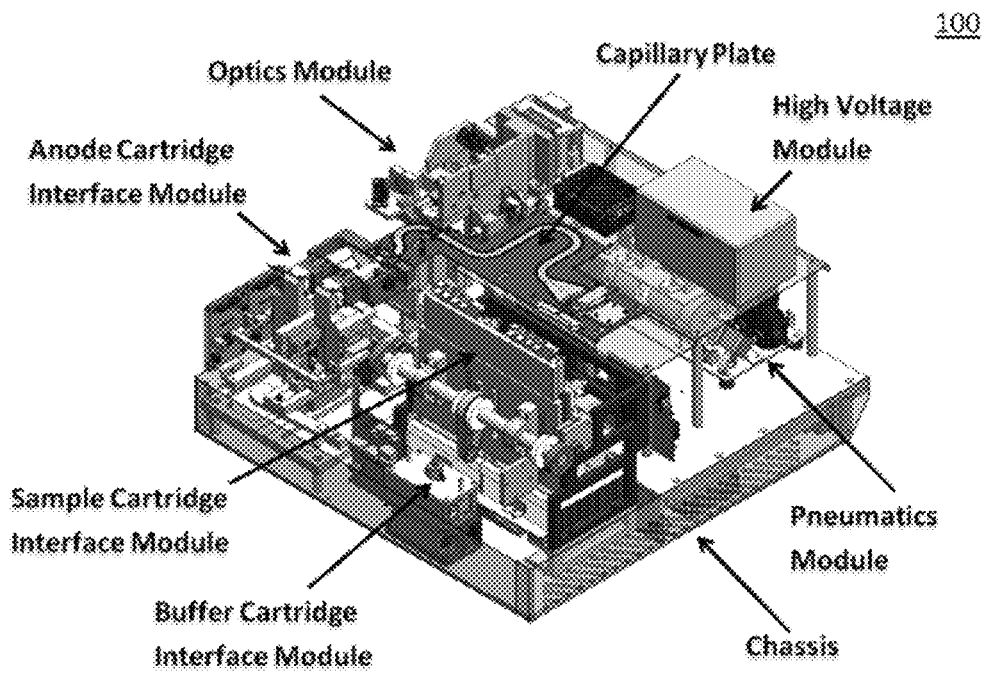
FIG. 2 shows the system of FIG. 1, in accordance with an embodiment of the invention.

FIG. 2 shows the system 100 of FIG. 1 in further detail. The system 100 includes a sample cartridge interface module for holding the cartridges 103 and 105. A buffer cartridge interface module enables a user to provide a buffer for use by the system 100. The system 100 includes a chassis for structural support, which may be formed of a metallic material, such as aluminum or steel or a polymeric material. The chassis may be structured so as to minimize the weight of the system 100. A pneumatics module provides air (or other gas) to operate the valves (e.g., MOVe) valves included in the cartridges 103 and 105. A power supply provides power to the system, including a controller of the system (e.g., central processing unit, CPU), system memory, cache, hard disks, and other electronic components of the system 100. A high voltage module can provide stepped up voltage to the electrophoresis system for separation of analytes. The system also includes a capillary plate, an optics module and anode cartridge interface module.

The system 100 can include a communications bus for enabling various modules of the system 100 to communicate with a controller of the system 100. The communications bus can be in electrical communication with the high voltage module, thereby enabling power to be provided to the various modules of the system.

The system of FIGS. 1 and 2 can be used in forensics analysis to determine a genetic profile of an organism. In some situations, the system 100 processes a biological sample from a subject in 20 steps or less, 15 steps or less, or 10 steps or less. In certain embodiments the steps are selected from cell lysis, DNA capture, DNA purification; DNA amplification; amplicon/analyte dilution; amplicon/analyte injection; amplicon/analyte separation; amplicon/analyte detection; and analysis of detected products. In some embodiments, the system 100 can determine the genetic profile of a subject in 3 hours, 2 hours, 1.5 hours, 1 hour, or less. Forensics analysis can include short tandem repeat (STR) analysis or restriction fragment length polymorphism (RFLP) analysis. In such a case, STR analysis may be performed within a time period of 3 hours, 2 hours, 1.5 hours, 1 hour, or less.

In some embodiments, the system 100 of FIGS. 1 and 2 is used for automated forensics. The system 100 can be used to determine a genetic profile of a subject in no more than any of 20 steps, 15 steps, 10 steps, using a fully integrated sample processing system having a volume of no more than any of 20 ft$^3$, 16 ft$^3$, 15 ft$^3$, 10 ft$^3$, 5 ft$^3$.

In some embodiments, the system is a complete sample-to-answer system, in some cases requiring coupling steps together to match volumes and concentrations. An integrated system can be configured to receive a sample comprising nucleic acid, e.g., a biological sample, and produce a genetic profile of the nucleic acid, e.g., an allelic analysis or an STR analysis, in the form of a computer file, e.g., a CODIS compatible file. It can also use the profile in the performance of kinship analysis. Kinship analysis involves comparing the genetic profiles (e.g., STR profiles) of two or more persons and estimating the likelihood of a familial relationship between the people, for example, whether two people are parent and child, siblings, cousins, second cousins, grandparent and grandchild, uncle/aunt and niece/nephew, etc.

The invention provides systems and methods for sample processing and/or analysis, including sample preparation. Such systems can process a sample for analysis by the system or another device. Some embodiments provide systems that facilitate sample processing with the aid of removable cassettes having reagents for sample processing and/or analysis, such as, for example, beads and nucleic acid amplification reagents. In some embodiments the system is a sample-to-answer system that receives a sample containing an analyte and reports a metric or characteristic of the analyte. The analyte can be, for example, a biological molecule such as a nucleic acid (e.g., DNA or RNA), a protein or a polysaccharide. The metric reported can be an amount of the analyte in the sample (including presence or absence or the analyte). The characteristic reported can be, for example, the identity of the analyte, the chemical composition of the analyte, the form or makeup of the analyte (e.g., the presence, form, size or identity of an allele at a locus (e.g., a genetic locus)).

An aspect of the invention provides a system for sample processing and/or analysis. The system can be configured for amplification, such as polymerase chain reaction (PCR) amplification or proteomics, which may be used for forensics analysis, animal (e.g., human) identification or kinship analysis. In some cases, the system is integrated and fully automated. In some cases, the system can process a sample for forensics analysis with little to no user involvement. In some embodiments, the system comprises subsystems configured to perform the following functions: nucleic acid (e.g., DNA) isolation from a sample (e.g., a sample containing a mixture of biological molecules); optionally purification of the nucleic acid; amplification of selected nucleotide sequences within the isolated nucleic acid (e.g., sequences from one or more genetic loci, each locus containing one or more allelic forms in a species) to produce amplification products; optional purification of the selected amplified nucleotide sequences; dilution or resuspension with a fragment size standard; separation and detection of the amplification products (e.g., production of an electropherogram) and analysis of the detected amplification products electropherogram (e.g., identification of alleles at each locus (e.g., genetic locus)).

In some embodiments, a system for sample processing implements a macro-to-micro downscaling of sample volume during sample processing. In some cases, such a system implements a macro-to-micro and subsequently a micro-to-macro change in sample volume. Systems provided herein can decrease, e.g., minimize, if not eliminate, contamination during processing, providing improved reliability, performance, and coefficient of variation. This advantageously enables reliability in sample processing and analysis from one system to another.

II. Analyte Preparation Module

Figure 48:
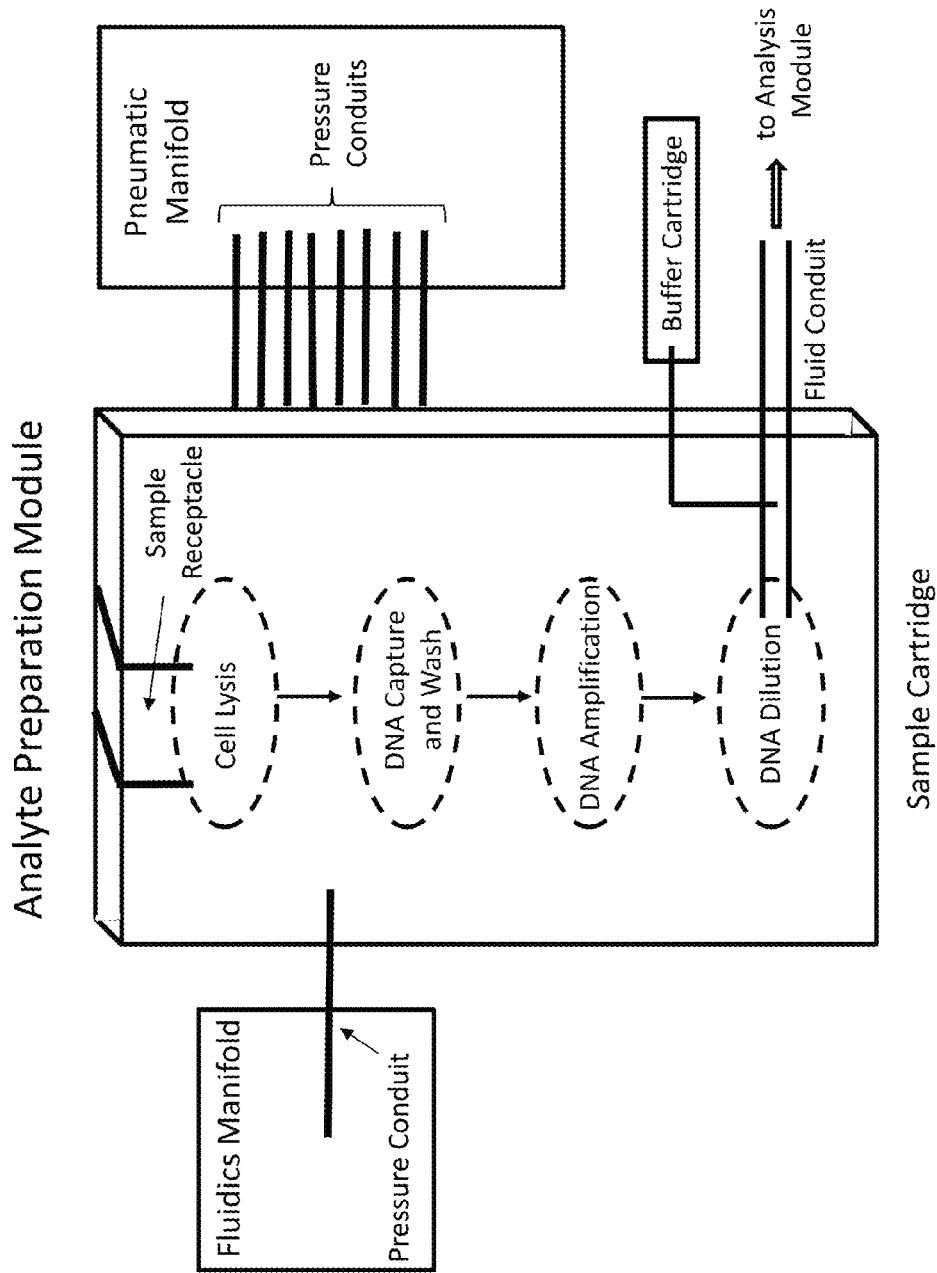
FIG. 48 shows a schematic of an analyte preparation module useful in the systems of this invention.

FIG. 48 shows an embodiment of an analyte preparation module of this invention. An analyte preparation module can comprise a sample cartridge module that receives a sample cartridge and is configured to move fluids within the cartridge. The sample cartridge comprises a sample receptacle to receive a sample and areas to perform functions such as cell lysis, DNA capture and wash, DNA amplification and DNA dilution. A fluidics manifold connected to a source of pressure can deliver pressure, e.g., air pressure, into the cartridge to move liquids within the sample cartridge. A reagent cartridge connected to a source of pressure can move reagents, such as buffer and/or water into the sample cartridge. Sample and buffer can be moved out of the cartridge through a fluid conduit to an analysis assembly. In one embodiment, the sample cartridge comprises a fluidic chip that comprises a fluidics layer comprising fluidic channels, an actuation layer comprising actuation channels and an elastomer layer sandwiched between them. The chip can include valves and pumps actuated by the actuation layer. In such an embodiment, the sample cartridge module can include a pneumatic manifold connected to a source of pressure that transmits pressure to the cartridge pneumatics when the manifold engages the cartridge. This pneumatic pressure can operate pumps and valves in the cartridge to move fluids around the cartridge and out of the cartridge.

A. Sample Cartridge

This invention provides a cassette that can be pre-loaded with reagents for performing one or a series of chemical or biochemical reactions. The cassette includes a container (see, e.g., FIG. 8) having closed compartments that can contain the reagents and that are, initially, fluidically separated from each other. Accordingly, the cassette is configured to prevent leakage of the reagents from the cassette, or of mixture of the reagents until desired. Such a configuration is useful for shipping or otherwise transporting reagents in isolation. The compartments in the container can have friable seals that can be punctured to provide access to the compartment and its contents. The cassette further includes a fluidic device having fluidic passages or channels. The fluidic device can be a microfluidic device containing microfluidic passages or channels. The fluidic device also can have puncturing elements adapted to puncture the friable seals of the container. The puncturing element, itself, can have an opening that is in fluidic communication with a fluidic channel in the fluidic device. The cassette is configured so that the fluidic device is engagable with the container. Engagement can be accomplished, for example, by pressing the container upon the fluidic device. Upon engagement, puncturing elements puncture the friable seals and put punctured compartments in fluidic communication with fluidic passages in the fluidic device.

In certain arrangements two previously isolated compartments are put in fluidic communication with each other through a common fluidic channel. In other arrangements, two fluidic channels are put in fluidic communication with a single compartment, for example, by puncturing the seal of a single compartment in two different places. For example, the device can be configured such that engagement, (1) creates a flow path between two compartments through a fluidic channel (e.g., a segment of a channel) on the fluidic device; and/or (2) creates a flow path between two fluidic channels (e.g., channel segments) on the fluidic device through a single compartment. In certain embodiments, the flow path between two compartments through a channel or between two channels through a compartment does not include a branch in the flow path. In other arrangements, a port leading out of the fluidic device that is in fluidic communication with a fluidic channel is put in fluidic communication with a compartment through the fluidic channel. The channels can include controllable valves. Such valves can be used to route the passage of fluids in the channels, e.g., between a first pathway and a second pathway. Fluid can be moved through the device by on-device pumps, such as diaphragm pumps. Alternatively, fluidic channels opening at ports can be connected to an outside source of pressure, e.g., pneumatic pressure, used to move fluids, especially bulk fluid volumes, through the device. The fluidic channels opening at ports can be connected to outside sources of reagents when desired. Accordingly, in certain arrangements, engagement of the fluidic device with the container creates fluidic paths that connect compartments in the container with each other and with ports leading off the cassette through fluidic paths in the fluidic device. The cassette also can comprise chambers which, when the cassette is engaged by a receiving element of a control instrument, becomes in thermal contact with a thermal control element. For example, the thermal control element can perform thermal cycling with heating and cooling. A pressure sensor can be used to indicate whether a port (e.g., a fluidic port or a pneumatic port) is blocked or has a leak and to identify the location of a blocked or leaking port.

In some cases, the plurality of closed and fluidically isolated chambers can be microfluidic chambers. Such chambers are configured to hold fluid volumes from microliters to nanoliters or lower. In other cases, the plurality of closed and fluidically isolated chambers are macrofluidic chambers, which are configured to hold fluid volumes on the order of at least one microliter or more.

An aspect of the invention provides cartridges (or cassettes) for sample processing, including sample preparation. Cartridges of the invention can be used with sample processing and/or analysis systems, such as the system 100 of FIG. 1. In some embodiments, a cartridge for processing a sample comprises a container (e.g., a reagent pack) comprising a plurality of closed and fluidically isolated chambers. The cartridge can be similar or identical to the cartridge of FIG. 4. Each of the plurality of chambers comprises a friable seal. In some cases, the cartridge further includes a microfluidic device comprising a plurality of puncturing elements and a microfluidic channel in fluid communication with one or more ports. Multiple puncturing elements are disposed opposite each of the plurality of chambers. Engaging the microfluidic device with the container punctures the friable seal of each of the plurality of chambers and creates a fluid flow path between each of the fluidically isolated chambers and the microfluidic channel. In some embodiments, engaging the microfluidic device with the container fluidically connects two isolated chambers. In some cases, this permits fluid flow from one chamber to another.

In some embodiments, 2, or 3, or 4, or 5, or 6, or 7, or 8, or 9, or 10, or more puncturing elements are disposed adjacent to each of the plurality of chambers of the container. At least some of the plurality of chambers can be prefilled with a reagent, such as a wash solution or buffer (see below). In an example, two puncturing elements are disposed adjacent to a chamber. In another example, three puncturing elements are disposed adjacent to a chamber. In another example, two puncturing elements are disposed adjacent to a first chamber and three puncturing elements are disposed adjacent to a second chamber.

The plurality of puncturing elements can include openings (or ports) that are in fluid communication with the microfluidic channel. Alternatively, the openings can be disposed adjacent to the puncturing elements. The openings may have various geometric shapes and sizes. In some cases, the openings are circular, triangular, square, rectangular, pentagonal, hexagonal, or have other polygonal cross-sections or partial cross-sections (e.g., semi-circular).

During processing, the flow of a fluid having a sample from a sample chamber to the microfluidic channel can effect a macro-to-microscale downscaling of fluid volume, and the flow of the fluid from the microfluidic channel to a chamber of the container preloaded with a liquid can effect a micro-to-macroscale upscaling of fluid volume.

In some embodiments, a cassette for processing a biological sample comprises a microfluidic device comprising a microfluidic channel in fluid communication with one or more ports. The microfluidic device includes a plurality of puncturing elements. The cassette further comprises a container disposed over adjacent to microfluidic device. The container has a plurality of sealed chambers. Each of the plurality of sealed chambers comprises a friable seal. The container can be attached to the microfluidic device with the aid of a layer of deformable material or an adhesive material (e.g., a material that is adhesive on both sides). Engaging the microfluidic device with the container punctures the friable seal of each of the plurality of sealed chambers and creates a fluid flow path between each of the sealed chambers and the microfluidic channel. In certain embodiments, puncture of the friable seal creates a flow path from a first channel segment in the microfluidic device, into the chamber, out of the chamber and into a second channel segment in the microfluidic device. In another embodiment, puncture of the friable seal creates a flow path from a port in the microfluidic device, through a first channel segment and into the chamber. In another embodiment, puncture of the friable seal creates a flow path from a first port in the microfluidic device, through a first channel segment, into the chamber, out of the chamber, into a second channel segment and out a second port in the microfluidic device.

In some cases, the friable seal is formed of a metallic material, such as aluminum. In other cases, the friable seal is formed of a polymeric material.

Figure 4:
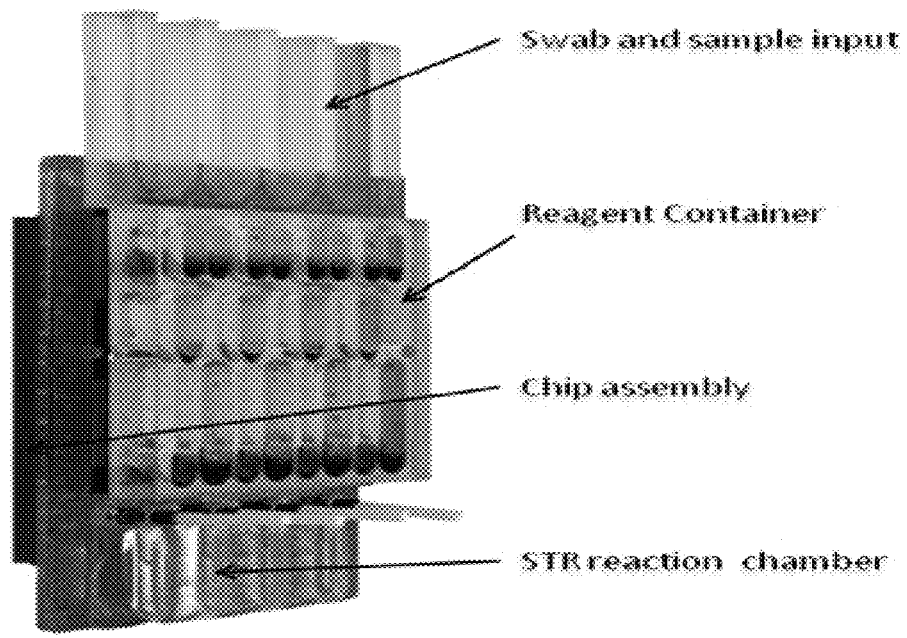
FIG. 4 shows a cartridge, in accordance with an embodiment of the invention.

FIG. 4 shows a cartridge for use with the system 100. In some embodiments, the cartridge is configured to perform all or substantially all sample processing, including fluidic sample preparation operations. The cartridge includes a swab and sample input port, a reagent container, a chip assembly with various microfluidic channels, valves and ports, and a reaction chamber. The cartridge is configured for insertion into the sample cartridge interface module either vertically or angled in relation to a horizontal plane having the system 100. For example, the system 100 can receive the cartridge at an angle of about 10°, 20°, 30°, 40°, 50°, 60°, 70°, 80°, or less than 90° in relation to the horizontal plane.

Figure 31:
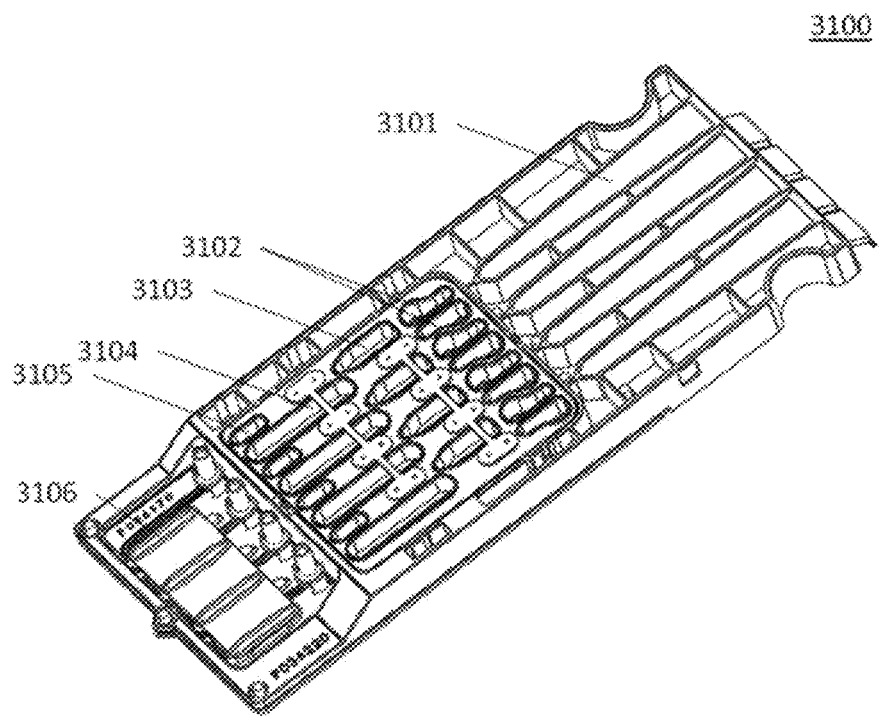
FIG. 31 shows an integrated cartridge, in accordance with an embodiment of the invention.
Figure 32:
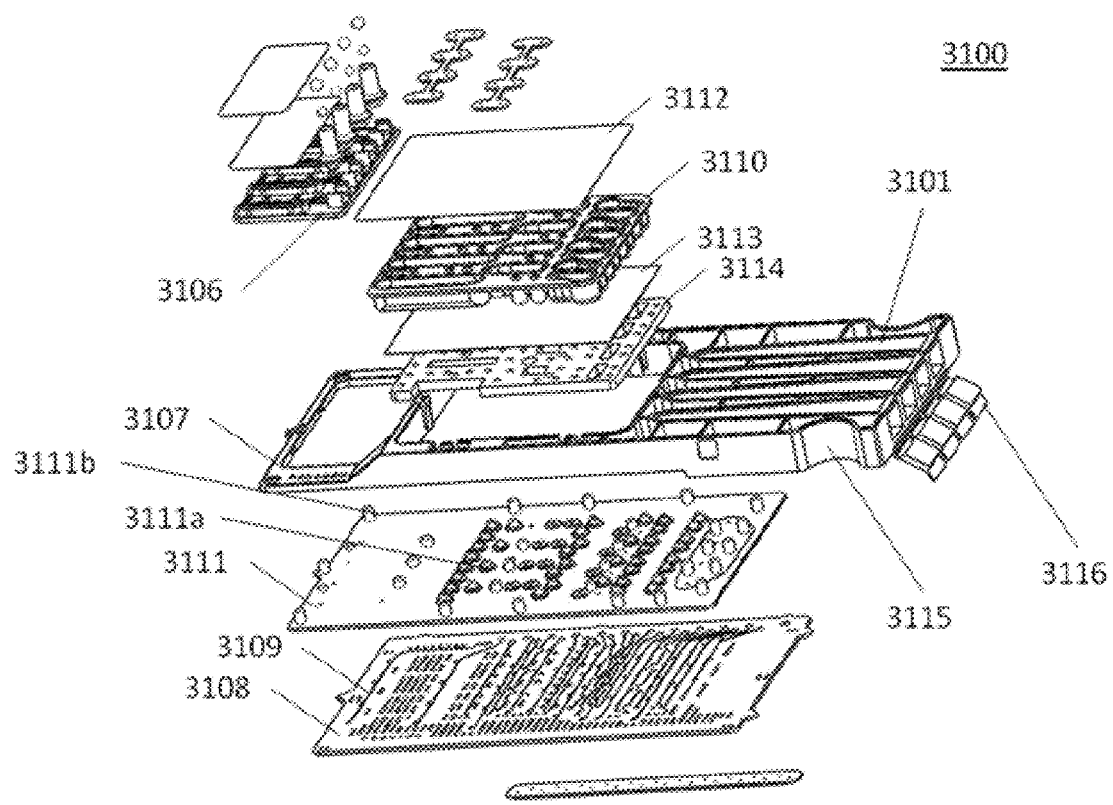
FIG. 32 is an exploded view of the cartridge of FIG. 31, in accordance with an embodiment of the invention.

In an embodiment, shown, for example, in FIG. 31 and FIG. 32, a sample cartridge comprises a) a fluidic device comprising one or a plurality of fluidic channels (e.g., a microfluidic channels) arranged substantially in a first plane; b) a sample container comprising one or a plurality of sample receptacles, each receptacle having an elongate shape defined by an axis in a long dimension of the shape (e.g., an axis along which a swab can be inserted), wherein each elongate axis is arranged substantially in a second plane; and, optionally, c) a reagent container comprising one or a plurality of reagent chambers, each reagent chamber having an elongate shape defined by an axis in a long dimension of the shape (e.g., chamber 3104) wherein each elongate axis is arranged substantially in a third plane; and d) a reaction container comprising one or a plurality of reaction chambers, each reaction chamber having an elongate shape defined by an axis in a long dimension of the shape, wherein each elongate axis is arranged substantially in a fourth plane (e.g., 3106). The fluidic channels, the sample receptacles, the reagent chambers and the reaction chambers are fluidically connected to one another; and the first, second, third and fourth planes are substantially parallel to each other. In an embodiment, a sample cartridge comprises a) a fluidic device comprising one or a plurality of fluidic channels arranged substantially in a first plane; and b) a sample container comprising one or a plurality of sample receptacles, wherein the fluidic channels and the sample receptacles are fluidically connected to one another. The sample cartridge is configured to be loaded with sample into sample receptacles and move analyte from the sample into the fluidic channels when the sample cartridge is engaged with a cartridge module configured to receive the sample cartridge, and the first plane is oriented at least 10°, at least 20°, at least 30°, at least 40°, at least 50°, at least 60°, at least 70°, at least 80°, or at least 90° off horizontal. (See., e.g., FIG. 1 or FIG. 39.)

Figure 8:
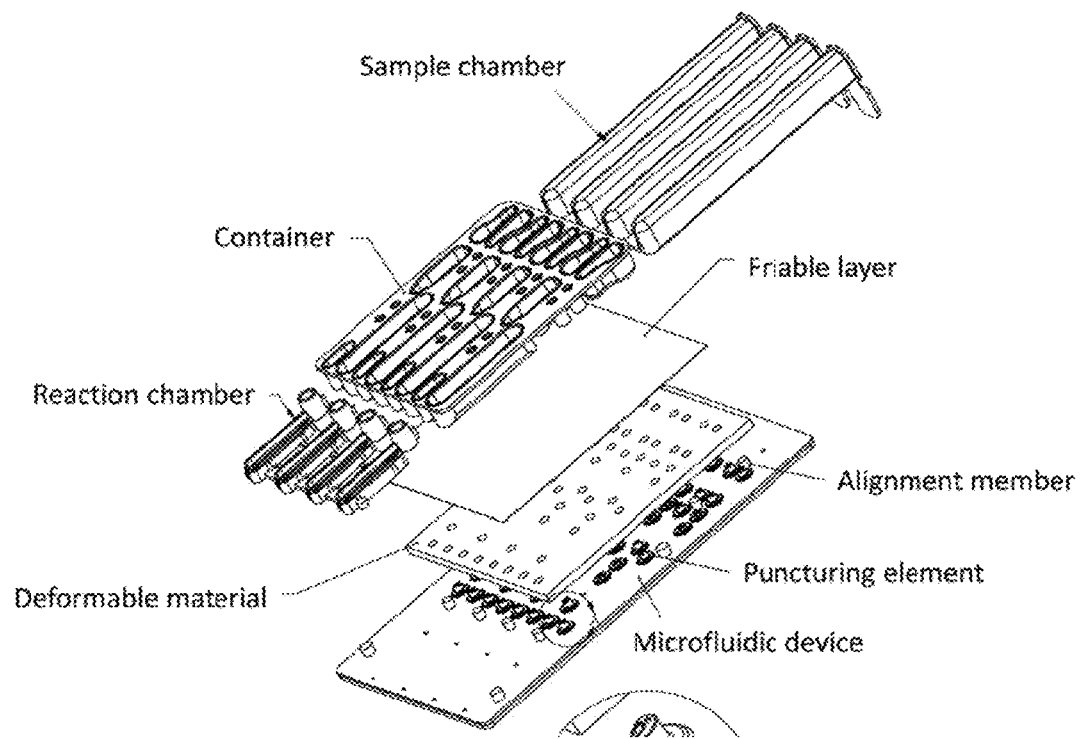
FIG. 8 shows a cassette for use with systems provided herein, in accordance with an embodiment of the invention.

FIG. 8 is an exploded view of a cartridge for use with sample preparation and processing, in accordance with an embodiment of the invention. The cartridge includes a container having a plurality of chambers for holding one or more reagents, and a microfluidic device having microfluidic channels. The chambers are also for use during sample preparation and processing. Each of the chambers is sealed with the aid of a friable seal, which may be formed of a polymeric material or a metallic material. The cartridge includes a deformable layer (e.g., layer of deformable material) with holes (or openings) that are aligned with various puncturing elements (see FIG. 9) and alignment members of the microfluidic device configured to be disposed adjacent to the container. In some situations, two or more of the plurality of puncturing elements are disposed opposite each of the plurality of closed and fluidically isolated chambers. A sample chamber is configured to be mounted adjacent to the microfluidic device and the container, in the general orientation shown in the figure.

The cartridge can include a single friable seal adjacent to each chamber, or a plurality of friable seals. For instance, each individual chamber of the container can be sealed with a separate friable seal.

As described below, the sample cartridge interface module (cartridge module) includes a clamping system, such as, e.g., a cam driven clamping system for engaging the microfluidic device (or layer) of the cartridge with the container. In some situations, the cam applies a predetermined pressure against the cartridge, which presses the container of the cartridge against the microfluidic device of the cartridge. In some cases, the applied pressure can be constant or gradually increased.

The microfluidic channel can include one or more selectably closable channels. The selectably closable channels can be opened and closed with the aid of valves, such as diaphragm valves (or pumps). The microfluidic channel can be in fluid communication with one or more diaphragm valves, such as 1, 2, 3, 4, 5, 6, 7, 8, 9, 10 or more valves. A diaphragm valve can include a layer of a pressure-deformable material (e.g., elastomeric material) that is configured to rest against a valve seat, thereby regulating fluid flow. The one or more valves can be pneumatically-actuated valves, such as actuated with the aid of positive pressure or negative pressure (vacuum). In some cases, the one or more valves are piezoelectric valves, which are configured to open or close upon the application of an electrical potential to a piezoelectric material.

Figure 42:
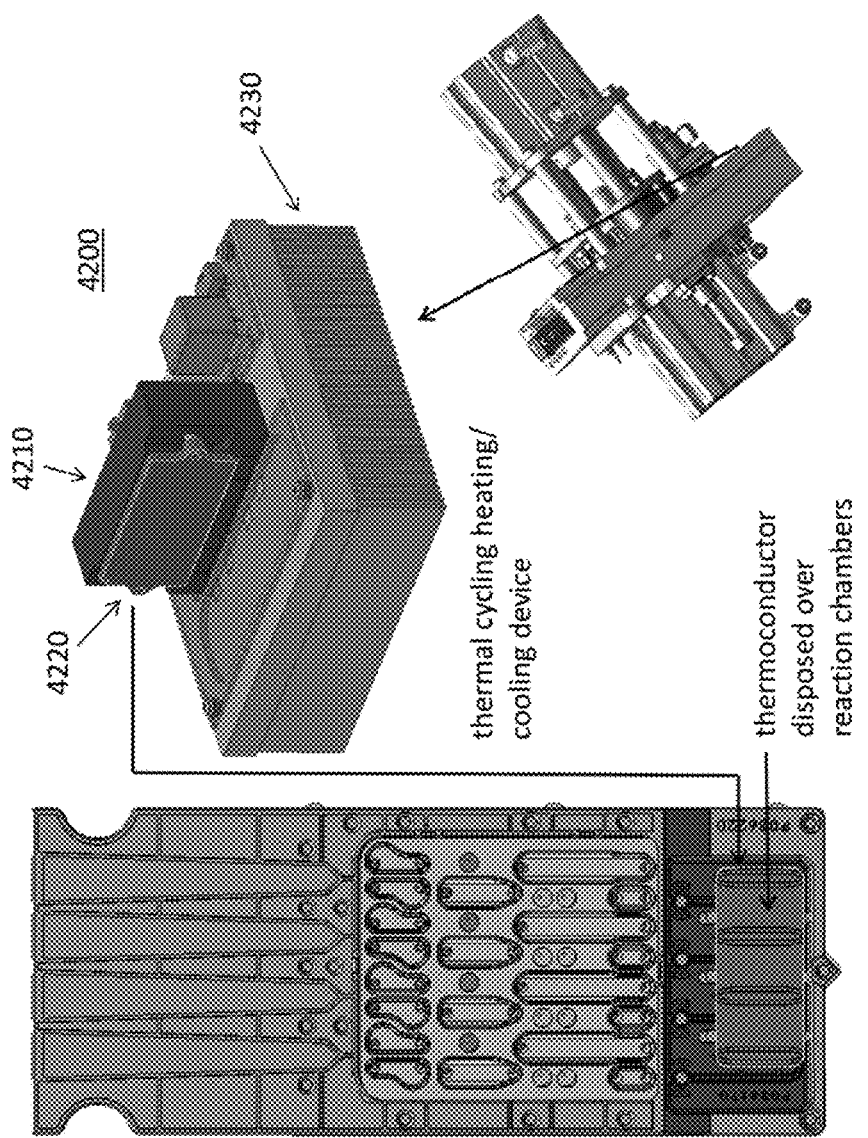
FIG. 42 shows an embodiment of a thermocycler assembly including four reaction chambers in a sample or control cartridge, a thermal conductor (or thermoconductor) disposed over the reaction chambers, and a thermal cycling heating and cooling device (including, e.g., a Peltier heating and cooling device).

In an embodiment, a cartridge comprises a frame that is attached on one side to a microfluidic chip that has a port leading to sample chambers (e.g., sample receptacles). The sample chambers are each adapted to accept a sample from a sample holder (e.g., cotton swab, punch or liquid). The cartridge also includes a hole (e.g., a slot, a receptacle, a receiving element, a compartment) adapted to accept a container having a plurality of chambers preloaded with reagents for sample processing. The cartridge includes a slot or receiving element that accepts part or all of a thermocycler assembly, e.g., a plurality of reaction chambers (thermocycling chambers) configured to perform amplification (e.g., by PCR) with thermal cycling and a plurality of reagent (premix) chambers for providing amplification reagents (e.g., an amplification premix) to the reaction chambers. Thermocycling chambers are in fluid communication with microfluidic channels in the microfluidic chip, which microfluidic channels are in communication with chambers of the container. In some cases, the thermocycling chambers are raised in relation to the microfluidic device and have openings that are in contact with or adjacent to a heat spreader (or thermoconductor that can spread/distribute heat and cooling), which in turn is in contact with or adjacent to a temperature control element (e.g., a heating element and/or a cooling element, such as a Peltier heating and cooling device) that is configured to perform thermal cycling. In certain embodiments, the temperature control element (e.g., a heating and cooling element, such as a Peltier heating and cooling device) is configured to move to come into contact with or become adjacent to the heat spreader or the reaction chambers. FIG. 42 illustrates an embodiment of a thermal cycling heating and cooling device that contacts the thermoconductor disposed over the reaction chambers when the cartridge is engaged with the cartridge module.

In some embodiments, the cartridge further comprises a sample receptacle that has a sample chamber adapted to receive a sample. The sample chamber has an opening that is parallel to a surface of the microfluidic device disposed between the microfluidic device and the container. Such a configuration can advantageously permit a user to insert a tissue sample (e.g., cotton swab) using various tools and apparatuses for collecting the tissue sample, such as a Q-tip or a ball of cotton of various shapes and sizes. The alignment of the opening permits the cartridge to be inserted into a system (e.g., the system 100 of FIG. 1) in a configuration that is vertical or angled with respect to a plane having the system.

A sample cartridge can comprise one or a plurality of lanes, each lane configured to process a sample or a control. Lanes can comprise a fluidic circuit that comprises channels, compartments and fluid control elements such as valves and pumps. Lanes in a sample cartridge can be fluidically isolated from one another, e.g., fluid from one lane cannot cross into another lane.

In some cases, the sample receptacle is unitary (or single-piece) with the microfluidic device. Such construction can help minimize processing cost, as the sample receptacle and microfluidic device may be formed during one or more overlapping processing steps.

The microfluidic channel can comprise a sample channel in fluid communication with the sample chamber. When the container has engaged the microfluidic device, the container covers all or a substantial portion of the sample channel.

The microfluidic device can comprise a reagent channel in fluid communication with a reagent chamber of the plurality of closed and fluidically isolated chambers. When the container has engaged the microfluidic device, the container covers all or a substantial portion of the reagent channel.

In some embodiments, the plurality of closed and fluidically isolated chambers comprise a first chamber holding a diluent, a second chamber holding one or more lysis reagents, a third chamber having capture particles, and a fourth and/or fifth chamber having a wash solution. The second chamber is in fluid communication with the sample chamber. In some cases, the second chamber is a waste chamber configured to hold a waste material.

In some embodiments, the cartridge comprises a layer of deformable material between the container and the microfluidic device. In some situations, the layer of deformable material is formed of closed foam, such as ethylene propylene diene monomer (EPDM), an open foam, such as ethylene vinyl acetate (EVA), or other polymeric material, such as silicone. The layer of deformable material may have a thickness between about 0.5 mm and 20 mm, or 1 mm and 5 mm. In an implementation, the layer of deformable material has a thickness of about 3 mm. The layer of deformable material can be compressed to a thickness between about 10 micrometers ("microns") and 1000 microns, or 100 microns and 800 microns, or 300 microns and 600 microns. The container is attached to the microfluidic device with the aid of the layer of deformable material. In some situations, the layer of deformable material has a first sticky side and a second sticky side opposite from the first sticky side. The first sticky side is adjacent to the microfluidic device and the second sticky side is adjacent to the container. In some cases, the layer of deformable material is formed of a compressible material. In other cases, the layer of deformable material is formed of a heat pliable material. In an example, the layer of deformable material comprises springs or a polymeric material that is configured to compress upon the application of pressure to the layer of deformable material.

The microfluidic device includes pneumatically actuated valves. In some cases, a plurality of valves defines a pump. A pump can include at least 2, 3, 4, 5, 6, 7, 8, 9, 10, or more valves in a serial configuration.

Figure 55:
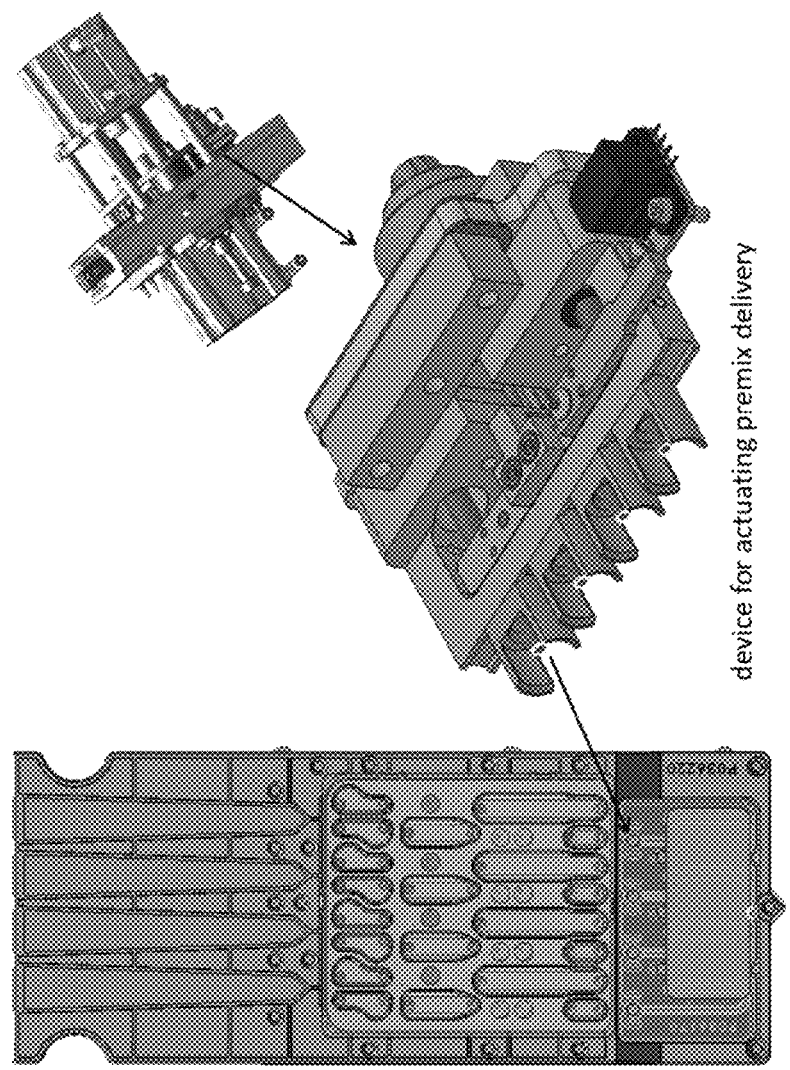
FIG. 55 illustrates an embodiment of a device configured to actuate delivery of amplification reagents from a premix vessel or chamber to a reaction chamber.

With reference to FIG. 8, the cartridge includes a thermocycler assembly for use in polymerase chain reaction (PCR). In the illustrated example, the thermocycler assembly in the cartridge includes four reaction chambers (thermocycling chambers) configured to perform nucleic acid amplification by PCR with thermal cycling, each thermocycling chamber in fluid communication with a channel of the microfluidic device. The thermocycler assembly further includes a plurality of reagent (premix) chambers for delivering a premix of amplification reagents to the thermocycling chambers. FIG. 55 illustrates an embodiment of a device configured to actuate delivery of amplification reagents from a premix chamber to a PCR reaction chamber. Such a device functions as a premix application member and can comprise, e.g., a plunger and/or a pneumatically actuated device for delivering positive pressure to deliver the premix during sample processing. The thermocycling assembly can optionally include optical elements to allow interrogation of the thermocycling chamber to perform assays such a real-time or quantitative PCR; the optical elements can include fiber optic delivery of a light source such as a laser or LED, and collection of fluorescent light for delivery to a detector such as a CCD, CMOS, photodetector, photo diode, or photomultiplier detector. The optical detection can be used to quantify the amount of DNA in the sample which can be further used to, for example, dilute the sample to known concentration of DNA, or to adjust the number of thermal cycles, or injection parameters.

In some embodiments, each chamber of the container is sealed from a top side by a sealing member, which may be transparent or opaque. A bottom side of the container, which is configured to rest adjacent to the microfluidic device, is sealed with the aid of the friable seal. The friable seal can form a hermetic (or airtight) seal between the container and the external environment.

Figure 9:
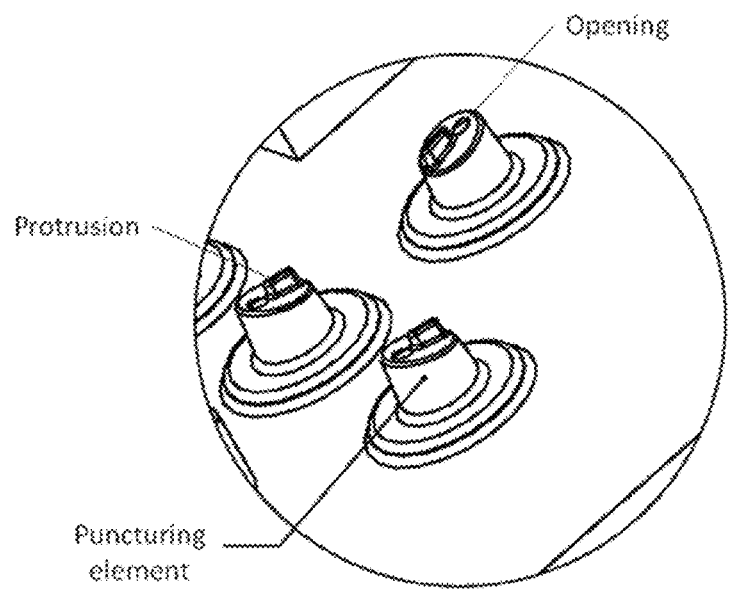
FIG. 9 show puncturing elements, in accordance with an embodiment of the invention.

FIG. 9 shows puncturing elements formed in the microfluidic device, in accordance with an embodiment of the invention. The puncturing elements are configured to form holes in the friable seal of the cartridge when the container is pressed against the microfluidic device. The puncturing elements include holes that are configured to bring the chambers of the container in fluidic communication with microfluidic channels in the microfluidic device, and various ports, including the sample chamber. This permits the flow of a fluid from the chambers of the container and the sample chamber through the microfluidic channels of the microfluidic device. The puncturing elements also include protrusions or raised ridges for facilitating the formation of holes in the friable seal.

Figure 10:
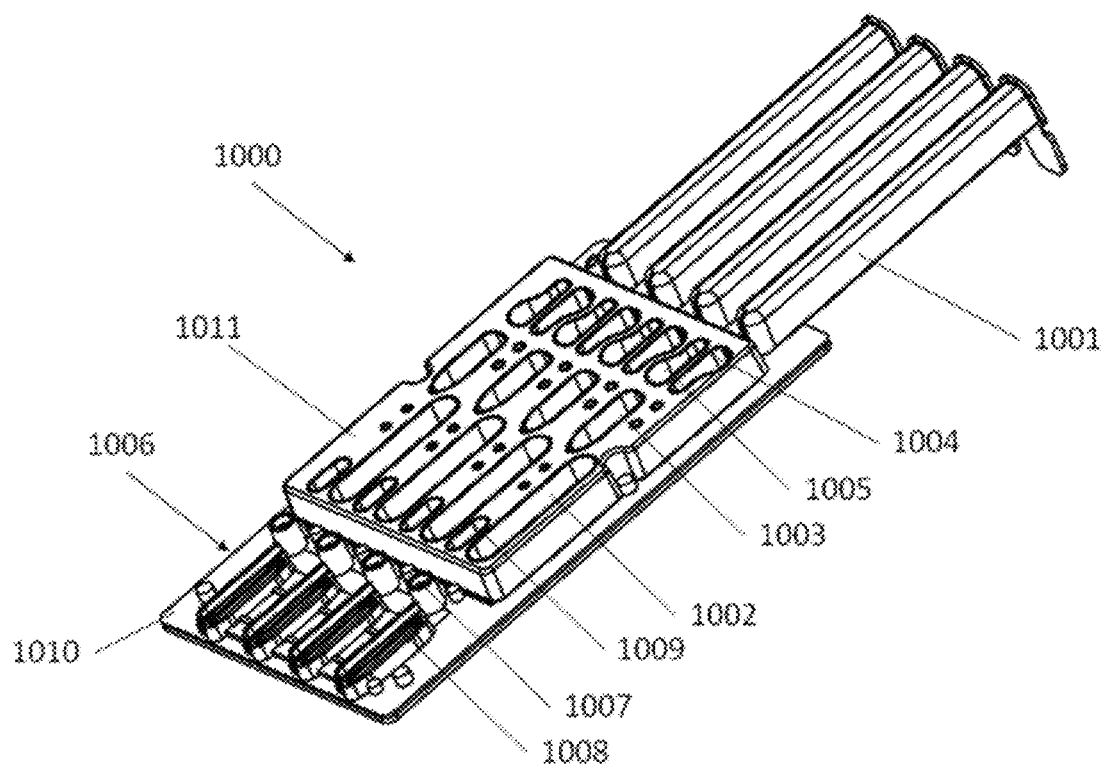
FIG. 10 shows an integrated cartridge, in accordance with an embodiment of the invention.

FIG. 10 schematically illustrates the cartridge when the container and microfluidic device (including the intervening layers) have been engaged with one another, in accordance with an embodiment of the invention. The cartridge of FIG. 10 includes a plurality of separate or separable components, but in some embodiments one or more components of cartridge can be single piece. For instance, the sample chamber can be formed in the microfluidic device.

With reference to FIG. 10, the cartridge 1000 includes a plurality of sample chambers 1001 and a container 1011 adjacent to a microfluidic device 1010 with microfluidic channels. The container 1011 includes four lysis reagent storage and waste chambers 1002, four bead suspension and capture chambers 1003, four pairs of first wash solution/buffer chamber 1004 and second wash solution/buffer chamber 1005, a thermocycler assembly 1006 having four pairs of premix chamber 1007 and reaction chamber 1008, and four diluent (or dilution) chambers 1009. The cartridge 1000 includes four pairs of premix chamber 1007 and reaction chamber 1008 in parallel (four pairs shown). Each of the chambers of the container 1011 is in fluid communication with a channel of the microfluidic device 1010 (see FIG. 15) of the cartridge 1000. In some embodiments, all of the sample chambers, wash chambers, bead suspension/capture chambers, lysis reagent/waste chambers, diluent chambers, and reaction chambers are substantially co-planar.

The container 1011 can be prefilled with the first wash solution or buffer, second wash solution or buffer, premix and beads. This advantageously provides for automated sample preparation, processing and analysis with minimal or no user intervention. The reagents can be those necessary to perform STR analysis. For example, the reagents can include Promega® DNA IQ® and/or PowerPlex® reagents.

The cartridge 1000 includes four processing channels for parallel processing, such as processing samples in parallel (i.e., at the same time), or processing a sample and a control in parallel. A sample chamber 1001, microfluidic channel in the microfluidic device 1010 and a thermocycling chamber are comprised in a single processing channel or lane of the cartridge.

In some embodiments, the first and second wash solutions or buffers include water and a salt, such as sodium chloride. In other embodiments, the first wash solution and the second wash solution are aqueous solutions containing an alcohol, e.g., ethanol. The first wash solution and the second wash solution can contain any concentration of the alcohol in water (e.g., about 60% to about 95%, or about 70% to about 90%) suitable for purifying nucleic acid (e.g., DNA) captured to a substrate (e.g., magnetically responsive particles). In an embodiment, the first wash solution contains about 90% ethanol in water, and the second wash solution contains about 70% ethanol in water. In another embodiment, both the first wash solution and the second wash solution contain about 70% ethanol in water.

In some embodiments, the lysis reagent or buffer comprises a chemical or biochemical lysis reagent and a detergent/surfactant. Non-limiting examples of chemical lysis reagents that can be used for extraction of nucleic acid from cells include guanidinium salts (e.g., guanidinium thiocyanate and guanidinium hydrochloride) and urea. In certain embodiments, the detergent/surfactant comprises a zwitterionic detergent/surfactant and/or a non-ionic detergent/surfactant. Examples of zwitterionic detergents/surfactants include without limitation 3-[(3-cholamidopropryl)dimethylammonio]-1-propanesulfonate (CHAPS), cocamidopropyl hydroxysultaine, and cocamidopropyl betaine. Non-limiting examples of non-ionic detergents/surfactants include polyoxyethylene glycol alkyl ethers (e.g., octaethylene glycol monododecyl ether and pentaethylene glycol monododecyl ether), polyoxypropylene glycol alkyl ethers, block copolymers of polyethylene glycol and polypropylene glycol (e.g., poloxamers (Pluronics®)), polyoxyethylene glycol octylphenol ethers (e.g., Tritons®, such as Triton® X-100 and Triton® X-114), polyoxyethylene glycol alkylphenol ethers (e.g., NP-40 and Nonoxynol-9), polyoxyethylene glycol sorbitan alkyl esters (e.g., Polysorbates/Tweens®, such as Polysorbate/Tween® 20), sorbitan alkyl esters (e.g., sorbitan monolaurate), glycerol alkyl esters (e.g., glyceryl laurate), and glucoside alkyl ethers (e.g., decyl glucoside, lauryl glucoside, and octyl glucoside). In certain embodiments, the lysis reagent or buffer comprises a guanidinium salt (e.g., guanidinium thiocyanate or guanidinium hydrochloride), a Triton® detergent/surfactant (e.g., Triton® X-100 or Triton® X-114), and CHAPS. In an embodiment, the lysis reagent or buffer includes about 50-70% guanidinium thiocyanate, less than about 2% polyethylene glycol tert-octylphenyl ether (Triton® X-114), less than about 2% 3-[(3-cholamidopryl)dimethylammonio]propanesulfonic acid (CHAPS), and about 44.2% water.

In further embodiments, the lysis reagent or buffer comprises a chemical or biochemical lysis reagent, a detergent/surfactant, and a buffering agent. In some embodiments, the buffering agent provides buffering in a basic pH range (e.g., about pH 8-11, about pH 8-10, about pH 10-11, about pH 9-10, or about pH 8-9). Non-limiting examples of buffering agents that provide buffering in a basic pH range include borate, N,N-bis(2-hydroxyethyl)glycine (bicine), N-tris(hydroxymethyl)methylglycine (tricine), tris(hydroxymethyl)methylamine (Tris), 3-amino-1-propanesulfonic acid, 4-(cyclohexylamino)-1-butanesulfonic acid (CABS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N-(2-hydroxyethyl)piperazine-N'-(3-propanesulfonic acid) (EPPS), and 3-{[tris(hydroxymethyl)methyl]amino}-propanesulfonic acid (TAPS).

In additional embodiments, the lysis reagent or buffer comprises: 1) a chemical or biochemical lysis reagent, a detergent/surfactant, and an anti-foaming agent (also called defoamer); or 2) a chemical or biochemical lysis reagent, a detergent/surfactant, a buffering agent, and an anti-foaming agent. Non-limiting examples of anti-foaming agents (defoamers) include water-based defoamers, silicone-based defoamers (e.g., defoamers containing a silicate or a siloxane (e.g., polydimethylsiloxane)), and EO/PO-based defoamers containing a copolymer of polyethylene glycol and polypropylene glycol.

If a sample is stored on a cellulosic substrate such as a piece of paper (e.g., FTA® paper), a lysis reagent or buffer suitable for extracting nucleic acid (e.g., DNA) from cells stored on the piece of paper can be utilized. A suitable lysis reagent or buffer includes without limitation GenSolve® (available from IntegenX Inc.), which can optionally contain one or more additional agents (e.g., an anti-foaming agent) for use in the system or instrument described herein.

Other reagents for use during processing may include an elution buffer having, for example, 10 mM Tris (pH 8.0), 0.1 mM EDTA. DNA captured on beads may or may not be eluted off the beads as desired.

The diluent in the dilution chamber can be an aqueous solution. In some embodiments, the liquid of the diluent is water. The diluent can also comprise a control—e.g., 1) a size standard in a lane running a sample, 2) a size standard in a lane running a positive control, 3) a size standard in a lane running a negative control, and 4) both an allelic ladder and a size standard in a lane running neither a sample, a positive control nor a negative control.

Figure 11:
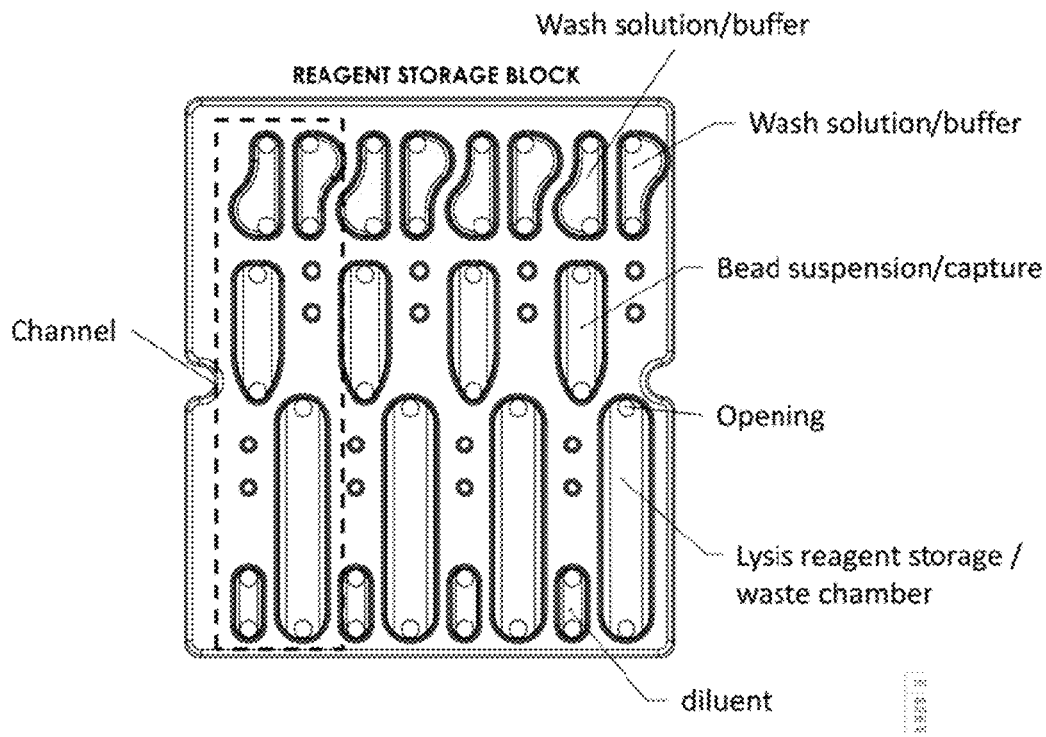
FIG. 11 shows a container having chambers for sample processing, in accordance with an embodiment of the invention.

FIG. 11 is a schematic top view of the container showing various chambers, in accordance with an embodiment of the invention. The container includes wash solution/buffer chambers, a bead suspension and capture chamber, a lysis reagent storage chamber, and a diluent chamber. The lysis reagent storage chamber is used as a waste chamber during processing. The chambers define a single channel of the cartridge; the cartridge as illustrated has four channels for parallel processing of the sample or different samples. When the container is pressed against the microfluidic device, the puncturing elements form openings in the chambers. As illustrated, two openings are formed in each chamber. The openings permit fluid flow to and from the channels of the microfluidic device.

Figure 12:
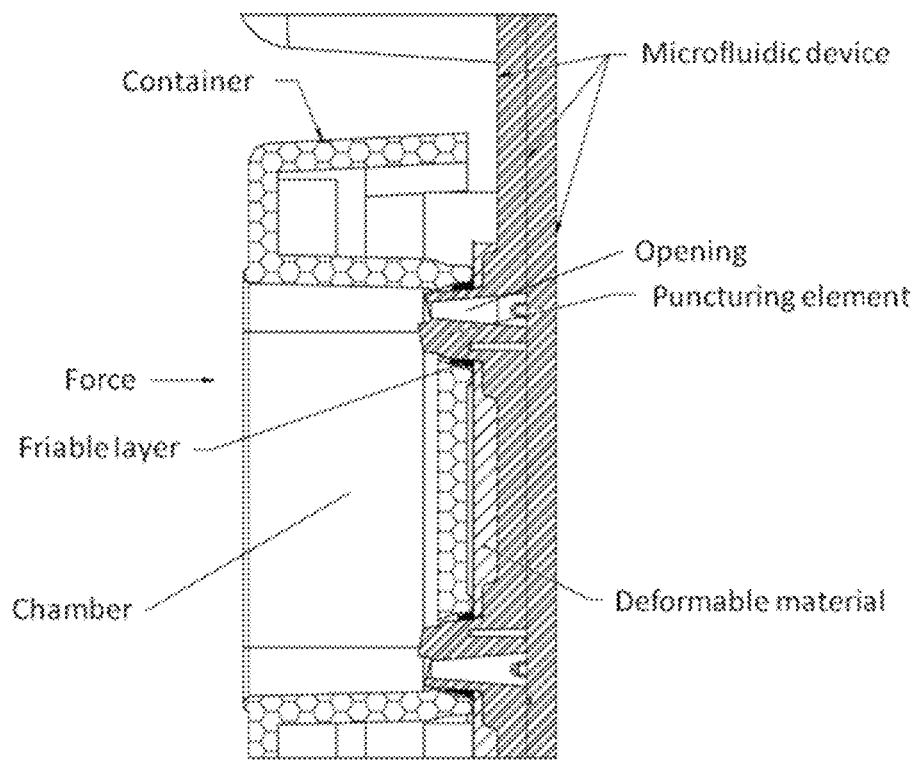
FIG. 12 is a schematic side view of a cartridge, in accordance with an embodiment of the invention.

FIG. 12 is a schematic side view of the cartridge, in accordance with an embodiment of the invention. The puncturing elements have pierced the friable layer (or seal) of the cartridge, bringing the openings of the puncturing elements and the microfluidic channels of the microfluidic device in fluid communication with a chamber of the container.

Figures 13A, 13B:
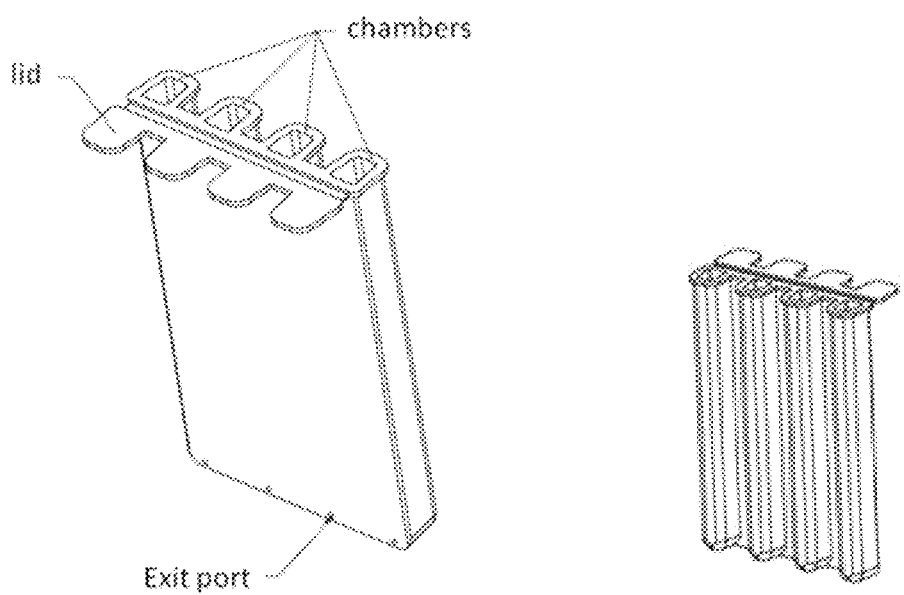
FIGS. 13A and 13B show a sample receptacle, in accordance with an embodiment of the invention.

FIGS. 13A and 13A show the sample receptacle, in accordance with an embodiment of the invention. The sample receptacle includes a plurality of sample chambers, one chamber per channel of the cartridge. The sample chambers are configured to accept a sample, e.g., a cotton swab, such as with the aid of a Q-tip or ball of cotton or analyte contained in another material. The sample receptacle can include a lid for sealing the sample chambers during processing.

Figure 14:
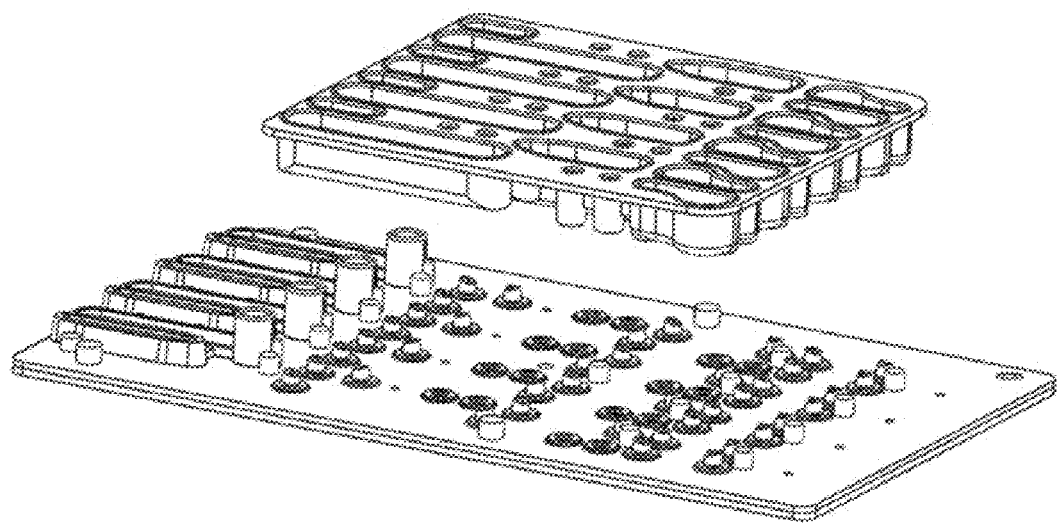
FIG. 14 shows a cartridge having a microfluidic device and a container, in accordance with an embodiment of the invention.
Figure 15:
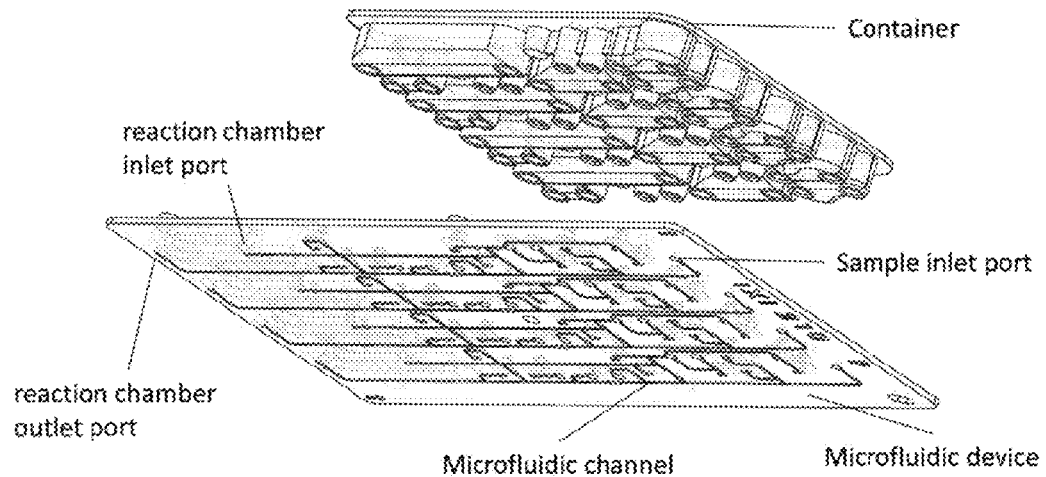
FIG. 15 is a bottom view of the microfluidic device and container of FIG. 14, in accordance with an embodiment of the invention.

FIG. 14 shows the container and the microfluidic device, in accordance with an embodiment of the invention. A pair of puncturing elements are configured to bring channels in the microfluidic device in fluid communication with a chamber of the container. A bottom view of the cartridge is shown in FIG. 15. The microfluidic device has a microfluidic channel network per channel of the cartridge. The microfluidic device of FIG. 15 includes four reaction channels for parallel processing. A sample inlet port is configured to bring various chambers of the container in fluid communication with the sample chamber. A reaction chamber inlet port is configured to bring a microfluidic channel of the microfluidic device in fluid communication with a reaction chamber configured to perform nucleic acid amplification (e.g., by PCR) with thermal cycling (sometimes also referred to as a "thermocycling chamber" herein). A reaction chamber outlet port brings a reaction chamber in fluid communication directly or indirectly with a separation system, such as the electrophoresis capillaries. A reaction chamber can be in fluid communication with a diluent chamber, which can dilute amplification products with a diluent (e.g., water), can comprise a control (e.g., a size standard), and can in turn be in fluid communication with the separation system.

Figure 16:
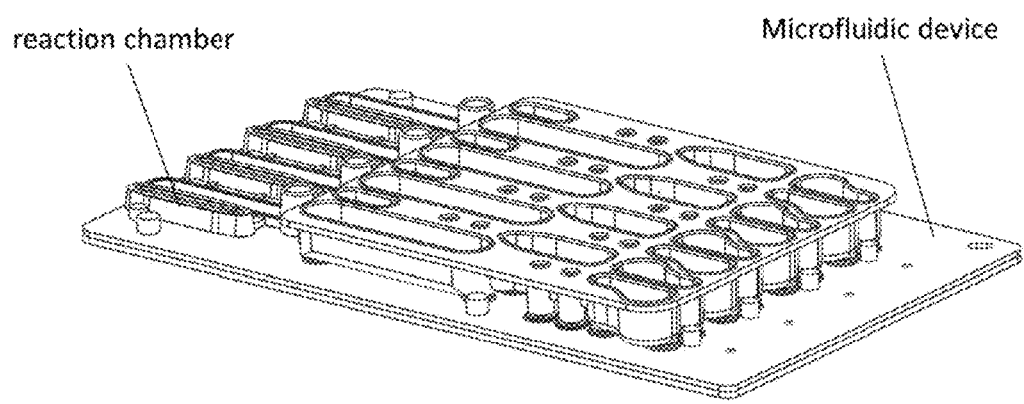
FIG. 16 is a schematic top view of the microfluidic device and container of FIGS. 14 and 15, showing the container mounted on the microfluidic device, in accordance with an embodiment of the invention.

FIG. 16 is a schematic side view of the cartridge, showing the container engaged with the microfluidic device, and the thermocycler assembly comprising four reaction chambers and attached to the microfluidic device, in accordance with an embodiment of the invention.

Figure 17:
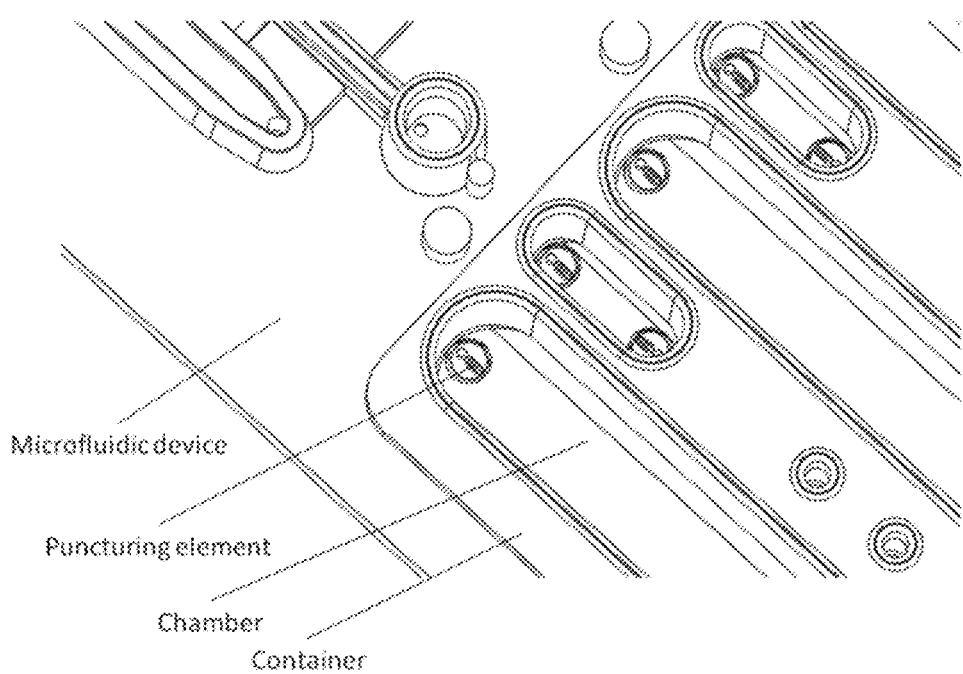
FIG. 17 shows various features of the microfluidic device and container of FIGS. 14-16, in accordance with an embodiment of the invention.

With reference to FIG. 17, a puncturing element of the microfluidic device is in fluid communication with a chamber of the container. An opening of the puncturing element brings the chamber in fluid communication with a microfluidic channel of the microfluidic device.

The cartridge can be a disposable, single-use cartridge. In some embodiments, the cartridge has a size and shape that minimizes environmental waste after use and even environmental waste (e.g., $CO_2$ and $NO_x$ emission) during construction. The cartridge can have a thickness that provides a smaller footprint in relation to other sample processing and/or analysis systems. In some cases, the size and thickness of the cartridge enables the minimization of the size of the system 100, which in turn enables ready transport of the system 100 and even a reduction of manufacturing costs and expenses during construction of the system 100.

Figure 35A:
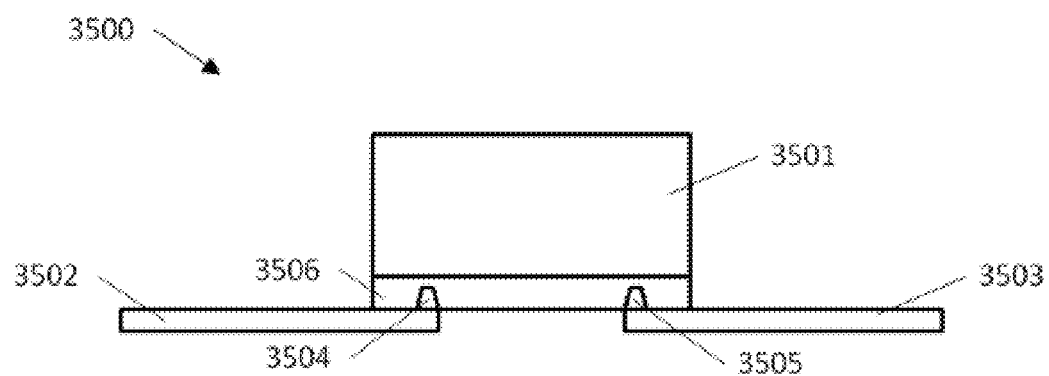
FIGS. 35A and 35B schematically illustrate a container engaging a microfluidic device, in accordance with en embodiment of the invention.
Figure 35B:
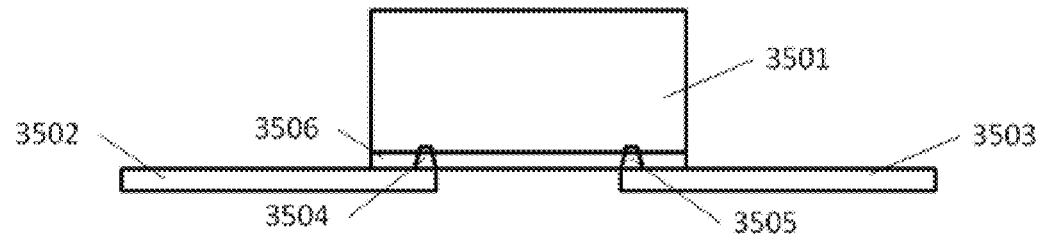

In some embodiments, engaging the container with the microfluidic device creates a fluid flow path from a first channel to a second channel through a chamber of the container. FIG. 35A shows a cartridge 3500 having a container with a chamber 3501, and a microfluidic device adjacent to the container. The microfluidic device comprises a first channel 3502 and a second channel 3503. The first channel is in fluid communication with a puncturing element 3504 and the second channel 3503 is in fluid communication with a second puncturing element 3505. The container 3501 is attached to the microfluidic device having the first channel 3502 and the second channel 3503 through a layer of deformable material 3506. The chamber 3501 is sealed at a side adjacent to the layer of deformable material 3506 with the aid of a friable (or puncturable) seal. The first channel 3502 can be in fluid communication with a first port to permit a fluid to enter or leave the first channel 3502, and the second channel 3503 can be in fluid communication with a second port for permitting a fluid to enter or leave the second channel 3503. The layer of deformable material 3506 supports the container but, absent sufficient force, keeps the puncturing elements 3504 and 3505 from piercing the friable seal. With reference to FIG. 35B, engaging the container against the microfluidic device deforms the layer of deformable material 3506 and brings the puncturing elements 3504 and 3505 in contact with a friable seal of the container. The puncturing elements pierce the layer of friable material and bring the chamber in fluid communication with the first channel 3502 and the second channel 3503.

Cassettes provided herein can be formed of multiple components and assembled to form an integrated unit. In some embodiments, assembling is performed prior to use by an end user.

FIG. 31 shows an integrated cassette 3100 for use with systems provided herein. An individual processing channel of the cassette 3100 has sample and lysis chambers 3101, wash solution/buffer chambers 3102, a bead suspension and capture chamber 3103, a lysis reagent storage and waste chamber 3104 and a diluent chamber 3105. The cassette 3100 has a thermocycler assembly comprising four reaction chambers 3106 configured to perform nucleic acid amplification (e.g., by PCR) with thermal cycling. The cassette 3100 has four processing channels or lanes.

With reference to FIG. 32, the cassette 3100 includes a holder 3107 that includes the lysis chamber 3101, a microfluidic device 3108 having a plurality of microfluidic channels 3109 and pneumatically actuated valves (e.g., MOVe valve), and a container 3110 having the chambers 3102-3105. A fluidic member 3111 brings the chambers 3102-3105 in fluid communication with the channels 3109. The fluidic member 3111 effects a macro-to-micro scale transition in fluid volume. The fluidic member 3111 includes puncturing elements 3111a and guides 3111b for coupling the fluidic member 3111 to the holder 3107.

The microfluidic device 3108 includes valves having a pneumatic layer, fluidic layer and an elastomeric layer disposed between the pneumatic layer and the fluidic layer. The valves are in fluid communication with a positive or negative pressure source for actuating the valves (see, e.g., FIGS. 36A and 36B). During use, the valves of the microfluidic device 3108 move fluid in and out of the chambers 3102-3105. The flow of fluid in and out of the chambers can be facilitated upon the application of positive or negative pressure to each of the chambers 3102-3105 through a space adjacent to each of the chambers 3102-3105, at a side opposite of the microfluidic device 3108.

The chambers 3102-3105 are sealed with the aid of layers 3112 and 3113. The layer 3113 is formed of a friable material, such as a polymeric material (e.g., elastomeric material) or other materials provided herein. The cassette 3100 includes a layer of deformable material 3114 that is configured to bring the puncturing elements in the fluidic member 3111 in contact with the layer 3113. The layers 3112 and 3113 formed a hermetic seal in each of the chambers 3102-3105.

The cassette 3100 includes gripping members 3115 for enabling a user to grip the cassette 3100 with one or both of the user's hand. The gripping members 3115 are angular depressions in side walls of the cassette. In other instances, the gripping members may be ridges on a surface of the side walls.

The sample chamber 3101 is configured to hold a sample, such as with the aid of a swab (e.g., a cotton swab or a brush swab) or a cellulosic substrate (e.g., a paper, such as FTA® paper). The chamber 3101 is sealed with the aid of a door 3116 that is configured to be manually closed or, alternatively, closed with the aid of a motorized mechanism or actuation mechanism. The wash solution/buffer chambers 3102 can be preloaded with wash solutions or wash buffers. The bead suspension and capture chamber 3103 can be preloaded with beads for processing, such as magnetic (magnetically responsive) beads or particles. In some embodiments, the bead suspension/capture chamber comprises (e.g., is preloaded with) silica-coated magnetic beads (e.g., Magnacel® beads from Promega). The lysis storage chamber 3104 can be preloaded with a lysis reagent. The diluent chamber 3105 can be preloaded with a diluent (e.g., water) that can comprise a control (e.g., a size standard).

FIGS. 8, 10, 11, 14, 16, 31 and 32 show two holes to the left of each reagent storage/waste chamber (viewing from the reaction chamber to the sample chamber), and two holes to the right of each bead suspension/capture chamber. In another embodiment, a cartridge comprises two holes to the left of each reagent storage/waste chamber, and one hole to the right of each bead suspension/capture chamber. In additional embodiments, viewing from the reaction chamber to the sample chamber, a cartridge comprises: (1) two or more holes to the left of each reagent storage/waste chamber and one or more holes to the right of each bead suspension/capture chamber; (2) two or more holes to the right of each reagent storage/waste chamber and one or more holes to the left of each bead suspension/capture chamber; (3) two or more holes to the left of each reagent storage/waste chamber and one or more holes to the left of each bead suspension/capture chamber; or (4) two or more holes to the right of each reagent storage/waste chamber and one or more holes to the right of each bead suspension/capture chamber.

B. Microfluidic Devices

The sample cartridges of this invention include fluidic devices. In certain embodiments, the devices are microfluidic devices.

In some embodiments, a passage is considered to be microfluidic if it has at least one cross-sectional dimension of no more than about 1 mm or 0.5 mm, e.g., if a sphere having a diameter of about 1 mm or 0.5 mm can pass through the passage without restriction. In other embodiments, a passage is considered to be microfluidic if it has no cross-sectional dimension greater than about 1 mm or 0.5 mm In some embodiments, a microfluidic volume is a volume of no more than about 1 microliter. In further embodiments, a macrofluidic volume is a volume of greater than about 1 microliter, e.g., at least about 2 microliters, at least about 10 microliters, at least about 100 microliters, or at least about 1 milliliter.

In some embodiments, the microfluidic device comprises selectably closable channels that are opened and closed with the aid of Micro-scale On-chip Valves (MOVe) device that miniaturize and automate complex workflows. Collectively, the MOVe devices, pumps, and routers and the instrumentation to operate them can be referred to as a microfluidic device (or microchip fluid processing platform). A MOVe device can include a series of three or more valves (e.g., diaphragm valves) in series. An individual valve of the MOVe device includes, in sequence, a pneumatic-actuation (also "pneumatic" herein) layer, elastomeric layer and fluidic layer. In certain embodiments, the actuation layer employs hydraulic actuation. The fluidic layer includes a valve seat, which may be a portion of a dome or cavity of the valve that is in fluid communication with the fluidic layer. The pneumatic layer is configured to provide positive or negative pressure to the elastomeric layer, thereby moving the elastomeric layer toward or away from the valve seat, which closes and opens the valve. In some cases, absent positive or negative pressure (i.e., actuation) from the pneumatic layer, the valve is in a normally open configuration in which elastomeric layer is disposed away from valve seat, thereby permitting fluid flow through the fluid layer. Upon actuation, the elastomeric layer comes in contact with a valve seat to close the valve and impede fluid flow through the valve. In other cases, absent positive or negative pressure from the pneumatic layer, the valve is in a normally closed configuration in which the elastomeric layer is in contact with the valve seat, thereby preventing fluid flow through the fluidic layer. Upon actuation, the elastomeric layer moves away from the valve seat to open the valve and permit fluid flow through the valve.

Accordingly, certain microfluidic devices used in this invention can have a pneumatic layer, fluidic layer and an elastomeric layer disposed between the pneumatic layer and the fluidic layer. In certain embodiments, the fluidic channels are comprised on the surface of the fluidics layer that faces the elastomeric layer. A valve can be formed where an interruption interrupts the channel. In this case, the port comprises that portion of the channel that meets the interruption and that will open into the valve chamber when the diaphragm is deflected. In another embodiment, a fluidic channel travels within a fluidics layer. In such an embodiment, the fluidics layer can comprise a plurality of layers. Certain layers can include vias, or bores, that put two sides of the layer in fluid communication with each other. Certain layers can comprise channels. Such channels can be closed when two layers are sandwiched together. In this case, ports are formed where two vias made in the fluidics layer communicate between two channels and the elastic layer across from an actuation valve body. (The two adjacent vias are separated by an interruption that can function as a valve seat.) For example, the structure can comprise four layers: two layers comprising a fluidics layer, an elastomeric layer and a pneumatics layer. In another embodiment, a fluidic channel is formed as a bore that traverses from one surface of the fluidic layer to the opposite surface which faces the elastic layer. A pair of such bores separated by an interruption can function as a valve. When the elastic layer is deformed away from the interruption (to which it is not bonded), a passage is created that allows the bores to communicate and for fluid to travel in one bore, through the valve and out the other bore.

MOVe valves are described in further detail in U.S. Patent Publication Nos. 2004/0209354 to Mathies et al. ("FLUID CONTROL STRUCTURES IN MICROFLUIDIC DEVICES") and 2011/0005932 to Jovanovich et al. ("UNIVERSAL SAMPLE PREPARATION SYSTEM AND USE IN AN INTEGRATED ANALYSIS SYSTEM") ("Jovanovich"), U.S. Patent Publication 2010/0303687, U.S. Patent Publication 2011/0005932, U.S. Patent Publication 2011/0126911, which are entirely incorporated herein by reference.

MOVe valves, pumps and routers may have a normally open or normally closed configuration. In a normally closed configuration, absent actuation, a MOVe valve, pump or router is closed, thereby blocking fluid flow. A normally closed MOVe valve can be opened upon actuation, such as with the aid of positive pressure or a vacuum to move an elastomeric layer of the MOVe valve away from a valve seat of the valve. In a normally open configuration, absent actuation, a MOVe valve, pump or router is open, thereby permitting fluid flow. A normally open MOVe valve can be closed upon actuation, such as with the aid of positive pressure or vacuum to move an elastomeric layer of the MOVe valve to and in contact with a valve seat of the valve.

The MOVe valves and pumps can combine two glass and/or plastic microfluidic layers with an elastomeric layer, e.g., polydimethyl siloxane (PDMS) that opens and closes the valve, and a pneumatic layer to deform the membrane and actuate the valve. The microfluidic channel etched in the top glass fluidic wafer is discontinuous and leads to a valve seat which is normally closed. When a vacuum is applied to the pneumatic displacement chamber by conventional-scale vacuum and pressure sources, the normally closed PDMS membrane lifts from the valve seat to open the valve. PDMS can be bonded to plastic by coating the plastic with a layer of an oxide, e.g., a metal oxide, and then contacting the PDMS to the plastic, optionally with heat and pressure.

In some embodiments, the microfluidic device is provided in a cartridge. The cartridge can include sample capture and purification, micro-separations, micro-valves, -pumps, and -routers, nanofluidic control, and nano-scale biochemistry systems. MOVe pumps, valves, and routers transport, process, and enable analysis of samples. These externally actuated, pneumatically-driven, on-chip valves, pumps, and routers can control fluidic flow at manipulate volumes from 20 nL to 10 µL.

Figures 52A, 52B:
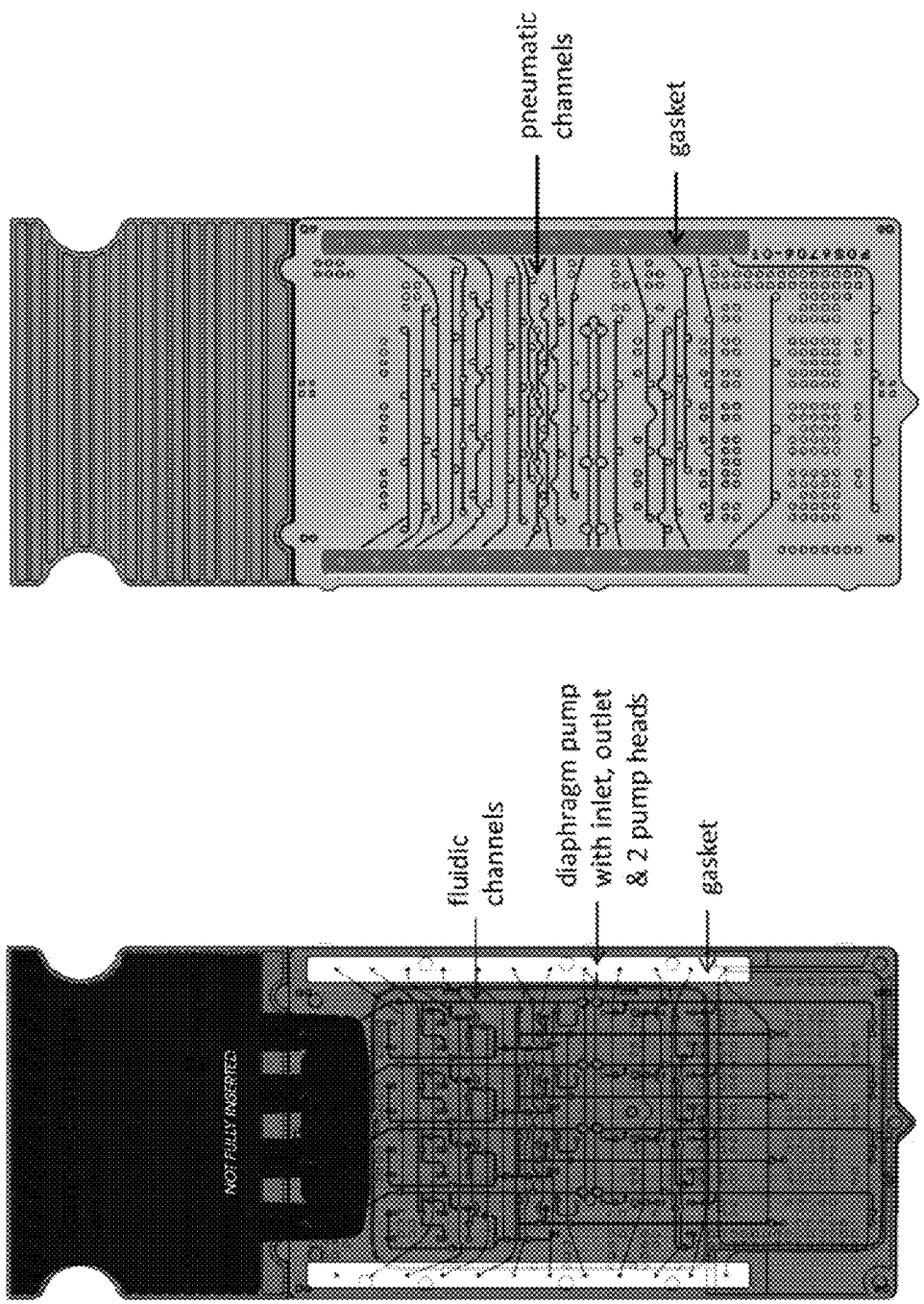
FIG. 52A shows a layout for a fluidics side of a microfluidic chip usable in a cartridge of this invention.
FIG. 52B shows a layout for a pneumatic side of a microfluidic chip usable in a cartridge of this invention.

Three valves can be used to make a pump on a microchip to move fluids through a microfluidic channel. The valves can be microvalves or nanovalves, configured to move microliter or nanoliter fluid volumes, respectively. The fluids are moved by three or more valves. The valves can be created actuation of a deformable structure. In some implementations a valve seat is created and in other embodiments no valve seat may be needed. In one embodiment, a diaphragm pump can comprise an inlet (e.g., a valve such as a normally open valve), a pump head (e.g., one or two or more pumping chambers, optionally operated in tandem) and an outlet (e.g., a valve such as a normally open valve). (See, e.g., FIG. 52.)

Arrays of MOVe valves, pumps, and routers are readily fabricated on microchips. Significantly, all the MOVe valves, pumps, and routers on a microchip are created at the same time in a simple manufacturing process using a single sheet of PDMS membrane. In some cases, the manufacture of five MOVe micropumps on a microchip may be the same as the manufacture of five hundred micropumps.

Devices and methods useful in the present invention are described, for example, in U.S. Pat. No. 7,445,926, U.S. Patent Publications 2004/0209354, 2005/0161669, 2006/0073484, 2007/0248958, 2008/0014576, 2009/0253181, 2010/0165784, 2010/0303687, 2011/0005932, 2011/0126911, 2011/0240127, 2012/0181460, 2012/0240127 and 2012/0290648; and PCT Publications WO 2008/115626, WO 2011/011172, and WO 2012/024657.

In some embodiments, a valve is in a normally open configuration. Alternatively, a valve can be in a normally closed configuration. In a normally open configuration, absent actuation the deformable membrane layer is not in contact with the seat, and the valve permits fluid flow through a dome (or chamber) of the valve. Actuating the deformable membrane layer causes the deformable membrane layer to contact the seat, thereby closing the valve. In a normally closed configuration, absent actuation the deformable membrane layer is in contact with the valve seat, which obstructs the flow of fluid through the dome of the valve. Actuating the deformable membrane layer causes the deformable membrane layer to move away from the valve seat, thereby opening the valve. Actuation of the deformable membrane layer is achieved with the application of positive or negative pressure through a pneumatic line to increase or decrease the pressure in a pneumatic chamber relative to the microfluidic channel, which can deform the deformable membrane layer.

Figure 43:
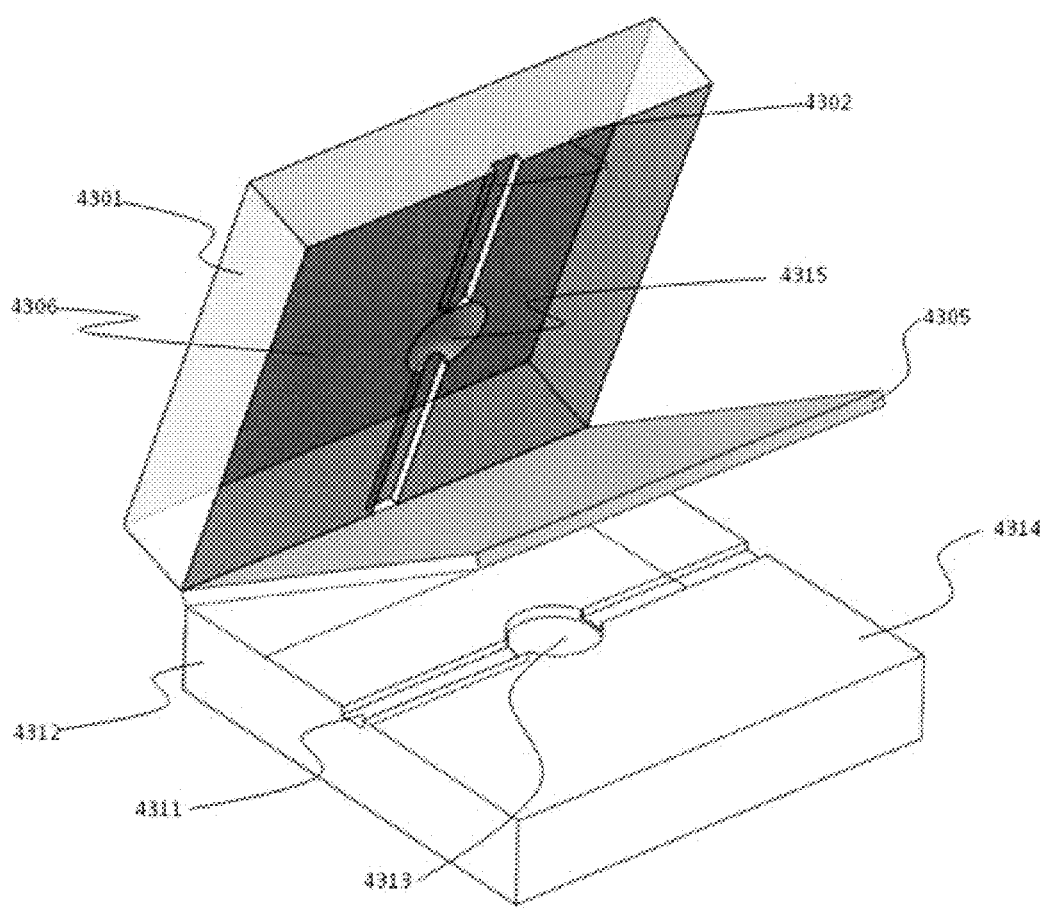
FIG. 43 is a schematic illustration of a diaphragm valve in a normally open configuration.

In an example, FIG. 43 shows a clamshell view of an embodiment of a normally open diaphragm valve of this invention, as can be used with microfluidic devices of the invention. A fluidics layer 4301 comprises a fluid conduit comprising a fluidic channel 4302, which opens into a recessed dome 4315 that functions as a valve seat. When no pressure or negative pressure is exerted on elastic layer 4305, the elastic layer 4305 sits away from the valve seat, allowing for an open valve in which a fluid path between the channels entering the valve are in fluidic contact, creating a fluid path. When positive pressure is exerted on elastic layer 4305, the elastic layer 4305 deforms toward the valve seat to close the valve.

In an embodiment of a normally open valve, the valve seat is not configured as an interruption in a fluidic conduit. Rather, it takes the form of a recess with respect to surface of the fluidics layer that normally contacts the elastic layer, so that the elastic layer does not sit against the recessed surface without application of pressure on the elastic layer, e.g. through the actuation chamber. In this case, the valve may not have a discrete valve chamber in the fluidics layer that is separate from the valve seat. The valve seat can take a curved shape that is concave with respect to the surface of the fluidic layer, against which the elastic layer can conform. For example, the valve shape can be an inverted dimple or a dome. Its shape can substantially conform to the shape of the elastic layer when deformed by pressure. It can take the shape substantially of a parabola or a portion of a sphere. Such a configuration decreases the dead volume of the valve, e.g., by not including a valve chamber that contains liquid while the valve is closed. This valve also comprises a surface against which the elastic layer can conform easily to close the valve. Also, this configuration eliminates the need to create a surface patterned so that valves do not comprise surface hydroxyl groups, e.g., for bonding with a polysiloxane elastomer such as PDMS), because the recessed surfaces do not bond with the elastic layer against which they are laid during construction. In another embodiment, the concave surface can comprise within it a sub-section having a convex surface, e.g., an inverted dimple comprising an extraverted dimple within it forming, for example, a saddle shape. The convex area rises up to meet the elastic layer under pressure, creating a better seal for the valve.

In some embodiments of a normally open valve, the concavity is recessed less than the channels to which it is connected. For example, the deepest part of the concavity can be about one-third to one-half the depth of the channel (e.g., 30 microns to 50 microns for the concavity versus 100 microns for the channel). For example, the elastic layer may be about 250 microns, the channels about 100 microns deep and the valve seat about 30 microns deep. The thinner the elastic layer, the deeper that the concavity can be, because the elastic layer can conform to the concavity without excessive deformation. In certain embodiments the channels can enter partially into the concavity, for example forming a vault. In certain embodiments, the channels and concavity are formed by micromachining. In other embodiments they may be formed by hot embossing or injection molding or other methods. The actuation layer can comprise a valve relief into which the diaphragm deflects for opening the valve.

In some embodiments, a diaphragm valve is formed from a body comprising a chamber in the actuation layer (e.g., a valve relief) and the in the fluidics layer (e.g., a pumping chamber), but without an interruption. In this embodiment, deforming the diaphragm into the actuation chamber creates a volume to accept fluid, and deforming the diaphragm into the fluidics chamber pumps liquid out of the chamber. In this configuration, the position of the diaphragm alters the effective cross-section of the fluidic conduit and, thus, can regulate the speed of flow through the valve. In such a configuration, the valve may not completely block the flow of fluid in the conduit.

Valves with concave valve seats displace defined volumes of liquid upon closing. Therefore, such valves are useful and pumps where pumping of uniform volumes is desired. Typically, pumping valves have greater volumes of than closing valves. For example, a pumping valve can have a displacement volume of between 50 μL to 150 μL, e.g., about 100 μL. To pumping valves can be placed in series, e.g., without intervening features, to provide variable volume pumps. Such pumping valves typically are placed between two closing valves that function as pump inlets and pump outlets. The pump head can be configured such that an elastomer membrane, when actuated in the pump head, does not completely stop fluid from passing through the pump head. This contrasts with a closable valve.

In some embodiments, a microfluidic device is fabricated from an elastomeric polymer, such as GE RTV 615 (formulation), a vinyl-silane crosslinked (type) silicone elastomer (family). However, a microfluidic device is not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in Unger et al. (2000) Science 288:113-116, and PCT Publications WO 02/43615 (Unger et al.), and WO 01/01025 (Unger et al.), which are entirely incorporated herein by reference.

C. Thermocycler Assembly

The analyte preparation module can include a thermocycler assembly. The thermocycler assembly can be comprised in a combination of the sample cartridge and the cartridge module. The thermocycler assembly can be configured to deliver analyte (e.g., a polynucleotide, such as DNA) and reagents to a reaction chamber (or thermocycling chamber) and to cycle temperature (e.g., heating and cooling) of a liquid in the thermocycling chamber.

In one embodiment, the thermal cycling chamber is attached to the sample cartridge and in fluidic communication with the fluidic device. An amplification reagent container can be fluidically isolated from the thermal cycling chamber and can be configured to deliver reagents to the chamber upon actuation. A device configured to actuate delivery of the reagents can be comprised in the cartridge module (see, e.g., FIG. 55). A thermal controller, such as a Peltier device, can be configured to heat and cool for thermal cycling and can be comprised in the cartridge module (see, e.g., FIG. 42), which can be configured to move the thermal controller into thermal contact with the thermal cycling chambers, e.g., through a heat spreader (or thermoconductor that can spread/distribute heat and cooling) disposed over each of the reaction chambers as shown in the embodiment of FIG. 42.

In some embodiments, the cartridge comprises a thermocycler assembly having one or more (e.g., 4, 8, 10, 16, 24, 32, 40, 48 or more) thermocycling chambers, each thermocycling chamber in fluid communication with a microfluidic channel. The one or more thermocycling chambers can be configured for nucleic acid amplification, such as by polymerase chain reaction (PCR). In some situations, the cartridge includes a premix vessel or chamber in fluid communication with a thermocycling chamber. The premix vessel or chamber includes a premix, which can comprise one or more primers for amplifying one or more selected nucleotide sequences, a buffer, a metal salt (e.g., magnesium chloride) and an enzyme (e.g., a DNA polymerase, such as a Taq polymerase) for nucleic acid amplification, such as by PCR, rolling circle amplification or other amplification methods.

Each of the one or more reaction chambers of the thermocycler assembly can be configured to perform standard PCR and variants thereof, such as allele-specific PCR, assembly PCR, asymmetric PCR, hot-start PCR, intersequence-specific PCR, inverse PCR, isothermal PCR (e.g., helicase-dependent amplification and PAN-AC), ligation-mediated PCR, mini-primer PCR, multiplex PCR, nested PCR, picotiter PCR, quantitative PCR, real-time PCR, restriction fragment length polymorphism PCR, reverse transcription PCR, single-cell PCR, solid-phase PCR (e.g., bridge PCR), thermal asymmetric interlaced PCR, touchdown (step-down) PCR, and universal fast walking PCR. Prior to PCR amplification, whole genome amplification can be performed to improve amplification of a low copy-number DNA or a degraded DNA. DNA can also be amplified using other methodologies that can be isothermal or can involve thermal cycling, such as ligase chain reaction and strand displacement assay.

Uracil-DNA-glycosylase (also known as uracil-N-glycosylase, UNG or UDG) in combination with deoxyuridine triphosphate (dUTP) can be used to prevent carry-over DNA contamination in PCR amplification of loci (e.g., STR loci). Amplification performed in the presence of dUTP in place of deoxythymidine triphosphate (dTTP) results in uracil-containing STR amplicons. Prior to amplification, a PCR reaction mixture can be pre-treated with UNG, which specifically degrades any uracil-containing PCR products carried over from previous PCR amplifications, thereby preventing their unwanted amplification. UNG is heat-inactivated during a subsequent PCR amplification, and only DNA from the specific sample of interest is amplified. It may be desirable to generate an allelic ladder with incorporated uracil bases in place of thymidine bases since the electrophoretic migration of uracil-containing STR fragments may differ from the electrophoretic migration of their thymidine-containing counterparts.

Carry-over contamination with products of previous PCR amplifications can also be minimized by UV irradiation at a suitable wavelength (e.g., 254 nm). For example, a solution potentially containing DNA contaminants can be UV-irradiated at a suitable wavelength (e.g., 254 nm) and at a suitable distance (e.g., 1 cm) from a UV bulb for a suitable period of time (e.g., 10 minutes) in a suitable instrument (e.g., a Stratalinker® UV Crosslinker 2400 device (Stratagene, Cedar Creek, USA) or a Spectrolinker XL 1500 UV crosslinker device (Spectronics Corp., Westbury, N.Y.)).

In some embodiments, the cassette further comprises a magnetic field application member adjacent to the thermocycling chamber. The magnetic field application member may be configured to apply a magnetic field using a permanent magnet or an electromagnet, in which case the magnetic field application member includes a permanent magnet or an electromagnet. A permanent magnet can be comprised in the sample cartridge. Alternatively, the magnetic field application member can be a moveable magnet (e.g., permanent magnet or electromagnet) that can be moved to become adjacent to the thermocycling chamber.

In some embodiments, a thermocycler assembly includes one or more (e.g., 4, 8, 10, 16, 24, 32, 40, 48 or more) pairs of premix vessels/chambers and reaction chambers for nucleic acid amplification (e.g., by PCR). The thermocycler assembly in some cases comprises a polymeric material (e.g., plastic) that is attached to an external surface of a microfluidic device of the cartridge. In an example, at least a portion of the thermocycler assembly (e.g., a reaction chamber) is mechanically attached to the microfluidic device, e.g., bolted or snapped onto the microfluidic device. Alternatively, at least a portion of the thermocycler assembly is attached to the microfluidic device through adhesion, e.g., through a glue or an adhesive tape.

The thermocycler assembly can include a plurality of reaction chambers for nucleic acid amplification. Each reaction chamber can have an elongate shape. In some cases each chamber is an open container, such as a trough having a depth (as measured from an opening of the trough to a floor of the trough) of about 1 micron to 10,000 microns, or 10 microns to 800 microns, or 50 microns to 600 microns. A trough can have a volume between about 100 nanoliters and 1 microliter, 1 microliter and 100 microliters, or 5 microliters and 50 microliters, or 10 microliters and 30 microliters. In an example, a trough has a depth of about 510 microns, and a volume of about 20 microliters. In some cases the chamber is a closed container that is cylindrical or rectangular in shape.

In some embodiments, the reaction chambers of the thermocycler assembly are in thermal contact with a thermal conductor (e.g., a heat spreader) for conducting heat and cooling to each reaction chamber and a sample in the reaction chamber during sample processing. The thermal conductor can rest over each reaction chamber of the thermocycler assembly, and away from the microfluidic device (see, e.g., layer 3406 of FIG. 34A, FIG. 42 and FIG. 44). The thermal conductor can be formed of graphite, graphene, aluminum, copper or a copper-containing alloy, though other metals or materials with suitable thermal conductivities can be used. In some cases, the thermal conductor is formed of a plurality of layers, such as a layer of a thermally conductive material (e.g, graphite) adapted to come in thermal communication with a temperature control element (e.g., heating element and/or cooling element), and a layer of a polymeric material (e.g., polypropylene) adjacent to the layer of the thermally conductive material that is adapted to come in contact with each reaction chamber or a sample in each reaction chamber of the thermocycler assembly. As an alternative, the thermal conductor can be adjacent to the microfluidic device of the cartridge, such as between the thermocycler assembly and the microfluidic device, or integrated into the thermocycler assembly and disposed adjacent to the cartridge.

During processing, a temperature control element (e.g., a heating element and/or a cooling element, which can be a heating and cooling element) is disposed adjacent to one or more reaction chambers of the thermocycler assembly, such as adjacent to the cartridge or over the reaction chambers and disposed away from the cartridge. The temperature control element of the thermocycler assembly can be integrated in the microfluidic device or the cartridge module, or brought in proximity to the thermocycler assembly chambers. The temperature control element can be a Peltier temperature control element (e.g., a Peltier heating and cooling element), which is configured to generate heat upon the application of an electrical potential across electrodes of the Peltier temperature control element. The temperature control element can be in thermal communication with the thermal conductor, which can aid in directing heat to the sample during sample processing. The Peltier can aid in maintaining a constant temperature in each chamber, or increase the temperature or decrease the temperature at a desired or otherwise predetermined heating or cooling rate, respectively. Alternative heating and cooling elements such as circulating air, water or other gases or liquids of different temperatures, IR heating, and other methods well known to one skilled in the art are also possible with air temperature control and IR heating providing advantages of non-contact.

FIG. 42 illustrates an embodiment of a thermal cycling device 4200 that can heat and cool. Thermal cycling device (or thermocycler) 4200 can be employed to perform thermal cycling for, e.g., nucleic acid amplification by PCR. Thermal cycling device 4200 comprises a heat sink 4230, a metal block 4210 composed of a suitable metal (e.g., copper), and a cold plate 4220 composed of a suitable metal (e.g., aluminum). A Peltier heat and cooling element (not shown) is sandwiched between metal block 4210 and cold plate 4220. In the embodiment of FIG. 42, thermal cycling device 4200 is included in a cartridge module. Thermal cycling device 4200 floats in the cartridge module and is engaged with a sample/control cartridge by being pressed against the cartridge, which results in cold plate 4220 contacting the thermoconductor disposed over the reaction chambers of the cartridge. Once thermal cycling device 4200 is engaged with the cartridge, the device is held in place. The Peltier heat and cooling element both heats and cools (e.g., by thermoelectric heating and cooling), and the thermoconductor on the cartridge can spread/distribute thermal changes involving both heating and cooling. Because cold plate 4220 of thermal cycling device 4200 contacts the thermoconductor, heating and cooling of the Peltier element results in (e.g., conductive) heating and cooling of the thermoconductor, which in turn distributes heat and cooling to each of the four reaction chambers in the cartridge.

Figure 18A:
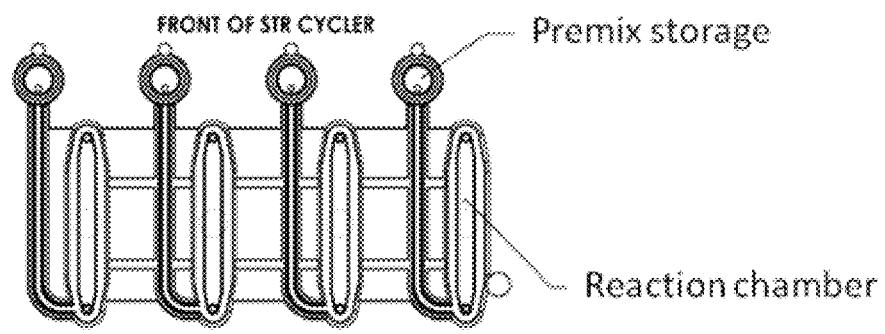
FIGS. 18A-18D show a thermocycler assembly comprising four reagent (premix) chambers and four reaction chambers configured to perform amplification (e.g., by PCR) with thermal cycling, in accordance with an embodiment of the invention.
Figure 18B:
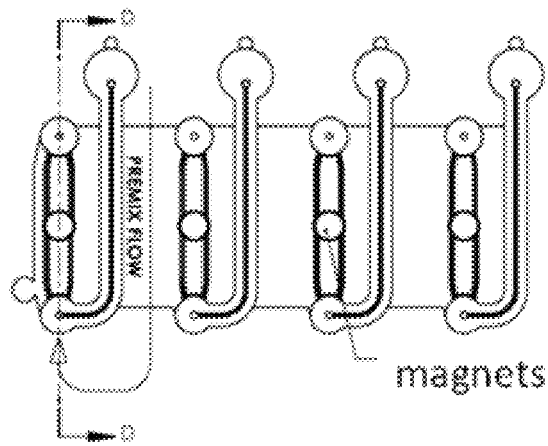
Figure 18C:
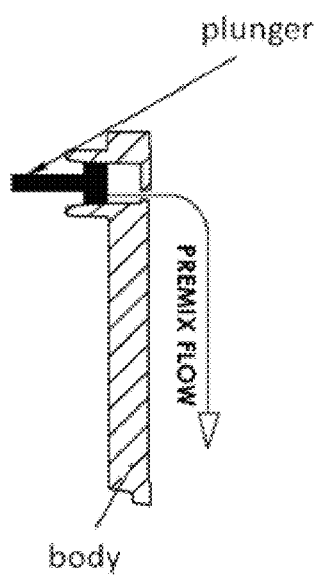
Figure 18D:
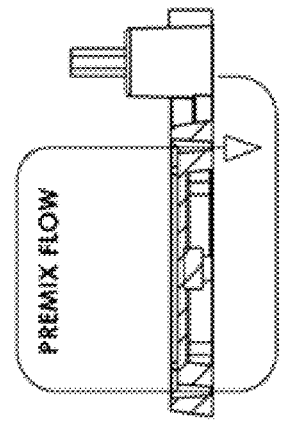
Figure 45:
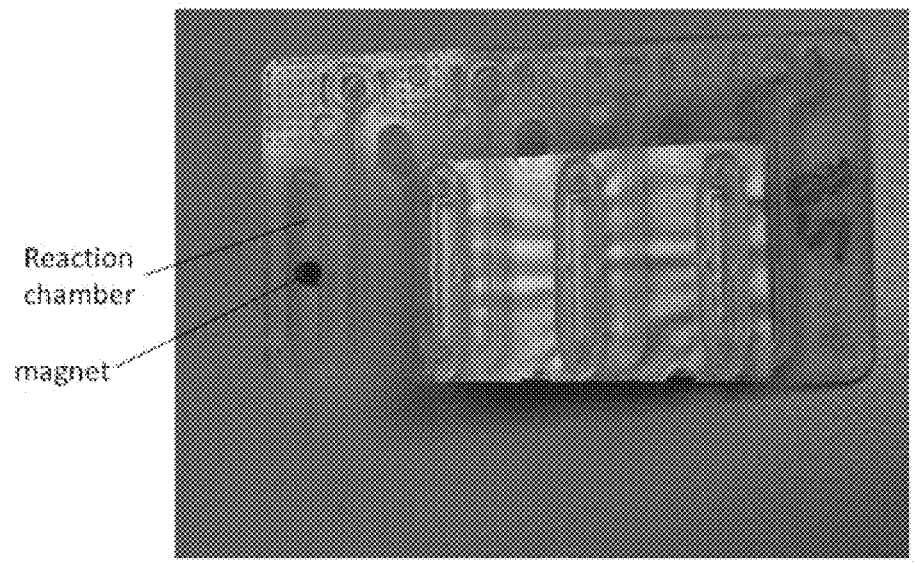
FIG. 45 shows a bottom view of a thermocycler assembly having four reaction chambers, with each reaction chamber having a magnet, in accordance with an embodiment of the invention.

FIGS. 18A-18D schematically illustrate a thermocycler assembly, in accordance with an embodiment of the invention. Four thermocycling chambers are illustrated, one thermocycling chamber per channel or lane of the cartridge described above. The thermocycler assembly includes a premix storage chamber for storing and providing a premix to each thermocycling chamber, as shown in FIG. 18A. The premix can include primers, buffers and enzymes for reaction. The thermocycler assembly includes four reaction chambers for holding a sample and reagents during a reaction (e.g., PCR). In some embodiments, nucleic acid (e.g., DNA) obtained from a sample is captured on magnetic beads and the beads are held in place in a reaction chamber with the aid of a magnetic field, as can be supplied by a magnetic field source (e.g., magnet, induction coil), as shown in FIGS. 18B and 45. Premix is provided from a premix storage chamber to the reaction chamber with the aid of, e.g., a plunger, as shown in FIG. 18C. FIG. 18D shows an exemplary premix (or reagent) flow path.

Figure 34A:
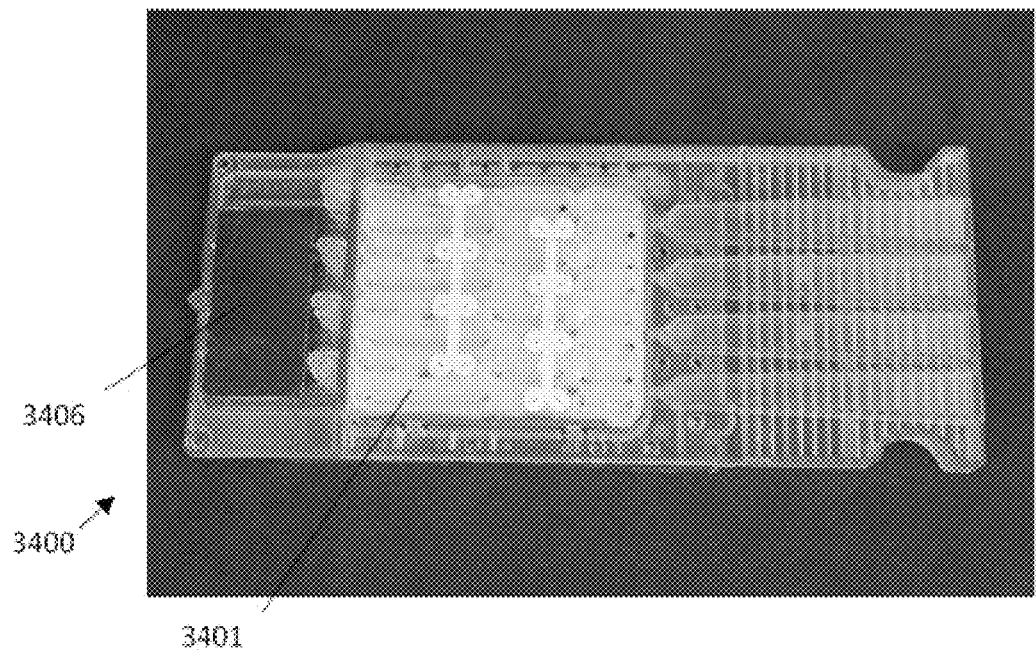
FIGS. 34A-34D shows various components of a cartridge, in accordance with embodiments of the invention.

The thermocycler assembly of FIGS. 18A-18D can be bolted or otherwise secured onto the body of a microfluidic device. (See, e.g., 3106.) In an example, FIG. 16 shows four thermocycling chambers attached to a microfluidic device. The thermocycler assemblys include reaction chambers for sample processing (e.g., PCR). With reference to FIG. 34A, during sample processing, a temperature control element (e.g., heating element and/or cooling element such as a Peltier heating and cooling element) is configured to come in thermal communication with each chamber with the aid of a layer of a thermal conductor 3406 disposed over the chambers. The thermal conductor 3406 can include graphite, graphene, copper, tantalum, or aluminum, to name a few examples. In an example, the temperature control element (e.g., heating element and/or cooling element) rests against the thermal conductor 3406 during sample processing. Alternatively, the cartridge can include an integrated temperature control element which, for example, can be disposed between the microfluidic device and the thermocycler assembly. Accordingly, in certain embodiments, such as cassettes that include a microfluidic chip comprising channels and diaphragm valves involving polysiloxane membranes, such as PDMS, the reaction chamber does not have to be included within the microfluidic chip. In other embodiments, the surfaces of the reaction chamber can be configured to not inhibit the activity of the enzymes either by selection of an appropriate material (e.g., polypropylene) for making the reaction chamber or by surface modification of the material by, for example, grafting polyethylene glycol (PEG) groups, silanization, plasma treatment, chemical vapor deposition or other methods.

In some cases, an amplification premix is provided to a sample prior to nucleic acid amplification (e.g., PCR), and the sample with the premix is subsequently thermally annealed to initiate nucleic acid amplification. The premix includes the reagents (e.g., primers, enzymes) for facilitating nucleic acid amplification. The premix can be a PCR premix, which can include short tandem repeat (STR) premix reagents.

There are various approaches for delivering a nucleic acid amplification premix to a processed or partially-processed sample prior to amplification. Following delivery of the premix, the temperature of the sample is raised, and in some cases cycled, in a thermocycling chamber in fluid communication with a channel that is coupled to the cartridge.

In some embodiments, the premix is delivered to the sample with the aid of a plunger. In other embodiments, the premix is delivered to the sample with the aid of a rehydration delivery device.

Figure 33A:
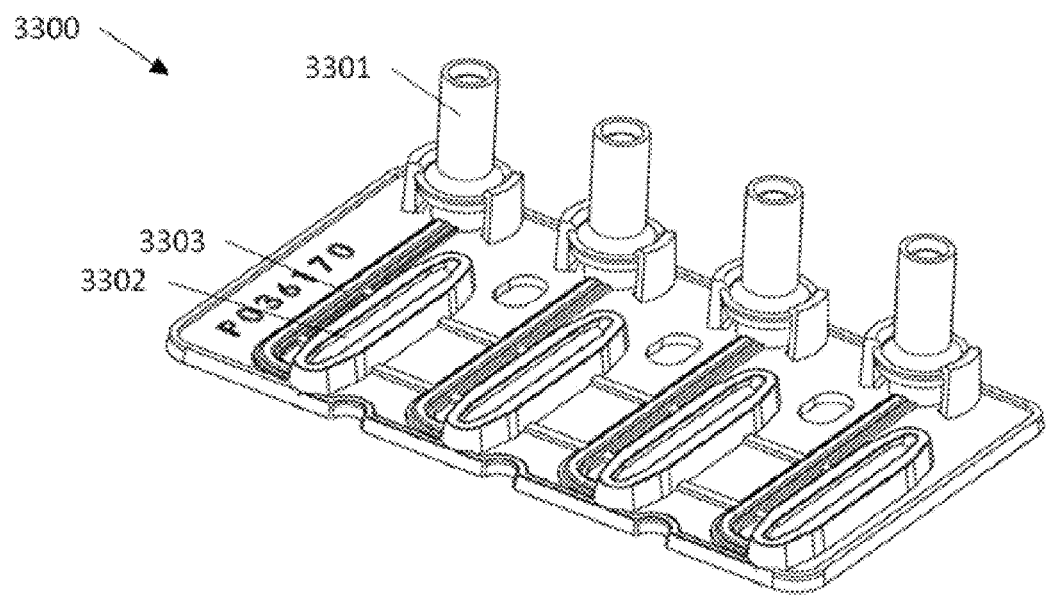
FIGS. 33A-33F show various views and features of a thermocycler assembly comprising four reagent (premix) chambers and four reaction chambers configured to perform amplification (e.g., by PCR) with thermal cycling, in accordance with various embodiments of the invention.
Figure 33B:
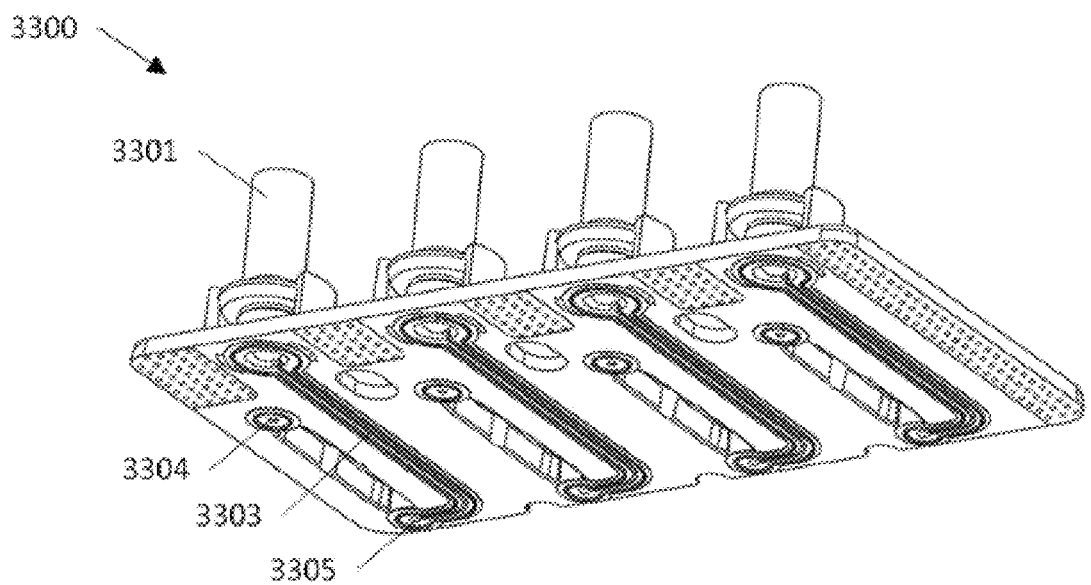

FIGS. 33A-33E illustrate a thermocycler assembly 3300 as can be used with systems and methods provided herein. The thermocycler assembly 3300 can be the thermocycler assembly 3106 of FIGS. 31 and 32. FIG. 33A is a schematic top view of the thermocycler assembly 3300. The thermocycler assembly 3300 includes four reagent delivery members 3301 (or reagent (or premix) vessels/chambers) for delivering a premix or other reagents to four thermocycling (or reaction) chambers 3302 of the thermocycler assembly 3300. In some cases, the thermocycling chamber 3302 is a trough that has an opening along the length of the thermocycling chamber 3302. The reagents or premix is delivered from a reagent delivery member 3301 to a thermocycling chamber 3302 through a channel 3303 in fluid communication with the reagent chamber and the thermocycling chamber 3302. In some embodiments, channel 3303 does not comprise a valve. The reagents or premix can be delivered to a thermocycling chamber with the aid of a plunger or an actuating device such as that shown in FIG. 55. FIG. 33B is a schematic bottom view of the thermocycler assembly 3300. An inlet port 3304 and outlet port 3305 are configured to come in fluid communication with an inlet port and outlet port, respectively, of a microfluidic device disposed adjacent to the thermocycler assembly 3300, such as the microfluidic device 3108 of FIG. 32.

For example, a sample to be processed is directed from the inlet port of the microfluidic device to the inlet port 3304 and to the thermocycling chamber 3302. The reagent delivery member (or reagent vessel/chamber) 3301 delivers a reagent (e.g., premix) to the thermocycling chamber 3302. The sample is processed (e.g., STR processing). The processed sample is then directed to the outlet port 3305 and the outlet port of the microfluidic device for analysis, such as with the aid of capillary array electrophoresis. In some embodiments the electrophoresis system and include a memory device that records the number of times a capillary has been used.

Figure 33C:
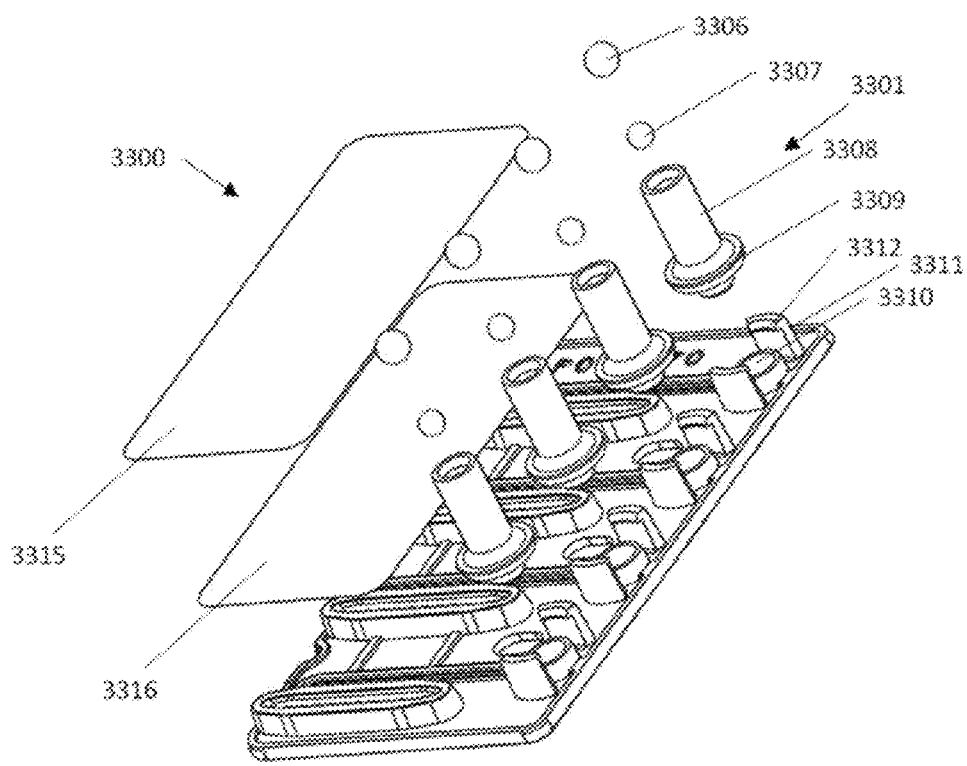

FIG. 33C is an exploded view of the thermocycler assembly 3300 showing the reagent delivery member (or reagent vessel/chamber) 3301. In some embodiments, the reagent delivery member is a dual plunger sealed chamber having a first stopper 3306 and a second stopper 3307, in this case configured as balls. The stoppers 3306 and 3307 seal a receptacle (e.g., a column or tube) 3308 having a reagent (e.g., premix, master mix), such as an STR master mix is. The application of force to the first stopper ball 3306 (such as, e.g., with the aid of a plunger or a syringe) actuates the movement of the second stopper ball 3307 ball into a larger chamber, cavity or channel that creates a flow path for the master mix to pass through the channel 3303 into the thermocycling chamber 3302. The thermocycler assembly 3300 includes a thermal conductor formed of a layer of a thermally conductive material 3315, such as graphite, laminated to a layer of a polymeric material 3316, such a polypropylene.

In some embodiments, the system 100 includes dual thermocycler (also "thermal cycler" herein) units for use during sample processing (see below). The dual thermocycler units apply heat and cooling to each of the control and sample cartridges during processing. The thermocyclers can apply heat at a power output of at least about 10 watts (W), 20 W, 30 W, 40 W, 50 W, 100 W, 200 W, 300 W, 400 W, 500 W, or more. FIG. 42 illustrates an embodiment of a thermocycler that can be used as each of two thermocyclers included in a sample cartridge interface module. As described above, because cold plate 4220 contacts the thermoconductor disposed over the reaction chambers when the sample/control cartridge is engaged with the cartridge module, a Peltier heating and cooling element (not shown in FIG. 42) sandwiched between metal block 4210 and cold plate 4220 can conductively heat and cool the thermoductor and hence the reaction chambers. In other embodiments, the thermocyclers may operate via resistive or radiative heating and cooling, though convective heating and cooling may be employed in some circumstances. An automated capture magnet of the system 100, which is disposed adjacent to the sample cartridge interface module, is used during processing in some cases to hold magnetically-attractable particles in place.

The flow of a reagent from the reagent delivery member (or reagent vessel/chamber) 3301 is activated by applying force to a stopper ball, such as with the aid of positive pressure to the first stopper ball 3306 or the application of negative pressure (or vacuum) to the second stopper ball 3307. Force may be applied with the aid of a mechanical device, pneumatics, or other force delivery mechanism or device, such as the device shown in FIG. 55. In some cases, force is delivered with the aid of a plunger in fluid communication with the stopper balls 3306 and 3307 and the receptacle (e.g., a column or tube) 3308. The plunger can be a metal plunger or a syringe-type device.

In some embodiments, the first stopper ball 3306 has a larger diameter than the second stopper ball 3307. In some situations, the first stopper ball 3306 has a shape that is different from the second stopper ball 3307.

The receptacle (e.g., a column or tube) 3308 can include one or more reagents. The stopper balls 3306 and 3307 can be used to compartmentalize the reagents in fluidically isolated containers. In some situations, upon the application of force to the first stopper ball 3306 (or, alternatively, the application of vacuum to the second stopper ball 3307, the fluids may mix.

The stopper balls 3306 and 3307 can be spherical or other geometric shapes i.e., the stopper balls 3306 and 3307 can have shapes that are not necessarily spherical. In some embodiments, the stopper balls 3306 and 3307 can have cross-sections that are circular, triangular, square, rectangular, pentagonal, hexagonal, heptagonal or octagonal, or partial shapes, such as semi-circular.

In other embodiments, the reagent application member comprises the second stopper ball 3307 and a plunger instead of the first stopper ball 3306. The force delivery mechanism or device for such a reagent application member can be the same as or substantially similar to that for a reagent application member comprising the first stopper ball 3306 and the second stopper ball 3307.

Figure 33D:
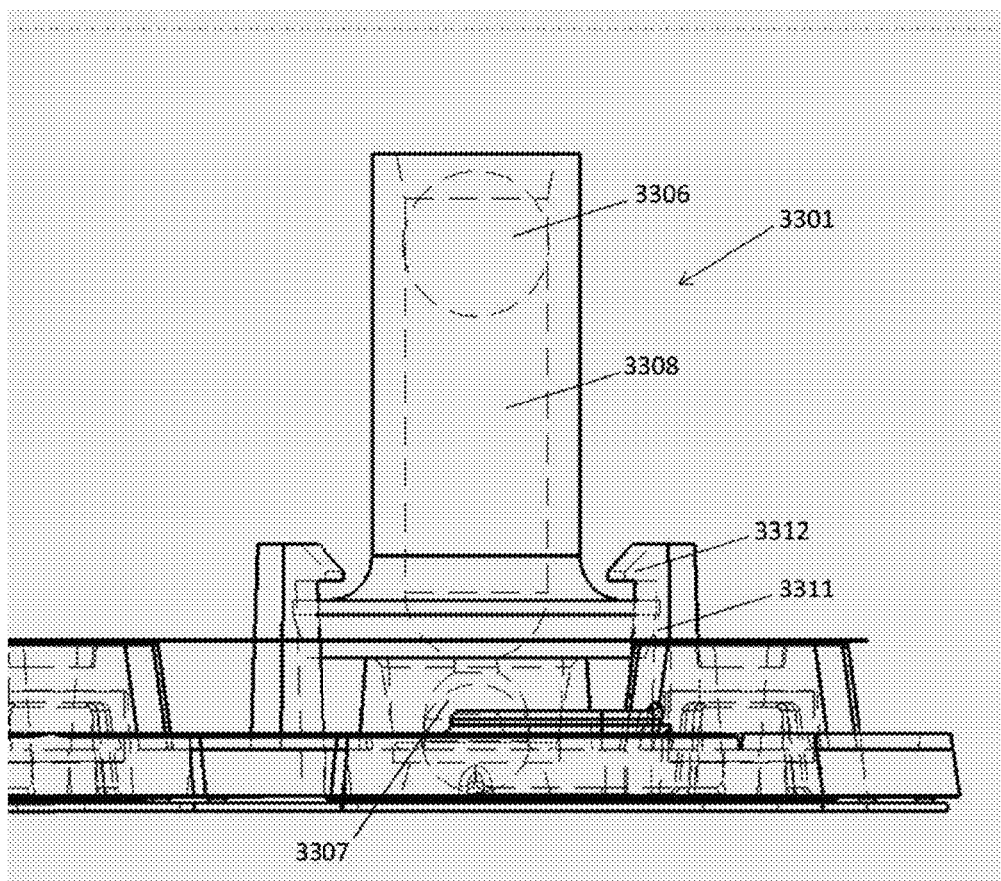

With reference to FIGS. 33C and 33D, the reagent delivery member (or reagent vessel/chamber) 3301 has a flange or collar 3309 that is configured to mate with a receptacle 3310 having two enclosing walls 3311 with protrusions 3312 for mating with the collar 3309. In an example, the reagent delivery member 3301 is configured to snap in place.

Figure 33E:
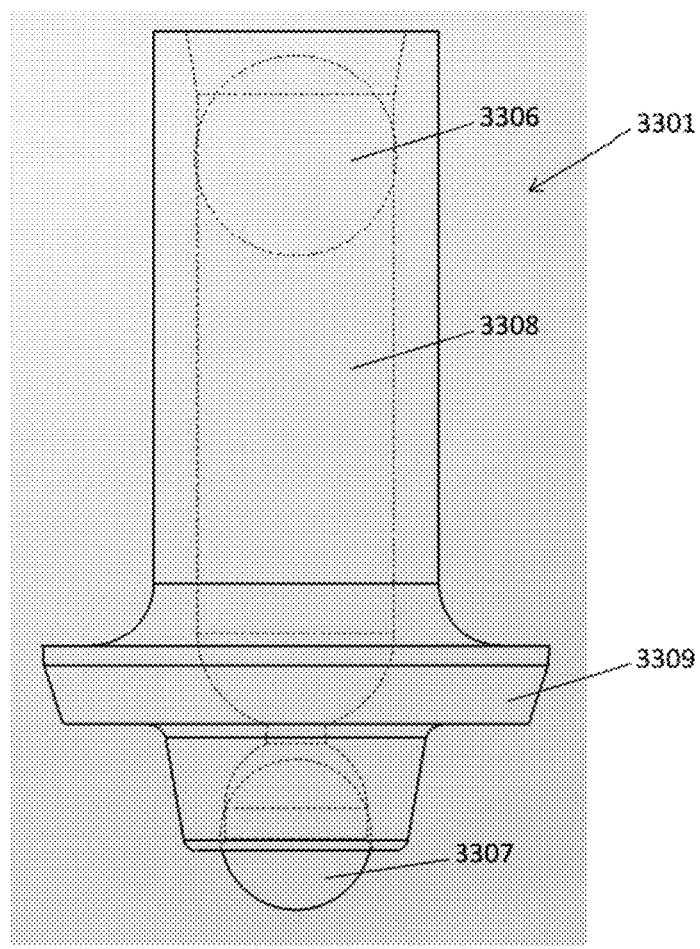

With reference to FIG. 33D, the first stopper ball 3306 is in fluid communication with the second stopper ball 3307 through the receptacle (e.g., a column or tube) 3308 (which includes a chamber for holding a reagent). In the illustrated example, the stopper balls 3306 and 3307 are in contact with walls of the reagent delivery member 3301, which configuration may not permit fluid flow. The configuration of the stopper balls 3306 and 3307 in such a case is shown in FIG. 33E.

Figure 33F:
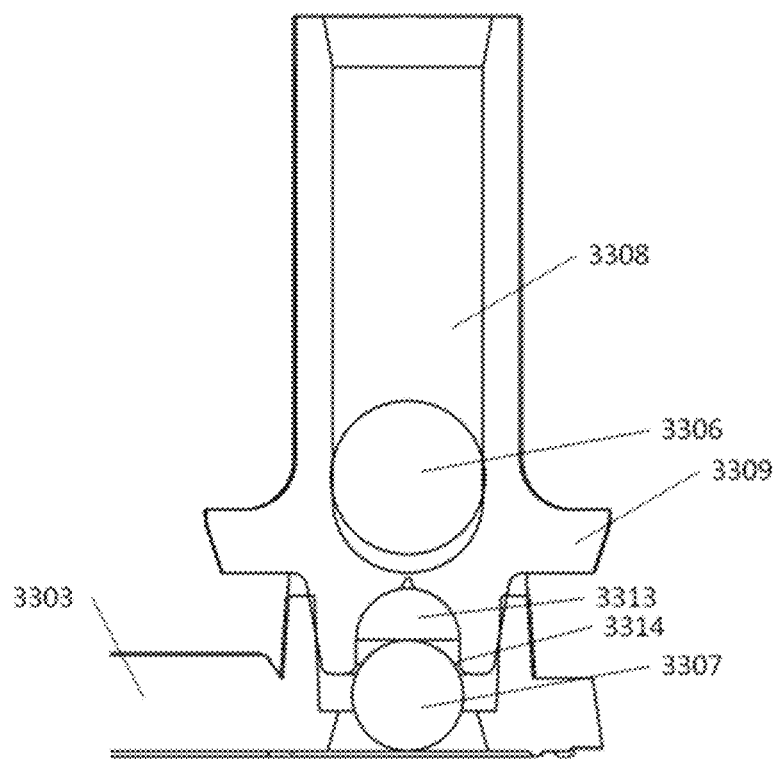

Upon the application of positive pressure to the first stopper ball 3306 or negative pressure to the second stopper ball 3307, fluid will from the receptacle (e.g., a column or tube) 3308 into the channel 3303 and subsequently the thermocycling chamber 3302. In some embodiments, upon the application of positive pressure to the first stopper ball 3306, the first stopper ball moves laterally along the co receptacle (e.g., a column or tube) lumen 3308 toward the second stopper ball 3307, as shown in FIG. 33F. Fluid pressure drives the second stopper ball 3307 out of a holding chamber 3313 having the second stopper ball 3307, thereby providing a fluid flow path 3314 around the second stopper ball 3307. Fluid will subsequently flow to the channel 3303.

In some embodiments, the reagent delivery member (or reagent vessel/chamber) 3301 can effect fluid mixing. For instance, the second stopper ball 3307 can be moved by a plunger (e.g., attached to a plunger) that enables the second stopper ball 3307 to retract into the holding chamber 3313. During use, the second ball 3307 can be expelled from the holding chamber 3313 upon the application of pressure to the second stopper ball 3307 and subsequently retracted into the holding chamber 3313. As such, fluid can be expelled from the holding chamber 3313 and retracted into the holding chamber (e.g., from the channel 3303), which effects fluid mixing.

Nucleic acid amplification premixes can be delivered to a sample in liquid form. The reagent delivery (or application) member 3301 of FIGS. 33A-33F, for instance, is configured to deliver a liquid premix. In some embodiments, PCR reagents in liquid form are stored in a vial connected to the amplification reaction chamber via a delivery channel. The vial is sealed at the bottom by a rubber ball and at the top by a second rubber ball or a plunger. The liquid PCR reagents are delivered to the reaction chamber by pushing on the top ball or the plunger to break the seal formed by the lower ball, thereby delivering the liquid PCR reagents from the vial, through the delivery channel and to the amplification reaction chamber.

Prolonged storage of PCR reagents in liquid form at ambient temperature may potentially result in degradation of PCR primers, which may lead to non-specific amplification and reduced amplification efficiency. To minimize degradation of a reagent, in some embodiments PCR reagents (or reagents for other biochemical reactions) in liquid form are stored at about 4° C. or cooler. In other embodiments, PCR reagents or reagents for other biochemical reactions are stored in a solid (e.g., lyophilized) form, a dry form or other stabilized form, which can be rehydrated for use in biochemical reactions as appropriate.

The PCR vial, the top plunger and the bottom seal can independently be made of any suitable material (e.g., one or more polymers) using any suitable technique (e.g., injection molding). For example, the PCR vial, the top plunger and the bottom seal can independently be made of one or more polymers selected from cycloolefin polymers and copolymers, synthetic rubbers, ethylene propylene diene monomer (EPDM), polypropylene, polyoxymethylene, and liquid silicone rubber. The selection of material can depend on factors such as ease of manufacturing (e.g., injection molding), PCR compatibility, etc. In some embodiments, the PCR vial is made of polypropylene or a cycloolefin polymer or copolymer. In certain embodiments, the top plunger and the bottom seal are made of polypropylene.

D. Cartridge Module Assembly

Figure 3:
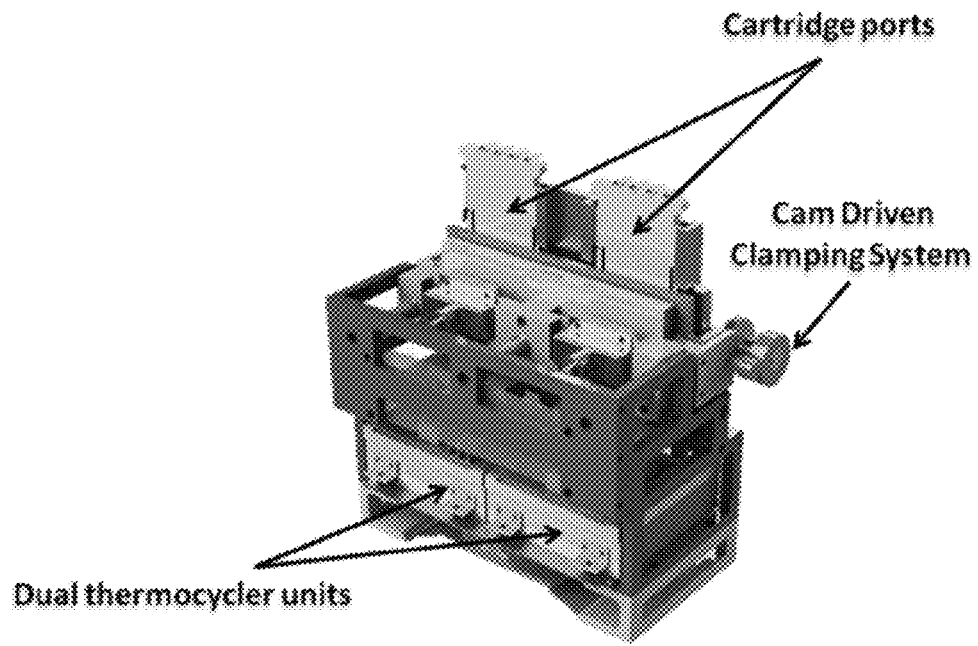
FIG. 3 shows a sample cartridge interface module, in accordance with an embodiment of the invention.
Figure 39:
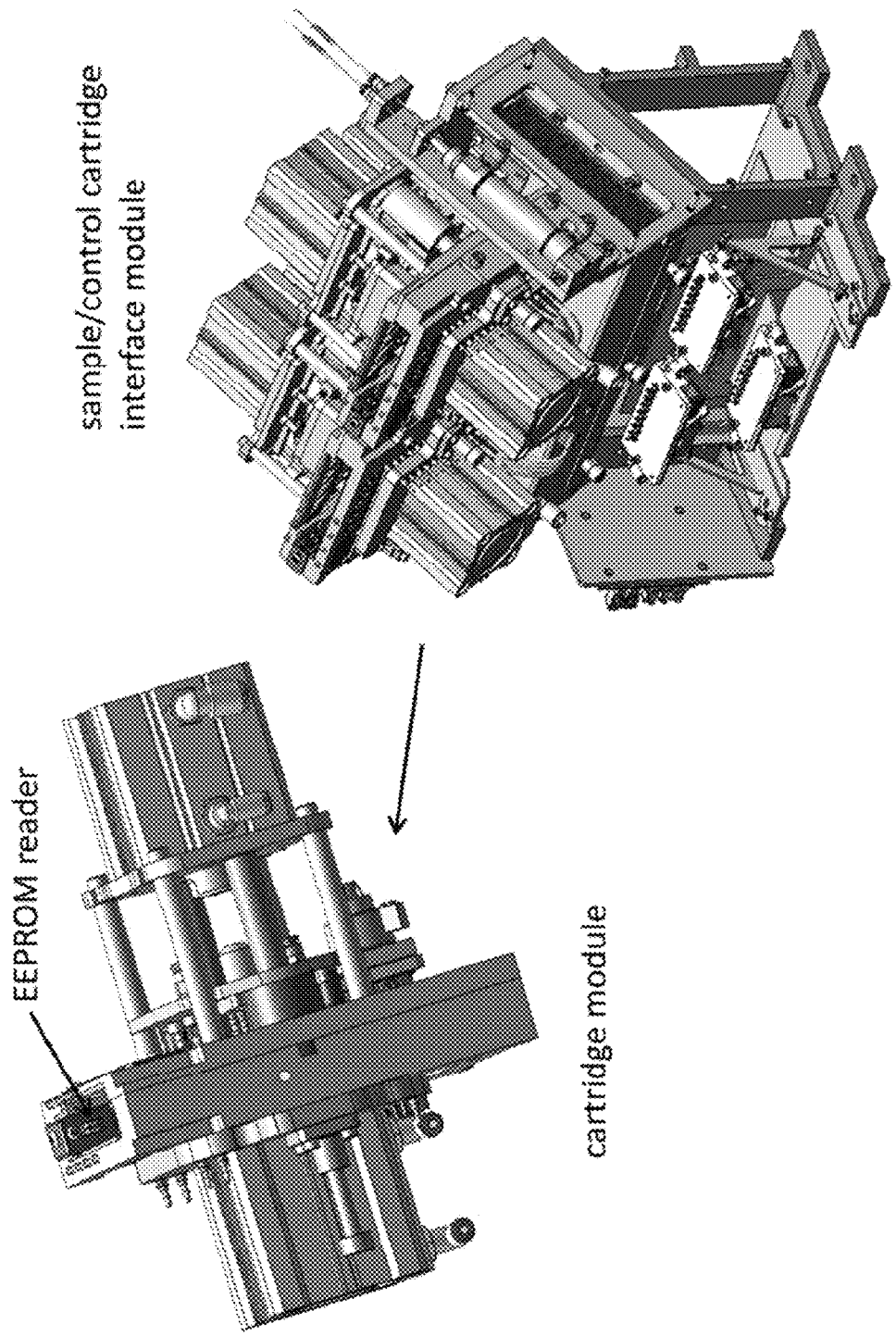
FIG. 39 depicts an embodiment of a cartridge module and a sample/control cartridge interface module having two cartridge modules for accepting two sample cartridges or a sample cartridge and a control cartridge.
Figure 40:
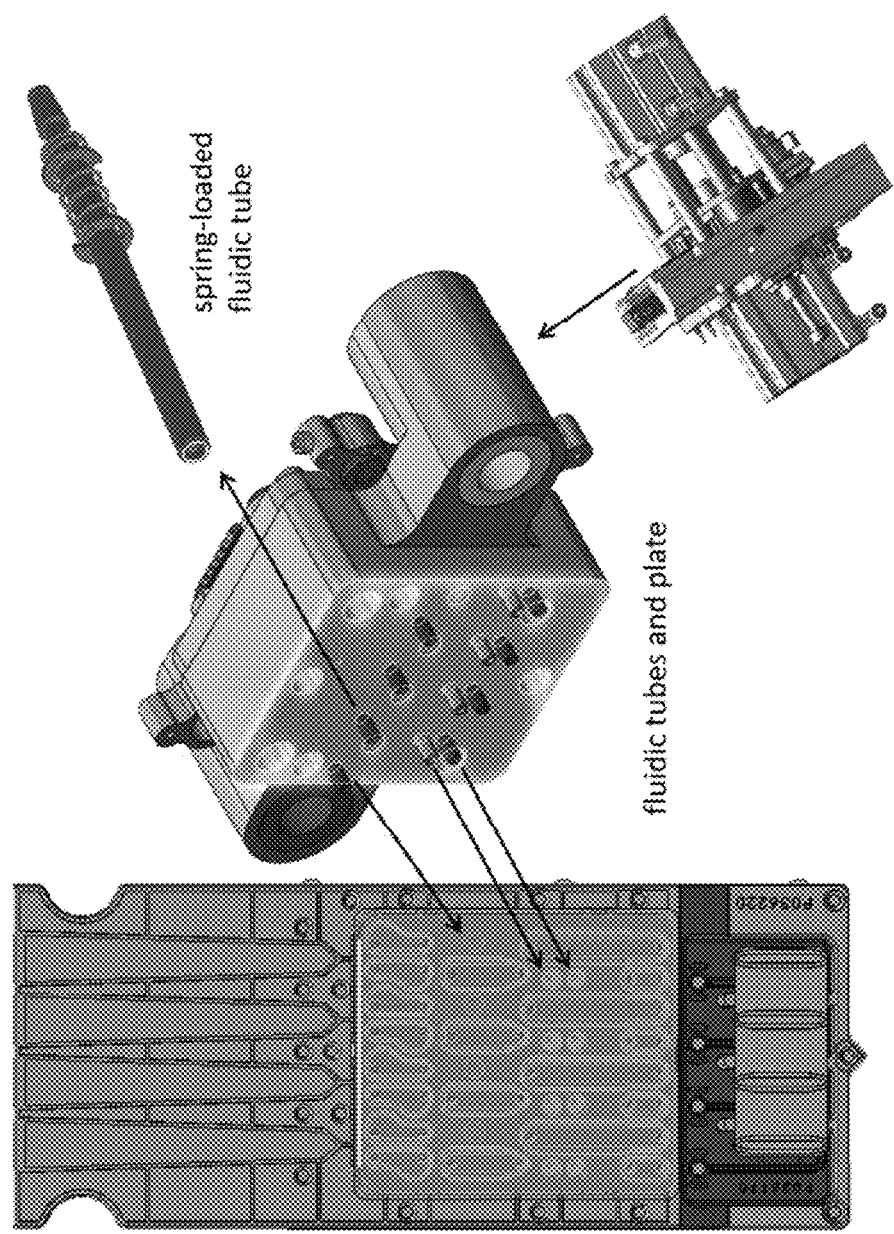
FIG. 40 shows embodiment of a fluidic manifold of a cartridge module indicating mating of tubes with ports in a sample cartridge.
Figure 41:
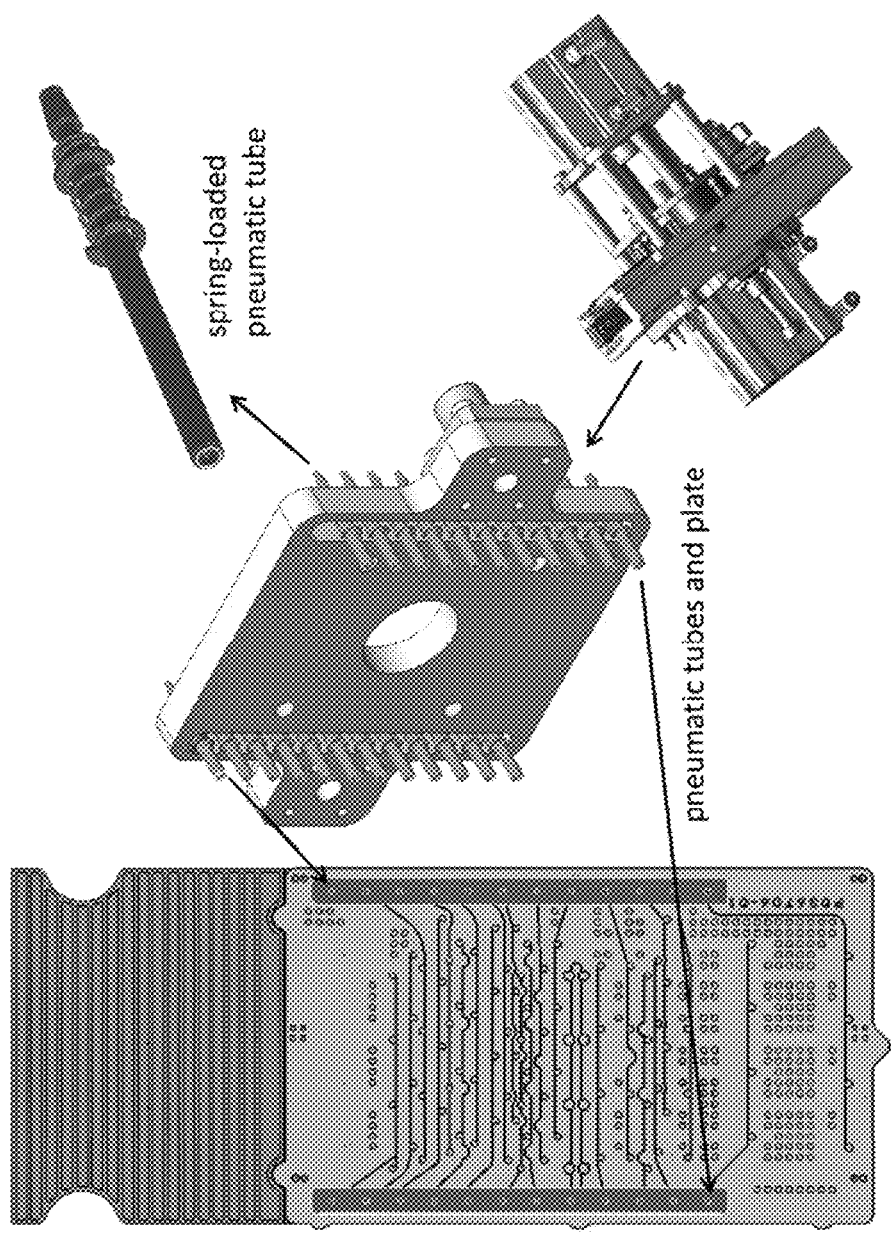
FIG. 41 shows an embodiment of a pneumatic manifold and a pneumatic side of a sample cartridge with ports for mating with pneumatic tubes.

With reference to FIG. 3 and FIG. 39, the sample cartridge interface module includes two cartridge modules for accepting sample cartridges, such as a control cartridge and a sample cartridge or two sample cartridges. The sample cartridge is for providing one or a plurality of samples (e.g., a fluid FTA card punch, solid material or tissue sample with genetic material) to be prepared, processed and analyzed. The control cartridge can be provided for a control sample having, for example, a known genetic profile and/or a negative control (e.g., containing no DNA sequences that can be amplified by the analyte preparation process). Controls can include an allelic ladder, a positive control having, for example, a known genetic profile and a negative control which does not have any DNA of interest, e.g. no human DNA. The control cartridge can also process one or more samples depending on the configuration.

In the embodiments shown in FIG. 3 and FIG. 39, the sample cartridge interface module comprises two cartridge modules. In other embodiments, the sample cartridge interface module comprises a single cartridge module for receiving a single sample cartridge. A sample cartridge interface module configured to receive a single sample cartridge would not need to provide pneumatic and fluidic connections to multiple (e.g., two) sample cartridges, which could reduce the weight and complexity of the system or instrument. Whether a sample cartridge interface module comprises a single cartridge module or multiple (e.g., two) cartridge modules, a sample cartridge can be configured to have 4, 8, 10, 16, 24, 32, 40, 48 or more sets of sample chamber, reagent chambers (e.g., one or more wash chambers, DNA capture chamber, lysis reagent/waste chamber, and diluent chamber), reaction chamber, and reaction reagent (e.g., premix) chamber, for receiving and processing 4, 8, 10, 16, 24, 32, 40, 48 or more samples, where one or more controls (e.g., an allelic ladder, a positive control and/or a negative control) can be run instead of one or more samples.

In some embodiments, the clamping system engages the cartridge and brings macroscale chambers of the cartridge in fluid communication with one another. In an example, the clamping system engages the cartridge and brings a lysis chamber in fluid communication with a buffer chamber through a microfluidic channel of the cartridge. The system 100, with the aid of the cartridge, is thus configured to effect a macro-to-micro downscaling of fluid volume, and also a micro-to-macro upscaling of fluid volume.

In some embodiments, the system comprises a receptacle for receiving a cassette having a container comprising a plurality of closed and fluidically isolated chambers and a microfluidic device comprising a plurality of puncturing elements and a microfluidic channel in fluid communication with one or more ports. Each of the plurality of closed and fluidically isolated chambers comprises a friable seal. The system further includes a pressure application member for engaging the microfluidic device with the container. Engaging the microfluidic device with the container punctures the friable seal of each of the plurality of closed and fluidically isolated chambers and creates a fluid flow path between each of the plurality of closed and fluidically isolated chambers and the microfluidic channel.

In some embodiments, the system comprises a cartridge module having a receptacle for accepting a cartridge and a first assembly having a first pressure manifold that engages a first side of the cartridge and brings the one or more chambers in fluid communication with a pressure source. A second assembly has a second pressure manifold that engages a second side of the cartridge and brings the one or more valves in fluid communication with a pressure source for actuation, e.g., pneumatic or hydraulic actuation. An elongation or moving member moves one or both of the first assembly and the second assembly towards the cartridge module and adjacent to the cartridge.

The elongation or moving member can be coupled to one or both of the first assembly and the second assembly through a cable, such as a Bowden cable. The elongation or moving member can move one or both of the first pressure manifold and the second pressure manifold away from the cartridge module. In some situations, the elongation or moving member comprises an air-driven piston the movement of which moves one or both of the first assembly and the second assembly towards the cartridge module. A pneumatic piston can have one or more sensors to monitor motion of the piston. For example, a pneumatic piston can have two sensors to indicate whether the piston is fully withdrawn or fully engaged.

1. Fluidic and Pneumatic Manifolds

Figure 36A:
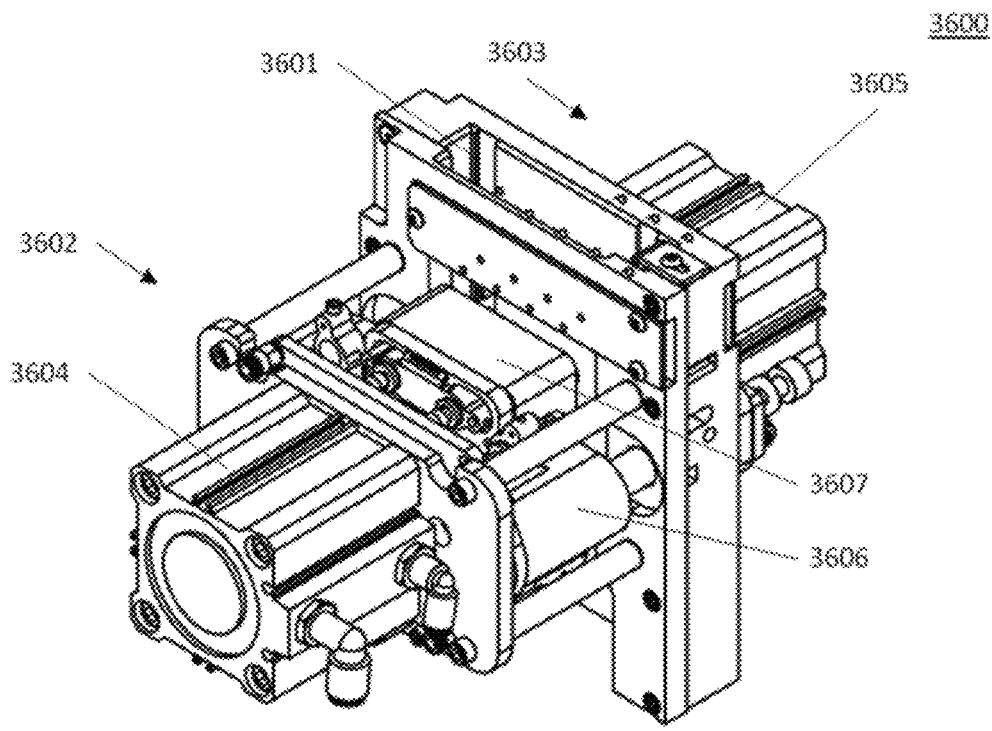
FIGS. 36A and 36B are schematic perspective side views of a cartridge module, in accordance with embodiment of the invention.

FIG. 36A shows a cartridge module 3600 that is configured to accept a cartridge, in accordance with an embodiment of the invention. The cartridge module 3600 includes a cartridge receptacle 3601, a first assembly 3602 and a second assembly 3603. The first assembly 3602 includes a first air cylinder 3604 and the second assembly 3603 includes a second air cylinder 3605. The air cylinders are each in fluid communication with a positive or negative pressure source. In an example, the first air cylinder 3604 is in fluid communication with a positive pressure source, and the second air cylinder 3605 is in fluid communication with a positive pressure source.

The first air cylinder 3604 provides positive or negative pressure (vacuum) to chambers of the cartridge (e.g., the waste chamber 3104 of FIG. 31) when the first assembly has engaged the cartridge. The second air cylinder 3605 actuates the valves in a microfluidic device of a cartridge, as described elsewhere herein.

With continued reference to FIG. 36A, the first assembly 3602 comprises a fluidic pusher assembly 3606. The fluid pusher assembly includes a manifold 3607 that is configured to rest adjacent to a cartridge that has been inserted into the cartridge receptacle 3601, and direct positive or negative pressure to one or more chambers of the cartridge. In some situations, the manifold 3607 directs positive pressure to the chambers of the cartridge to facilitate fluid flow. The first assembly can include an STR plunger assembly for actuating an STR plunger of the cartridge.

With a cartridge inserted in the cartridge receptacle 3601, the manifold 3607 is moved against the chambers of the cartridge with the aid of an elongation or moving member (not shown). The elongation or moving member can be coupled to the manifold 3607 through a cable, such as a Bowden cable.

Figure 36B:
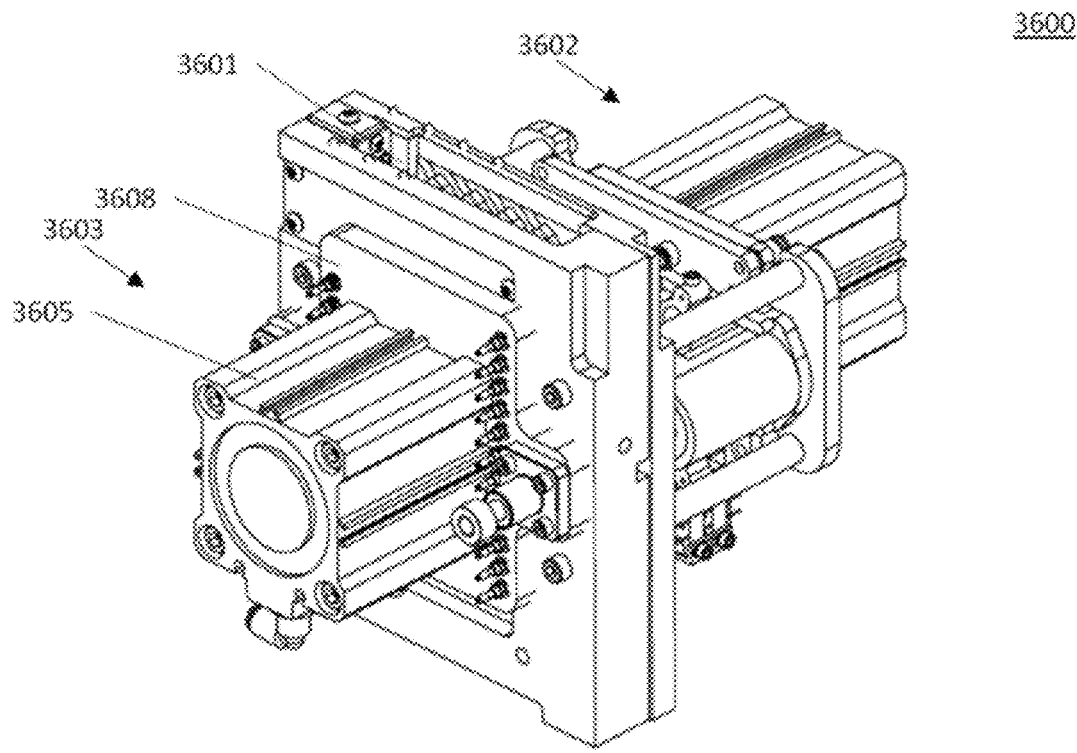
Figure 37:
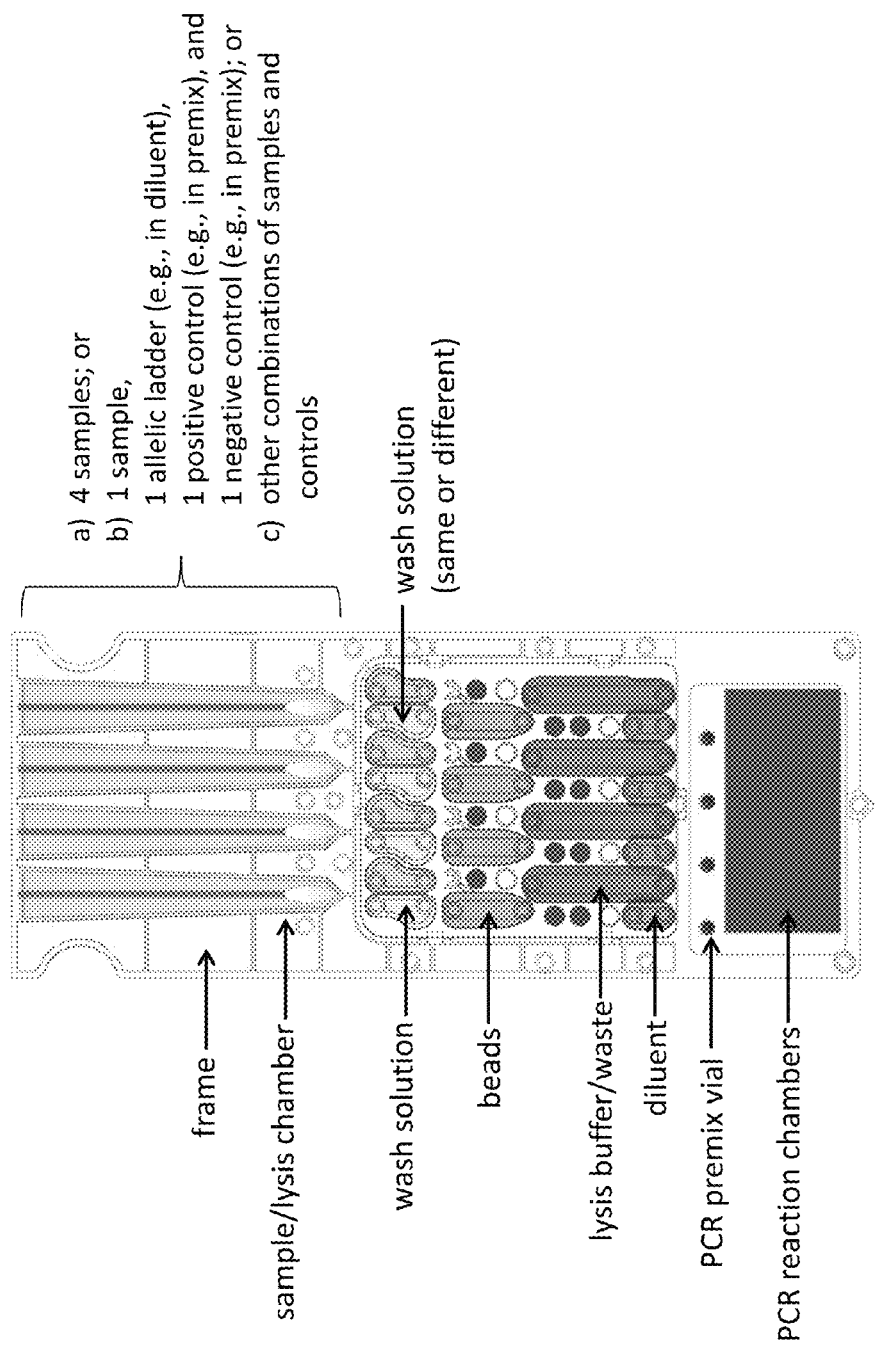
FIG. 37 shows an illustration of a sample cartridge of this invention.

FIG. 36B shows a perspective of cartridge module 3600 in which the cartridge module is rotated 180 degrees with respect to the cartridge module shown in FIG. 36A. With reference to FIG. 36B, the second air cylinder 3605 is disposed adjacent to a pneumatic pusher assembly (or pressure manifold) 3608. The second air cylinder 3605 provides air to the pneumatic pusher assembly 3608 that is in fluid communication with individual valves of the microfluidic device of the cartridge. The second air cylinder 3605 and pneumatic pusher assembly 3608 are configured to actuate the valves of the microfluidic device.

In some embodiments, the instrument or system of the present disclosure comprises tubes made of a suitable material (e.g., a metal or metal alloy, such as stainless steel) which facilitate fluidic communication described herein by engaging ports. Such a tube can have the same or different dimensions with respect to other such tubes, and can have the same or different dimensions along the length of the tube. The tubes can comprise a rigid material. Each tube can independently biased against the port to which it is aligned. For example, each tube can be driven by a different pressure source, e.g., a different spring. Independent biasing can ensure proper sealing of each tube with each port, especially in situations in which the cartridge has limited compliance.

In some embodiments, the instrument or system comprises 10 or more tubes (e.g., tubes 3620 in FIG. 46) that reversibly contact gaskets on the pneumatic side of the microfluidic device, engage pneumatic ports, and facilitate fluidic communication via actuation of valves by application of pressure or vacuum. In some embodiments, the instrument or system comprises 15 or more, 20 or more, 25 or more, or 30 or more such tubes. In further embodiments, the instrument or system comprises from 20 to 30 such tubes. In certain embodiments, the instrument or system comprises 23, 24 or 25 such tubes. In some embodiments, the second pressure manifold of the second assembly of the system described herein comprises such tubes.

The system configured to engage the cassette can include a pneumatic manifold that mates with pneumatic ports on the pneumatic layer of the fluidic chip and a fluidic manifold that mates with ports on the fluidic layer. A pneumatic assembly comprising a pneumatic manifold can be controlled by solenoid valves to deliver pressure and vacuum. A fluidic assembly can comprise a fluidic manifold that engages ports on the cassette and includes channels that connect passages in the cassette with an analytic assembly, e.g., capillary electrophoresis.

When fully engaged, the pneumatic manifold engages the pneumatic ports. In some cases, a pressure manifold is in fluid communication with one or more chambers of the cartridge. The pressure manifold provides positive or negative pressure to the one or more chambers. On the other side, the cassette has ports that communicate with ports on the chip that communicate with the microfluidic channels. In some cases, these first ports are engaged with a source of pressure to pump liquids not by the diaphragm pumps but by outside pressure.

The pneumatics module may include compressors and/or pumps for providing a pressurized gas (e.g., pressure greater than 1 atm) and/or vacuum to various pneumatically actuated valves, such as valves of the cartridges 103 and 105. The system 100 may include actuation conduits in fluid communication with the pneumatics module for providing communication of pressure (positive or negative) between the valves and the pneumatic module. Each actuation conduit is in fluid communication with a positive pressure source compared to ambient (e.g., air compressor) or a negative pressure source compared to ambient (e.g., vacuum pump), or both that is, the system 100 may be configured to actuate valves with the aid of both positive and negative pressure, such as, for example, closing normally open valves using positive pressure, and opening the normally open valves using negative pressure. A pneumatics module also can provide pressure to a port in the fluidics of the sample cartridge and to a buffer module to move buffer from the buffer module to the fluidic system of the sample cartridge.

In further embodiments, the instrument or system comprises 4 or more tubes (e.g., tubes 3610 in FIG. 46) that traverse through one or more holes to the right (or to the left) of each bead suspension/capture chamber, reversibly contact gaskets on the fluidic side of the microfluidic device, engage ports of fluidic channels, and facilitate fluid movement between various places (e.g., between chambers) by application of pressure (e.g., air or liquid pressure). In an embodiment, the instrument or system comprises 4 such tubes that each separately traverse through one hole to the right (or to the left) of each of 4 bead suspension/capture chambers, one such tube for each such hole. In another embodiment, the instrument or system comprises 8 such tubes that each separately traverse through one of two holes to the right (or to the left) of each of 4 bead suspension/capture chambers, one such tube for each such hole. It is understood that the number of such tubes can be based on the number of hole(s) to the right (or to the left) of each bead suspension/capture chamber and the number of bead suspension/capture chambers, or the number of fluidic ports to be engaged by such tubes. In some embodiments, the first pressure manifold of the first assembly of the system described herein comprises such tubes.

In additional embodiments, the instrument or system comprises 8 or more tubes (e.g., tubes 3614 and 3616 in FIG. 46) that traverse through two or more holes to the left (or to the right) of each reagent storage/waste chamber, reversibly contact gaskets on the fluidic side of the microfluidic device, engage fluidic ports, and are conduits of fluid. In an embodiment, the instrument or system comprises 8 such tubes that each separately traverse through one of two holes to the left (or to the right) of each of 4 reagent storage/waste chambers, one such tube for each such hole. In certain embodiments, the tubes (e.g., tubes 3614 in FIG. 46) traversing through the upper hole to the left (or to the right) of each reagent storage/waste chamber connect the sample cartridge (the cartridge containing sample chambers) to a capillary electrophoresis system by application of pressure (e.g., spring-driven pressure), and the tubes (e.g., tubes 3616 in FIG. 46) traversing through the lower hole to the left (or to the right) of each reagent storage/waste chamber connect the sample cartridge to a buffer cartridge by application of pressure (e.g., spring-driven pressure). The tubes can be connected to a conduit, such as flexible tubing, that transports sample from the cartridge to an electrophoresis capillary. It is understood that the number of such tubes can be based on the number of holes to the left (or to the right) of each reagent storage/waste chamber and the number of reagent storage/waste chambers, or the number of fluidic ports to be engaged by such tubes. In some embodiments, the first pressure manifold of the first assembly of the system described herein comprises such tubes.

In some embodiments, the manifold structure used to interface a sample cartridge (e.g., the first pressure manifold of the first assembly or the second pressure manifold of the second assembly of the system described herein) comprises a base pressure plate, a plurality of tube spring assemblies, and a pressure actuator. In certain embodiments, a tube spring assembly comprises a tube that has two snap ring grooves, two snap rings, a tip with an orifice that is surrounded by a raised sealing edge, a hose barb structure opposite the tip, and a coil spring. The coil spring is contained between the two snap rings and a thrust plate. The thrust plate comprises a plurality of tube spring assemblies in an arrangement configured to interface ports of the cartridge. The plurality of tubes are configured to fluidically interface the cartridge simultaneously, as groups or individually, e.g., if more than one thrust plate is used. The tubes are configured to individually impart a force sufficient to make a reliable seal with the corresponding port (or an intervening gasket) for the tube on the cartridge. For all of the tubes to make a reliable seal, the array of tubes does not need to be a highly precise planar structure, and the cartridge does not need to be a highly precise structure. Each of the tubes can move and engage independently of the others to optimize each seal. By comparison, a monolithic solid sealing "block" may be less effective in sealing ports of the cartridge because the two planes of the sealing block and the cartridge may require a high degree of accuracy (e.g., within about 0.001 inch) and the force distribution on the seals may not be suitably uniform given the overall system accuracy.

Figure 46:
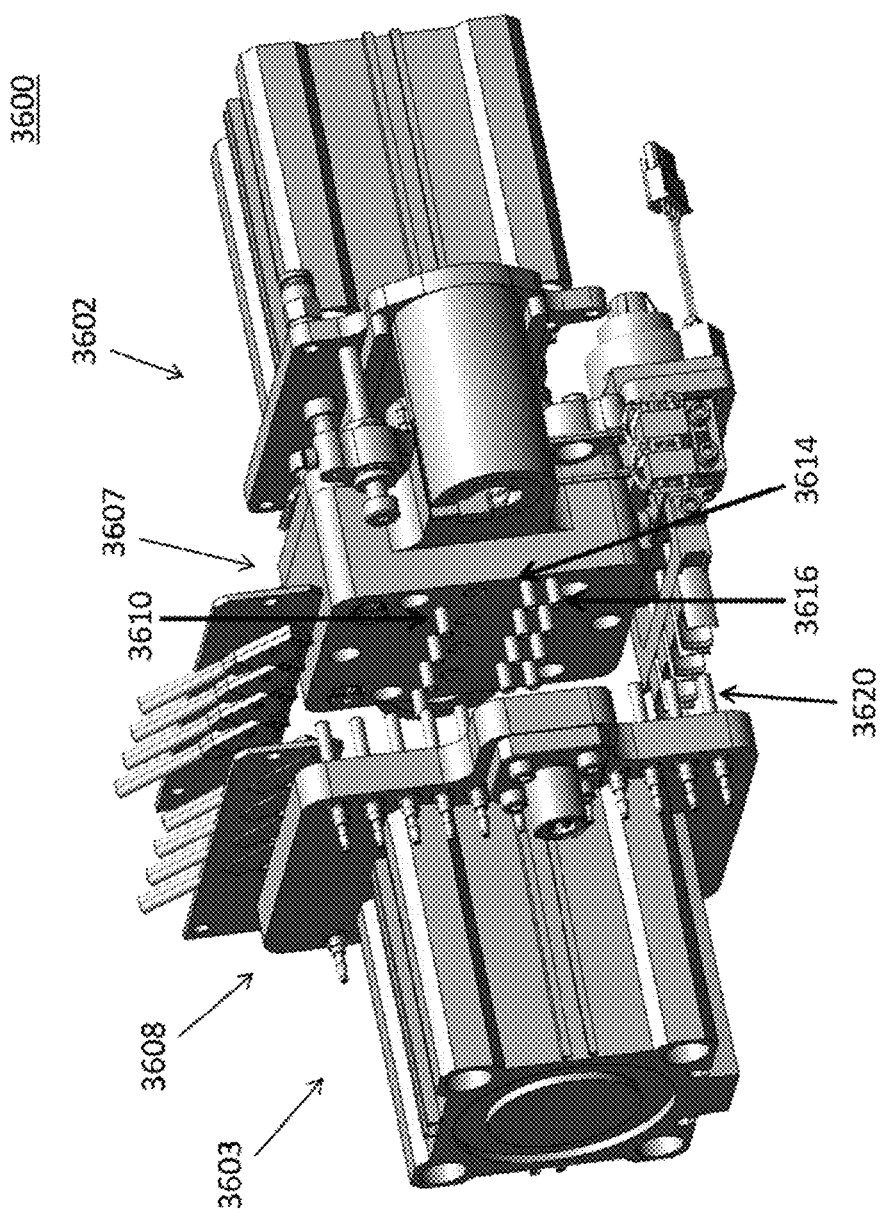
FIG. 46 shows an embodiment of cartridge module 3600 in which the first pressure manifold 3607 of the first assembly 3602 comprises tubes 3610, tubes 3614 and tubes 3616 that each engage ports on the fluidic side of the microfluidic device of a cartridge, and the second pressure manifold 3608 of the second assembly 3603 comprises tubes 3620 that each engage ports on the pneumatic side of the microfluidic device.
Figure 47:
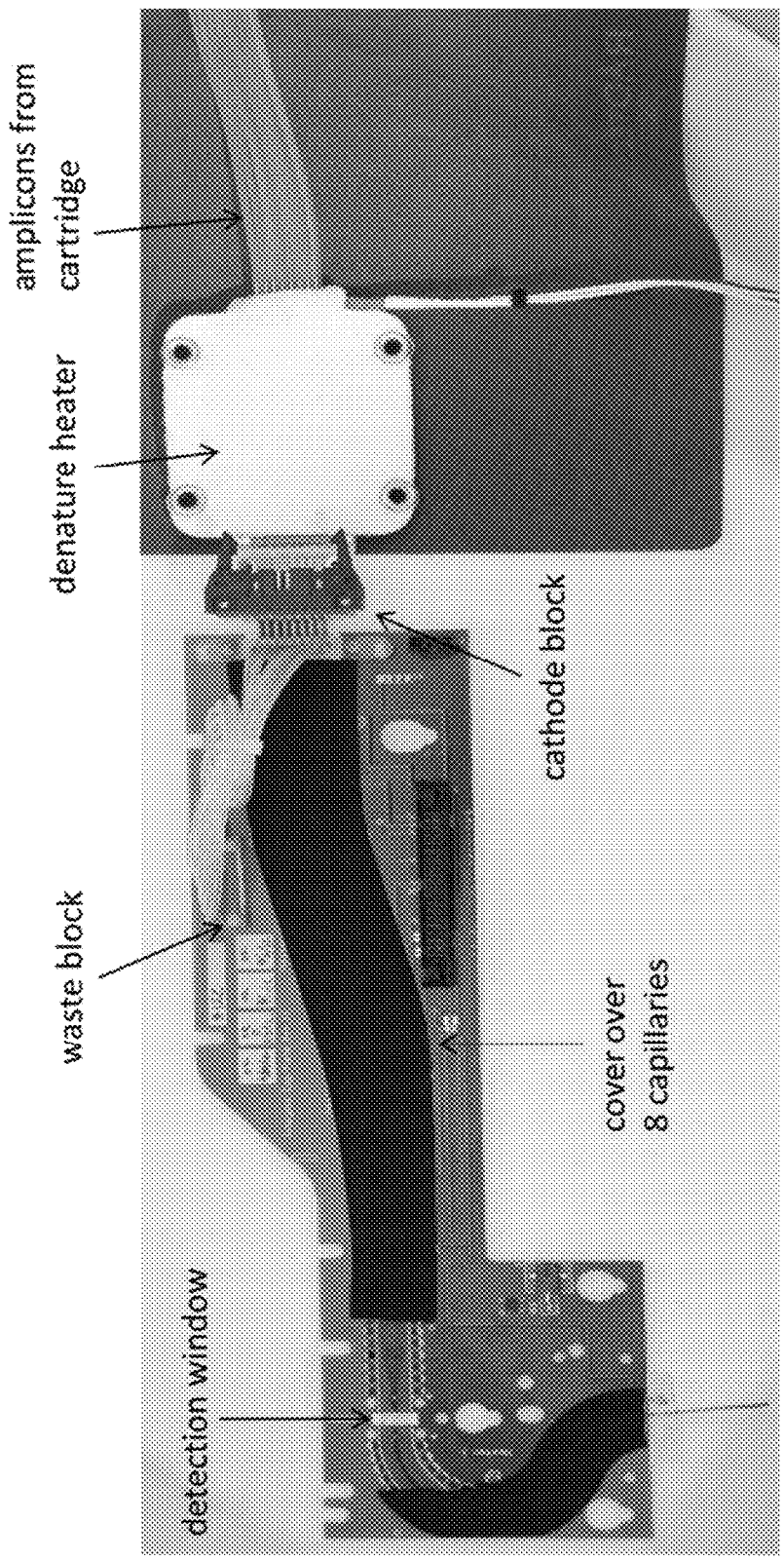
FIG. 47 shows an embodiment of a capillary electrophesis array having a capillary board and a denature heater.

FIG. 46 shows an embodiment of cartridge module 3600. In the embodiment of FIG. 46, the first pressure manifold 3607 of the first assembly 3602 comprises four tubes 3610 that each separately traverse through one hole to the right (or to the left) of each bead suspension/capture chamber, one such tube for each such hole, and engage ports on the fluidic side of the microfluidic device of a cartridge. The first pressure manifold of the first assembly also comprises four tubes 3614 and four tubes 3616 that each separately traverse through the upper hole and the lower hole, respectively, to the left (or to the right) of each reagent storage/waste chamber, one such tube for each such hole, and engage ports on the fluidic side of the microfluidic device. In the embodiment of FIG. 46, the second pressure manifold 3608 of the second assembly 3603 comprises 23 or 24 tubes 3620 that each engage ports on the pneumatic side of the microfluidic device.

In some embodiments, to obviate potential contamination (e.g., run-to-run contamination or cross-lane contamination) by a contaminant (e.g., a DNA contaminant, such as a potentially amplifiable allelic ladder or size standard), a membrane comprising a hydrophobic material is placed between fluidic ports and the terminus of tubes that traverse through one or more holes to the right (or to the left) of each bead suspension/capture chamber and engage such ports (e.g., tubes 3610 in FIG. 46). In an embodiment, a hydrophobic membrane is placed underneath the gasket that contacts such tubes. The hydrophobic membrane is designed to allow gas to pass through it but not a hydrophilic liquid (e.g., an aqueous solution). Non-limiting examples of material composing the hydrophobic membrane include fluorinated and perfluorinated polymers {e.g., perfluoroalkoxy (PFA) polymers, polytetrafluoroethylene (PTFE, Teflon®), fluorinated ethylene-propylene (FEP) polymers, polyethylenetetrafluoroethylene (PETFE), polyvinylfluoride (PVF), polyvinylidene fluoride (PVDF), polyethylene chlorotrifluoroethylene (PECTFE), and polychlorotrifluoroethylene (PCTFE)}, hydrocarbon polymers (e.g., polyethylene and polypropylene), and silicon-containing materials (e.g., silicon-containing polymers and silica).

In further embodiments, to preclude potential contamination (e.g., run-to-run contamination or cross-lane contamination) by a contaminant (e.g., a DNA contaminant, such as a potentially amplifiable allelic ladder or size standard), tubes (e.g., the inside thereof) that traverse through one or more holes to the right (or to the left) of each bead suspension/capture chamber and engage fluidic ports (e.g., tubes 3610 in FIG. 46) are washed with a decontaminating agent (e.g., bleach) upon completion of a sample-to-answer protocol. For example, a decontamination cartridge containing an aqueous solution of a decontaminating agent (e.g., bleach), and optionally other solution(s) (e.g., water and/or ethanol), can be used to wash the inside of such tubes with such solution(s) upon completion of a sample-to-answer protocol. Such a decontamination cartridge can be integrated with the instrument or system described herein or can be inserted into the instrument or system after completion of a sample-to-answer protocol.

In additional embodiments, to obviate potential contamination (e.g., run-to-run contamination or cross-lane contamination) by a contaminant (e.g., a DNA contaminant, such as a potentially amplifiable allelic ladder or size standard), a conformable or spongy material impregnated with a cleaning solution is placed under the container of FIG. 8. The conformable or spongy material can be the deformable material of FIG. 8, a material used in place of the deformable material, or a material adjacent to (e.g., above) the deformable material. Contact of a contaminant (e.g., a DNA contaminant) with the conformable or spongy material impregnated with the cleaning solution can degrade the contaminant. The cleaning solution can contain a decontaminating agent (e.g., bleach).

2. Buffer Cartridge Module

Figure 7:
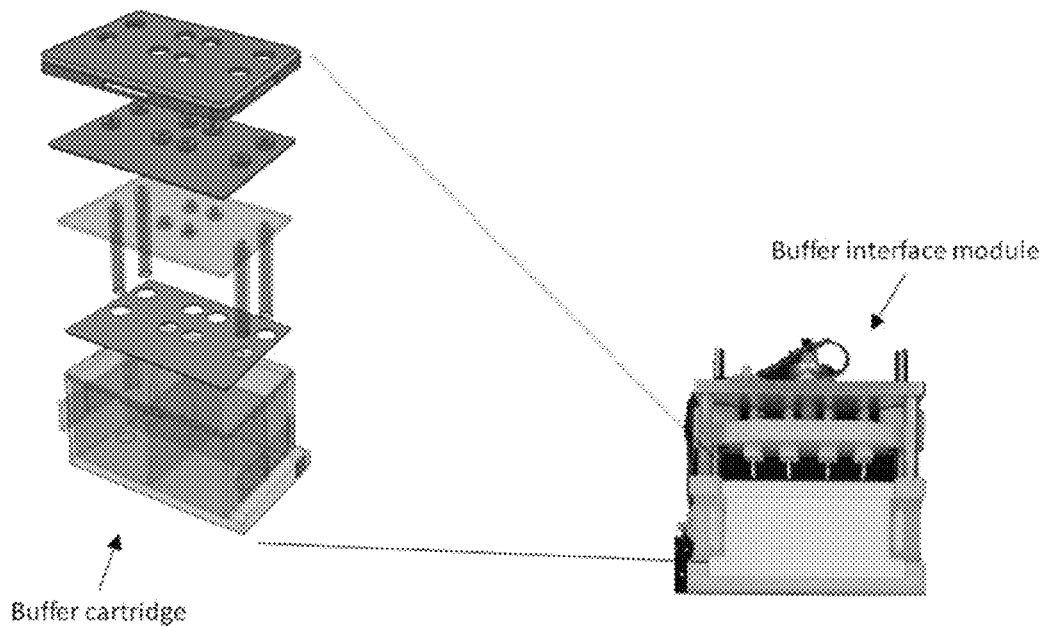
FIG. 7 shows a buffer interface module and a buffer cartridge, in accordance with an embodiment of the invention.

The buffer cartridge and interface module of the system 100 are shown in FIG. 7. The buffer cartridge and interface module includes a buffer interface module and a buffer cartridge. An exploded view of the buffer cartridge is shown on a left side of the figure. The buffer cartridge interface module includes an automated engagement mechanism for accepting the buffer cartridge, which may comprise (e.g., be prefilled) with one or more buffers and/or water. One or more buffers may be used for electrophoresis (e.g., capillary electrophoresis).

In some embodiments, the buffer cartridge comprises (e.g., is pre-loaded with) an aqueous buffer for electrophoresis which contains one or more buffering agents selected from N,N-bis(2-hydroxyethyl)glycine (bicine), N-tris(hydroxymethyl)methylglycine (tricine), tris(hydroxymethyl)methylamine (Tris), 3-amino-1-propanesulfonic acid, 4-(cyclohexylamino)-1-butanesulfonic acid (CABS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N-(2-hydroxyethyl)piperazine-N'-(3-propanesulfonic acid) (EPPS), and 3-{[tris(hydroxymethyl)methyl]amino}-propanesulfonic acid (TAPS). In an embodiment, the buffer cartridge comprises an aqueous buffer containing Tris and TAPS. In additional embodiments, the buffer cartridge further comprises (e.g., is further pre-loaded with) water, which can be used for, e.g., cathode preparation and clean up. In certain embodiments, the aqueous buffer and/or the water further contain a metal chelator. Non-limiting examples of metal chelators include aurintricarboxylic acid (ATA), boric acid, citric acid, salicylic acid, 1,2-bis(o-aminophenoxy) ethane-N,N,N,N-tetraacetic acid (BAPTA), diethylene triamine pentaacetic acid (DTPA), ethylenediaminetetraacetic acid (EDTA), ethylene glycol tetraacetic acid (EGTA), glycoletherdiaminetetraacetic acid (GEDTA), N-(2-hydroxyethyl)ethylenediamine-N,N',N'-triacetic acid (HEDTA), nitrilotriacetic acid (NTA), 2,2'-bipyridine, o-phenanthroline, triethanolamine, and salts thereof. In an embodiment, the metal chelator comprises EDTA. In additional embodiments, the buffer cartridge is further configured to collect waste material.

A buffer and/or water is provided from the buffer cartridge with the aid of pressure (e.g., positive or negative pressure). A pressure/vent line can connect the buffer cartridge to a pressure solenoid valve. To capture any liquid that may come out of the buffer cartridge (e.g., due to overpressure in the cartridge) and enter the pressure/vent line, a liquid trap can be placed in the pressure/vent line between the buffer cartridge and the pressure solenoid valve. The liquid trap prevents liquid from migrating to the pressure solenoid valve. A check valve can also be placed in a line connecting a pressure source (e.g., a 10 psi pump) to the pressure solenoid valve. The check valve is designed to protect the pressure solenoid valve, e.g., by creating a static volume of air and no flow. A liquid trap and/or a check valve can also be used in other places of the instrument or system described herein where it is not desired for liquid to get into a line connecting a source of liquid to a valve or other structure. The buffer interface module includes an EEPROM reader for reading an on-board EEPROM of the buffer cartridge, which can be removably mounted on the buffer interface module. The buffer interface module may have a relatively small foot print. In some situations, the buffer interface module has a length of about 4.5 inches or less, a width of about 2.5 inches or less, and a height of about 5 inches or less. The buffer interface module of the system 100 advantageously permits a user to load the system 100 with different types of buffers. The buffer cartridge interface module also can include a chamber for receiving liquids (e.g., waste) from the fluidic conduit that moves liquids from the sample cartridge to the cathode assembly.

E. Methods For Processing Samples

In another aspect of the invention, methods for processing samples are provided. Methods provided herein can be used with systems provided herein, such as the system 100 of FIG. 1 and the cartridge of FIGS. 8-18.

In some embodiments, a method for processing a biological sample comprises (a) providing a cassette as described above, (b) providing a biological sample in the sample chamber, (c) engaging the microfluidic device with the container to form a fluid flow path between each of the plurality of closed and fluidically isolated chambers and the microfluidic channel, and (d) processing the biological sample. In some cases, the plurality of closed and fluidically isolated chambers comprise a first chamber holding a diluent, a second chamber holding one or more lysis reagents, a third chamber having capture particles, and a fourth chamber having a wash solution. The second chamber is in fluid communication with the sample chamber. In some cases, engaging the microfluidic device with the container comprises applying pressure against the container in the direction of the microfluidic device.

In some embodiments, the sample is processed by directing the one or more lysis reagents from the second chamber to the sample chamber, contacting the one or more lysis reagents with the biological sample in the sample chamber, thereby extracting a nucleic acid sample from the biological sample, directing the nucleic acid sample from the sample chamber to the third chamber, thereby attaching at least a portion of the nucleic acid sample to capture particles, and directing the capture particles to a reaction chamber (or thermocycling chamber) in fluid communication with the third chamber through the microfluidic channel.

In some cases, the lysis reagents are directed from the second chamber to the sample chamber with the aid of negative or positive pressure, such as negative pressure provided by one or more pumps disposed in the microfluidic device.

In some situations, the sample includes a nucleic acid. During processing, the nucleic acid is amplified in a reaction chamber (e.g., a reaction chamber configured to perform PCR with thermal cycling) of the cassette. The nucleic acid may be attached to capture particles (e.g., beads). In some cases, the nucleic acid sample is amplified by directing the capture particles to a reaction chamber of the thermal cycler assembly, providing a premix with primers, a buffer that can contain a metal salt (e.g., magnesium chloride), and an enzyme (e.g., a DNA polymerase, such as a Taq polymerase) to the reaction chamber, heating the nucleic acid to amplify the nucleic acid, and subsequently directing the amplified nucleic acid to a separation system.

In an example, a cartridge, such as the cartridge 1000 of FIG. 10 having a microfluidic device 1010, is provided in a sample preparation, processing and analysis system, such as the system 100 of FIG. 1. A sample, such as a cotton swab containing nucleic acid or a cell-containing sample, is provided into the sample chamber 1001 either before or after the cartridge 1000 is provided in the system. The chambers of the cartridge 1000 are then engaged with the microfluidic device 1010, thereby bringing the chambers in fluid communication with microfluidic channels of the microfluidic device 1010. Engaging the chambers with the microfluidic device 1010 also brings the chambers in fluid communication with one another through the microfluidic channels of the microfluidic device 1010. A manifold of a fluid pusher assembly (see, e.g., FIGS. 36A and 36B) is then brought in fluid communication with reagent and processing chambers of the cartridge 1000.

Lysis buffer, contained in the lysis reagent storage chamber 1002, is pumped through the microfluidic device 1010 (having a microfluidic channel) into the sample chamber 1001, where the lysis buffer (e.g., NaOH and a detergent, such SDS; or a guanidinium salt (e.g., guanidinium thiocyanate), a zwitterionic detergent/surfactant (e.g., CHAPS) and/or a nonionic detergent/surfactant (e.g., Triton® X-114, and optionally an anti-foaming agent) lyses cells in the sample, releasing nucleic acids of the sample. Bubbling of air or another gas can provide mild agitation to improve lysis. Heating can also improve lysis, as can application of an ultrasonic field. The resulting lysate is pumped into the bead suspension/capture chamber 1003. The bead capture chamber 1003 comprises magnetically responsive particles adapted to capture nucleic acids. In some embodiments, the bead capture chamber 1003 comprises silica-coated magnetic beads (e.g., Magnacel® beads from Promega). Upon nucleic acid capture, a magnetic field is used to immobilize the particles and captured nucleic acid in the bead capture chamber 1003, which is generally a multi-use chamber. The magnetic field may be applied inductively or using a rare earth magnet, such as neodymium, which is preferably moved closer to capture the beads and further away to release the beads. Any lysate material that is not captured by the magnetically responsive particles is transferred to the waste chamber 1002 while the particles and captured nucleic acid are immobilized in the bead capture chamber 1003. Next, a first wash solution or buffer (e.g., Tris EDTA and a salt; or an aqueous alcohol solution, e.g., 90% ethanol in water or 70% ethanol in water) from a first wash solution/buffer chamber 1004 is moved through the microfluidic device into the bead capture chamber 1003. The first wash solution or buffer washes the particles, removing waste. The first wash solution or buffer and dissolved wastes are then moved into the waste chamber 1002 while the capture particles and captured nucleic acid are immobilized in the bead capture chamber 1003. Next, a second wash solution or buffer (e.g., Tris EDTA and a salt; or an aqueous alcohol solution, e.g., 70% ethanol in water) is moved from a second wash solution/buffer chamber 1005 into the bead capture chamber 1003. Next, the magnetic force is released, allowing the particles to mix with the second wash solution or buffer. The second wash solution or buffer, along with capture particles and captured target nucleic acid, are moved into the reaction chamber 1008 of the thermocycler assembly 1006 (see above). The device 1000 includes four reaction chambers in parallel which are configured to perform nucleic acid amplification (e.g., by PCR) with thermal cycling. A magnet adjacent to each reaction chamber 1008 immobilizes magnetically responsive particles having samples attached thereto in the reaction chamber 1008 of the thermocycler assembly 1006. The remaining solution is moved to the waste multi-use chamber 1002. A master mix (or premix) containing reagents sufficient to perform short tandem repeat (STR) amplification on selected loci is directed into the reaction chamber 1008. The master mix is moved from the premix chamber 1007 to the reaction chamber 1008 of the thermocycler assembly 1006 with the aid of, e.g., a plunger, a blister pack as described elsewhere herein, or an actuating device such as that shown in FIG. 55. The temperature of the reaction chamber 1008 and sample in the chamber 1008 can be cycled with the aid of a heating and cooling device (e.g., a Peltier temperature control element) in proximity to the reaction chamber 1008. The heating and cooling device (e.g., a Peltier device) can be contained, e.g., in the cartridge module (see, e.g., FIG. 42) and can be moved to come into proximity with each reaction chamber 1008. Cycling the temperature amplifies STRs defined by primers in the master mix, producing an amplified product. A solution containing amplified product is moved from the reaction chamber 1008 into a diluent (or dilution) chamber 1009, which contains an amount of diluent (e.g., water) and, optionally, a size standard, selected to dilute the product for injection into the capillary array electrophoresis. The amplified product can be diluted by any suitable amount, e.g., diluted about 5-fold to about 20-fold, or about 10-fold. The diluted product is then moved from dilution chamber to the capillary array injector (see FIGS. 2 and 5) through the manifold adjacent to the cartridge 1000. For example, diluted product in each fluidic circuit in the cartridge can be transported from the chamber that holds it to the capillary for electrophoresis through a path that leads from the chamber, through a channel, out a port in the cartridge, through a tube that engages the port (e.g., tubes 3614 in FIG. 46), through a fluidic conduit (e.g., a sample line) to the capillary. In certain embodiments, the fluidic conduit can continue to a receptacle, e.g., a waste chamber, e.g., in the buffer cartridge.

F. Reagents and Controls

In some embodiments, one or more controls for determining the size, mass or length of nucleic acids (e.g., DNA and/or RNA) are employed. In an embodiment, a size standard (also called size marker, internal lane standard or molecular weight ladder) is used. In preferred embodiments, the size standard is provided in every lane that contains a sample. In another embodiment, an allelic ladder (a plurality of alleles at each of one or more loci) is used. In preferred embodiments, the allelic ladder is provided in a lane that contains no sample. In certain embodiments, the allelic ladder comprises a plurality of alleles at each of one or more STR loci, such as those STR loci used in a forensic database (e.g., CODIS). In some embodiments, the allelic ladder comprises a plurality of alleles at, and optionally adjacent to, one or more, or all, STR loci used in CODIS, and optionally a plurality of alleles of amelogenin (AMEL) and the STR loci designated Penta D and Penta E. CODIS presently uses STR loci designated CSF1PO, D3S1358, D5S818, D7S820, D8S1179, D13S317, D16S539, D18S51, D21S11, FGA, TH01, TPOX and vWA for human identification, and amelogenin for sex determination. In an embodiment, the allelic ladder comprises a plurality of alleles at, and optionally adjacent to, all the CODIS STR loci, plus amelogenin, Penta D and Penta E. In yet another embodiment, both a size standard and an allelic ladder are used. In preferred embodiments, the size standard is provided in every lane that contains a sample, the allelic ladder is provided in a lane that contains no sample, and the lane containing the allelic ladder also contains the size standard.

The size standard and/or the allelic ladder can be provided (e.g., pre-loaded) in any appropriate chamber. In an embodiment, the size standard and/or the allelic ladder are provided (e.g., pre-loaded) in the premix chamber. To obviate potential contamination (e.g., run-to-run contamination or cross-lane contamination) by a potentially amplifiable size standard and/or by a potentially amplifiable allelic ladder, the size standard and/or the allelic ladder can be provided (e.g., pre-loaded) in a post-amplification chamber or in the chamber immediately preceding introduction to a capillary electrophoresis system. In a preferred embodiment, the size standard and/or the allelic ladder are provided (e.g., pre-loaded) in the diluent (or dilution) chamber.

If both a size standard and an allelic ladder are employed, the size standard and the allelic ladder can be provided (e.g., pre-loaded) in any appropriate chamber(s). In an embodiment, the size standard and the allelic ladder are provided (e.g., pre-loaded) in the premix chamber of the same lane or separate lanes. In another embodiment, the size standard is provided (e.g., pre-loaded) in the premix chamber of a lane, and the allelic ladder is provided (e.g., pre-loaded) in the diluent chamber of the same lane or a separate lane. In a further embodiment, the size standard is provided (e.g., pre-loaded) in the diluent chamber of a lane, and the allelic ladder is provided (e.g., pre-loaded) in the premix chamber of the same lane or a separate lane. In an additional embodiment, the size standard and the allelic ladder are provided (e.g., pre-loaded) in the diluent chamber of the same lane or separate lanes. In preferred embodiments, the size standard is provided (e.g., pre-loaded) in the diluent chamber of every lane that contains a sample, the allelic ladder is provided (e.g., pre-loaded) in the diluent chamber of a lane that contains no sample, and the diluent chamber containing the allelic ladder also contains (e.g., is also pre-loaded with) the size standard.

In further embodiments, a positive control is used. In some embodiments, the positive control comprises purified genomic DNA of a known or unknown subject (e.g., a known or unknown human). In other embodiments, the positive control can be control nucleic acids bound to a swab or in a liquid. In certain embodiments, the DNA of the positive control undergoes PCR amplification at the same loci (e.g., all the CODIS STR loci, plus optionally Penta D, Penta E and amelogenin) as the DNA from a regular sample. In preferred embodiments, the lane containing the positive control also contains a size standard. The positive control and the size standard can be provided (e.g., pre-loaded) in any appropriate chamber(s). For example, the DNA of the positive control can be provided (e.g., pre-loaded) in the sample chamber or the premix chamber, and the size standard can be provided (e.g., pre-loaded) in the premix chamber or the diluent chamber. In preferred embodiments, the DNA of the positive control is provided (e.g., pre-loaded) in the premix chamber, and the size standard is provided (e.g., pre-loaded) in the diluent chamber.

In further embodiments, an internal positive control DNA can be provided by using a sequence not found in the STR panel of interest, or a non-human DNA, including an artificial DNA, can be used. The internal positive control DNA can be provided (e.g., pre-loaded) in any or every lane as desired. The primers and fluorescent dyes would be designed to have the amplification products generated from the internal positive control not overlap any of the alleles of the STR panel of interest, e.g., either in fluorescent color or fragment size. An advantage of this approach is that every sample could have an internal positive control without using a complete lane for the positive control, thus allowing one more sample to be analyzed per run, reducing cost and potentially improving the quality of the positive control.

In additional embodiments, a negative control is used. In some embodiments, the negative control contains no DNA to be amplified, but rather contains the same premix reagents, including the same dye-labeled primer oligonucleotides, used to amplify by PCR selected loci (e.g., selected STR loci, such as all the CODIS STR loci plus optionally Penta D, Penta E and amelogenin) of the DNA of a sample. In preferred embodiments, the lane containing the negative control also contains a size standard. The negative control and the size standard can be provided (e.g., pre-loaded) in any appropriate chamber(s). For example, the negative control can be provided (e.g., pre-loaded) in the premix chamber, and the size standard can be provided (e.g., pre-loaded) in the premix chamber or the diluent chamber. In preferred embodiments, the negative control is provided (e.g., pre-loaded) in the premix chamber, and the size standard is provided (e.g., pre-loaded) in the diluent chamber.

In certain embodiments, an allelic ladder, a positive control and a negative control are provided (e.g., pre-loaded) in a control cartridge, which optionally can also take a sample.

III. Detection and Analysis Module

An analysis and detection module can include a capillary electrophoresis assembly, a detection assembly and an analysis assembly.

Figure 49:
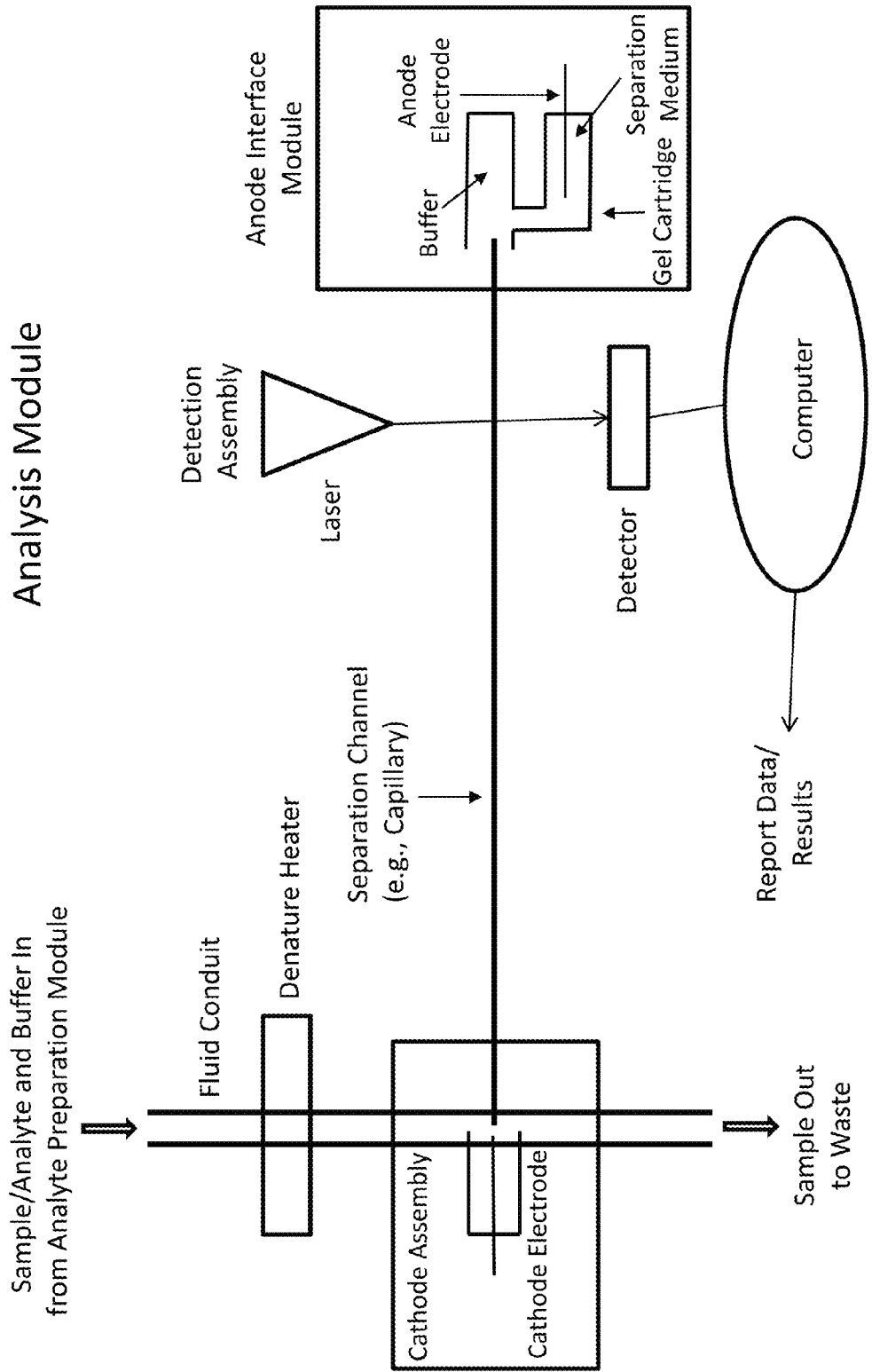
FIG. 49 shows a schematic of an analysis module useful in the systems of this invention.

FIG. 49 shows a schematic of an analysis module useful in the systems of this invention. Sample (e.g., amplified DNA or controls) and buffer (e.g., electrophoresis buffer) flow through a fluidic conduit, such as a tube, from a analyte preparation module in a path that can include a denature heater, a cathode assembly for injecting analyte into a capillary, and out to waste. A denature heater heats fluid containing DNA and denatures strands in double stranded DNA into single strands. The cathode assembly can include an electrode, such as a forked electrode, connected to a source of voltage. When a sample to be analyzed is positioned for injection, the electrode can provide voltage to inject the analyte into the capillary. The capillary is filled with a separation medium, such as linear polyacrylamide (e.g., LPA V2e, available from IntegenX Inc., Pleasanton, Calif.). The capillary ends are electrically connected to a voltage source, e.g., an anode and a cathode. Separated analyte is detected with a detection module. The detection module can employ, for example, a laser and a detector, such as a CCD camera, CMOS, photomultiplier, or photodiode. The anode assembly (e.g., anode cartridge interface) can include an anode in electrical connection with the capillary and a source of voltage. The anode assembly also can include a source of separation medium and a source of pressure for introducing separation medium into a capillary. The anode assembly can include electrophoresis buffer. The separation medium and/or the electrophoresis buffer can be included in an anode cartridge. The anode cartridge can be configured for removable insertion into the anode assembly. It can contain separation medium and/or electrophoresis buffer sufficient for one or more than one run.

A. Capillary Electrophoresis Assembly

The capillary electrophoresis assembly can include an injection assembly that can include a denture assembly, a cathode assembly; a capillary assembly; an anode assembly; a capillary filling assembly for filling a capillary with separation medium; a positioning assembly for positioning an analyte (or sample) for capillary injection; and a power source for applying a voltage between the anode and the cathode.

Figure 54:
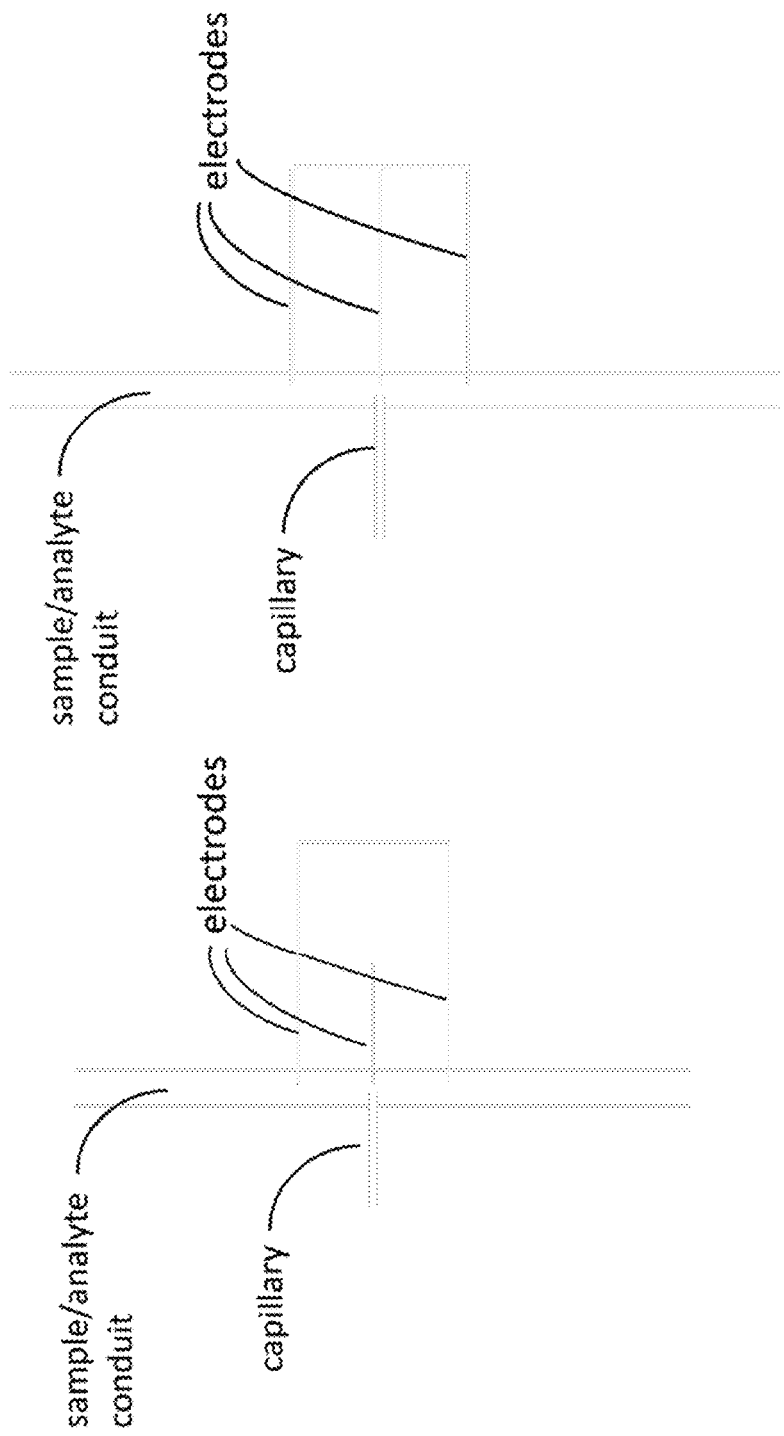
FIG. 54 shows an injection system for injecting a sample into an electrophoresis capillary.

The capillary electrophoresis system can include one or more capillaries for facilitating sample or product separation, which can aid in analysis. In some embodiments, a fluid flow path directs a sample or product from the cartridge to an intersection between the fluid flow path and a separation channel. (See, e.g., FIGS. 49 and 54.) The sample is directed from the fluid flow path to the separation channel, and is directed through the separation channel with the aid of an electric field, as can be generated upon the application of an electrical potential across an anode and a cathode of the system (see below). U.S. Patent Publication No. 2011/0005932 ("UNIVERSAL SAMPLE PREPARATION SYSTEM AND USE IN AN INTEGRATED ANALYSIS SYSTEM"), which is entirely incorporated herein, provides examples of electrophoresis capillaries for use in analysis, as may be used with systems herein. The capillary can be inserted into the fluidic conduit for fluidic and electric communication.

1. Cathode Assembly

A cathode also can be in electric communication with the capillary through an electric communication with fluid in the fluidic conduit. The cathode can be disposed in the fluidic conduit near the connection with the capillary. For example the cathode can be positioned opposite the point at which the capillary connects with the fluidic conduit (e.g., neither upstream nor downstream of the connection). This can aid injection of the sample into the capillary and/or to provide voltage for the electrophoresis run. In certain embodiments, the cathode can comprise a forked electrode in which one fork is positioned upstream and one fork is positioned downstream of the point of connection of the capillary and the fluidic conduit. In other embodiments, the cathode comprises both a forked electrode and a third electrode positioned near the connection between the fluidic conduit and the capillary.

An electrophoresis sample (e.g., amplification products) can be prepared for injection into a separation channel (e.g., a capillary) by any suitable method. As an example, field-amplified stacking (FAS) can be performed by positioning in an electrophoresis sample channel a diluted mixture comprising the sample of lower salt concentration or lower ionic strength between areas comprising an electrophoresis buffer of higher salt concentration or higher ionic strength. As another example, a bolus of a material (e.g., air) can be positioned downstream of the sample in the sample channel, wherein the material has an electrical conductivity that differs from the electrical conductivity of the electrophoresis buffer or the sample, as described below. When the sample is positioned across the separation channel, the sample can be electrokinetically injected into the separation channel at an appropriate voltage (e.g., about 3 kV to about 5 kV, or about 4 kV) over an appropriate amount of time (e.g., about 10 sec to about 20 sec, or about 15 sec).

2. Capillary Assembly

Figure 5:
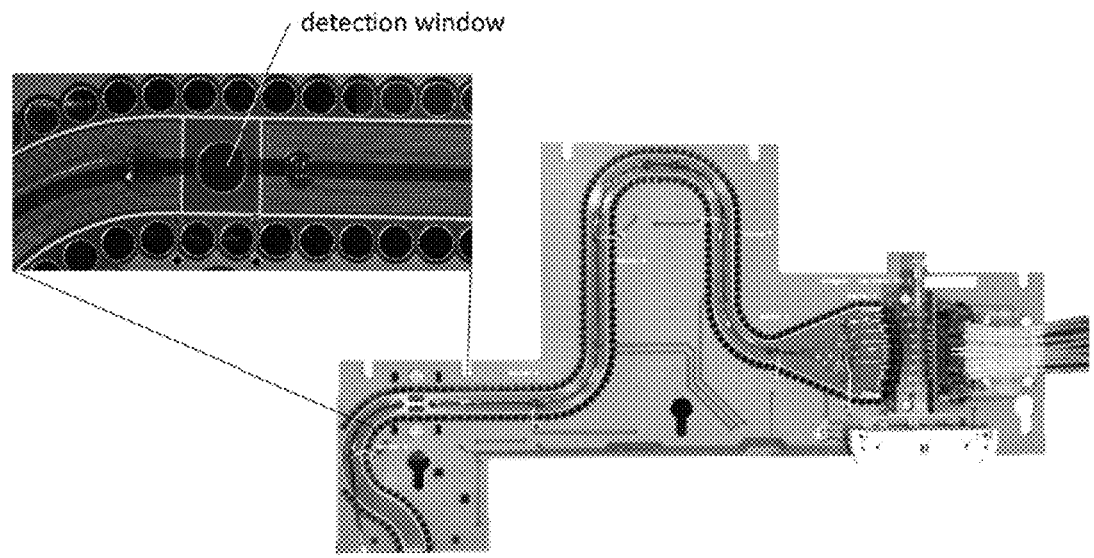
FIG. 5 shows capillaries for electrophoresis, in accordance with an embodiment of the invention.

The system 100 is configured for sample (or sample product) analysis, such as with the aid of a capillary board. The capillary board (or plate) of the system 100 is shown in FIG. 5. The capillary board includes individual capillaries and integrated capillary and denature heaters. The capillary plate includes individual capillaries to be used in capillary electrophoresis on at least one sample. In some situations, the capillary board is for performing capillary electrophoresis on a plurality of samples, such as 1, 2, 3, 4, 5, 6, 7, 8, 9, 10, or more than 10 samples. To collect any liquid that may leak from, e.g., a capillary or the cathode of the electrophoresis system, a spill tray of sufficient collection capacity (e.g., up to about 50 mL, 75 mL, 100 mL, 125 mL or 150 mL) can be placed under the capillary board. The spill tray can optionally have a leak sensor for detection of any leak. A spill tray of sufficient collection capacity (e.g., up to about 50 mL, 75 mL, 100 mL, 125 mL or 150 mL) can also be placed under other components of the instrument or system described herein which may potentially leak liquid, e.g., under the buffer cartridge or the interface therefor, under the sample cartridge or the interface therefor, and/or under the anode cartridge or the interface therefor, where the spill tray can optionally have a leak sensor.

The system 100 includes a device for regulating the temperature of each of the electrophoresis capillaries. The capillaries may be held on an electrically insulating circuit board that has a generally curved path or a substantially straight path for placement of capillaries. In some embodiments, the capillaries are provided in one or more curvilinear paths, such as, e.g., a generally S-shaped path or a plurality of S-shaped paths. The path can be distributed into a plurality of sections. Each of the sections separately regulates the temperature in a portion of the capillaries in thermal communication with the section. Temperature is regulated with the aid of resistive heating, though other temperature control elements (e.g., heating element and/or cooling element) or devices may be used. Temperature can be measured with the aid of a temperature sensing device, such as a thermocouple, a thermistor or a resistive temperature device (RTD) in each section. Each of the different sections includes an electrical path that traverses the capillaries of each section. In some cases, the electrical path traverses back and forth (e.g., in a serpentine shape in that section). The electrical path includes one or more temperature control elements (e.g., heating elements and/or cooling elements) (e.g., resistive heaters) for providing heat to the capillaries. A portion of the electrical path is shown in the inset of FIG. 5.

On a circuit board, such as the circuit board shown in FIG. 5, electrophoresis capillaries are attached to a path (e.g., S-shaped path) with the aid of an adhesive, for example. In the illustrated embodiment, a bundle of eight capillaries are provided. In other embodiments, the path may include any number of capillaries, ranging from 1 to a higher number, depending on the requirements of a particular electrophoresis for parallel processing of analytes.

In some cases, an entrance of the capillaries has fanned out ends to facilitate injection of analytes into the different capillaries. One end of the capillaries may be bundled or the capillaries may be separate depending on whether all capillaries are filled together or if each capillary will be filled separately.

A thermal sensor is in contact with each of the separately thermally regulated areas or sections of the path. Examples of temperature sensors are thermistors or other temperature-varying resistance, or thermocouples or other temperature-varying voltage source. In some cases, the temperature data of the separately thermally regulated sections is not gathered by discrete temperature sensor, but by the electrical paths themselves such as by the resistances of the electrical paths. External temperature sensors may also be used.

Each section of the capillaries may be marked by a heater comprising one or more resistive heating elements. The heaters may be distributed across a path of the capillaries to provide temperature control.

With reference to FIG. 5, the electrophoresis separation channels (e.g., capillaries) can be electrically connected to a cathode and anode. The cathode and anode can be electrically connected to the high voltage module. The cathode is part of the capillary array and held in place by electrophoresis system hardware. The anode is part of the anode cartridge interface module and is connected to the electrophoresis system hardware (FIG. 5). High voltage is supplied to the anode electrode while cathode electrodes (e.g., sixteen cathode electrodes, two per channel) are held at ground. Current monitoring can be done between the cathodes and ground and can be monitored for individual channels on a high voltage board. The cathode electrodes are part of the capillary array and connections are made to the high voltage system during array installation.

Electrophoresis can be conducted at any voltage and over any period of time suitable for achieving good separation of the analyte (e.g., amplification products). In some embodiments, amplification products are separated at a voltage of about 6 kV to about 12 kV, or about 8 kV to about 10 kV, or about 9 kV, over a period of about 10 min to about 30 min, or about 15 min to about 25 min, or about 20 min. The length of the separation channels (e.g., capillaries) can also be selected to achieve good separation of the analyte. In certain embodiments, the length of a separation channel to the detection window is about 10 cm to about 40 cm, or about 15 cm to about 35 cm, or about 20 cm to about 30 cm, or about 25 cm.

The electrophoresis channels can be filled with a separation matrix (e.g., a separation polymer or gel) from the anode cartridge. Examples of separation polymers and gels that can be used to separate nucleic acid fragments by electrophoresis include polyacrylamide (e.g., the LPA line (including LPA-1) of separation gels (Beckman Coulter), the POP™ line (including POP-4™, POP-6™ and POP-7™) of separation polymers (Life Technologies), and a modified LPA with a self-coating polymer (e.g., LPA V2E (IntegenX Inc.)), agarose, hydroxyethylcellulose, and other biopolymers. To separate single-stranded nucleic acid fragments, denaturing gel electrophoresis can be performed using a separation polymer or gel that comprises a chemical denaturant (e.g., urea, formamide or N-methyl-pyrrolidone) or at a temperature (e.g., about 65° C., 75° C., 85° C. or 90° C. or higher) that denatures double-stranded nucleic acid fragments. Heat can be applied to nucleic acid fragments prior to their injection into a separation channel using a denature heater as described below, and/or during separation using a thermally controlled solid-state heating system (e.g., a heating system comprising one or more metal wires (e.g., copper wires) adjacent to the separation channels (e.g., under the board containing the capillary electrophoresis array)) as described herein.

3. Anode Assembly

Figure 6:
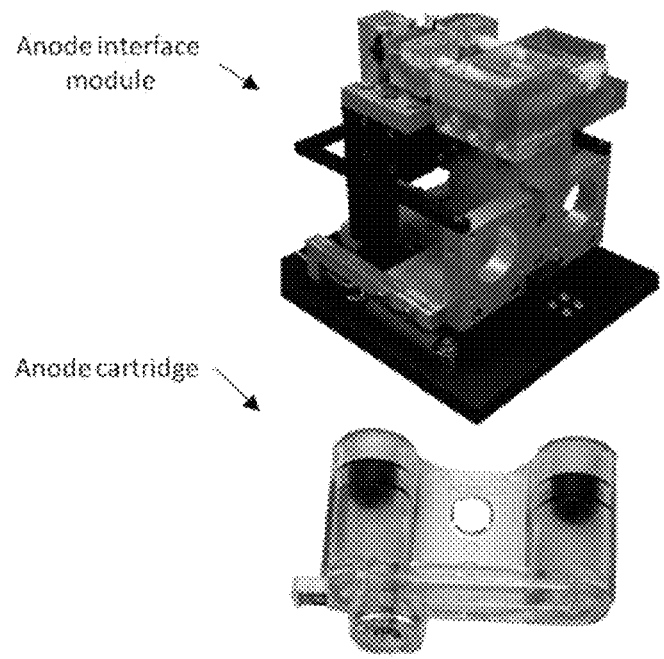
FIG. 6 shows an anode interface module and an anode cartridge, in accordance with an embodiment of the invention.

FIG. 6 shows an anode assembly (e.g., anode cartridge interface module) of the system 100. The anode cartridge interface module includes an anode interface module (top) and an anode cartridge (bottom). The anode cartridge in some cases is a disposable, limited use (e.g., single-use) cartridge. The anode cartridge may be formed by injection molding a polymeric material or by other methods. In one embodiment the anode cartridge can comprise two chambers. One chamber can contain separation matrix and the other chamber can contain electrophoresis buffer. In another embodiment, both chambers can contain separation matrix. In yet another embodiment, the anode cartridge can comprise a single chamber containing buffered separation matrix. The chamber comprising electrophoresis buffer can be in electrical communication with the anode. It also can be in electrical communication with the capillaries and with the chamber comprising the separation matrix, e.g., through one or more fluidic channels. Each chamber can comprise a plunger operatively linked with a pressure source and adapted to move separation matrix and/or buffer out of the chambers. Each plunger can be independently operable. The anode cartridge can be prefilled with a separation matrix and buffer. In some embodiments, the anode cartridge has an on-board memory, such as an electrically erasable programmable read-only memory (EEPROM), which may include calibration details and/or device configuration.

The anode cartridge is configured to be inserted into a port of the anode interface module. The anode interface module includes an automated engagement mechanism for engaging with the anode cartridge. In some cases, an integrated high voltage electrode in the anode interface module provides power to the anode cartridge. The anode interface module comprises a memory reader for being communicatively coupled to the on-board memory of the anode cartridge. In some situations, the memory reader is an EEPROM reader configured to communicate with (and read from) an EEPROM of the anode cartridge.

4. Filling Assembly

The anode cartridge includes (e.g., is pre-loaded with) a separation matrix (e.g., polymer or gel) that is used in electrophoresis. In some embodiments, the anode cartridge further comprises (e.g., is further pre-loaded with) an aqueous buffer for electrophoresis which contains one or more buffering agents selected from bicine, tricine, Tris, 3-amino-1-propanesulfonic acid, CABS, CAPS, CAPSO, CHES, EPPS, and TAPS. In an embodiment, the anode cartridge comprises an aqueous buffer containing Tris and TAPS. In certain embodiments, the aqueous buffer further contains a metal chelator, such as a metal chelator described herein. In an embodiment, the metal chelator comprises EDTA. The anode cartridge can further comprise a readable and/or writable memory device (e.g., an EEPROM chip) configured to store, receive and transmit information relating to the cartridge (e.g., the batch number of the cartridge, a recommended use-by date for the cartridge, the composition and the remaining amount of the aqueous buffer, the composition and the remaining amount of the separation matrix, and the condition of the anode electrode).

In one embodiment, during electrophoresis, high voltage is supplied to the anode electrode while cathode electrodes (e.g., two per channel) are held at ground. Current monitoring is done between the cathodes and ground and is monitored for individual channels on a system board. The separation matrix may be a separation polymer or gel. The separation polymer may be provided to the separation channels (e.g., capillaries) (see, e.g., FIG. 5) through an interface at the anode that connects to the electrophoresis system hardware for anode high voltage supply and control. The anode cartridge attaches to the anode interface module and supplies pressure and reagent for every run. The system is pressure driven and can be controlled by solenoids managed by the electronics. Pressure can be monitored by electronic transducers monitored by the electronic safety of the system 100. Safety can be provided by passive and active pressure relief paths and by current shut-off when any access doors are opened during a run.

After a separation run in a separation channel is completed, the same separation matrix (e.g., polymer or gel) can be re-used in one or more subsequent separation runs, or the separation matrix can be discarded and the separation channel can be re-filled with new separation matrix from the same anode cartridge. An anode cartridge can be filled with an amount of separation matrix and an amount of electrophoresis buffer sufficient for a desired number of separation runs.

5. Positioning Assembly

In one embodiment, this invention provides a method for positioning a sample for injection into a capillary. According to one embodiment the method involves providing a fluidic conduit in fluid communication with a sample-containing container and capillary, wherein the capillary intersects a fluidic path of the fluidic conduit and wherein the capillary is in electric communication with an anode and a cathode and wherein the cathode is inserted into the fluidic conduit; positioning a bolus of a material having electrical conductivity that is distinctive from the electrical conductivity of either electrophoresis buffer or sample (e.g., the material comprises air) downstream of the sample in fluidic conduit; moving the bolus of material and the sample in the direction of the capillary while monitoring a current across the anode and the cathode; detecting a distinct current (e.g., a change in current) corresponding to movement of the bolus into an electrical path in the conduit between the cathode and the anode; based on detecting, moving the sample into the electrical path in the conduit between the cathode and the anode. Alternatively, an optical sensor can also be used to detect and control the position of a bolus. The method can further comprise applying an injection voltage and/or a run voltage to inject the sample into the capillary and to run the sample in the capillary. The bolus can be positioned by, for example, pumping a bolus of the material into the conduit using a pump such an on-chip pump in a cartridge containing the sample, e.g., a diaphragm pump; or a pumping mechanism that is not on the cartridge such as a peristaltic pump, syringe pump, etc. Accordingly, in another embodiment, the sample delivery subsystem is configured as (a) a sample channel having a channel inlet and a channel outlet; (b) an electrophoresis capillary having a capillary inlet and a capillary outlet, wherein the capillary comprises an electrically conductive medium and is in communication with the sample channel at a point of connection; (c) an anode and a cathode configured to apply a voltage across the capillary inlet and capillary outlet, wherein one of the anode or cathode comprises a forked electrode wherein the forks are in electrical communication with the sample channel on different sides of the point of connection; and (d) a second electrode in electrical communication with the sample channel substantially opposite the point of connection. In one embodiment of the device, the second electrode is comprised as a third fork in the forked electrode.

6. Denature Heater

Figure 53:
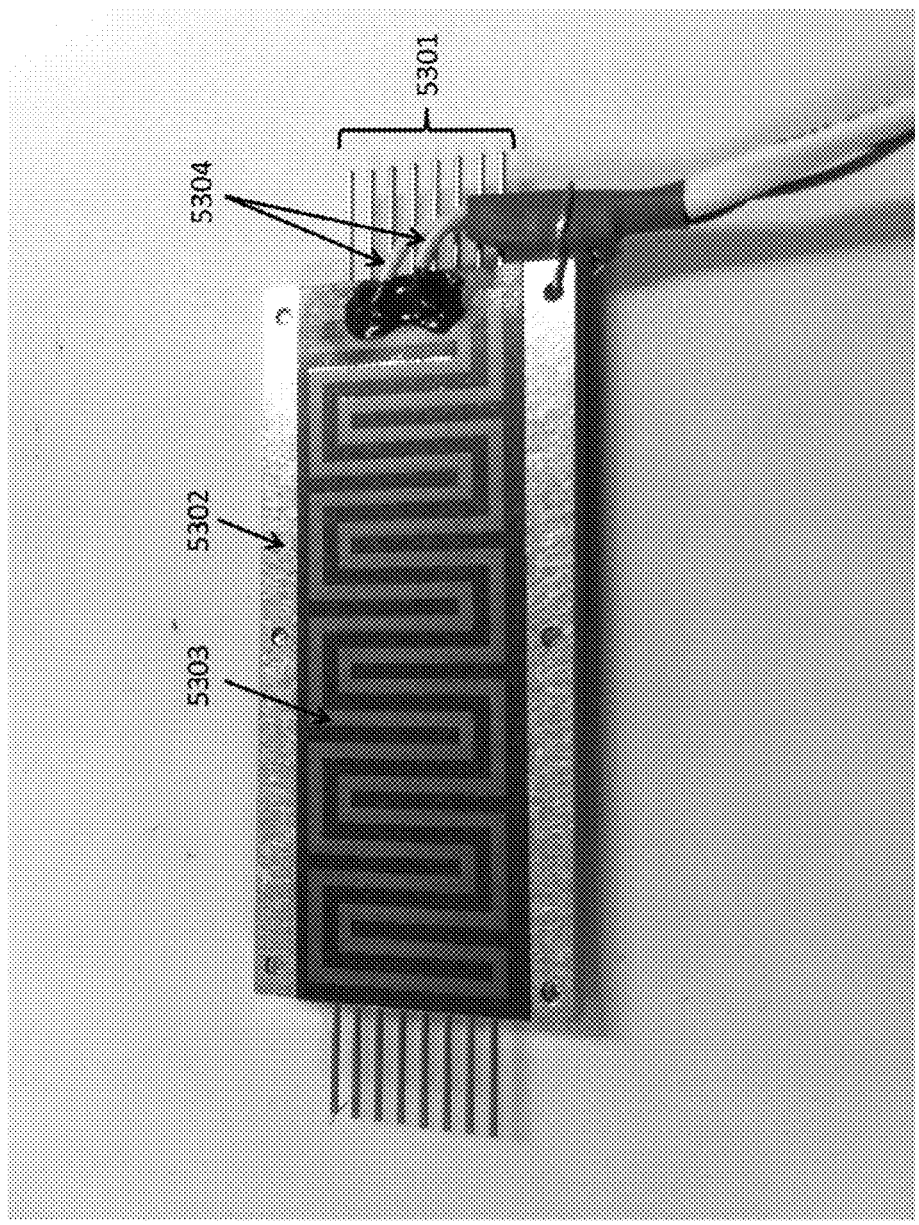
FIG. 53 shows a denature heater of this invention.

In certain embodiments a denature heater is configured as a cannula (or a plurality of cannulae) in thermal contact with a heating element. The cannula can be fluidically connected on one end to the dilution chamber (see, e.g., chamber 1009 in FIG. 10) and on the other end to the capillary sample injector. The assembly comprising the cannula and the heating element can be configured to heat fluid inside the cannula to a temperature that denatures double-stranded nucleic acid such as DNA. In certain embodiments, the cannula can comprise a heat-conducting material, such as a metal tube. The heating element can comprise a resistive heater or other type of heating mechanism. For example, the heating element can comprise an electrically resistive material connected to a source of voltage. The cannula can be clamped between elements of a resistive heater, such as plates. The denature heater can be configured to electrically isolate each of a plurality of cannulae in the heater from each other and from the heating element. For example, the cannulae can be separated from each other and from the heating element by an electrically resistant material. For example, the cannulae can be embedded in an epoxy. The denature heater also can comprise an insulator configured to insulate elements in proximity to the denature heater from heat generated by it. FIG. 53 shows a denature heater of this invention. It includes cannulae 5301, heating element 5302 comprising resistive heater 5303 attached to wires 5304 leading to a source of voltage.

B. Detection Assembly

A detector can be used to observe or monitor materials in the electrophoresis capillaries (or channels). The detector can be, e.g., a charge-coupled device (CCD) camera-based system or a complementary metal oxide semiconductor (CMOS) camera-based system.

The system can include multiple (e.g., 4, 8, 10, 16, 24, 32, 40, 48 or more) electrophoresis separation channels (e.g., capillaries), a light source (e.g., a laser device or a light-emitting diode), an optical detector, and an optical selector. The laser device is positioned to deliver a beam from the laser device to at least one electrophoresis capillary. The optical detector is optically coupled to receive an optical signal from at least one electrophoresis capillary. The laser device, optical detector, and optical selector are in an arrangement that allows the optical detector to selectively detect an optical signal from any one or more of the multiple electrophoresis capillaries.

The laser device can be selected in part based on an output wavelength suitable for distinguishing the separated analyte (e.g., nucleic acid fragments). The nucleic acid fragments can be labeled with a certain number of (e.g., 2, 3, 4, 5 or more) spectrally resolvable fluorescent dyes (e.g., by using primers labeled with those dyes in amplification) so that fragments having different sequences but having the same size and the same electrophoretic mobility can still be distinguished from one another by virtue of being labeled with dyes having spectrally resolvable emission spectra. The laser device can be selected to have one or two output wavelengths that efficiently excite the fluorescent dyes used to label the nucleic acid fragments. The laser device can have a single output wavelength (e.g., about 488 nm) or dual wavelengths (e.g., about 488 nm and about 514 nm). The laser device can scan across the interior of each separation channel at an appropriate rate (e.g., about 1 Hz to about 5 Hz, or about 2 or 3 Hz). The fluorescence emission of each dye excited by the laser device can pass through a filter and a prism and can be imaged onto, e.g., a CCD camera or a CMOS camera.

In one embodiment, the capillaries are arranged as an array. In one embodiment, the optical selector is optically positioned between the laser device and the multiple electrophoresis capillaries. The beam from the laser device is delivered to a single electrophoresis capillary and not delivered to other electrophoresis capillaries. In one embodiment, the optical selector is a scanning objective directing the beam from the laser device to the single electrophoresis capillary and not to other electrophoresis capillaries. In one embodiment, the scanning objective is adapted to make a traversing motion relative to the beam from the laser device entering the scanning objective. In another embodiment, the optical selector is an aperture passing the beam from the laser device to the single electrophoresis capillary and not to other electrophoresis capillaries. One embodiment further includes a capillary alignment detector optically coupled to receive a reflection of the beam from the single electrophoresis capillary. The reflection indicates an alignment of the beam with the single electrophoresis capillary.

In one embodiment, the optical selector is optically positioned between the multiple electrophoresis capillaries and the optical detector. The optical signal from the multiple electrophoresis capillaries to the optical detector is limited to a single electrophoresis capillary.

Various embodiments further include a wavelength dependent beam combiner optically coupled between the laser device and the optical detector, or a spatial beam combiner optically coupled between the laser device and the optical detector.

C. Analysis Assembly

An analysis assembly can comprise a computer comprising memory and a processor for executing code in the computer for receiving the data output of the detection assembly, processing the data and producing a file that reports a metric or characteristic of the analyte(s) analyzed (e.g., an answer).

In a preferred embodiment, the analysis module can comprise memory and a processor that executes code that performs the analysis to classify STR fragments by length and by the spectral characteristics of an attached dye and then use this information along with ancillary information such as the separation of an allelic ladder to determine which STR alleles are present in the detected amplification products; this process is typically referred to as calling the STR alleles. In the case of STR analysis, the analysis assembly can receive raw electropherogram data, transform it into a format that is recognizable by, e.g., allele calling software, and, using the allele calling software, identify alleles and report them in a format understandable by a user or recognized by a database. For example, the analysis assembly can take an electropherogram and produce a CODIS file recognized by, e.g., the FBI's National DNA Index System (NDIS).

An electropherogram generated from separation of amplified STR fragments can be analyzed in the following way. The detection modality of the system (e.g., optical detection) will produce a data stream that is an amalgam of the signals coming from fluorescent dyes attached to the STR fragments as well as a host of optical and electronic background effects. This data stream can be processed into a form that is consumable by the STR calling software (e.g., an expert system).

The input data that is expected by most commercial STR-calling expert systems typically contains arrays of numbers of dimensionality N×M, where N is the number of dyes that are detected by the system, and M is a time sequence of points taken during the separation. Some expert systems have upper limits on N and M, and this can vary from product to product. There are a number of ancillary assumptions that commercial expert systems make about these data streams:

(1) Most electronic and optical noise from the detection mode has been removed.
(2) Each of the N channels nominally referenced to the same dark signal, defined to be "zero."
(3) Enough measurements have been taken of each fragment to insure sufficient base-pair resolution for the minimum-size repeat pattern in the STR kit. Nominally, this means a sampling frequency sufficient to obtain 5-10 measurements over the time that it takes a fragment to migrate past the detector.
(4) Each individual channel in the N dimension represents the photonic signal coming from a single dye as much as is possible for the detection mode. To the degree that this condition isn't satisfied, it is called "bleed-through".

The functionality that STR calling software can provide includes:

(1) Sizing of fragments relative to an in-lane size standard.
(2) Calibration of allele bins using a (potentially optional) allelic ladder.
(3) Allele calling with morphological rejection filters (for common PCR effects such as stutter).
(4) Quality flag assignment based on mathematical measures such as signal-to-noise.
(5) Call summary output generation as text.

The practitioner can to properly tune the performance of the STR calling software to minimize the false-positive measurement set. The procedures for this are known in the art and, for commercially available software, can be contained in the product documentation.

As described above, expert systems will provide services that identify the base pair size of fragments found in the data stream and attach a preliminary allele assignment to each fragment if such exists. In addition, a quality flag can be assigned to the allele call which is reported to the analyst. The practitioner then decides what the STR profile actually is based on information from the flags. The process can be further automated by putting into place a rules engine to process the calls and quality flags into a final profile. This rules engine can be trained on the system's data to know when to keep and when to reject an allele based on the specific content of the quality flags coming from the system.

Figure 50:
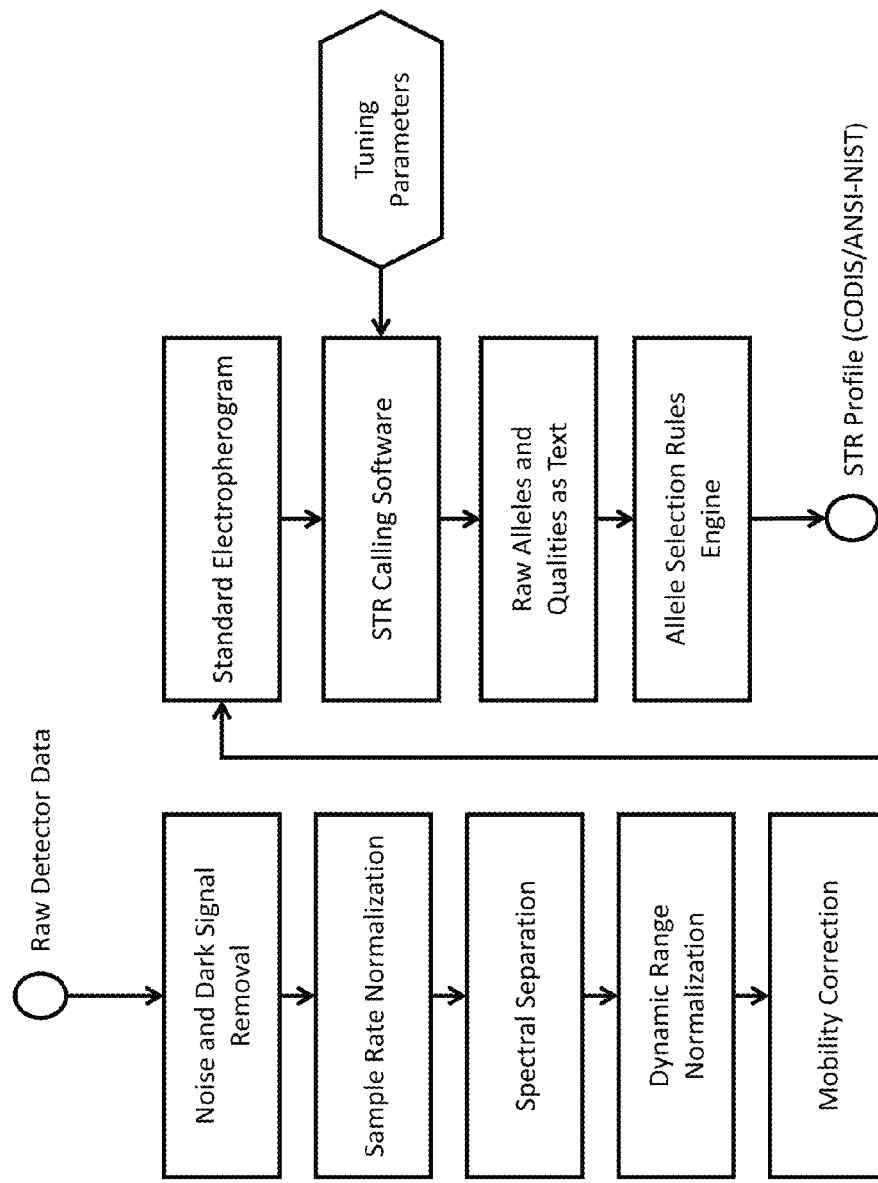
FIG. 50 shows a process for transforming data from an electropherogram into a format usable by STR allele-calling software.

An entire process is shown in FIG. 50: The first five boxes on the left of the diagram show how to generically process data in a way that reflects the input assumptions 1-4 mentioned above. Some of these steps may be optional depending on the quality of the separation and type of detector used. These steps culminate in the generation of an electropherogram in a standard format, typically *.fsa. These are fed to the STR calling package that processes the electropherograms using an implementer-supplied parameter tuning. Finally, these calls are filtered by a rules engine to create the final, reliable STR profile.

Software to perform STR and kinship analysis are commercially available from, for example, GeneMarker®HID STR Human Identity software and GeneMarker kinship analysis software (SoftGenetics, State College, Pa., USA)); DNA-VIEW™ v29.11 (Charles Brenner); LISA (Future Technologies Inc., Fairfax, Va., USA); KInCALcv3.1 (California Department of Justice); GeneMapper (Life Technologies, Carlsbad, Calif.).)

More methods for transforming electropherograms are described here:

1. Segmentation Base-Lining

In some specific embodiments, a system as described herein may include or work with a separable logic module or method for improved base-lining in electrophoresis data. A "base line" or "zero level" in signal processing generally refers to the level below which signal and signal variations is considered due to noise or otherwise not of interest. Base-lining in signal processing generally describes methods for determining, for an entire signal or for specific samples or locations of a signal, which level of the signal is due to noise and removing or subtracting that level from the signal. Correctly determining a baseline level for capillary electrophoresis signals and similar signals is challenging when the signals are rapidly changing and/or are collected over a time period during which the baseline noise may change. In rapidly changing signals with a variable signal noise, it can be very difficult to accurately determine a base-line correction.

In one embodiment, a novel segmentation base-lining logic module or method first determines segments or periods of the collected data where no signal of interest is determined to be present (referred to at times as "flat" segments) and areas of high variation that contain signal of interest (referred to at times as "signal segments" or "variable segments"). Generally, the flat regions and signal regions alternate, such that each signal region is bounded by two flat regions. A base line correction curve can be determined for each of the flat regions. In a preferred embodiment, this determination is done separately for each region and is generally a polynomial fit curve, which can be linear or some higher order. The end-points for the base-line correction for the two different flat regions are then used to determine a base-line correction for the signal region. The base line correction for the signal region is also a polynomial and can be a line or a spline and is generally fit so as to be continuous to the flat regions on either side at least to the 1st derivative or forward difference and optionally also to the 2nd derivative or forward difference.

With the flat and varying regions identified, various curve fitting techniques are applied to different segments to construct a piece-wise continuous overall curve representing the baseline correction. This curve effectively is then subtracted from the data stream (for example, data derived from a detector such as a chromatogram trace or binned chromatogram trace as described herein) to provide a "baselined" or "zeroed" data set. It has been found that in some embodiments or situations and in some systems such as described herein, a segmented baselining approach provides more accurate results.

2. Dynamic Spectral Correction

In some specific embodiments, a system as described herein may include or work with a separable logic module or method for dynamic spectral correction. Capillary electrophoresis systems typically use fluorescently labeled to primers to help distinguish to which locus a particular DNA fragment is related. Because some alleles from different loci might overlap in terms of their by length, the different spectral profile or color of each dye is used to distinguish to which locus a particular detected allele is related. However, labeling dyes have somewhat broad and overlapping spectral response. As a result, a single dye in a multi-spectral-channel detector causes a signal in multiple spectral channels. The characteristic frequency response of a dye is a times referred to as the dye's spectral profile. Thus, a detection in multiple channels at a particular time period may involve a complex mixture of signal from different dyes. Many electrophoresis systems employ some type of spectral calibration in which a matrix is created. This matrix is used to determine the detection of specific dyes from the multi-channel data. Thus, in many systems, overlap of spectral profiles is automatically calculated and subtracted using fluorescence "matrix" standards.

However, the spectral profiles of different dyes as detected can vary in different electrophoresis runs. In a preferred embodiment, a dynamic spectral correction module examines the collected data and determines time periods when the spectral energy detected is from one dye only. Machine learning and/or clustering algorithms (for example, Principal Component Analysis) are used to identify the pure multi-spectral peaks. The three highest intensity value from those peaks can then be used to determine a corrective phase shift whereby the spectral profile for one or more dyes can be resampled in software and the spectral correction matrix recalculated on a per-chromatogram or per-trace basis.

3. Differential Mobility Correction

As referenced above, capillary electrophoresis data is typically gathered over a relatively long periods (e.g., 10-45 minutes). This creates numerous problems in determining various calibrations for the capillary electrophoresis data to particular systems and run conditions. One such calibration is typically made to the reference allele (or allelic) ladder that is used to call particular detected alleles in a sample. In one form, the allelic ladder is a reference set of sequence lengths that generate reference signal peaks at particular base-pair (bp) lengths that are compared to the sample peaks in order to identify (or call) the allele of the particular peaks in the sample.

When an allele ladder mixture is placed into an electrophoresis capillary for reading (generally alongside a sample capillary) both the ladder and the sample can also include a set of known length DNA fragments, referred to as a "size standard," and "internal size standard" or a "size ladder". After the electrophoresis of the allele ladder is run, it is often the case that the peaks produced as indexed by the Size Standard peaks are not at the locations (or within the bins) indicated by the expected allele values. This can lead to both false positives and false negatives in allele calling. Many systems use automated methods to provide some adjustments to the allele ladder to correspond to the expected allele values. These methods can work when migration characteristics are varying slowly. However, there are cases where strong non-linearities in the migration (which generally takes place over a period of time of about 10-45 minutes) cause marked shifts in ladder peak locations relative to the sizing peaks A Differential Mobility Correction module as described above uses a three phase adjustment where a metric is calculated representing the quality of the allelic ladder panel fit to the expected bins. This metric is calculated (1) first for the allelic ladder panel as a whole, (2) then for each locus in the allelic ladder panel in turn, and (3) then for each allele bin of the allelic ladder individually. During locus calibration, a special optimal metric search is used that contains monotonic telescoping of spacing to prevent phase shifting in locus alignment to peaks.

IV. Control Module

A. Computer

Systems provided herein include various hardware and software. In some embodiments, a system for sample preparation, processing and analysis, such as the system 100 of FIG. 1 (or any other system provided herein), includes a controller with a central processing unit, memory (random-access memory and/or read-only memory), a communications interface, a data storage unit and a display. The communications interface includes a network interface for enabling a system to interact with an intranet, including other systems and subsystems, and the Internet, including the World Wide Web. The data storage unit includes one or more hard disks and/or cache for data transfer and storage. The data storage unit may include one or more databases, such as a relational database. In some cases, the system further includes a data warehouse for storing information, such user information (e.g., profiles) and results. In some cases, the data warehouse resides on a computer system remote from the system. In some embodiments, the system may include a relational database and one or more servers, such as, for example, data servers. The system 100 may include one or more communication ports (COM PORTS), one or more input/output (I/O) modules, such as an I/O interface. The processor may be a central processing unit (CPU) or a plurality of CPU's for parallel processing.

The system 100 may be configured for data mining and extract, transform and load (ETL) operations, which may permit the system to load information from a raw data source (or mined data) into a data warehouse. The data warehouse may be configured for use with a business intelligence system (e.g., Microstrategy®, Business Objects®). It also can be configured for use with a forensic database such as the National DNA Index System (NDIS)) in the USA or NDAD in the United Kingdom, State DNA Index Systems (SDIS), or Local DNA Index Systems (LDIS) or other databases that contain profiles from known and unknown subjects, forensics samples, or other sample types such as organism identifications.

Aspects of the systems and methods provided herein may be embodied in programming. Various aspects of the technology may be thought of as "products" or "articles of manufacture" typically in the form of executable code and/or associated data that is carried on or embodied in a type of machine readable medium. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Figure 19:
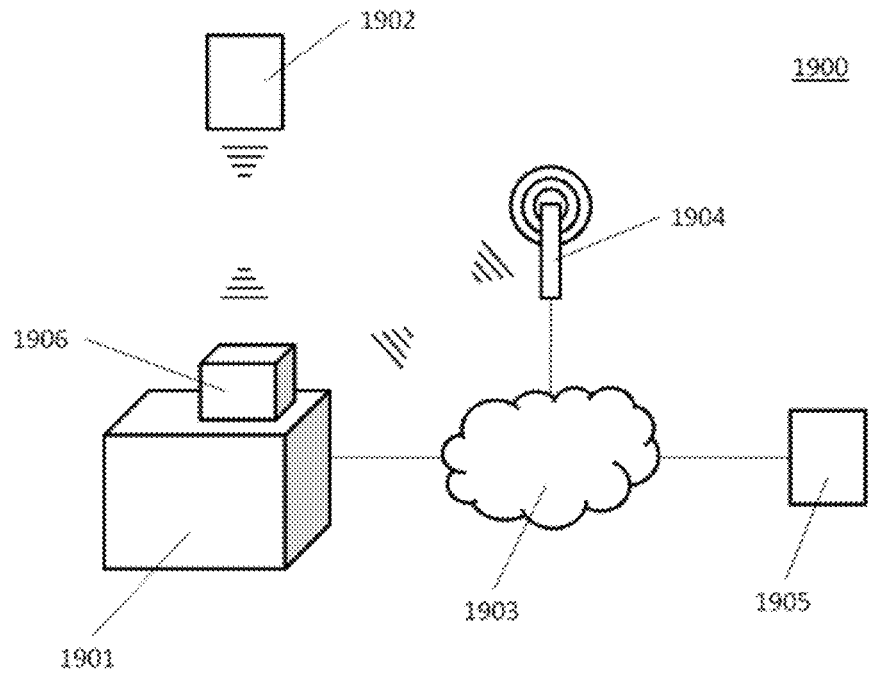
FIG. 19 shows a system for sample processing, in accordance with an embodiment of the invention.

In some embodiments, the system 100 is configured to communicate with one or more remote devices, such as a remote electronic device (see FIG. 19). Such remote connection is facilitated using the communications interface. In some situations, the system 100 presents information to (or requests information of actions from) the user by way of a user interface on an electronic device of the user (see below). The user interface can be a graphical user interface (GUI). In some cases, the GUI operates on an electronic device of the user, such as a portable electronic device (e.g., mobile phone, Smart phone). The electronic device can include an operating system for executing software and the graphical user interface of the electronic device.

Figure 38B:
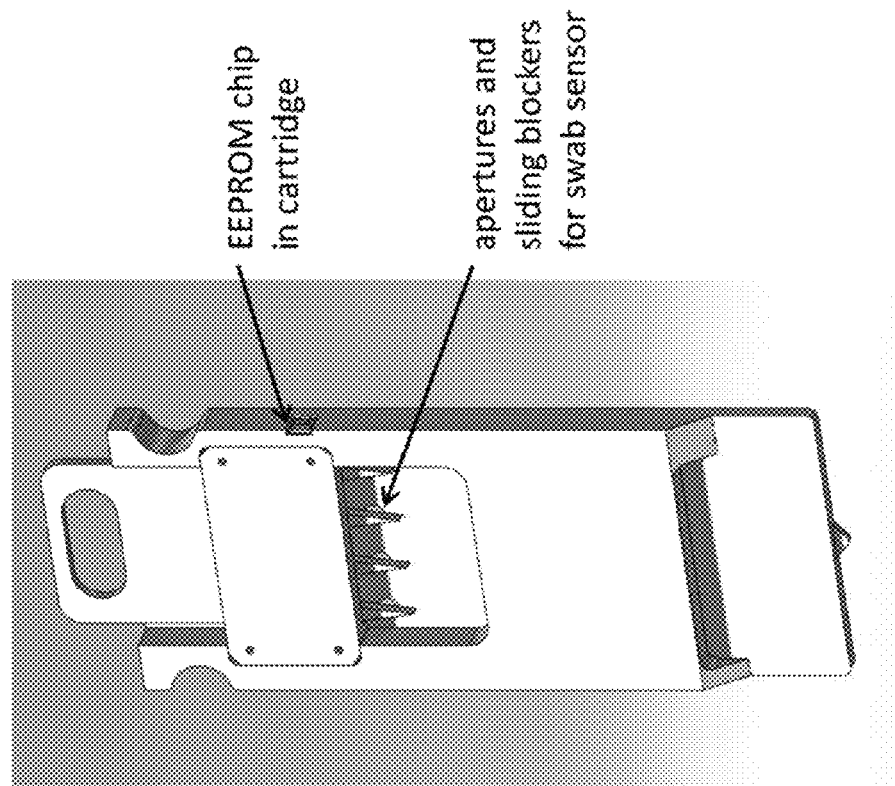
FIG. 38B shows an embodiment of a cartridge comprising an embedded EEPROM chip and apertures and sliding blockers for swab sensing.
Figure 38A:
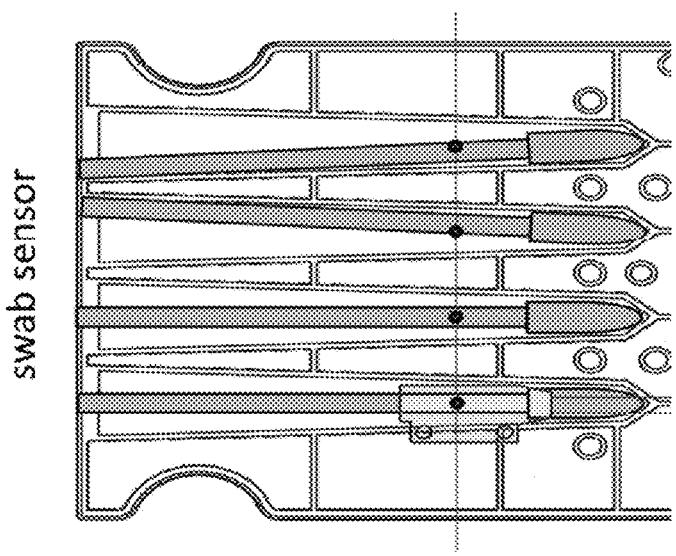
FIG. 38A shows an embodiment of a swab sensor.

In some embodiments, the system 100 provides alerts, updates, notifications, warnings, and/or other communications to the user by way of a graphical user interface (GUI) operating on the system or an electronic device of the user. The GUI may permit the user to access the system to, for example, create or update a profile, view status updates, setup the system 100 for sample preparation and processing, or view the results of sample preparation, processing and/or analysis. The system can be configured to operate only when a user provides indicia of permission, such as a key card and/or a password. The system can record and provide information on sample chain of custody, contamination or tampering. Systems to record and provide such information can include controls on access to operate the system (e.g., operator permission requirements); sample control (e.g., sensors to indicate introduction or removal of a sample from a cartridge) (see, e.g., FIGS. 38A and 38B); enclosure control (e.g., sensors indicating door opening and closing) and cartridge control (e.g, sensors for indicating insertion, proper seating and removal of cartridge).

In some embodiments, the system includes one or more modules for sample processing and/or analysis, and a controller for facilitating sample processing and/or analysis. The controller can include one or more processors, such as a central processing unit (CPU), multiple CPU's, or a multi-core CPU for executing machine-readable code for implementing sample processing and/or analysis. The system in some cases directs a sample sequentially from one module to another, such as from a sample preparation module to an electrophoresis module.

B. User Interface

In another aspect of the invention, a user interface is provided for enabling a user to interact with systems provided herein. In some embodiments, the user interface is a graphical user interface (GUI) that includes various graphical objects (e.g., icons, etc.) and, in some cases, auditory elements for permitting a user to interact with a sample preparation, processing and analysis system ("the system"), such as the system 100 of FIG. 1. The GUI can be configured to recognize gestures or other visual or auditory user commands for implementing a predetermined task or by touching or swiping a touch screen or by use of a 'mouse' or other standard input devices. In some cases, a particular gesture is linked to a particular task. The GUI is configured to be displayed on a display of the system or a remote electronic device (see FIG. 19 and the related text). In an example, the GUI is configured to be displayed on the display 101 of the system 100 of FIG. 1.

Figure 20:
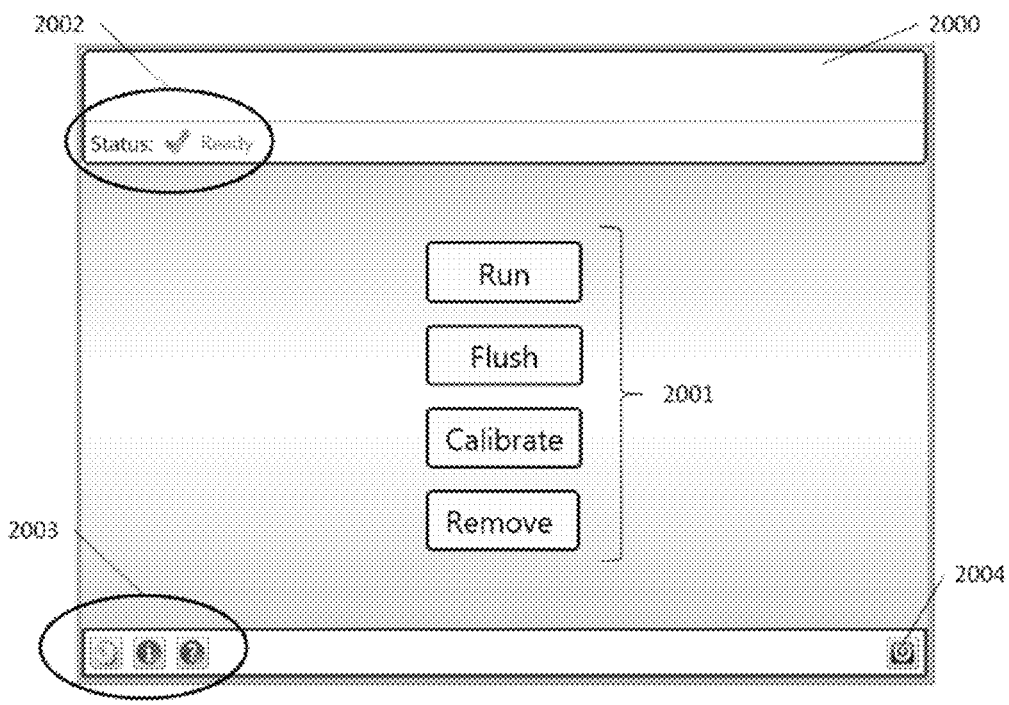
FIGS. 20-30 show a graphical user interface for use with a system for processing a sample, in accordance with various embodiments of the invention.

In some embodiments, a graphical user interface is provided that includes various visual elements for enabling a user to execute various commands of a system having the GUI. FIG. 20 shows a GUI 2000 having "Run", "Flush", "Calibrate" and "Remove" buttons 2001 for implementing various commands, in accordance with an embodiment of the invention. The "Run" button starts sample preparation and processing. The "Flush" button flushes the capillary with buffer or other solution. The "Calibrate" button is used to calibrate the system and verify data generated by the system. The "Remove" button initiates the process for removing the capillary.

The term "button" in this context refers to two or pseudo-three dimensional graphical elements that may resemble buttons, but that may be activated (or depressed) with the aid of user touch or an electronic pointing device, such as a mouse. The GUI 2000 includes a status indicator for providing the status of the system. In the illustrated example, the system (e.g., the system 100 of FIG. 1) is ready for sample preparation, processing and analysis ("Ready"). The GUI 2000 also includes buttons 2003 for providing help and information about the system (right button), providing menu and run status information (middle button), and enabling a user to access system settings (left button). A power button 2004 enables a user to turn the system on and off.

In some cases, the system is configured to enter an "off" state after a predetermined period of inactivity. A user can then turn the system "on" by pressing the button 2004. In some situations, the GUI 2000 may require a user to input a password or provide other identifying information as part of a security measure to help prevent unauthorized use of the system.

Figure 21:
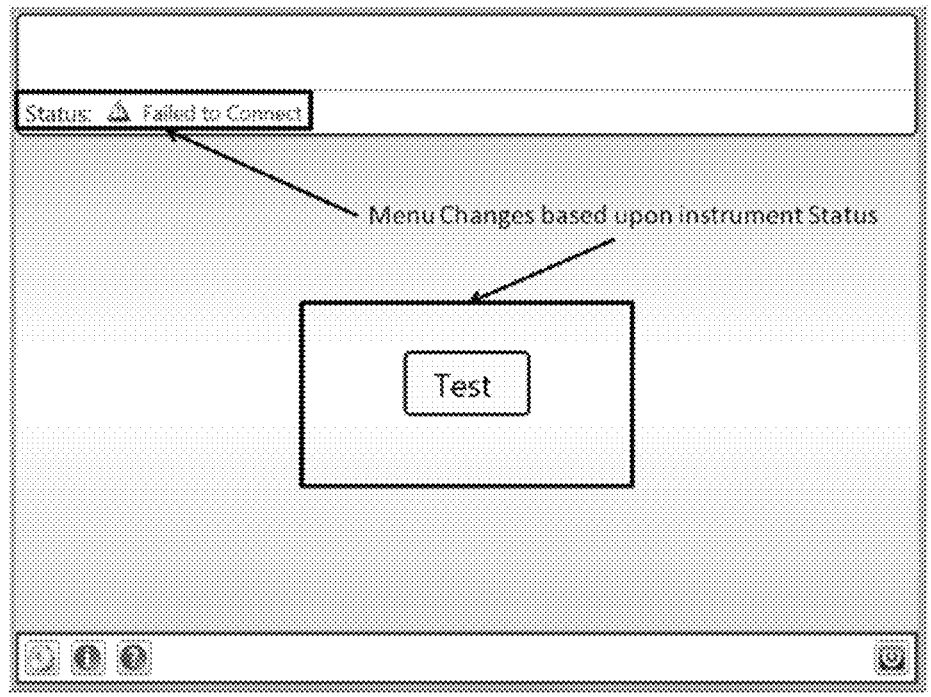

The GUI 2000 is configured to present system updates and other status information at predetermined intervals or in real time. With reference to FIG. 21, the status menu has changed from "Ready" to "Failed to Connect" in response to a change in the status of the system. The GUI 2000 presents the user with a "Test" button to run various diagnostic tests to determine whether there are any issues with the system.

The GUI 2000 is configured to guide a user through various stages of sample preparation, processing and analysis, and to request user input when required. The GUI communicates to the user various instructions or system requests, such as inputting a cartridge. The GUI 2000 presents the user with a progress indicator (i.e., the present progress in relation to the number of steps required to reach completion) which can be at a bottom panel of the GUI or in other locations.

Figure 22:
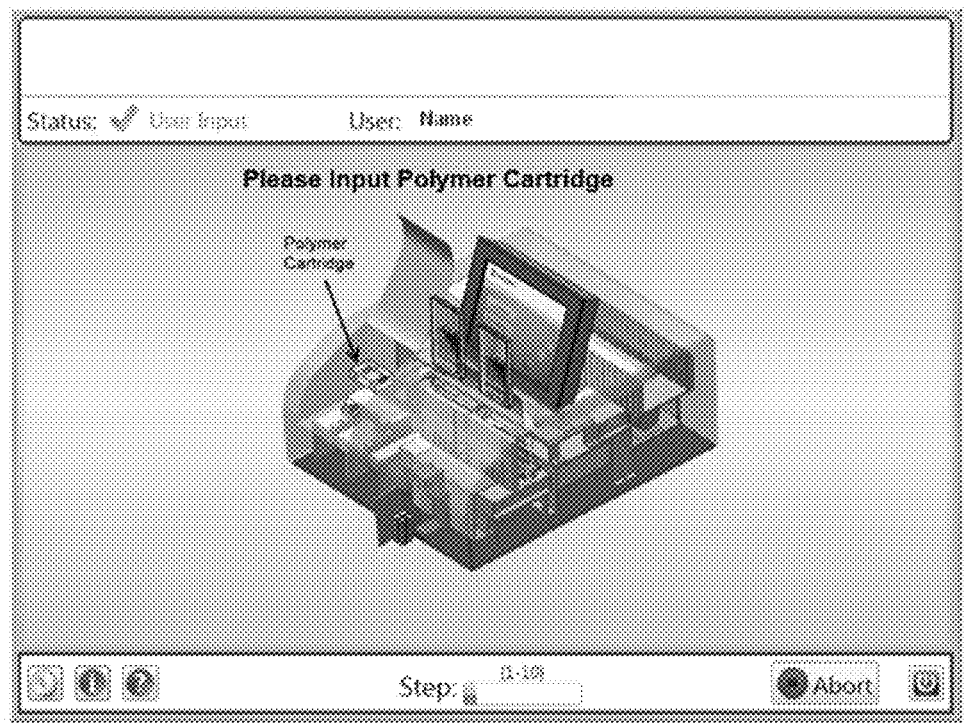
Figure 23:
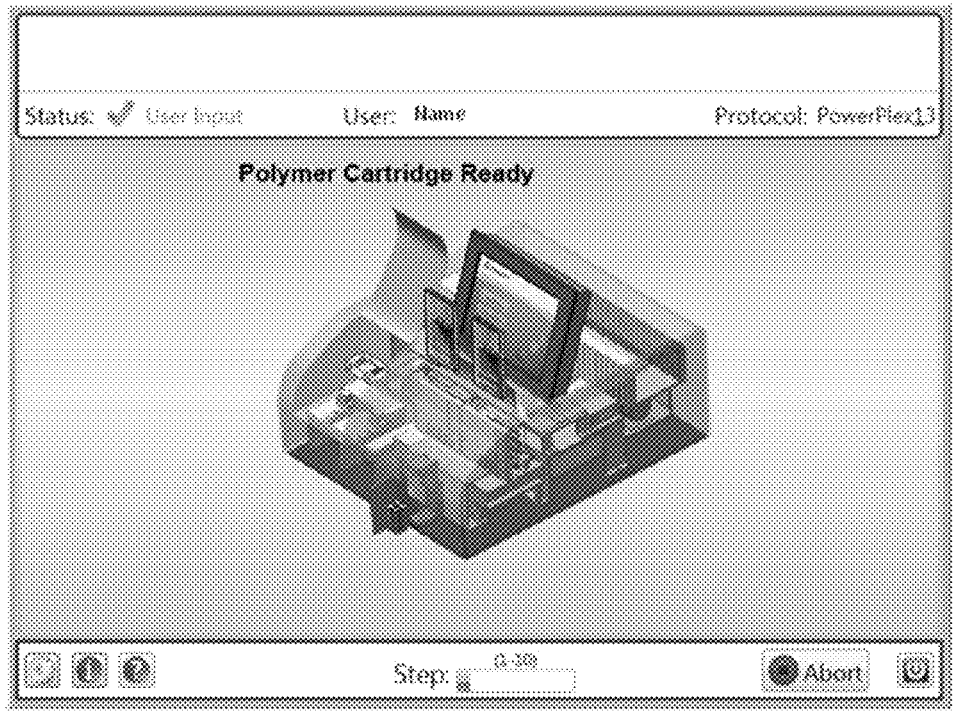
Figure 24:
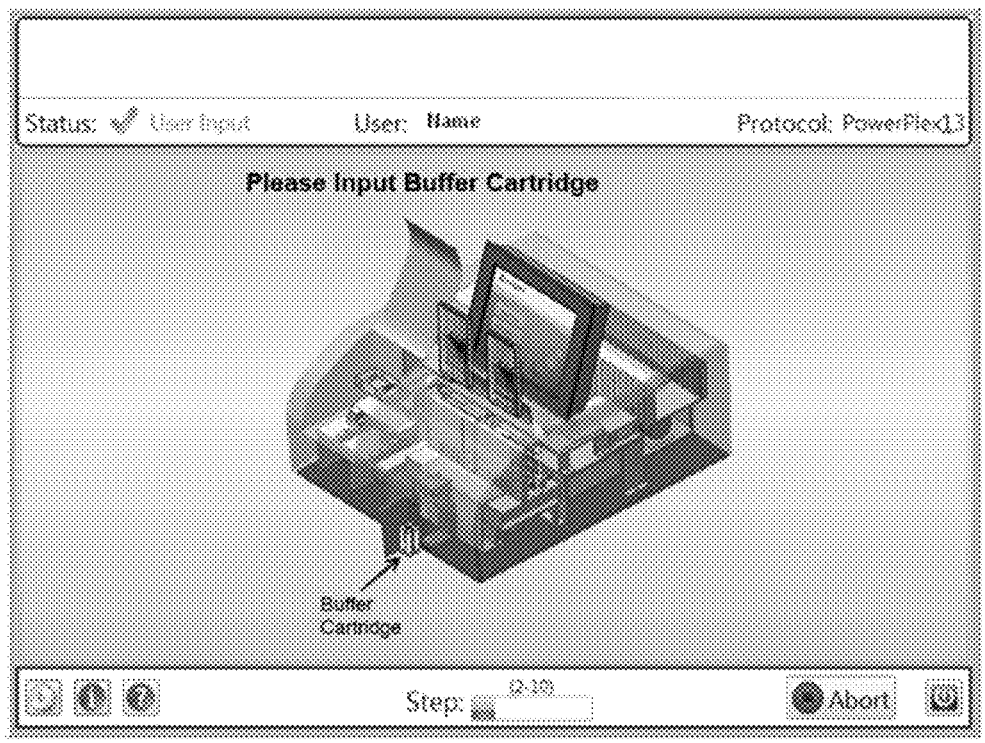
Figure 25:
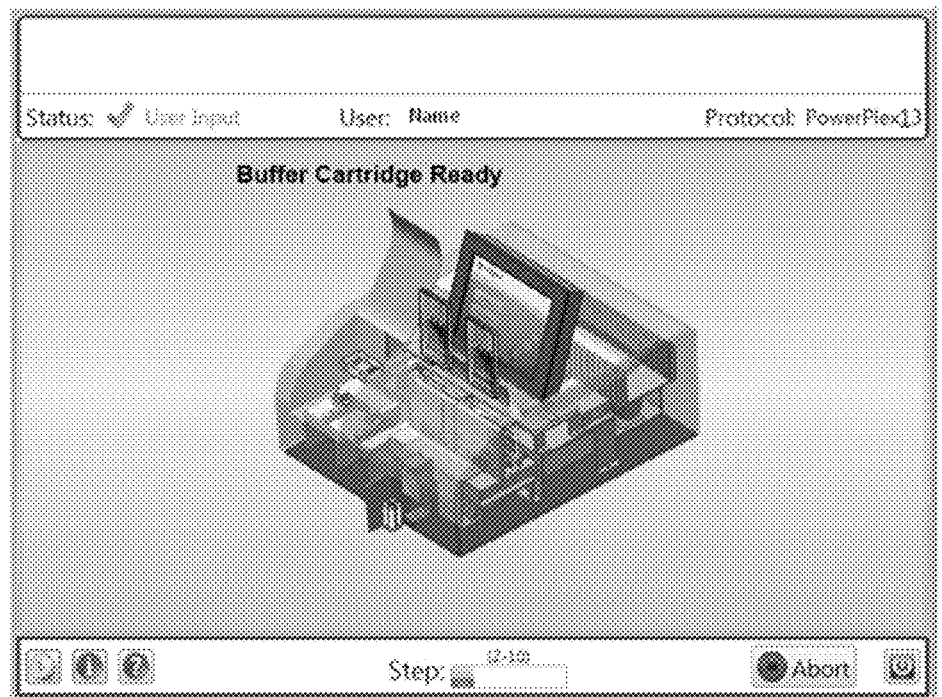
Figure 26:
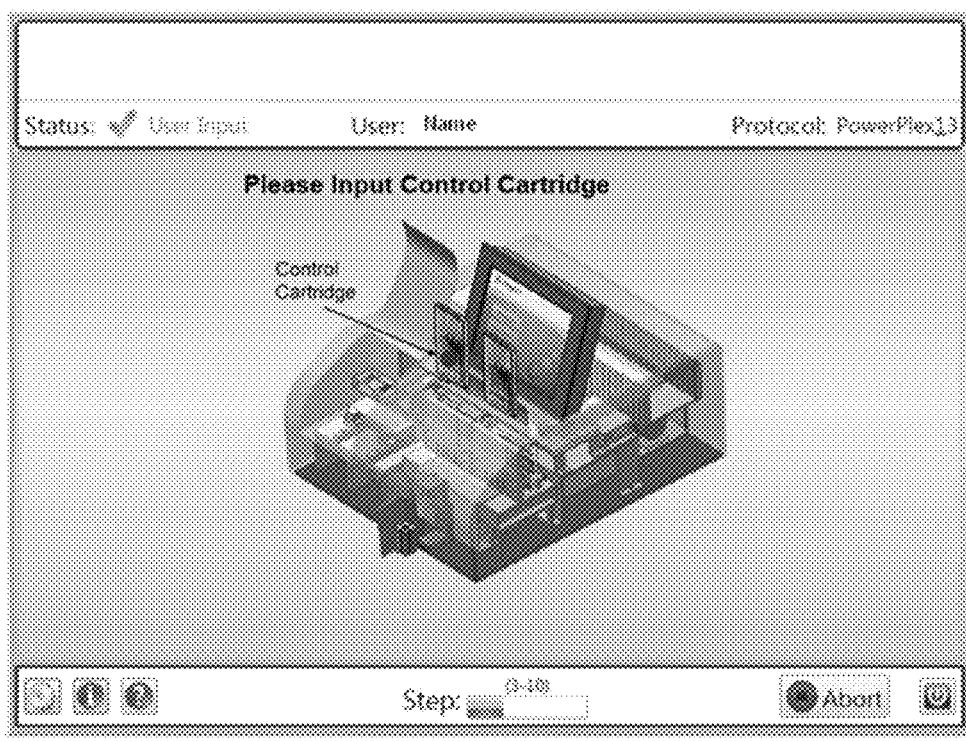
Figure 27:
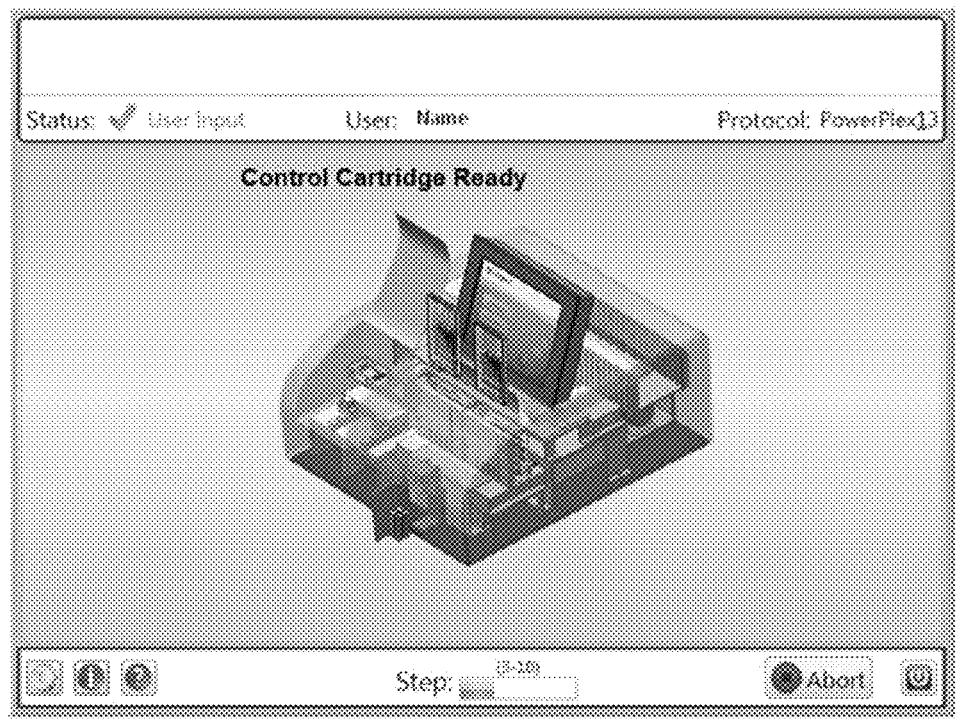
Figure 28:
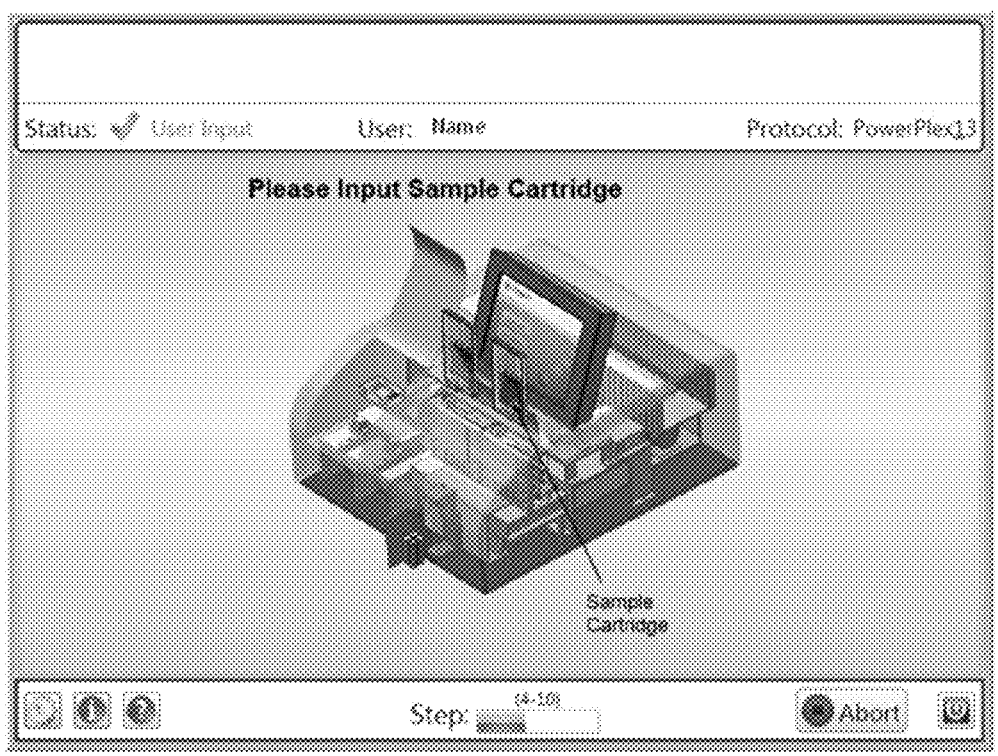
Figure 29:
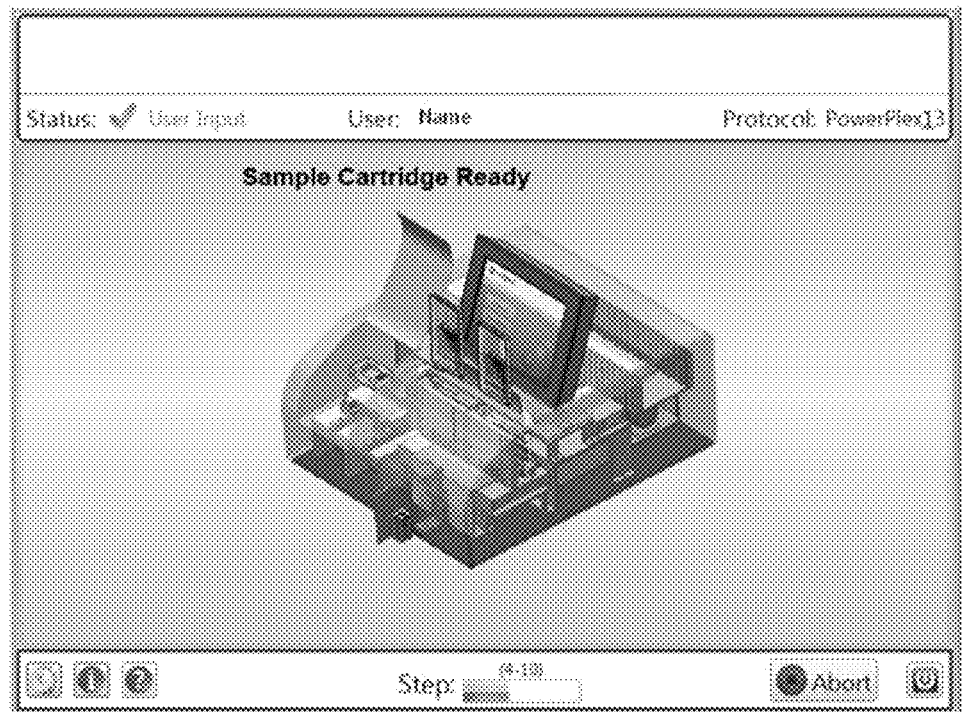

With reference to FIG. 22, the GUI 2000 requests that the user input a polymer cartridge into the anode interface module of the system (see FIG. 6). The progress indicator shows that the user is at a first step ("Step: (1-10)"). The system waits for user input or enables the user to abort by pressing the "Abort" button. The GUI then indicates that the polymer cartridge is ready for use, as shown in FIG. 23. With reference to FIG. 24, the GUI indicates that the system has requested that the user input a buffer cartridge (see FIG. 7). Upon the user inserting the buffer cartridge, the system indicates that the buffer cartridge is ready, as shown in FIG. 25. In FIG. 26 the GUI instructs the user to input a control cartridge. Upon successfully insertion of the control cartridge (FIG. 27), the GUI instructs the user to input a sample cartridge, as shown in FIG. 28. The GUI then indicates that the sample cartridge is ready for use, as shown in FIG. 29.

Figure 30:
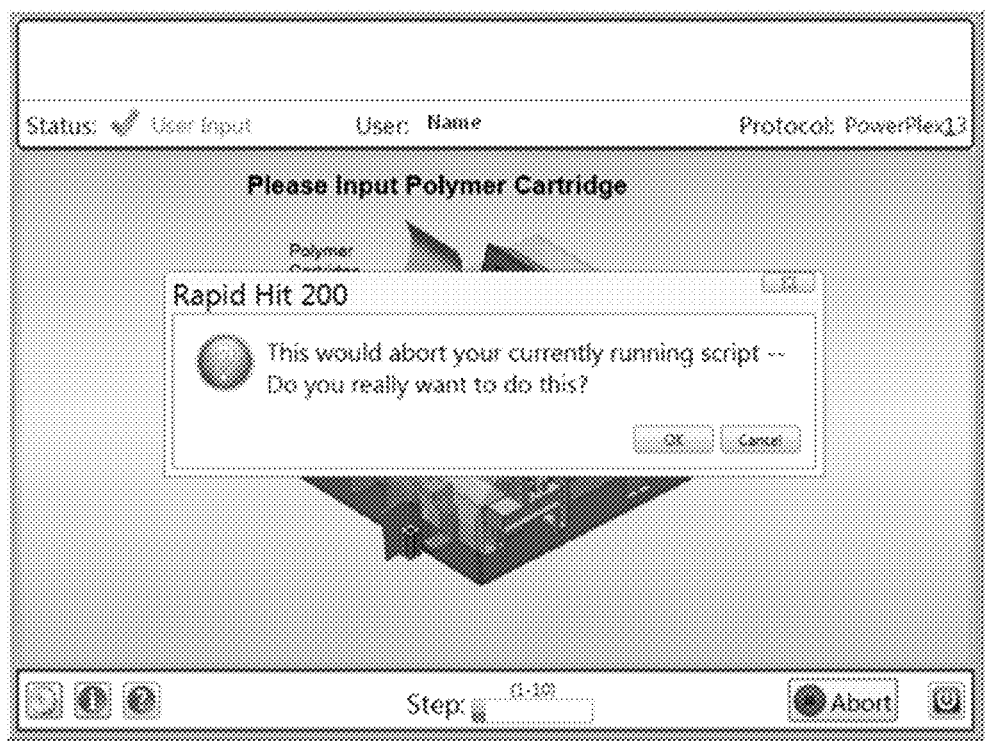

With reference to FIG. 30, at any point during system setup, the user can abort the setup process by pressing the "Abort" button. The user or another user may then start a new process prior to sample preparation, processing and analysis. In some cases, the system starts the setup process where a previous user aborted the setup process. For instance, if a previous user aborted the setup process after inputting a buffer cartridge and a new user desires to use the system, the system may not require the new user to input a buffer cartridge. In some cases, however, where a particular type of buffer is required for certain processing, the system may recognize (e.g., with the aid of on-board EEPROM) that the buffer cartridge presently in the system is not adequate for use and request that the user input the required buffer cartridge.

The GUI 2000 can be implemented on a display of the system (e.g., the display 101 of the system 100 of FIG. 1) or a display of a remote system (e.g., the portable electronic device 1902 or electronic device 1905 of FIG. 19). In some situations, remote access may enable a user to interact with the system and to setup and run sample processing remotely. The results of sample processing and/or analysis, such as the genetic information of or related to a sample, may be obtained remotely.

C. Timing Control in an Integrated and Automated System

In some embodiments, the instrument or system described herein performs sample-to-answer processing and analysis (e.g., "commence process" to answer display) in no more than 2 hours, e.g., in no more than about 90 minutes. The functions performed include: DNA isolation; DNA amplification; amplicon separation and data collection; and system wrap up (e.g., disengagement of instrument from consumable cartridges, line clearing) and data analysis. In a system that performs sample-to-answer processing in no more than about 2 hours, DNA isolation can be performed in about 20% of the time; DNA amplification can be performed in about 33% of the time; amplicon separation and data collection can be performed in about 33% of the time and system wrap up and data analysis can be performed in about 10% of the time. For example, times for each of these functions in a 90 minute run can be as follows: DNA isolation: ~20 minutes; DNA amplification: ~30 minutes; amplicon separation and data collection: ~30 minutes; system wrap up and data analysis: ~10 minutes.

In some embodiments, the instrument or system described herein performs sample-to-answer processing and analysis in no more than about 4 hours (hr), 3.5 hr, 3 hr, 2.5 hr, 2 hr, 1.5 hr, 1 hr or 0.5 hr. In further embodiments, the instrument or system performs sample-to-answer processing and analysis in about 0.5 hr to about 3 hr, or about 0.5 hr to about 2 hr, or about 0.5 hr to about 1.5 hr, or about 0.5 hr to about 1 hr, or about 1 hr to about 2 hr, or about 1 hr to about 1.5 hr, or about 1.5 hr to about 2 hr. In some embodiments, sample-to-answer processing and analysis time comprises the time from starting sample processing (e.g., pressing a start or run button of the instrument or system, or initiating the sample-to-answer protocol) to generation of a nucleic acid profile (e.g., a DNA profile, such as a profile of one or more, or all, STR loci used in a forensic database (e.g., CODIS), and optionally of other loci useful in human identification or sex determination (e.g., Penta D, Penta E and amelogenin)) in a computer system or computer-readable medium of the instrument or system or on a screen thereof. In further embodiments, sample-to-answer processing and analysis time comprises the time from pressing the start or run button of the instrument or system, or initiating the sample-to-answer protocol, to posting of the nucleic acid profile onto an internal or external database.

In some embodiments, sample-to-answer processing and analysis comprise nucleic acid (e.g., DNA and/or RNA) extraction, nucleic acid amplification (e.g., by PCR), nucleic acid separation (e.g., by capillary electrophoresis) and collection of data on separated analytes, and analysis of collected data. In some embodiments, nucleic acid extraction comprises lysis of nucleic acid-containing cells, binding of nucleic acids to capture particles (e.g., magnetic or paramagnetic particles (e.g., beads)), and washing of nucleic acid-bound particles. In certain embodiments, the instrument or system described herein performs nucleic acid extraction in no more than about 2 hr, 1.5 hr, 1 hr, 45 minutes (min), 30 min, 20 min, 15 min, 10 min or 5 min In further embodiments, the instrument or system performs nucleic acid extraction in about 0.5 hr to about 2 hr, or about 0.5 hr to about 1.5 hr, or about 0.5 hr to about 1 hr, or about 1 hr to about 2 hr, or about 1 hr to about 1.5 hr, or about 5 min to about 30 min, or about 10 to about 20 min, or about 10 min to about 15 min. In certain embodiments, nucleic acid extraction begins when the start or run button of the instrument or system is pressed, or when the sample-to-answer protocol is initiated. The duration of nucleic acid extraction may depend on, e.g., the nature of the nucleic acid-containing medium. For example, extraction of nucleic acids from cells contained in a cellulosic medium (e.g., FTA® paper) may take longer time than extraction of nucleic acids from cells contained in swabs.

In certain embodiments, the instrument or system performs amplification (e.g., by PCR) of nucleic acids (e.g., at, and optionally adjacent to, one or more, or all, STR loci used in a forensic database (e.g., CODIS), and optionally other loci useful in human identification or sex determination (e.g., Penta D, Penta E and amelogenin)) in no more than about 2 hr, 1.5 hr, 1 hr, 45 min, 40 min, 30 min, 20 min, 15 min, 10 min, or 5 min. In further the instrument or system performs amplification (e.g., by PCR) of nucleic acids (e.g., at, and optionally adjacent to, one or more, or all, STR loci used in a forensic database (e.g., CODIS), and optionally other loci useful in human identification or sex determination (e.g., Penta D, Penta E and amelogenin)) in about 5 or 10 min to about 2 hr, or about 20 min to about 1 hr, or about 20 min to about 40 min, or about 20 min to about 30 min, or about 30 min to about 40 min. The duration of nucleic acid amplification may depend on, e.g., the number of loci amplified, the temperature ramp rate, the hold time at a particular temperature, or the number of amplification cycles.

In some embodiments, nucleic acid separation comprises separation (e.g., by capillary electrophoresis) of nucleic acid fragments (e.g., those resulting from PCR amplification at one or more, or all, CODIS STR loci, and optionally other loci) and collection of data (e.g., collection of laser-induced fluorescence by a CCD camera). In certain embodiments, the instrument or system performs nucleic acid separation in no more than about 1 hr, 45 min, 40 min, 30 min, 20 min, 15 min, 10 min, or 5 min. In further embodiments, the instrument or system performs nucleic acid separation in about 5 or 10 min to about 1 hr, or about 15 min to about 45 min, or about 20 min to about 40 min, or about 20 min to about 30 min, or about 30 min to about 40 min. The duration of nucleic acid separation may depend on, e.g., the gel used, the length of the electrophoretic capillary, the voltage ramp rate, or the size of the nucleic acid fragments.

In some embodiments, the system processes a biological sample within a time period of 4 hours or less, or 3.5 hours or less, or 2.5 hours or less, or 2 hours or less, or 1.5 hours or less, or 1 hour or less, or 45 minutes or less, or 30 minutes or less, or 15 minutes or less, or 10 minutes or less, or 5 minutes or less. In other embodiments, the system processes and analyzes a biological sample within a time period of 4 hours or less, or 3.5 hours or less, or 2.5 hours or less, or 2 hours or less, or 1.5 hours or less, or 1 hour or less, or 45 minutes or less, or 30 minutes or less, or 15 minutes or less, or 10 minutes or less, or 5 minutes or less.

In some embodiments, analysis comprises analysis of collected data and generation of a nucleic acid profile (e.g., a DNA profile, such as a profile of one or more, or all, STR loci used in a forensic database (e.g., CODIS), and optionally of other loci useful in human identification or sex determination (e.g., Penta D, Penta E and amelogenin)) in a computer system or computer-readable medium of the instrument or system or on a screen thereof. In other embodiments, analysis further comprises posting of the nucleic acid profile onto an internal or external database. In certain embodiments, the instrument or system performs analysis in no more than about 15 min, 10 min, 5 min, 3 min, 2 min, 1 min, 30 sec, or 10 sec. In further embodiments, the instrument or system performs analysis in about 2 min to about 10 min, or about 2 min to about 5 min, or about 2 min to about 4 min, or about 3 min to about 4 min, or about 10 sec to about 2 min, or about 30 sec to about 2 min, or about 30 sec to about 1 min.

In additional embodiments, sample-to-answer processing and analysis further comprise transfer of nucleic acid-bound beads from the bead suspension/capture chamber to the reaction chamber, delivery of a premix reagent to the reaction chamber, transfer of the amplification reaction product to the diluent chamber, and delivery of the diluted amplification product to a separation (e.g., capillary electrophoresis) system. The premix reagent can be in liquid or lyophilized form and can contain, e.g., primers, polymerase, buffer and any other reagent suitable for amplification (e.g., a salt, such as magnesium chloride). In certain embodiments, the instrument or system transfers nucleic acid-bound beads from the bead suspension/capture chamber to the reaction chamber in no more than about 10 min, 5 min, 4 min, 3 min, 2 min, 1 min or 30 sec, or in about 30 sec or 1 min to about 5 min, or about 2 min to about 4 min, or about 2 min to about 3 min, or about 1 min to about 2 min In further embodiments, the instrument or system delivers the premix reagent to the reaction chamber in no more than about 10 min, 8 min, 6 min, 5 min, 4 min, 3 min, 2 min or 1 min, or in about 5 min to about 10 min, or about 5 min to about 8 min, or about 6 min to about 8 min, or about 0.5 min to about 5 min, or about 1 min to about 5 min, or about 2 min to about 5 min, or about 0.5 min to about 3 min, or about 1 min to about 3 min, or about 1 min to about 2 min Delivery of a lyophilized premix reagent to the reaction chamber may take longer time than delivery of a premix reagent in liquid form due to, e.g., the need to rehydrate the lyophilized reagent.

In certain embodiments, the instrument or system transfers the amplification reaction product to the diluent chamber in no more than about 3 min, 2 min, 1 min, 30 sec or 10 sec, or in about 10 or 30 sec to about 3 min, or about 1 min to about 3 min, or about 1 min to about 2 min In some embodiments, delivery of the diluted amplification product to the separation (e.g., capillary electrophoresis) system comprises transfer of the diluted amplification product to an injector and injection of the diluted amplification product into the capillary. In certain embodiments, the instrument or system delivers the diluted amplification product to the separation system in no more than about 8 min, 6 min, 5 min, 4 min, 3 min, 2 min, 1 min or 30 sec, or in about 30 sec or 1 min to about 6 min, or about 2 min to about 5 min, or about 2 min to about 4 min, or about 1 min to about 3 min.

In some embodiments of processing of a sample (e.g., a swab having nucleic acid-containing cells), the instrument or system described herein delivers lysis reagents to the sample chamber and performs lysis of nucleic acid-containing cells in no more than about 15 min, 10 min, 8 min, 6 min, 5 min, 4 min or 3 min, or in about 2 min to about 10 min, or about 5 min to about 10 min, or about 4 min to about 8 min, or about 2 min to about 5 min In certain embodiments, the instrument or system transfers the resulting lysate from the sample chamber to the bead suspension/capture chamber in no more than about 5 min, 4 min, 3 min, 2 min or 1 min, or in about 0.5 min to about 5 min, or about 0.5 min to about 3 min, or about 1 min to about 3 min, or about 1 min to about 2 min In further embodiments, the instrument or system performs binding (or capture) of nucleic acids (e.g., DNA and/or RNA) to magnetic or paramagnetic particles (e.g., beads) in the bead suspension/capture chamber in no more than about 10 min, 8 min, 6 min, 5 min, 4 min, 3 min or 2 min, or in about 1 min to about 10 min, or about 2 min to about 8 min, or about 4 min to about 8 min, or about 4 min to about 6 min In some embodiments, the first wash chamber delivers to the bead suspension/capture chamber a reagent or solution (e.g., 95%-100% ethanol, 90% ethanol in water or 70% ethanol in water) that promotes binding of nucleic acids to the beads, and the second wash chamber delivers to the bead chamber a reagent or solution (e.g., 70% ethanol in water) that removes impurities (e.g., salts) while promoting retention of nucleic acids to the beads. In certain embodiments, the instrument or system performs washing of the nucleic acid-bound beads with the reagent or solution from the second wash chamber in no more than about 3 min, 2 min, 1 min or 0.5 min, or in about 0.5 min to about 2 min, or about 1 min to about 2 min, or about 0.5 min to about 1.5 min, or about 0.5 min to about 1 min In further embodiments, while the beads are retained in the bead suspension/capture chamber by magnetization, the instrument or system transfers the liquid from the bead chamber to the waste chamber after completion of bead capture and before addition of the reagent or solution from the second wash chamber, and/or after addition of the reagent or solution from the second wash chamber, in no more than about 2 min, 1 min or 0.5 min, or in about 15 seconds (sec) to about 2 min, or about 0.5 min to about 1.5 min, or about 0.5 min to about 1 min.

In additional embodiments, the instrument or system transfers the nucleic acid-bound beads from the bead suspension/capture chamber to the reaction chamber in no more than about 5 min, 4 min, 3 min, 2 min or 1 min, or in about 0.5 min to about 5 min, or about 1 min to about 4 min, or about 2 min to about 3 min In certain embodiments, the instrument or system delivers the premix reagent (e.g., in liquid form) to the reaction chamber in no more than about 5 min, 4 min, 3 min, 2 min or 1 min, or in about 0.5 min to about 5 min, or about 0.5 min to about 3 min, or about 0.5 min to about 2 min, or about 0.5 min to about 1 min In further embodiments, the instrument or system performs PCR amplification of nucleic acids (e.g., at, and optionally adjacent to, one or more, or all, STR loci used in a forensic database (e.g., CODIS), and optionally other loci useful in human identification or sex determination (e.g., Penta D, Penta E and amelogenin)) in no more than about 1 hr, 50 min, 40 min, 30 min, 20 min, or 10 min, or in about 10 min to about 1 hr, or about 20 min to about 40 min, or about 30 min to about 40 min, or about 20 min to about 30 min In certain embodiments, the instrument or system transfers the amplification reaction product from the reaction chamber to the diluent chamber in no more than about 3 min, 2 min or 1 min, or in about 0.5 min to about 3 min, or about 1 min to about 2 min, or about 0.5 min to about 1 min In some embodiments, the diluent chamber contains a size standard and a suitable solvent (e.g., water). In further embodiments, the instrument or system transfers the diluted amplification product from the diluent chamber to an injector in no more than about 5 min, 4 min, 3 min, 2 min or 1 min, or in about 0.5 min to about 5 min, or about 1 min to about 4 min, or about 0.5 min to about 3 min, or about 1 min to about 2 min. In certain embodiments, the injector injects the amplification product into a separation channel (e.g., a capillary) of an electrophoresis system in no more than about 2 min, 1 min, 30 sec or 15 sec, or in about 10 sec to about 2 min, or about 10 sec to about 1.5 min, or about 0.5 min to about 1 min.

In some embodiments, the instrument or system performs nucleic acid separation by electrophoresis (e.g., capillary electrophoresis), optionally at elevated temperature (e.g., at about 60° C.), and collection of data in no more than about 1 hr, 40 min, 30 min, 20 min or 10 min, or in 15 min to about 45 min, or about 10 min to about 40 min, or about 20 min to about 40 min, or about 15 min to about 30 min, or about 20 min to about 30 min In further embodiments, the instrument or system analyzes collected data and generates a nucleic acid profile (e.g., a DNA profile, such as a profile of one or more, or all, STR loci used in a forensic database (e.g., CODIS), and optionally of other loci useful in human identification or sex determination (e.g., Penta D, Penta E and amelogenin)) in a computer system or computer-readable medium of the instrument or system or on a screen thereof, and optionally posts the nucleic acid profile onto an internal or external database, in no more than about 10 min, 6 min, 5 min, 4 min, 3 min, 2 min, 1 min or 30 sec, or in about 30 sec or 1 min to about 10 min, or about 2 min to about 6 min, or about 2 min to about 4 min FIG. 51A shows a typical electropherogram that can be generated from the data collected. FIG. 51B shows a typical plot of the nucleic acid profile generated from the data collected.

In certain embodiments, the time from start (e.g., initiation of the sample-to-answer protocol) to production of purified DNA (e.g., completion of capture of DNA to beads and bead wash after lysis) takes no more than about 65 minutes (if a sample is stored on a paper (e.g., FTA® paper), extraction of DNA from cells stored on the paper can take longer than extraction of DNA from cells stored on a swab), the time from production of purified DNA to beginning of electrophoresis (e.g., capillary injection) takes no more than about 80 minutes, the time from beginning of electrophoresis to completion of data collection takes no more than about 80 minutes, and the time from completion of data collection to generation of a data file (e.g., a file containing a DNA profile) takes no more than about 15 minutes, for a total of no more than about 240 minutes.

In further embodiments, the time from start (e.g., initiation of the sample-to-answer protocol) to production of purified DNA (e.g., completion of capture of DNA to beads and bead wash after lysis) takes no more than about 30 minutes, the time from production of purified DNA to beginning of electrophoresis (e.g., capillary injection) takes no more than about 45 minutes, the time from beginning of electrophoresis to completion of data collection takes no more than about 40 minutes, and the time from completion of data collection to generation of a data file (e.g., a file containing a DNA profile) takes no more than about 5 minutes, for a total of no more than about 120 minutes.

In additional embodiments, the time from start (e.g., initiation of the sample-to-answer protocol) to production of purified DNA (e.g., completion of capture of DNA to beads and bead wash after lysis) takes no more than about 20 minutes, the time from production of purified DNA to beginning of electrophoresis (e.g., capillary injection) takes no more than about 35 minutes, the time from beginning of electrophoresis to completion of data collection takes no more than about 30 minutes, and the time from completion of data collection to generation of a data file (e.g., a file containing a DNA profile) takes no more than about 5 minutes, for a total of no more than about 90 minutes.

In some embodiments, the system processes a biological sample at a coefficient of variation that is less than about 20%, 15%, 10%, 5%, 1%, 0.5%, 0.1% or less. In some cases, the system processes a biological sample at an accuracy of at least about 80%, 90%, 95%, 99%, 99.9%, or more.

D. Monitoring Systems

A system facilitates sample processing and/or analysis with the aid of a cartridge (or cassette) that is configured to accept a sample and perform various processing routines. The system includes a receptacle for accepting the cartridge. The cartridge can be removable from the system. The cartridge can include identifying information, such as a bar code, serial number or electrically erasable programmable read-only memory (EEPROM) or an electrically programmable read-only memory (EPROM) or a radio frequency ID (RFID) tag. In some examples, such identifying information enables a controller of the system to identify the cartridge and configure the system for an appropriate processing and/or analysis routine. Accordingly, each fluidic circuit in the cassette can be labeled with information about the sample being loaded. For example, information taken, e.g., at a collection site can be associated with the cassette in a fluidic circuit corresponding to the sample. Such information can include, for example, time of collection, place of collection, and information about a subject from whom a sample is taken.

For example, the cartridge can include a readable and/or writable memory device (e.g., an EEPROM chip) configured to store information and to communicate with the system to transmit or receive various kinds of information. Such information can include, for example, information about the configuration and/or the history of the cartridge, such as the batch number of the cartridge, place/time source information, expiration date of the cartridge, pumping parameters/sequences of the cartridge, identification of chemistries performed by each lane of the cartridge (e.g., reagents on board, chemical reactions performed), and locations of samples and/or controls. The memory device can be utilized, e.g., to identify and track the cartridge and to customize sample processing. The memory device also can be configured to transmit a signal to the system when the cartridge is properly engaged, e.g., seated, in the cartridge receptacle. The signal can be transmitted if, for example, an electrical connection is made between the memory device and the cartridge receptacle. The system can be configured to run only if a signal from the memory device indicates that the cartridge is properly seated. The memory device can be configured to receive information about the nature of the samples being run in particular lanes, for example date, time and location sample collected, method of collection, type of sample (e.g., blood, saliva), identity of person from whom taken. The memory device can be configured to record a signal from the system indicating that the cartridge has been run or if the cartridge lot number has expired, and the system can be configured not to run a cartridge carrying a record that the cartridge has previously been run. The memory device also can be configured to receive information about results of the run. For example, the memory device can be configured to record information about the time and date of run, results from the run (e.g., record an STR profile or the presence or absence of an analyte).

Sensors that detect the presence of a cartridge in its appropriate slot/receptacle and the condition of the cartridge in the system at any time assist in determining the chain of custody of the cartridge. The cartridge sensors can be EEPROM memory chips that recognize, read and store the state of each cartridge inserted in the system. The software recognizes the presence of a cartridge in a slot/receptacle, and denotes an empty slot/receptacle as EMPTY. The software also recognizes the state of a cartridge in a slot/receptacle as, e.g., NEW, USED or EXPIRED. Sample and control cartridges, or the system, can also have sensors that indicate the insertion of, e.g., a swab into a sample chamber or the removal of a swab from a sample chamber, as described herein, which also assists in determining the chain of custody of a cartridge or a sample.

In some embodiments, the cartridge is physically altered to prevent reuse, such as puncturing a friable seal or PDMS layer of the cartridge, or physically breaking, chemically degrading or otherwise altering the cartridge to prevent reuse of the cartridge. In some cases, an on-board EEPROM of the cartridge can be reset, and/or a reagent chamber of the cartridge can be refilled.

In some embodiments the system is configured to detect the presence or absence of an article in the sample receptacle. The article can be, for example, an article configured to hold a biological sample for analysis, such as a swab (e.g., a cotton swab or a brush swab) or a piece of paper (e.g., FTA® paper). The cartridge module, when engaged with the cartridge, can comprise a sensor configured to detect the presence or absence of an article in the receptacle. The sensor can be configured to detect, for example, changes in transmission of light or in an electrical field. Changes in an electrical field can be detected using capacitive or inductive sensors. Changes in transmission of light can be detected using a light source and a detector. For example, the system can comprise a light source that produces light that travels along an optical path that traverses the sample receptacle. The path can include, for example, windows in the module that are transparent to light. The system can comprise a light source, such as an LED or laser, and a detector, positioned to transmit light along the optical path. When the sample receptacle contains no article, or is empty or transparent, the light can traverse the optical path to the detector. When an article is introduced into the sample receptacle, it blocks or attenuates the optical path, decreasing or preventing light from the light source from reaching the detector. The presence or absence of an article in the sample receptacle, as determined by lack of detection or detection, respectively, of a signal from the light source, is reported to software that can run a number of sub-routines based on the result. For example, the software can report the status of each sample receptacle to a user, e.g., whether or not each receptacle contains does not contain an article, or whether or not an article has been introduced and then removed from a receptacle. The software can run a sub-routine based on these results, for example, if an article has been introduced and then removed from a receptacle, the sub-routine can prompt the user to run or nullify the results from the article in the receptacle. The system also can include a door which closes to enclose the cartridge within the system. The system can further comprise a sensor that indicates whether the door is open or closed and whether and when, after having been closed, the door has been opened during a run. This information can be written to a database or displayed on a user display.

To enhance maintenance of the chain of custody of a sample-containing article (e.g., a swab), a radio frequency identification (RFID) tag or a 2-D bar code can be affixed (e.g., permanently affixed) to a portion of the article, e.g., to a portion of the article (e.g., an end of a swab) that would not contact a reagent or a liquid in a sample receptacle/chamber of a cartridge. The RFID tag or 2-D bar code can be used to keep track of the sample-containing article throughout the whole process including collection of the sample, testing of the sample, storage of the sample, and transfer of the sample to any other possessor.

E. Remote Communication And Data Storage

In another aspect of the invention, a sample preparation, processing and analysis system is communicatively coupled to one or more remote systems. This permits the system, such as the system 100 described above, to transmit information to and from a remote system. This can be used for remote data storage or for interrogation of a remote database or to provide the information to a remote analysis. Remote communication can be used for cloud computing.

FIG. 19 shows a system 1900 having a sample preparation, processing and analysis device 1901 (which may be the system 100 of FIG. 1) that is operatively coupled to various components. The sample preparation, processing and analysis system is configured to communicate with a remote portable electronic device 1902, such as a portable personal computer (PC), Smart phone (e.g., Apple iPhone®, Android enabled phone, Black Berry), a tablet or slate PC (e.g., Apple iPad®, Galaxy Tab), or other portable device. The portable electronic device 1902 may include a graphical user interface for permitting a user to interact with the device 1901. This can enable a user to review results and setup processing tasks remotely. The device 1901 may communicate with the portable electronic device 1902 wirelessly, such as with the aid of a wireless network interface (e.g., WiFi interface) or Bluetooth.

With continued reference to FIG. 19, the device 1901 is configured to communicate with a network 1903 (e.g., an intranet or the Internet) via wired or wireless network connectivity, or a satellite. The system may wirelessly communicate with the network 1903 with the aid of a wireless communications device 1904, which may be a wireless router or a cell tower for various over-the-air communications protocols (e.g., 2G, 3G, 4G or LTE connectivity). An electronic device 1905 is in communication with the device 1901 with the aid of the network 1903. In some situations, the electronic device 1905 is a remote computer to permit a user to interact with the device 1901 remotely. In other situations, the electronic device 1905 is a data storage system, such as a computer system having one or more databases for storing preparation, processing and/or analysis data remotely. This can advantageously permit the device 1901 to store information remotely and retrieve information when required. In some instance, the remote data storage system can permit the device 1901 to backup information and/or retrieve information from storage.

In some situations, the device 1901 is device 100 described above in the context of FIG. 1. The device 1901 may include a display 1906 that has a user interface, such as a graphical user interface (GUI), to permit a user to interact with the device 1901. In some embodiments, the device 1901 includes a controller with one or more processors, such as, e.g., one or more central processing units (CPU's). The device 1901 in some cases also includes one or more of memory (e.g., read-only memory, random access memory), cache, and hard disks.

The display of the device 1901, the portable electronic device 1902 and the electronic device 1905 may be a touch screen, such as a capacitive touch or resistive touch screen, which may permit a user to interact with a graphical user interface (GUI) of the electronic devices using the user's fingers. Device 1901 can also be controlled by voice commands or other input modalities.

The system 1900 may permit sample preparation, processing and analysis to be performed on the device 1901 in a first location, and information retrieved for use from a second location that is different from the first location. In an example, the device 1901 is used to process a tissue sample in the first location, and data is transmitted wirelessly to the second location, which is remote from the first location, for analysis. Such analysis may include data comparison for a match. The system 1900 can be advantageous in cases in which data comparison is required to be done in a remote location different from the location at which a sample is processed.

The data collected can be transferred to a database located either within the system or outside the system using either a copy function, a USB drive or over an ethernet connection. The collected data can be transferred in its raw format or the data may be broken into components amenable for searches. For example, electropherogram data may be broken into numbers that represent the peak height, arrival times, or STR count for a particular locus. The database stores the parsed data from runs to create a population of individuals considered possible matches with the donor of a biological sample. Search function allows a quick search of the data in the database against an STR profile derived from the donor sample (minimum search speed: 100 trial matches per second) or against any other numbers parsed into the database. Matches can be performed at various defined levels of stringency. Matching data record can be displayed, including identifying information and ancillary biometrics data, if available.

V. Kits

Also provided are kits comprising consumable reagents. The kits can comprise a first container configured to receive a sample for analysis and a second container comprising at least one consumable reagent for use in analysis of the sample. Consumable reagents for use in sample analysis can include, for example, solutions (e.g., wash solutions, reaction buffers or electrophoresis buffers), enzymes for performing chemical or biochemical reactions (e.g., polymerases), chemical reagents (e.g., amplification primers, labeling reagents). One or more of the containers can be cartridges that are configured to engage an assembly of an analytical instrument that performs part or all of the sample analysis. For example, the container adapted to receive a sample can be a sample cartridge of this invention. A container comprising at least one consumable reagent can be a buffer cartridge or an anode cartridge of this invention. In some embodiments the first container or cartridge also can comprise consumable reagents for use in sample analysis. For example, the sample cartridge can contain one or more than one reagent necessary for performing a chemical reaction on an analyte. In some embodiments, the containers in the kits provided can be configured for a single analysis run in an instrument. The containers can be disposable. Accordingly, the kit can include a disposable single-use container (e.g., cartridge) for receiving a sample (and, optionally, for performing a chemical, e.g., biochemical, reaction on an analyte in the sample). In further embodiments, second containers, e.g., cartridges, containing at least one consumable reagent can be figured for one or more than one analysis run. Containers configured for more than one analysis run can contain consumable reagent sufficient for more than one analytical run. In some embodiments, the kit comprises a plurality of first containers, each first container configured receive a sample and configured for use in a single analysis run; and one or more second containers, each of the second containers containing one or more consumable reagents for use in the sample analysis in quantities sufficient for a number of analytical runs equal to the plurality of first containers. For example, the kit could contain ten sample cartridges and a consumable reagent cartridge with a reagent in an amount sufficient for ten analytical runs. In some embodiments, the kit can include all consumable reagents necessary for every step in an analysis run performed by an analytical instrument for which the kit is configured. For example, a kit for STR analysis can include reagents for DNA extraction from a sample (e.g., lysis buffer, capture particles, wash solutions), reagents for performing STR amplification (e.g., primers, polymerase) and reagents for electrophoresis (e.g., electrophoresis buffer, separation medium). Such a kit also can include controls and standards (e.g., allelic ladders, size standards).

VI. Portable Instrument or System

Some embodiments of the present disclosure relate to portable versions of the sample-to-answer instrument or system described herein which can be made sufficiently rugged for intended uses, e.g., by military or law enforcement personnel operating in the field. Non-limiting examples of applications of such a portable instrument or system include sensitive site exploitation, intelligence operations, confirmation or denial of hostages, expeditionary forensic capabilities, criminal identification and crime scene evaluation. Features of the portable instrument or system can include, e.g., reagents storable at ambient temperature, shorter sample-to-answer time (e.g., no more than about 45 min, 60 min, 75 min or 90 min), reduced weight, and enhanced ruggedization to withstand vibration and shock that may be encountered during transport across rough terrain and operation across a broad range of environmental conditions, including high altitude, extreme temperatures, and extreme humidity.

In some embodiments, the portable instrument or system is configured to be transportable in a container that can be carried by hand, by the shoulder or on the back (e.g., a backpack), where the instrument or system can comprise one or more modules, and where each of the one or more modules can be transported in a container (e.g., a backpack). In certain embodiments, each of the one or more modules weighs no more than about 30 pounds (lb), 35 lb, 40 lb, 45 lb, 50 lb, 55 lb, 60 lb, 65 lb or 70 lb. The weight of the portable instrument or system can be reduced, e.g., by reducing the weight of various components of the instrument or system, and/or by eliminating or redesigning certain components. For example, the instrument or system can be designed to use a single sample cartridge, which would not require a sample cartridge interface module that provides pneumatic and fluidic connections to two sample cartridges. The sample cartridge can be configured to receive and process a plurality of different samples, such as 8, 10, 16, 24, 32, 48 or more different samples. As another example, mounts having reduced weight can be used for various components, such as the anode cartridge interface module and/or the optics module. As a further example, each of the one or more modules can have a chassis and a case of reduced weight. For instance, each of the one or more modules can have a chassis and/or a case made of a lighter metal, such as aluminum or sheet metal.

Figure 56:
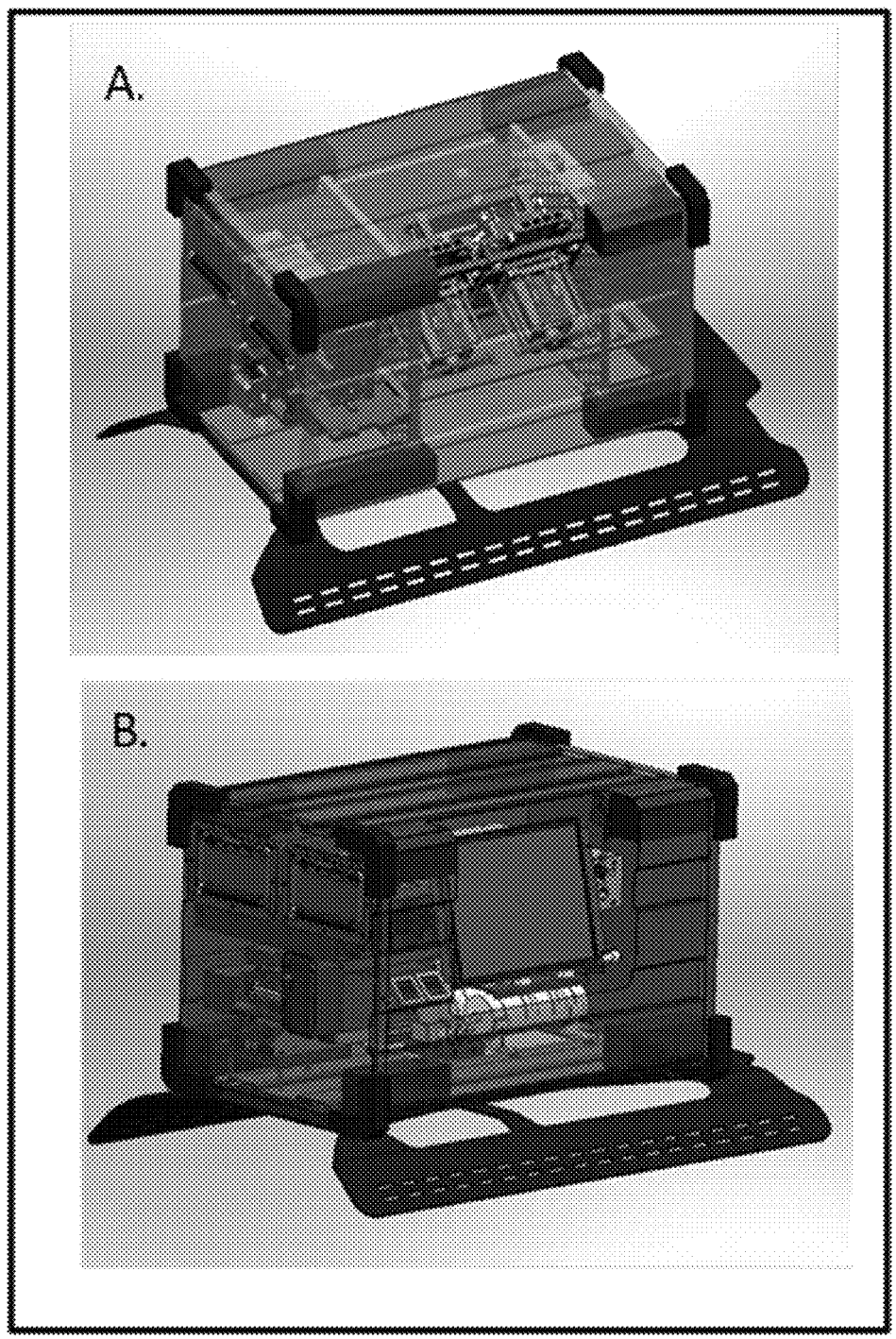
FIGS. 56A and 56B show embodiments of a portable instrument or system comprising two modules.

In certain embodiments, the portable instrument or system comprises two modules which each can be transported in a separate container that can be carried by hand, by the shoulder or on the back (e.g., a backpack), and which can be connected to each other at a destination point to create a functional nucleic acid (e.g., DNA) analysis instrument or system. FIGS. 56A and 56B show embodiments of a portable instrument or system comprising two modules that are transportable in a backpack format. In some embodiments, one of the two modules of the portable instrument or system is a sample analysis module (FIG. 56A) that comprises, among other components, an interface for one or more sample cartridges, a separation and detection system (including a capillary electrophoresis array, a pump for filling the capillaries with gel, and a detector), a means for rehydrating dried reagents, and a high voltage power supply. In certain embodiments, the sample analysis module is configured to take a single sample cartridge. In other embodiments, the sample analysis module is configured to take multiple sample cartridges (e.g., two sample cartridges). All sample processing, including DNA extraction and separation and detection of amplified DNA (e.g., STR) fragments, can be performed in the sample analysis module. In certain embodiments, the sample analysis module has dimensions of about 14.5 inches×about 14.5 inches×about 23 inches, or within about 10% or 20% less than or greater than those dimensions. In certain embodiments, the sample analysis module weighs about 50, 53 or 55 lb, or about 10% or 20% less than or greater than about 50, 53 or 55 lb. In further embodiments, the other module of the portable instrument or system is a support module (FIG. 56B) that comprises, among other components, a pump to supply vacuum and pressure to the one or more sample cartridges and the interface therefor, a computer system, and a touch screen display. In some embodiments, the support module has dimensions substantially similar to those of the sample analysis module. In certain embodiments, the support module weighs about 40, 42 or 45 lb, or about 10% or 20% less than or greater than about 40, 42 or 45 lb. FIGS. 56A and 56B show the sample analysis module and the support module each mounted on a backpack frame. In certain embodiments, the backpack frame for the sample analysis module and the support module weighs about 1 lb, 2 lb, 3 lb, 4 lb or 5 lb. The sample analysis module and the support module can be ruggedized to withstand vibration and shock, e.g., by having an internally sprung sub-frame. In other embodiments, one of the two modules comprises systems for performing nucleic acid extraction and purification and PCR amplification, and the other module comprises systems for performing separation, detection and data analysis.

In some embodiments, the portable instrument or system performs sample-to-answer processing and analysis in no more than about 45 min, 60 min, 75 min or 90 min. In some embodiments, the instrument or system achieves a shorter sample-to-answer time by employing a faster thermal cycler and/or a faster thermal cycling methodology. In certain embodiments, the instrument or system has a Peltier-based thermal cycling system that has a heating rate of about 10-15° C./sec or greater, and a cooling rate of about 5-10° C./sec or greater. A faster thermal cycler can allow PCR amplification (e.g., of STR loci) to be performed in about 30 min, 25 min, 20 min, 15 min or less. Faster PCR amplification can also be accomplished by utilizing a faster thermal cycling methodology, e.g., continuous flow PCR amplification. Continuous flow PCR amplification can achieve fast PCR amplification by having the PCR fluid undergo rapid temperature transitions as it moves between fixed temperature zones. Faster PCR amplification can also be achieved by performing shuttle cycling. In further embodiments, the portable instrument or system achieves a faster sample-to-answer time by separating DNA fragments (e.g., amplicons of STR loci) in a shorter time. Faster electrophoretic separation of DNA fragments can be accomplished in various ways, e.g., by decreasing the injected sample plug length and increasing the quantity of DNA injected into a capillary. As another example, a narrower sample injection plug can allow separation in a shorter capillary with sufficient resolution of DNA fragments. As a further example, use of an electrokinetic sample stacking injection process (e.g., transient isotachophoresis) can substantially increase the efficiency of sample injection in electrophoresis, which can result in improved sensitivity of sample detection and can decrease the number of PCR cycles required for amplification. Fewer PCR cycles can shorten the amplification time.

VII. Representative Embodiments

The following embodiments of the disclosure are provided by way of example only:
1. A cassette, comprising:
   (a) a container comprising a plurality of closed and fluidically isolated chambers, wherein each of the plurality of chambers comprises a friable seal; and
   (b) a microfluidic device comprising a plurality of puncturing elements and a microfluidic channel, wherein multiple puncturing elements are disposed opposite each of said plurality of chambers,
   wherein, upon engaging the microfluidic device with the container, said puncturing elements puncture the friable seal of each of the plurality of chambers, thereby creating a fluid flow path between said fluidically isolated chambers through said microfluidic channel.
2. The cassette of embodiment 1, further comprising a port that brings an individual chamber of said plurality of closed and fluidically isolated chambers in fluid communication with a pressure source.
3. The cassette of embodiment 1 or 2, wherein said fluid flow path is a multidirectional fluid flow path
4. The cassette of any one of the preceding embodiments, wherein said plurality of puncturing elements include openings that are in fluid communication with the microfluidic channel.
5. The cassette of any one of the preceding embodiments, wherein the microfluidic channel comprises one or more selectably closable channels.
6. The cassette of any one of the preceding embodiments, wherein the microfluidic channel is in fluid communication with one or more valves.
7. The cassette of embodiment 6, wherein the one or more valves are diaphragm valves.

8. The cassette of embodiment 6 or 7, wherein the one or more valves are pneumatically actuated valves.
9. The cassette of embodiment 6 or 7, wherein the one or more valves are piezoelectric valves.
10. The cassette of any one of the preceding embodiments, wherein:
the microfluidic channel comprises a plurality of microfluidic channels;
at least one, or each, of the plurality of chambers comprises a first port connectable to a microfluidic channel and a second port connectable to a microfluidic channel; and
engaging the microfluidic device with the container creates a fluid flow path comprising a microfluidic channel connected to the first port of a chamber, the chamber, and a microfluidic channel connected to the second port of the chamber.
11. The cassette of any one of the preceding embodiments, wherein said plurality of closed and fluidically isolated chambers comprise microfluidic chambers.
12. The cassette of any one of the preceding embodiments, wherein said plurality of closed and fluidically isolated chambers comprise macrofluidic chambers.
13. The cassette of any one of the preceding embodiments, further comprising a thermal cycler assembly adapted to receive a sample from said container and heat and cool the sample.
14. The cassette of embodiment 13, wherein said thermal cycler assembly is configured for polymerase chain reaction (PCR).
15. The cassette of embodiment 13 or 14, wherein said thermal cycler assembly comprises a thermal cycling chamber.
16. The cassette of embodiment 15, further comprising a premix application member in fluid communication with said microfluidic channel and said thermal cycling chamber.
17. The cassette of embodiment 15 or 16, further comprising a magnetic field application member adjacent to said thermal cycling chamber.
18. The cassette of any one of the preceding embodiments, wherein upon engaging the microfluidic device with the container, the container covers said microfluidic channel.
19. The cassette of any one of the preceding embodiments, further comprising a sample receptacle comprising a sample chamber adapted to receive a sample.
20. The cassette of embodiment 19, wherein said sample chamber has an opening that is parallel to a surface of the microfluidic device disposed between the microfluidic device and the container.
21. The cassette of embodiment 19 or 20, wherein said sample chamber is adapted to hold a swab (e.g., a cotton swab or a brush swab).
22. The cassette of any one of embodiments 19 to 21, wherein said microfluidic channel comprises a sample channel in fluid communication with said sample chamber.
23. The cassette of embodiment 22, wherein the container covers all or a substantial portion of the sample channel.
24. The cassette of any one of embodiments 19 to 23, wherein said sample receptacle is unitary with said microfluidic device.
25. The cassette of any one of the preceding embodiments, wherein said microfluidic channel comprises a reagent channel in fluid communication with a reagent chamber of said plurality of closed and fluidically isolated chambers.
26. The cassette of embodiment 25, wherein said container covers all or a substantial portion of the reagent channel.
27. The cassette of any one of the preceding embodiments, wherein said plurality of closed and fluidically isolated chambers comprise:
a first chamber holding a diluent;
a second chamber holding one or more lysis reagents, wherein the second chamber is in fluid communication with said sample chamber;
a third chamber having capture particles; and
a fourth chamber having a wash solution.
28. The cassette of embodiment 27, wherein said second chamber is a waste chamber configured to hold a waste material.
29. The cassette of embodiment 27 or 28, wherein:
the microfluidic channel comprises a plurality of microfluidic channels;
each of the first chamber, the second chamber, the third chamber and the fourth chamber comprises a first port connectable to a microfluidic channel and a second port connectable to a microfluidic channel; and
engaging the microfluidic device with the container creates a fluid flow path comprising a microfluidic channel connected to the first port of a chamber, the chamber, and a microfluidic channel connected to the second port of the chamber.
30. The cassette of any one of the preceding embodiments, further comprising a layer of deformable material between said container and said microfluidic device.
31. The cassette of embodiment 30, wherein said container is attached to said microfluidic device with the aid of said layer of deformable material.
32. The cassette of embodiment 30 or 31, wherein said layer of deformable material has a first sticky side and a second sticky side opposite from said first sticky side, wherein said first sticky side is adjacent to said microfluidic device and said second sticky side is adjacent to said container.
33. The cassette of any one of embodiments 30 to 32, wherein said deformable material is formed of a compressible material.
34. The cassette of any one of embodiments 30 to 33, wherein said deformable material is formed of a heat pliable material.
35. The cassette of any one of embodiments 30 to 34, wherein said deformable material comprises one or more springs.
36. The cassette of any one of the preceding embodiments, wherein said container is unitary with said microfluidic device.
37. The cassette of any one of the preceding embodiments, wherein said container is depressed into or compressed against said microfluidic device.
38. The cassette of any one of the preceding embodiments, wherein said friable seal is formed of a metallic material.
39. The cassette of any one of the preceding embodiments, wherein said friable seal is formed of a polymeric material.
40. The cassette of any one of the preceding embodiments, wherein said container is disposed over all or substantially all of said microfluidic channel.
41. A device for processing a biological sample, comprising:
(a) a microfluidic device comprising a microfluidic channel in fluid communication with one or more ports, wherein said microfluidic device includes a plurality of puncturing elements; and
(b) a container disposed over said microfluidic device, the container comprising a plurality of sealed chambers, wherein each of said plurality of sealed chambers is sealed with the aid of a friable seal, wherein the container is attached to the microfluidic device with the aid of a layer of deformable material,
wherein engaging the microfluidic device with the container punctures said friable seal and creates a fluid flow path between each of said sealed chambers and the microfluidic channel.

42. The device of embodiment 41, further comprising a port that brings an individual chamber of said plurality of sealed chambers in fluid communication with a pressure source.
43. The device of embodiment 41 or 42, wherein said fluid flow path is a multidirectional fluid flow path.
44. The device of any one of embodiments 41 to 43, wherein said plurality of puncturing elements include openings that are in fluid communication with the microfluidic channel.
45. The device of any one of embodiments 41 to 44, wherein the microfluidic channel comprises one or more selectably closable channels.
46. The device of any one of embodiments 41 to 45, wherein the microfluidic channel is in fluid communication with one or more valves.
47. The device of embodiment 46, wherein the one or more valves are diaphragm valves.
48. The device of embodiment 46 or 47, wherein the one or more valves are pneumatically actuated valves.
49. The device of embodiment 46 or 47, wherein the one or more valves are piezoelectric valves.
50. The device of any one of embodiments 41 to 49, wherein:
the microfluidic channel comprises a plurality of microfluidic channels;
at least one, or each, of the plurality of chambers comprises a first port connectable to a microfluidic channel and a second port connectable to a microfluidic channel; and
engaging the microfluidic device with the container creates a fluid flow path comprising a microfluidic channel connected to the first port of a chamber, the chamber, and a microfluidic channel connected to the second port of the chamber.
51. The device of any one of embodiments 41 to 50, wherein said plurality of sealed chambers comprise microfluidic chambers.
52. The device of any one of embodiments 41 to 51, wherein said plurality of sealed chambers comprise macrofluidic chambers.
53. The device of any one of embodiments 41 to 52, further comprising a thermal cycler assembly in fluid communication with said microfluidic channel.
54. The device of embodiment 53, wherein said thermal cycler assembly is configured for polymerase chain reaction (PCR).
55. The device of embodiment 53 or 54, wherein said thermal cycler assembly comprises a thermal cycling chamber.
56. The device of embodiment 55, further comprising a premix application member in fluid communication with said microfluidic channel and said thermal cycling chamber.
57. The device of embodiment 55 or 56, further comprising a magnetic field application member adjacent to said thermal cycling chamber.
58. The device of any one of embodiments 41 to 57, wherein said container covers a substantial portion of said microfluidic channel.
59. The device of any one of embodiments 41 to 58, further comprising a sample receptacle comprising a sample chamber adapted to receive a sample.
60. The device of embodiment 59, wherein said sample chamber has an opening that is parallel to a surface of the microfluidic device, the surface disposed between the microfluidic device and the container.
61. The device of embodiment 59 or 60, wherein said sample chamber is adapted to hold a swab or brush.
62. The device of any one of embodiments 59 to 61, wherein said microfluidic channel comprises a sample channel in fluid communication with said sample chamber.
63. The device of embodiment 62, wherein the container covers all or a substantial portion of the sample channel.
64. The device of any one of embodiments 59 to 63, wherein said sample receptacle is unitary with said microfluidic device.
65. The device of any one of embodiments 41 to 64, wherein said microfluidic channel comprises a reagent channel in fluid communication with a reagent chamber of said plurality of sealed chambers.
66. The device of embodiment 65, wherein said container covers all or a substantial portion of the reagent channel.
67. The device of any one of embodiments 41 to 66, wherein said plurality of sealed chambers comprise:
a first chamber holding a diluent;
a second chamber holding one or more lysis reagents, wherein the second chamber is in fluid communication with said sample chamber;
a third chamber having capture particles; and
a fourth chamber having a wash solution.
68. The device of embodiment 67, wherein said second chamber is a waste chamber configured to hold a waste material.
69. The device of embodiment 67 or 68, wherein:
the microfluidic channel comprises a plurality of microfluidic channels;
each of the first chamber, the second chamber, the third chamber and the fourth chamber comprises a first port connectable to a microfluidic channel and a second port connectable to a microfluidic channel; and
engaging the microfluidic device with the container creates a fluid flow path comprising a microfluidic channel connected to the first port of a chamber, the chamber, and a microfluidic channel connected to the second port of the chamber.
70. The device of any one of embodiments 41 to 69, further comprising a layer of deformable material between said container and said microfluidic device.
71. The device of embodiment 70, wherein said container is attached to said microfluidic device with the aid of said layer of deformable material.
72. The device of embodiment 70 or 71, wherein said layer of deformable material has a first sticky side and a second sticky side opposite from said first sticky side, wherein said first sticky side is adjacent to said microfluidic device and said second sticky side is adjacent to said container.
73. The device of any one of embodiments 70 to 72, wherein said deformable material is formed of a compressible material.
74. The device of any one of embodiments 70 to 73, wherein said deformable material is formed of a heat pliable material.
75. The device of any one of embodiments 70 to 74, wherein said deformable material comprises one or more springs.
76. The device of any one of embodiments 41 to 75, wherein said container is unitary with said microfluidic device.
77. The device of any one of embodiments 41 to 76, wherein said container is depressed into or compressed against said microfluidic device.
78. The device of any one of embodiments 41 to 77, wherein said friable seal is formed of a metallic material.
79. The device of any one of embodiments 41 to 78, wherein said friable seal is formed of a polymeric material.
80. The device of any one of embodiments 41 to 79, wherein said container is disposed over all or substantially all of said microfluidic channel.
81. A cassette for processing a biological sample, comprising:
(a) a microfluidic device comprising a microfluidic channel and one or more puncturing elements; and (b) a container comprising a plurality of chambers, said container disposed over all or a substantial portion of said microfluidic channel, wherein each of said plurality of chambers comprises a friable seal,
wherein upon clamping the microfluidic device against the container, said puncturing elements puncture the friable seal of each of the plurality of chambers, thereby forming a fluid flow path between each of said plurality of chambers and the microfluidic channel.

82. The cassette of embodiment 81, further comprising a port that brings an individual chamber of said plurality of chambers in fluid communication with a pressure source.

83. The cassette of embodiment 81 or 82, wherein:
the microfluidic channel comprises a plurality of microfluidic channels;
at least one, or each, of the plurality of chambers comprises a first port connectable to a microfluidic channel and a second port connectable to a microfluidic channel; and
clamping the microfluidic device against the container creates a fluid flow path comprising a microfluidic channel connected to the first port of a chamber, the chamber, and a microfluidic channel connected to the second port of the chamber.

84. The cassette of any one of embodiments 81 to 83, wherein said fluid flow path is a multidirectional fluid flow path.

85. The cassette of any one of embodiments 81 to 84, wherein said plurality of chambers comprise:
a first chamber holding a diluent;
a second chamber holding one or more lysis reagents, wherein the second chamber is in fluid communication with said sample chamber;
a third chamber having capture particles; and
a fourth chamber having a wash solution.

86. The cassette of embodiment 85, wherein said second chamber is a waste chamber configured to hold a waste material.

87. The cassette of embodiment 85 or 86, wherein:
the microfluidic channel comprises a plurality of microfluidic channels;
each of the first chamber, the second chamber, the third chamber and the fourth chamber comprises a first port connectable to a microfluidic channel and a second port connectable to a microfluidic channel; and
clamping the microfluidic device against the container creates a fluid flow path comprising a microfluidic channel connected to the first port of a chamber, the chamber, and a microfluidic channel connected to the second port of the chamber.

88. The cassette of any one of embodiments 81 to 87, wherein said friable seal is formed of a metallic material.

89. The cassette of any one of embodiments 81 to 88, wherein said friable seal is formed of a polymeric material.

90. The cassette of any one of embodiments 81 to 89, wherein said container is disposed over all or substantially all of said microfluidic channel.

91. The cassette of any one of embodiments 81 to 90, wherein the container covers all or a substantial portion of the microfluidic channel.

92. The cassette of any one of embodiments 81 to 91, further comprising a sample receptacle comprising a sample chamber adapted to receive a sample, said sample chamber in fluid communication with said microfluidic channel.

93. The cassette of embodiment 92, wherein said sample receptacle is unitary with said microfluidic device.

94. A cassette for processing a biological sample, comprising:
(a) a microfluidic device comprising a first microfluidic channel and a second microfluidic channel fluidically isolated from said first microfluidic channel, wherein said microfluidic device includes a plurality of puncturing elements; and
(b) a container comprising a first plurality of closed and fluidically isolated chambers and a second plurality of closed and fluidically isolated chambers, each of said first and second plurality of closed and fluidically isolated chambers comprising a friable seal,
wherein, upon engaging the microfluidic device with the container, said puncturing elements puncture the friable seal of each of the first and second plurality of closed and fluidically isolated chambers, thereby forming a fluid flow path between the first microfluidic channel and the first plurality of closed and fluidically isolated chambers and another fluid flow path between the second microfluidic channel and the second plurality of closed and fluidically isolated chambers.

95. The cassette of embodiment 94, further comprising a port for each of the fist and second plurality of closed and fluidically isolated chambers which brings an individual chamber of each of said first and second plurality of closed and fluidically isolated chambers in fluid communication with a pressure source.

96. The cassette of embodiment 94 or 95, wherein:
(1) the first microfluidic channel comprises a plurality of microfluidic channels;
at least one, or each, of the first plurality of chambers comprises a first port connectable to a microfluidic channel and a second port connectable to a microfluidic channel; and
engaging the microfluidic device with the container creates a fluid flow path comprising a microfluidic channel connected to the first port of a chamber of the first plurality of chambers, the chamber, and a microfluidic channel connected to the second port of the chamber; and
(2) the second microfluidic channel comprises a plurality of microfluidic channels;
at least one, or each, of the second plurality of chambers comprises a first port connectable to a microfluidic channel and a second port connectable to a microfluidic channel; and
engaging the microfluidic device with the container creates a fluid flow path comprising a microfluidic channel connected to the first port of a chamber of the second plurality of chambers, the chamber, and a microfluidic channel connected to the second port of the chamber.

97. The cassette of any one of embodiments 94 to 96, wherein said fluid flow paths are multidirectional fluid flow paths.

98. The cassette of any one of embodiment 94 to 97, wherein said first microfluidic channel is substantially parallel to and/or does not intersect said second microfluidic channel.

99. The cassette of any one of embodiments 94 to 98, further comprising a first sample receptacle comprising a first sample chamber adapted to receive a first sample, and a second sample receptacle comprising a second sample chamber adapted to receive a second sample.

100. The cassette of embodiment 99, wherein said first sample chamber is in fluid communication with said first microfluidic channel and said second sample chamber is in fluid communication with said second microfluidic channel.

101. The cassette of embodiment 99 or 100, wherein said first sample chamber includes a biological sample with a known genetic profile.

102. The cassette of any one of embodiments 94 to 101, wherein said sample receptacle is unitary with said microfluidic device.

103. A system, comprising:
(a) a receptacle for receiving a cassette;
(b) a cassette received in the receptacle, the cassette comprising:
(i) a container comprising a plurality of closed and fluidically isolated chambers, wherein each of the plurality of closed and fluidically isolated chambers comprises a friable seal; and
(ii) a microfluidic device comprising a plurality of puncturing elements and a microfluidic channel in fluid communication with one or more ports, wherein:
the container is attached to the microfluidic device with the aid of a layer of deformable material; and/or
two or more of said plurality of puncturing elements are disposed opposite each of said plurality of closed and fluidically isolated chambers; and
(c) a pressure application member for engaging the microfluidic device with the container, wherein engaging the microfluidic device with the container punctures the friable seal of each of the plurality of closed and fluidically isolated chambers and creates a fluid flow path between each of said plurality of closed and fluidically isolated chambers and the microfluidic channel.
104. The system of embodiment 103, wherein:
the microfluidic channel comprises a plurality of microfluidic channels;
at least one, or each, of the plurality of chambers comprises a first port connectable to a microfluidic channel and a second port connectable to a microfluidic channel; and
engaging the microfluidic device with the container creates a fluid flow path comprising a microfluidic channel connected to the first port of a chamber, the chamber, and a microfluidic channel connected to the second port of the chamber.
105. The system of embodiment 103 or 104, wherein the system processes, or processes and analyzes, a biological sample in about two hours or less, or in about 1.5 hours or less.
106. The system of any one of embodiments 103 to 105, wherein the system processes and/or analyzes a biological sample at a coefficient of variation less than about 20%.
107. The system of embodiment 106, wherein the system processes and/or analyzes a biological sample at a coefficient of variation less than about 10%.
108. The system of embodiment 107, wherein the system processes and/or analyzes a biological sample at a coefficient of variation less than about 1%.
109. The system of any one of embodiments 103 to 108, wherein the system processes and/or analyzes a biological sample at an accuracy of at least about 80%.
110. The system of embodiment 109, wherein the system processes and/or analyzes a biological sample at an accuracy of at least about 90%.
111. The system of embodiment 110, wherein the system processes and/or analyzes a biological sample at an accuracy of at least about 95% or 99%.
112. A method for processing a biological sample, comprising:
(a) providing a cassette as in embodiment 1;
(b) providing a sample in a sample chamber of said cassette, wherein said sample chamber is in fluid communication with the microfluidic channel of said cassette;
(c) engaging the microfluidic device with the container to form a fluid flow path between each of said plurality of closed and fluidically isolated chambers and the microfluidic channel; and
(d) processing the biological sample.

113. The method of embodiment 112, wherein said plurality of closed and fluidically isolated chambers comprise:
a first chamber holding a diluent;
a second chamber holding one or more lysis reagents, wherein the second chamber is in fluid communication with said sample chamber;
a third chamber having capture particles; and
a fourth chamber having a wash solution.
114. The method of embodiment 113, wherein:
the microfluidic channel comprises a plurality of microfluidic channels;
each of the first chamber, the second chamber, the third chamber and the fourth chamber comprises a first port connectable to a microfluidic channel and a second port connectable to a microfluidic channel; and
engaging the microfluidic device with the container creates a fluid flow path comprising a microfluidic channel connected to the first port of a chamber, the chamber, and a microfluidic channel connected to the second port of the chamber.
115. The method of any one of embodiments 112 to 114, wherein processing the biological sample comprises:
directing said one or more lysis reagents from the second chamber to the sample chamber;
contacting said one or more lysis reagents with the biological sample in the sample chamber, thereby extracting a nucleic acid sample from said biological sample;
directing the nucleic acid sample from the sample chamber to the third chamber, thereby attaching at least a portion of said nucleic acid sample to capture particles; and
directing the capture particles to a thermal cycling chamber in fluid communication with said third chamber through said microfluidic channel.
116. The method of embodiment 115, wherein the lysis reagents are directed from the second chamber to the sample chamber with the aid of negative or positive pressure.
117. The method of embodiment 115 or 116, further comprising amplifying the nucleic acid sample in the thermal cycling chamber.
118. The method of any one of embodiments 115 to 117, wherein directing the capture particles to a thermal cycling chamber comprises directing the capture particles to a thermal cycling chamber of a thermal cycler assembly.
119. The method of embodiment 118, further comprising providing a premix solution to the thermal cycling chamber.
120. The method of embodiment 119, further comprising thermal cycling the nucleic acid sample in the thermal cycling chamber, thereby amplifying the nucleic acid sample provided by said capture particles to produce nucleic acid amplification products.
121. The method of embodiment 120, further comprising directing the nucleic acid amplification products from said thermal cycling chamber to the first chamber.
122. The method of any one of embodiments 112 to 121, wherein engaging the microfluidic device with the container comprises applying pressure against the container in the direction of the microfluidic device.
123. A system for processing a biological sample, comprising:
a housing;
a receptacle in the housing, the receptacle configured to receive a cassette having a microfluidic device and a container that is adjacent to said microfluidic device,
wherein said container includes a chamber for sample processing, wherein said chamber is sealed with the aid of a friable seal, and wherein said microfluidic device comprises a port that brings said chamber in fluid communication with a pressure source;

an engagement member adjacent to said receptacle, wherein said engagement member engages the microfluidic device with the container, thereby puncturing said friable seal, wherein puncturing said friable seal brings said chamber in fluid communication with a microfluidic channel of the microfluidic device; and a controller in the housing, said controller having a processor and memory with machine executable code for implementing a method to process a biological sample with the aid of said cassette.

124. The system of embodiment 123, wherein:

the container comprises a plurality of chambers;

the microfluidic device comprises a plurality of microfluidic channels;

at least one, or each, of the plurality of chambers comprises a first port connectable to a microfluidic channel and a second port connectable to a microfluidic channel; and engaging the microfluidic device with the container creates a fluid flow path comprising a microfluidic channel connected to the first port of a chamber, the chamber, and a microfluidic channel connected to the second port of the chamber.

125. The system of embodiment 123 or 124, further comprising a display, wherein the display has a graphical user interface (GUI) operatively coupled to the controller, wherein the GUI enables a user to interact with the system.

126. A method for determining a genetic profile of an organism, comprising processing and analyzing a biological sample from said organism in 20 steps or less, or in 10 steps or less.

127. The method of embodiment 126, wherein the genetic profile is determined in about 3 hours or less.

128. The method of embodiment 127, wherein the genetic profile is determined in about 2 hours or less.

129. The method of embodiment 128, wherein the genetic profile is determined in about 1.5 hours or less, or about 1 hour or less, or about 45 min or less.

130. The method of any one of embodiments 126 to 129, wherein said determining comprises short tandem repeat (STR) analysis on the organism.

131. A method for automated forensics, comprising determining a genetic profile of an organism in 20 steps or less, or in 10 steps or less, using a fully integrated sample processing and analysis system having a volume of about 20 ft$^3$ or less.

132. The method of embodiment 131, wherein the fully integrated sample processing and analysis system has a volume of about 16 ft$^3$ or less.

133. The method of embodiment 132, wherein the fully integrated sample processing and analysis system has a volume of about 15 ft$^3$ or less.

134. The method of embodiment 133, wherein the fully integrated sample processing and analysis system has a volume of about 10 ft$^3$ or less.

135. The method of embodiment 134, wherein the fully integrated sample processing and analysis system has a volume of about 5 ft$^3$ or less.

136. A cassette, comprising:

(a) a container comprising at least one closed and fluidically isolated chamber, said chamber comprising a friable seal; and (b) a microfluidic device comprising a plurality of channels, wherein each of the plurality of channels terminates at a port, wherein engaging the microfluidic device with the container punctures the friable seal, thereby bringing said ports in fluid communication with one another through the chamber.

137. The cassette of embodiment 136, wherein each of the plurality of channels opens at a first port and terminates at a second port.

138. The cassette of embodiment 137, wherein said second port opens into the closed and fluidically isolated chamber where the microfluidic device has engaged the container.

139. The cassette of any one of embodiments 136 to 138, wherein at least one of said plurality of channels is in fluid communication with a plurality of chambers.

140. The cassette of any one of embodiments 136 to 139, wherein said container comprises two closed and fluidically isolated chambers, and wherein engaging the microfluidic device with the container brings said two closed and fluidically isolated chambers in fluid communication with one another through one or more channels in the microfluidic device.

141. A method for processing a sample, comprising:

engaging a container with a microfluidic device, wherein said container comprises at least one closed and fluidically isolated chamber, said chamber comprising a friable seal, wherein said microfluidic device comprises a plurality of channels, wherein each of the plurality of channels terminates at a port, wherein engaging the microfluidic device with the container punctures the friable seal, thereby bringing said ports in fluid communication with one another through the chamber.

142. A cassette, comprising:

(a) a container comprising a chamber that is closed and fluidically isolated with the aid of a friable seal; and (b) a microfluidic device comprising a first channel and second channel, each of which channels terminates at a port, and puncturing elements adjacent to said chamber, wherein, upon engaging the microfluidic device with the container, said puncturing elements puncture the friable seal, thereby creating a fluid flow path comprising said first channel, chamber and second channel.

143. The cassette of embodiment 142, wherein upon engaging the microfluidic device a port of each of the first channel and second channel opens into said chamber.

144. An article, comprising:

a body containing a passage between openings;

a first movable stopper and a second movable stopper positioned in the passage so as to define a compartment between them; and a fluid in the compartment, said fluid comprising an amplification premix, wherein external pressure exerted against the first movable stopper is transmitted to the second movable stopper to move the second movable stopper toward an opening.

145. The article of embodiment 144, wherein the body is configured as a barrel and the second movable stopper is configured as a spheroid.

146. The article of embodiment 144 or 145, wherein the first movable stopper is configured as a spheroid or a plunger.

147. The article of any one of embodiments 144 to 146, further comprising a lip adapted to engage a clip or clamp.

148. The article of any one of embodiments 144 to 147, wherein the second movable stopper is positioned toward a tapered end of the body.

149. The article of embodiment 148, wherein the tapered end engages a receiving element to form a swage seal.

150. A system for processing a biological sample, comprising:
- (a) a cassette having a chamber,
  - wherein said cassette includes a microfluidic device that is adjacent to said chamber, and
  - wherein said microfluidic device includes a plurality of diaphragm valves along a microfluidic channel of said microfluidic device, an individual diaphragm valve of said plurality of diaphragm valves having a fluidic layer, pneumatic layer and an elastic layer between said fluidic layer and pneumatic layer;
- (b) a pressure source in fluid communication with said chamber through a port of said microfluidic device, wherein said pressure source provides positive pressure or negative pressure to said chamber, thereby moving a fluid through said microfluidic channel at a flow rate of about 5000 microliters (ul)/s or less, or 1000 ul/s or less; and
- (c) a pneumatic manifold in fluid communication with said pneumatic layer, said pneumatic layer for actuating said elastic layer, thereby moving a fluid through said microfluidic channel at a flow rate of about 100 ul/s or less, or 10 ul/s or less.

151. The system of embodiment 150, wherein:
the pressure source can move the fluid through the microfluidic channel at a flow rate of less than or equal to about 5000 ul/s, 4000 ul/s, 3000 ul/s, 2000 ul/s, 1000 ul/s, 500 ul/s, 400 ul/s, 300 ul/s, 200 ul/s, 100 ul/s, 50 ul/s, or less; and
the actuation of the pneumatic layer can move a fluid through the microfluidic channel at a flow rate less than or equal to about 100 ul/s, 90 ul/s, 80 ul/s, 70 ul/s, 60 ul/s, 50 ul/s, 40 ul/s, 30 ul/s, 20 ul/s, 10 ul/s, 5 ul/s, 2.5 ul/s, 1 ul/s, or less.

152. The system of embodiment 151, wherein:
the pressure source can move the fluid through the microfluidic channel at a flow rate of less than or equal to about 100 ul/s or less; and
the actuation of the pneumatic layer can move a fluid through the microfluidic channel at a flow rate less than or equal to about 5 ul/s or less.

153. The system of any one of embodiments 150 to 152, wherein said microfluidic channel is in fluid communication with said chamber through a friable seal of said chamber.

154. A cartridge module, comprising:
a receptacle for accepting a cartridge that has a sample and one or more reagents for processing said sample, said cartridge having one or more chambers for sample processing and one or more valves for facilitating fluid flow to said one or more chambers;
a first assembly having a first pressure manifold that engages a first side of said cartridge and brings said one or more chambers in fluid communication with a pressure source;
a second assembly having a second pressure manifold that engages a second side of said cartridge and brings said one or more valves in fluid communication with a pressure source for pneumatic actuation; and
an elongation or moving member that moves one or both of said first pressure manifold and said second pressure manifold towards said cartridge.

155. The cartridge module of embodiment 154, wherein said elongation or moving member is coupled to one or both of said first assembly and said second assembly through a cable.

156. The cartridge module of embodiment 155, wherein said cable is Bowden cable.

157. The cartridge module of any one of embodiments 154 to 156, wherein said elongation or moving member moves one or both of said first pressure manifold and said second pressure manifold away from said cartridge.

158. The cartridge module of any one of embodiments 154 to 157, wherein said elongation or moving member comprises an air-driven piston the movement of which moves one or both of said first pressure manifold and said second pressure manifold towards said cartridge.

159. A cartridge comprising one or more sets of chambers and fluidic channels, wherein:
the cartridge is configured to be removably engagable with a cartridge module;
for a cartridge comprising a plurality of sets of chambers and fluidic channels, each set of chambers and fluidic channels is fluidically isolated from every other set of chambers and fluidic channels prior to and subsequent to engagement of the cartridge with the cartridge module;
each set of chambers and fluidic channels comprises a plurality of chambers that are closed and fluidically isolated from one another and from the fluidic channels prior to engagement of the cartridge with the cartridge module;
the chambers in each set of chambers and fluidic channels come into fluidic communication with one another via the fluidic channels when the cartridge is engaged with the cartridge module; and
for each of the plurality of closed and fluidically isolated chambers in each set of chambers and fluidic channels, engagement of the cartridge with the cartridge module creates a fluid flow path comprising a fluidic channel in fluidic communication with a first port of the chamber, the chamber, and a fluidic channel in fluidic communication with a second port of the chamber.

160. The cartridge of embodiment 159, wherein the first port and the second port of each of the plurality of closed and fluidically isolated chambers in each set of chambers and fluidic channels are on substantially the same plane, on the same surface, or at the base or the bottom of the chamber, or any combination thereof.

161. The cartridge of embodiment 159 or 160, wherein each of the plurality of closed and fluidically isolated chambers is closed and fluidically isolated, prior to engagement of the cartridge with the cartridge module, with the aid of a friable or puncturable seal.

162. The cartridge of embodiment 161, wherein when the cartridge is engaged with the cartridge module, two puncturing elements in the cartridge puncture the friable or puncturable seal of each of the plurality of closed and fluidically isolated chambers, thereby creating a fluid flow path comprising a fluidic channel in fluidic communication with a first port of the chamber, the chamber, and a fluidic channel in fluidic communication with a second port of the chamber.

163. The cartridge of embodiment 162, wherein the fluid flow path at each port of the chamber is sealed with the aid of one or more (e.g., two) gaskets.

164. The cartridge of embodiment 162 or 163, wherein each puncturing element has an opening that is in fluidic communication with a fluidic channel.

165. The cartridge of any one of embodiments 162 to 164, wherein each fluidic channel in fluidic communication with a port of a chamber can provide a fluid (e.g., a liquid or a gas) to the chamber.

166. The cartridge of any one of embodiments 161 to 165, wherein the friable or puncturable seal is composed of a metallic material (e.g., an aluminum foil).

167. The cartridge of any one of embodiments 161 to 166, wherein the friable or puncturable seal is composed of a polymeric material.

168. The cartridge of any one of embodiments 159 to 167, which further comprises one or more ports for each set of chambers and fluidic channels which bring the chambers in each set in fluidic communication with a source of positive pressure or negative pressure via the fluidic channels.

169. The cartridge of any one of embodiments 159 to 168, wherein for a cartridge comprising a plurality of sets of chambers and fluidic channels, the path of the fluidic channels in each set of chambers and fluidic channels is substantially parallel to and/or does not intersect the path of the fluidic channels in every other set of chambers and fluidic channels.

170. The cartridge of any one of embodiments 159 to 169, which is configured to:
    extract nucleic acid (e.g., DNA) from a sample;
    isolate the extracted nucleic acid (e.g., by capturing the extracted nucleic acid to a substrate (e.g., magnetically responsive particles));
    optionally purify the isolated nucleic acid;
    amplify one or more selected nucleotide (e.g., short tandem repeat (STR)) sequences of the isolated nucleic acid (e.g., by polymerase chain reaction (PCR)) to produce amplification products; and
    optionally separate, or optionally separate and detect, the amplification products (e.g., by electrophoresis).

171. The cartridge of embodiment 170, wherein each set of chambers comprises:
    (a) a chamber comprising a reagent (e.g., a lysis reagent) in a solution or buffer for extracting nucleic acid from a sample, and optionally an anti-foaming reagent;
    (b) a chamber comprising a substrate (e.g., magnetically responsive particles), optionally in a solution or buffer, for isolating extracted nucleic acid;
    (c) one or more (e.g., two) chambers comprising a solution (e.g., a wash solution or buffer) for purifying isolated nucleic acid; and
    (d) a chamber comprising a solution (e.g., water) for diluting amplification products prior to separation of the amplification products.

172. The cartridge of embodiment 171, wherein for each set of chambers:
    chamber (a) is configured to receive and/or store waste material; and
    chamber (d) optionally further comprises a control (e.g., a size standard in a set of chambers comprising a sample, or an allelic ladder (and optionally a size standard) in a set of chambers not comprising a sample).

173. The cartridge of embodiment 171 or 172, wherein for each set of chambers:
    chamber (a) is pre-loaded with a reagent (e.g., a lysis reagent) in a solution or buffer for extracting nucleic acid from a sample, and optionally an anti-foaming reagent;
    chamber (b) is pre-loaded with a substrate (e.g., magnetically responsive particles), optionally in a solution or buffer, for isolating extracted nucleic acid;
    one or more (e.g., two) chambers (c) are pre-loaded with a solution (e.g., a wash solution or buffer) for purifying isolated nucleic acid; and
    chamber (d) is pre-loaded with a solution (e.g., water) for diluting amplification products, and optionally a control (e.g., a size standard in a set of chambers that will comprise a sample, or an allelic ladder (and optionally a size standard) in a set of chambers that will not comprise a sample).

174. The cartridge of any one of embodiments 171 to 173, wherein for each set of chambers, chamber (b) comprises, or is pre-loaded with, an amount of magnetically responsive particles selected to control the amount of nucleic acid isolated.

175. The cartridge of any one of embodiments 171 to 174, wherein for each set of chambers:
    each of chambers (a), (b), (c) and (d) is closed and fluidically isolated prior to engagement of the cartridge with the cartridge module; and
    for each of chambers (a), (b), (c) and (d), engagement of the cartridge with the cartridge module creates a fluid flow path comprising a fluidic channel in fluidic communication with a first port of the chamber, the chamber, and a fluidic channel in fluidic communication with a second port of the chamber.

176. The cartridge of any one of embodiments 170 to 175, wherein each set of chambers comprises:
    a chamber configured to receive a sample; and
    a chamber configured to amplify one or more selected nucleotide sequences of isolated nucleic acid (e.g., by PCR).

177. The cartridge of embodiment 176, wherein the sample chamber is configured to receive a cellulosic substrate (e.g., FTA paper) or a swab (e.g., a cotton swab or a brush swab).

178. The cartridge of embodiment 176 or 177, wherein the sample chamber is further configured to extract nucleic acid from the sample.

179. The cartridge of any one of embodiments 176 to 178, wherein the nucleic acid amplification chamber is further configured to perform nucleic acid amplification with thermal cycling with the aid of a heating and cooling device (e.g., a Peltier heating and cooling element).

180. The cartridge of embodiment 179, further comprising a thermoconducting element configured to apply or distribute heat and cooling to the nucleic acid amplification chamber in each set of chambers.

181. The cartridge of embodiment 180, wherein the thermoconducting element is disposed over the nucleic acid amplification chamber in each set of chambers.

182. The cartridge of any one of embodiments 171 to 181, which further comprises a source of magnetic field (e.g., a magnet) adjacent to chamber (b) and/or the nucleic acid amplification chamber in each set of chambers.

183. The cartridge of any one of embodiments 176 to 182, wherein each set of chambers further comprises a chamber comprising reagents for amplifying one or more selected nucleotide sequences.

184. The cartridge of embodiment 183, wherein for each set of chambers, the amplification reagent chamber is pre-loaded with reagents for amplifying one or more selected nucleotide sequences.

185. The cartridge of embodiment 183 or 184, wherein the reagents for amplifying one or more selected nucleotide sequences comprise a DNA polymerase (e.g., a Taq polymerase), one or more pairs of forward and reverse primers for amplifying the one or more selected nucleotide sequences, deoxyribonucleotide triphosphates, and optionally a metal salt (e.g., magnesium chloride), and wherein the one or more pairs of forward and reverse primers optionally are labeled with a dye (e.g., a fluorescent dye).

186. The cartridge of any one of embodiments 183 to 185, wherein for each set of chambers, the amplification reagent chamber comes into fluidic communication with the nucleic acid amplification chamber upon actuation of a delivery mechanism (e.g., a plunger pushing down to break a seal at the bottom of the amplification reagent chamber).

187. The cartridge of any one of embodiments 183 to 186, wherein the reagents for amplifying one or more selected nucleotide sequences are delivered to the nucleic acid amplification chamber via a channel that does not comprise a valve.

188. The cartridge of any one of embodiments 183 to 187, wherein for a set of chambers that does not, or will not, comprise a sample, the amplification reagent chamber further comprises, or is further pre-loaded with, a positive control (e.g., a purified genomic DNA).

189. The cartridge of any one of embodiments 171 to 188, wherein for all of the one or more sets of chambers, all of chambers (a), (b), (c) and (d), the one or more sample chambers and the one or more nucleic acid amplification chambers, and optionally the one or more amplification reagent chambers, are all substantially co-planar.

190. The cartridge of any one of embodiments 170 to 189, which comprises a separation channel for each set of chambers and fluidic channels.

191. The cartridge of embodiment 190, which further comprises:
one or more heating elements configured to apply heat to denature amplification products during separation, or prior to and during separation; and
a thermal-control device configured to control heating of the amplification products.

192. The cartridge of any one of embodiments 159 to 191, wherein for each set of chambers, each of the chambers can be macrofluidic or microfluidic.

193. The cartridge of any one of embodiments 159 to 192, wherein one or more, or all, of the fluidic channels in each set of chambers and fluidic channels comprise one or more valves.

194. The cartridge of embodiment 193, wherein one or more, or all, of the one or more valves are diaphragm valves.

195. The cartridge of embodiment 194, wherein the diaphragm valves comprise normally open valves or normally closed valves, or both.

196. The cartridge of embodiment 195, wherein a normally open diaphragm valve is comprised in a combination that comprises a fluidic layer, a pneumatic layer and an elastic layer sandwiched between the fluidic layer and the pneumatic layer, and wherein the normally open diaphragm valve comprises:
(a) a diaphragm in the elastic layer and composed of an elastomeric material (e.g., polydimethylsiloxane (PDMS));
(b) a valve seat in the fluidic layer and recessed from a surface of the fluidic layer (e.g., the valve seat has a concave shape with respect to the surface of the fluidic layer) so that the diaphragm does not close the diaphragm valve unless positive pressure is exerted on the diaphragm; and
(c) a valve inlet and a valve outlet in the fluidic layer and in fluidic communication with a fluidic channel;
wherein the diaphragm is actuated by positive pressure or negative pressure transmitted to the diaphragm via a pneumatic conduit in the pneumatic layer.

197. The cartridge of any one of embodiments 193 to 196, wherein one or more, or all, of the one or more valves are pneumatically actuated valves.

198. The cartridge of any one of embodiments 193 to 197, wherein one or more, or all, of the one or more valves are electrically actuated valves.

199. The cartridge of any one of embodiments 159 to 198, wherein one or more, or all, of the fluidic channels in each set of chambers and fluidic channels comprise one or more pumps.

200. The cartridge of embodiment 199, wherein one or more, or all, of the one or more pumps comprise a plurality of (e.g., three or four) valves (e.g., diaphragm valves).

201. The cartridge of any one of embodiments 159 to 200, which comprises 4, 8, 10, 16, 24, 32, 40, 48 or more sets of chambers and fluidic channels, wherein each set of chambers and fluidic channels can be used to run a different sample, or one or more sets of chambers and fluidic channels can be used to run a different control (e.g., an allelic ladder, a positive control or a negative control) and every other set of chambers and fluidic channels can be used to run a different sample.

202. The cartridge of embodiment 201, wherein:
a first set of chambers comprises an allelic ladder and a size standard;
a second set of chambers comprises a positive control and a size standard;
a third set of chambers comprises a negative control and a size standard; and
every other set of chambers comprises a different sample and a size standard.

203. The cartridge of any one of embodiments 159 to 202, wherein one or more, or all, of the fluidic channels in each set of chambers and fluidic channels are microfluidic channels.

204. The cartridge of any one of embodiments 159 to 203, which can be configured for a single use or multiple uses.

205. The cartridge of any one of embodiments 159 to 204, which further comprises a readable and/or writable memory device (e.g., an EEPROM memory chip) configured to store, receive and/or transmit information relating to the cartridge (e.g., information relating to the history, a recommended use-by date, the current use (e.g., whether the cartridge is operably engaged with a cartridge module, information input from a user, and/or information generated by the system/instrument employing the cartridge in operation), the configurations, the conditions, the physical features and/or the chemical features of the cartridge).

206. The cartridge of any one of embodiments 159 to 205, wherein when the cartridge is engaged with the cartridge module, the longitudinal axis of the cartridge is at an angle of about 15-45 degrees, 20-40 degrees or 25-35 degrees, or about 30 degrees, relative to a vertical plane perpendicular to the plane of the surface on which a system comprising the cartridge module rests.

207. The cartridge of any one of embodiments 159 to 206, which is a sample cartridge or a control cartridge.

208. The cartridge of any one of embodiments 159 to 207, wherein at least abut 50%, 60%, 70%, 80%, 90%, 95% or 99% of the cartridge by mass, without addition of any sample or reagents, is composed of one or more polymeric materials (e.g., one or more plastics, such as a polyalkylene (e.g., polypropylene) and/or a cycloolefin homopolymer or copolymer (e.g., Zeonor® 1060R)).

209. The cartridge of embodiment 208, wherein the frame (including the outer portions), the chambers, the fluidic channels, and the fluidic layer and the pneumatic layer of valves (e.g., normally open valves and/or normally closed valves) of the cartridge are formed of one or more polymeric materials (e.g., one or more plastics, such as a polyalkylene (e.g., polypropylene) and/or a cycloolefin homopolymer or copolymer (e.g., Zeonor® 1060R)).

210. The cartridge of embodiment 208 or 209, wherein at least about 50%, 75%, 90% or 95% of the cartridge by mass is made by injection molding.

211. A cartridge comprising:
(a) a frame;
(b) a sample container comprising a plurality of sample chambers, wherein the sample container can be part of the frame or can be attached to a first side of the frame, and
wherein each sample chamber is configured to receive a different sample;

(c) a reagent container attached to the first side of the frame, wherein the reagent container comprises a plurality of reagent chambers for each sample chamber;

(d) a reaction container attached to the first side of the frame, wherein the reaction container comprises a plurality of reaction chambers, one reaction chamber for each sample chamber; and (e) a fluidic device attached to an opposing side of the frame, wherein the fluidic device comprises, for each set of sample chamber, reagent chambers and reaction chamber, a plurality of fluidic channels, a plurality of valves for regulating fluid flow to and from the chambers via the fluidic channels, and a plurality of ports for fluidic communication of the fluidic channels with the chambers;

wherein:
each of the sample chambers is in fluidic communication with a fluidic channel in the fluidic device through a port of the fluidic device;

for each set of sample chamber, reagent chambers, reaction chamber and fluidic channels, each of the reagent chambers is closed and fluidically isolated from every other chamber and from the fluidic channels prior to engagement of the reagent container with the fluidic device;

each of the reaction chambers is in fluidic communication with a fluidic channel in the fluidic device through a port of the fluidic device; and each set of sample chamber, reagent chambers, reaction chamber and fluidic channels is fluidically isolated from every other set of sample chamber, reagent chambers, reaction chamber and fluidic channels prior to and subsequent to engagement of the reagent container with the fluidic device.

212. The cartridge of embodiment 211, wherein each of the plurality of sample chambers is part of the frame of the cartridge.

213. The cartridge of embodiment 211 or 212, wherein the first side of the frame comprises slots or other means for mating with the reagent container and the reaction container, and slots or other means for mating with the sample container if the sample container is not part of the frame.

214. The cartridge of any one of embodiments 211 to 213, wherein for each set of sample chamber, reagent chambers, reaction chamber and fluidic channels, engagement of the reagent container with the fluidic device brings the chambers in fluidic communication with one another via the fluidic channels.

215. The cartridge of any one of embodiments 211 to 214, wherein for each of the closed and fluidically isolated reagent chambers in each set of chambers and fluidic channels, engagement of the reagent container with the fluidic device creates a fluid flow path comprising a fluidic channel in fluidic communication with a first port of the chamber, the chamber, and a fluidic channel in fluidic communication with a second port of the chamber.

216. The cartridge of embodiment 215, wherein the first port and the second port of each of the reagent chambers in each set of chambers are on substantially the same plane, on the same surface, or at the base or the bottom of the chamber, or any combination thereof.

217. The cartridge of any one of embodiments 211 to 216, wherein for each set of chambers, each of the reagent chambers is closed and fluidically isolated, prior to engagement of the reagent container with the fluidic device, with the aid of a friable or puncturable seal.

218. The cartridge of embodiment 217, wherein when the reagent container is engaged with the fluidic device, two puncturing elements on the fluidic device puncture the friable or puncturable seal of each of the reagent chambers, thereby creating a fluid flow path comprising a fluidic channel in fluidic communication with a first port of the chamber, the chamber, and a fluidic channel in fluidic communication with a second port of the chamber.

219. The cartridge of embodiment 218, wherein each puncturing element has an opening that is in fluidic communication with a fluidic channel.

220. The cartridge of any one of embodiments 211 to 219, wherein the reagent container becomes engaged with the fluidic device when the cartridge is received by and engages with a cartridge module.

221. The cartridge of embodiment 220, wherein when the cartridge is engaged with the cartridge module, the longitudinal axis of the cartridge is at an angle of about 15-45 degrees, 20-40 degrees or 25-35 degrees, or about 30 degrees, relative to a vertical plane perpendicular to the plane of the surface on which a system comprising the cartridge module rests.

222. The cartridge of any one of embodiments 211 to 221, wherein the fluidic device comprises one or more ports for each set of chambers and fluidic channels which bring the chambers in each set in fluidic communication with a source of positive pressure or negative pressure via the fluidic channels.

223. The cartridge of any one of embodiments 211 to 222, wherein the path of the fluidic channels in each set of chambers and fluidic channels is substantially parallel to and/or does not intersect the path of the fluidic channels in every other set of chambers and fluidic channels.

224. The cartridge of any one of embodiments 211 to 223, wherein for each set of chambers, the plurality of reagent chambers in the reagent container comprise:

(a) a chamber comprising (e.g., pre-loaded with) a reagent (e.g., a lysis reagent) in a solution or buffer for extracting nucleic acid from a sample, and optionally an anti-foaming reagent;

(b) a chamber comprising (e.g., pre-loaded with) a substrate (e.g., magnetically responsive particles), optionally in a solution or buffer, for isolating extracted nucleic acid;

(c) one or more (e.g., two) chambers comprising (e.g., pre-loaded with) a solution (e.g., a wash solution or buffer) for purifying isolated nucleic acid; and (d) a chamber comprising (e.g., pre-loaded with) a solution (e.g., water) for diluting amplification products prior to separation of the amplification products (e.g., by electrophoresis).

225. The cartridge of embodiment 224, wherein for each set of chambers:
chamber (a) is configured to receive and/or store waste material; and
chamber (d) optionally further comprises (e.g., optionally is further pre-loaded with) a control (e.g., a size standard in a set of chambers comprising a sample, or an allelic ladder (and optionally a size standard) in a set of chambers not comprising a sample).

226. The cartridge of embodiment 224 or 225, wherein for each set of chambers, chamber (b) comprises (e.g., is pre-loaded with) an amount of magnetically responsive particles selected to control the amount of nucleic acid isolated.

227. The cartridge of any one of embodiments 211 to 226, wherein each sample chamber is further configured to extract nucleic acid from a sample.

228. The cartridge of any one of embodiments 211 to 227, wherein each of the plurality of reaction chambers is configured to perform a chemical or biochemical reaction.
229. The cartridge of embodiment 228, wherein each of the reaction chambers is configured to amplify one or more selected nucleotide sequences of isolated nucleic acid (e.g., by PCR, such as isothermal PCR or PCR involving thermal cycling).
230. The cartridge of any one of embodiments 211 to 229, wherein the reaction container further comprises a thermoconducting element configured to apply or distribute heat and cooling to each of the reaction chambers.
231. The cartridge of embodiment 230, wherein the thermoconducting element is diposed over each of the reaction chambers.
232. The cartridge of any one of embodiments 224 to 231, which further comprises a source of magnetic field (e.g., a magnet) adjacent to chamber (b) and/or the reaction chamber in each set of chambers.
233. The cartridge of any one of embodiments 211 to 232, wherein the reaction container further comprises, for each reaction chamber, a chamber comprising (e.g., pre-loaded with) reagents for performing a chemical or biochemical reaction (e.g., for amplifying one or more selected nucleotide sequences).
234. The cartridge of embodiment 233, wherein the reagents for amplifying one or more selected nucleotide sequences comprise a DNA polymerase (e.g., a Taq polymerase), one or more pairs of forward and reverse primers for amplifying the one or more selected nucleotide sequences, deoxyribonucleotide triphosphates, and optionally a metal salt (e.g., magnesium chloride), and wherein the one or more pairs of forward and reverse primers optionally are labeled with a dye (e.g., a fluorescent dye).
235. The cartridge of embodiment 233 or 234, wherein for each set of chambers, the reaction reagent chamber comes in fluidic communication with the reaction chamber upon actuation of a delivery mechanism (e.g., a plunger pushing down to break a seal at the bottom of the reaction reagent chamber).
236. The cartridge of any one of embodiments 233 to 235, wherein for each set of chambers, the reagents for performing a chemical or biochemical reaction (e.g., for amplifying one or more selected nucleotide sequences) are delivered to the reaction chamber via a channel that does not comprise a valve.
237. The cartridge of any one of embodiments 233 to 236, wherein for a set of chambers that does not (or will not) comprise a sample, the reaction reagent chamber further comprises (e.g., is further pre-loaded with) a positive control (e.g., a purified genomic DNA).
238. The cartridge of any one of embodiments 224 to 237, wherein for all of the sets of chambers, all of chambers (a), (b), (c) and (d), the sample chambers and the reaction chambers, and optionally the reaction reagent chambers, are all substantially co-planar.
239. The cartridge of any one of embodiments 211 to 238, wherein for each set of chambers, each of the chambers can be macrofluidic or microfluidic.
240. The cartridge of any one of embodiments 211 to 239, wherein for each set of chambers and fluidic channels, one or more, or all, of the plurality of valves are diaphragm valves.
241. The cartridge of embodiment 240, wherein each diaphragm valve can be normally open or normally closed.
242. The cartridge of any one of embodiments 211 to 241, wherein for each set of chambers and fluidic channels, each of the valves can be pneumatically actuated or electrically actuated.
243. The cartridge of any one of embodiments 211 to 242, wherein for each set of chambers and fluidic channels, the fluidic device further comprises one or more pumps.
244. The cartridge of embodiment 243, wherein for each set of chambers and fluidic channels, one or more, or all, of the one or more pumps comprise a plurality of (e.g., three or four) valves (e.g., diaphragm vaves).
245. The cartridge of any one of embodiments 211 to 244, which comprises 4, 8, 10, 16, 24, 32, 40, 48 or more sets of chambers and fluidic channels, wherein each set of chambers and fluidic channels can be used to run a different sample, or one or more sets of chambers and fluidic channels can be used to run a different control (e.g., an allelic ladder, a positive control or a negative control) and every other set of chambers and fluidic channels can be used to run a different sample.
246. The cartridge of embodiment 245, wherein:
a first set of chambers comprises an allelic ladder and a size standard;
a second set of chambers comprises a positive control and a size standard;
a third set of chambers comprises a negative control and a size standard; and
every other set of chambers comprises a different sample and a size standard.
247. The cartridge of any one of embodiments 211 to 246, wherein the fluidic device is a microfluidic device, and one or more, or all, fluidic channels in each set of chambers and fluidic channels are microfluidic channels.
248. The cartridge of any one of embodiments 211 to 247, which can be configured for a single use or multiple uses.
249. The cartridge of any one of embodiments 211 to 248, which further comprises a readable and/or writable memory device (e.g., an EEPROM memory chip) configured to store, receive and/or transmit information relating to the cartridge (e.g., information relating to the history, a recommended use-by date, the current use (e.g., whether the cartridge is operably engaged with a cartridge module, information input from a user, and/or information generated by the system/instrument employing the cartridge in operation), the configurations, the conditions, the physical features and/or the chemical features of the cartridge).
250. The cartridge of any one of embodiments 211 to 249, which is a sample cartridge or a control cartridge.
251. The cartridge of any one of embodiments 211 to 250, wherein at least about 50%, 60%, 70%, 80%, 90%, 95% or 99% of the cartridge by mass, without addition of any sample or reagents, is composed of one or more polymeric materials (e.g., one or more plastics, such as a polyalkylene (e.g., polypropylene) and/or a cycloolefin homopolymer or copolymer (e.g., Zeonor® 1060R)).
252. The cartridge of embodiment 251, wherein the frame, the sample container, the reagent container, the reaction container, and the fluidic device are formed of one or more polymeric materials (e.g., one or more plastics, such as a polyalkylene (e.g., polypropylene) and/or a cycloolefin homopolymer or copolymer (e.g., Zeonor® 1060R)).
253. The cartridge of embodiment 251 or 252, wherein at least about 50%, 75%, 90% or 95% of the cartridge by mass is made by injection molding.

254. A cartridge module comprising:
a cartridge receptacle configured to receive and hold a cartridge that comprises a plurality of chambers and a plurality of valves for regulating fluid flow to and from the plurality of chambers;
a first assembly comprising a first pressure manifold configured to engage a first side of the cartridge and thereby bring the plurality of chambers in fluidic communication with a source of positive pressure or negative pressure;
a second assembly comprising a second pressure manifold configured to engage a second side of the cartridge and thereby bring the plurality of valves in fluidic communication with a source of positive pressure or negative pressure for pneumatic actuation of the valves; and
a moving member configured to move the first pressure manifold and/or the second pressure manifold toward or away from a cartridge held in the cartridge receptacle.

255. The cartridge module of embodiment 254, wherein the moving member comprises a pneumatic (e.g., air-driven) piston whose movement moves the first pressure manifold and/or the second pressure manifold toward or away from a cartridge held in the cartridge receptacle.

256. The cartridge module of embodiment 254 or 255, further comprising a memory device (e.g., EEPROM) reader.

257. The cartridge module of any one of embodiments 254 to 256, wherein the cartridge is the cartridge of any one of embodiments 159 to 210 or the cartridge of any one of embodiments 211 to 253.

258. The cartridge module of any one of embodiments 254 to 257, wherein the catridge receptacle is configured to receive and hold a sample cartridge or a control cartridge.

259. The cartridge module of any one of embodiments 254 to 258, which comprises a plurality of cartridge receptacles configured to receive and hold a plurality of cartridges.

260. A cartridge module comprising:
a cartridge receptacle configured to receive and hold a cartridge; and
a plurality of tubes, wherein each of the plurality of tubes is independently pressure-driven and is configured to sealingly engage with one of a plurality of ports of a cartridge held in the cartridge receptacle, and wherein engagement of an end of a tube with a port creates a fluidic communication between the port and an unengaged end of the tube.

261. The cartridge module of embodiment 260, wherein the cartridge receptacle is configured as a slot.

262. The cartridge module of embodiment 260 or 261, wherein two or more, or all, of the plurality of tubes are independently spring-biased (or spring-loaded).

263. The cartridge module of any one of embodiments 260 to 262, wherein the plurality of ports communicate with fluidic (e.g., microfluidic) channels in the cartridge.

264. The cartridge module of any one of embodiments 260 to 263, wherein the cartridge comprises a fluidic (e.g., microfluidic) device, and wherein the plurality of tubes engage ports on different (e.g., opposing) sides (e.g., a fluidic side and a pneumatic side) of the fluidic device.

265. The cartridge module of embodiment 264, wherein the fluidic device comprises fluidic channels and pneumatic channels, and wherein the plurality of tubes engage ports in fluidic communication with the fluidic channels and ports in fluidic communication with the pneumatic channels.

266. The cartridge module of any one of embodiments 260 to 265, wherein the plurality of tubes are configured to transmit positive pressure or negative pressure to conduits in the cartridge which are in fluidic communication with the plurality of ports.

267. The cartridge module of any one of embodiments 260 to 266, wherein the plurality of tubes are configured to transmit fluid (e.g., a liquid or a gas) into and/or out of conduits in the cartridge which are in fluidic communication with the plurality of ports.

268. The cartridge module of any one of embodiments 260 to 267, further comprising a memory device (e.g., EEPROM) reader.

269. The cartridge module of any one of embodiments 260 to 268, wherein the cartridge is the cartridge of any one of embodiments 159 to 210 or the cartridge of any one of embodiments 211 to 253.

270. The cartridge module of any one of embodiments 260 to 269, wherein the cartridge receptacle is configured to receive and hold a sample cartridge or a control cartridge.

271. The cartridge module of any one of embodiments 260 to 270, which comprises a plurality of cartridge receptacles configured to receive and hold a plurality of cartridges.

272. An integrated and automated system for performing a genetic analysis of a sample, comprising:
(a) an isolation module configured to isolate nucleic acid (e.g., DNA) from a sample;
(b) an amplification module configured to amplify one or more selected nucleotide sequences of the isolated nucleic acid to produce amplification products;
(c) a separation and detection module configured to separate and detect the amplification products;
(d) an analysis module configured to analyze the detected amplification products, wherein the analysis module comprises memory and a processor that executes code which identifies an allele of the one amplified nucleotide sequence, or alleles of at least one or all of the plurality of amplified nucleotide sequences;
(e) a cartridge module configured to receive and engage a cartridge; and
(f) a cartridge received by the cartridge module;
wherein:
the isolation module and the amplification module are part of the cartridge;
the cartridge comprises chambers that come into fluidic communication with one another via fluidic channels when the cartridge is engaged with the cartridge module; and
for one or more, or all, of the chambers, engagement of the cartridge with the cartridge module creates a fluid flow path comprising a fluidic channel in fluidic communication with a first port of a chamber, the chamber, and a fluidic channel in fluidic communication with a second port of the chamber.

273. The system of embodiment 272, wherein the cartridge further comprises valves (e.g., diaphragm valves) that regulate movement of reagents and/or fluid to and from the chambers via the fluidic channels.

274. The system of embodiment 272 or 273, wherein the isolation module is further configured to extract nucleic acid from the sample and to isolate the extracted nucleic acid by capturing the extracted nucleic acid to a substrate (e.g., magnetically responsive particles).

275. The system of any one of embodiments 272 to 274, wherein the isolation module is further configured to purify the isolated nucleic acid.

276. The system of any one of embodiments 272 to 275, wherein the amplification module is configured to amplify one or more selected nucleotide sequences of the isolated nucleic acid by polymerase chain reaction (PCR).

277. The system of any one of embodiments 272 to 276, wherein the amplification module or another component of the system (e.g., the cartridge module) comprises a heating and cooling device (e.g., a Peltier heating and cooling element) configured to perform thermal cycling for amplifying one or more selected nucleotide sequences of the isolated nucleic acid (e.g., by PCR).

278. The system of embodiment 277, wherein the cartridge and/or the heating and cooling device is configured to move so that a chamber in which one or more selected nucleotide sequences are amplified comes into contact with or becomes adjacent to (e.g., via a thermoconducting element contacting the chamber) the heating and cooling device during thermal cycling.

279. The system of any one of embodiments 272 to 278, wherein the amplification module is configured to amplify one or more selected short tandem repeat (STR) loci of the isolated nucleic acid.

280. The system of embodiment 279, wherein the one or more selected STR loci comprise at least five STR loci utilized in a forensic database (e.g., CODIS).

281. The system of embodiment 280, wherein the one or more selected STR loci comprise all STR loci utilized in CODIS (e.g., CSF1PO, D3S1358, D5S818, D7S820, D8S1179, D13S317, D16S539, D18S51, D21S11, FGA, TH01, TPOX and vWA).

282. The system of any one of embodiments 279 to 281, wherein the one or more selected nucleotide sequences further comprise Penta D, Penta E, and amelogenin.

283. The system of any one of embodiments 272 to 282, wherein the cartridge comprises:
(a) a chamber comprising a reagent (e.g., a lysis reagent) in a solution or buffer for extracting nucleic acid from a sample, and optionally an anti-foaming reagent;
(b) a chamber comprising a substrate (e.g., magnetically responsive particles), optionally in a solution or buffer, for isolating extracted nucleic acid;
(c) one or more (e.g., two) chambers comprising a solution (e.g., a wash solution or buffer) for purifying isolated nucleic acid; and
(d) a chamber comprising a solution (e.g., water) for diluting amplification products prior to separation of the amplification products.

284. The system of embodiment 283, wherein:
chamber (a) is configured to receive and/or store waste material; and
chamber (d) optionally comprises a control in the solution (e.g., a size standard in a lane running a sample, or an allelic ladder (and optionally a size standard) in a lane not running a sample).

285. The system of embodiment 283 or 284, wherein:
each of chambers (a), (b), (c) and (d) is closed and fluidically isolated prior to engagement of the cartridge with the cartridge module; and
for each of chambers (a), (b), (c) and (d), engagement of the cartridge with the cartridge module creates a fluid flow path comprising a fluidic channel in fluidic communication with a first port of the chamber, the chamber, and a fluidic channel in fluidic communication with a second port of the chamber.

286. The system of embodiment 285, wherein the first port and the second port of each of chambers (a), (b), (c) and (d) are on substantially the same plane, on the same surface, or at the base or the bottom of the chamber, or any combination thereof.

287. The system of any one of embodiments 272 to 286, wherein the cartridge comprises:
a chamber configured to receive a sample; and
a chamber configured to amplify one or more selected nucleotide sequences of isolated nucleic acid (e.g., by PCR).

288. The system of embodiment 287, wherein the sample chamber is further configured to extract nucleic acid from the sample.

289. The system of embodiment 287 or 288, wherein the cartridge further comprises a chamber comprising reagents for amplifying the one or more selected nucleotide sequences.

290. The system of embodiment 289, wherein the reagents for amplifying the one or more selected nucleotide sequences are delivered to the nucleic acid amplification chamber via a channel that does not comprise a valve.

291. The system of any one of embodiments 272 to 290, wherein the separation and detection module is configured to separate the amplification products by electrophoresis (e.g., capillary electrophoresis).

292. The system of any one of embodiments 272 to 291, wherein the separation and detection module comprises:
one or more heating elements configured to apply heat to denature the amplification products during separation; and
a thermal-control device configured to control heating of the amplification products.

293. The system of any one of embodiments 272 to 292, wherein the amplification products are separated in a separation channel (e.g., a capillary) that is part of the cartridge.

294. The system of any one of embodiments 272 to 292, wherein the amplification products are separated in a separation channel (e.g., a capillary) that is not part of the cartridge.

295. The system of embodiment 293 or 294, wherein the amplification products are heated by a denature heater prior to their introduction (e.g., injection) into the separation channel.

296. The system of any one of embodiments 293 to 295, wherein the separation and detection module is further configured to prepare the amplification products for injection into the separation channel by field-amplified stacking or by positioning a bolus of a material (e.g., air) having a different electrical conductivity downstream of the amplification products in a fluidic conduit (e.g., an electrophoresis sample channel) of an electrophoresis assembly.

297. The system of any one of embodiments 272 to 296, wherein one or more, or all, of the fluidic channels are microfluidic channels.

298. The system of any one of embodiments 272 to 297, wherein the cartridge further comprises a readable and/or writable memory device (e.g., an EEPROM memory chip) configured to store, receive and/or transmit information relating to the cartridge (e.g., information relating to the history, a recommended use-by date, the current use (e.g., whether the cartridge is operably engaged with the cartridge module, information input from a user, and/or information generated by the system in operation), the configurations, the conditions, the physical features and/or the chemical features of the cartridge).

299. The system of any one of embodiments 272 to 298, wherein when the cartridge is engaged with the cartridge module, the longitudinal axis of the cartridge is at an angle of about 15-45 degrees, 20-40 degrees or 25-35 degrees, or about 30 degrees, relative to a vertical plane perpendicular to the plane of the surface on which the system rests.

300. The system of any one of embodiments 272 to 299, wherein the cartridge can be configured for a single use or multiple uses.

301. The system of any one of embodiments 272 to 300, wherein the cartridge is the cartridge of any one of embodiments 159 to 210 or the cartridge of any one of embodiments 211 to 253.

302. The system of any one of embodiments 272 to 301, wherein the processor of the analysis module further executes code which determines a likelihood of a match between the source of the nucleic acid and an individual whose genetic profile is stored in a database (e.g., CODIS).

303. The system of any one of embodiments 272 to 302, wherein the processor of the analysis module further executes code which determines a likelihood of a genetic relationship (e.g., kinship) between the source of the nucleic acid and another individual.

304. The system of any one of embodiments 272 to 303, wherein the analysis module is further configured to transfer results of the genetic analysis (e.g., raw data, parsed data, a genetic profile of the source of the nucleic acid, a likelihood of a match between the source of the nucleic acid and an individual, or a likelihood of a genetic relationship between the source of the nucleic acid and another individual, or any combination thereof) to an internal database and/or an external database (e.g., a database used by law enforcement).

305. The system of any one of embodiments 272 to 304, which further comprises a display having a graphical user interface (GUI), wherein the GUI allows a user to perform a genetic analysis of the sample, to control the operation of the system, to see results of the genetic analysis (e.g., an electropherogram), and to handle (e.g., transfer) results of the genetic analysis.

306. The system of any one of embodiments 272 to 305, which is capable of identifying an allele of the one amplified nucleotide sequence, or alleles of at least one or all of the plurality of amplified nucleotide sequences (e.g., for human identification and/or kinship analysis), determining a likelihood of a match between the source of the nucleic acid and an individual, or determining a likelihood of a genetic relationship between the source of the nucleic acid and another individual, or any combination thereof, within about 2 hours, 1.5 hours or 1 hour after commencement of a protocol for performing a genetic analysis of the sample.

307. The system of any one of embodiments 272 to 306, which is capable of performing a genetic analysis (e.g., STR analysis for human identification and/or kinship determination) with a coefficient of variation of no more than about 10%, 5% or 1%, and/or with an accuracy of at least about 90%, 95% or 99%.

308. The system of any one of embodiments 272 to 307, which has a volume of about 10 ft$^3$ or less.

309. A method of performing a genetic analysis of a sample, comprising:
isolating nucleic acid (e.g., DNA) from a sample;
amplifying one or more selected nucleotide sequences of the isolated nucleic acid to produce amplification products;
separating and detecting the amplification products; and
analyzing the detected amplification products to identify an allele of the one amplified nucleotide sequence, or alleles of at least one or all of the plurality of amplified nucleotide sequences;
wherein:
the method is completed within about two hours;
the method is performed using an integrated and automated system that comprises a cartridge module configured to receive and engage a cartridge;
the isolating and the amplifying are performed using a cartridge that comprises chambers that come into fluidic communication with one another via fluidic channels when the cartridge is engaged with the cartridge module; and
for one or more, or all, of the chambers, engagement of the cartridge with the cartridge module creates a fluid flow path comprising a fluidic channel in fluidic communication with a first port of a chamber, the chamber, and a fluidic channel in fluidic communication with a second port of the chamber.

310. The method of embodiment 309, further comprising:
extracting nucleic acid from the sample prior to isolating nucleic acid; and
purifying the isolated nucleic acid prior to amplifying one or more selected nucleotide sequences of the isolated nucleic acid.

311. The method of embodiment 310, wherein extracting nucleic acid from the sample is performed with agitation with bubbles of a gas (e.g., air), and/or purifying the isolated nucleic acid (e.g., washing nucleic acid captured to magnetically responsive particles) is performed with agitation with bubbles of a gas (e.g., air).

312. The method of any one of embodiments 309 to 311, further comprising diluting the amplification products prior to separating the amplification products.

313. The method of any one of embodiments 309 to 312, wherein isolating the nucleic acid is performed by capturing the nucleic acid to a substrate.

314. The method of embodiment 313, wherein the capture substrate comprises magnetically responsive particles.

315. The method of embodiment 314, further comprising controlling the amount of nucleic acid isolated by controlling the amount of magnetically responsive particles used.

316. The method of any one of embodiments 309 to 315, wherein amplifying one or more selected nucleotide sequences of the isolated nucleic acid is performed by polymerase chain reaction (PCR).

317. The method of any one of embodiments 309 to 316, wherein amplifying one or more selected nucleotide sequences of the isolated nucleic acid (e.g., by PCR) comprises thermal cycling with the aid of a heating and cooling device (e.g., a Peltier heating and cooling element).

318. The method of any one of embodiments 309 to 317, wherein one or more selected short tandem repeat (STR) loci of the isolated nucleic acid are amplified.

319. The method of embodiment 318, wherein at least five STR loci utilized in a forensic database (e.g., CODIS) are amplified.

320. The method of embodiment 319, wherein all STR loci utilized in CODIS (e.g., CSF1PO, D3S1358, D5S818, D7S820, D8S1179, D13S317, D16S539, D18S51, D21S11, FGA, TH01, TPOX and vWA) are amplified.

321. The method of any one of embodiments 318 to 320, wherein the one or more selected nucleotide sequences that are amplified further comprise Penta D, Penta E, and amelogenin.

322. The method of any one of embodiments 309 to 321, wherein the cartridge comprises:
(a) a chamber comprising a reagent (e.g., a lysis reagent) in a solution or buffer for extracting nucleic acid from a sample, and optionally an anti-foaming reagent;
(b) a chamber comprising a substrate (e.g., magnetically responsive particles), optionally in a solution or buffer, for isolating extracted nucleic acid;
(c) one or more (e.g., two) chambers comprising a solution (e.g., a wash solution or buffer) for purifying isolated nucleic acid; and
(d) a chamber comprising a solution (e.g., water) for diluting amplification products prior to separation of the amplification products.

323. The method of embodiment 322, wherein:
chamber (a) is configured to receive and/or store waste material; and chamber (d) optionally further comprises a control in the solution (e.g., a size standard in a lane running a sample, or an allelic ladder (and optionally a size standard) in a lane not running a sample).

324. The method of embodiment 322 or 323, wherein:
   each of chambers (a), (b), (c) and (d) is closed and fluidically isolated prior to engagement of the cartridge with the cartridge module; and
   for each of chambers (a), (b), (c) and (d), engagement of the cartridge with the cartridge module creates a fluid flow path comprising a fluidic channel in fluidic communication with a first port of the chamber, the chamber, and a fluidic channel in fluidic communication with a second port of the chamber.

325. The method of embodiment 324, wherein the first port and the second port of each of chambers (a), (b), (c) and (d) are on substantially the same plane, on the same surface, or at the base or the bottom of the chamber, or any combination thereof.

326. The method of any one of embodiments 309 to 325, wherein the cartridge comprises:
   a chamber configured to receive a sample; and
   a chamber configured to amplify one or more selected nucleotide sequences of isolated nucleic acid.

327. The method of embodiment 326, wherein the sample chamber is further configured to extract nucleic acid from the sample.

328. The method of embodiment 326 or 327, wherein the cartridge further comprises a chamber comprising reagents for amplifying the one or more selected nucleotide sequences.

329. The method of any one of embodiments 309 to 328, wherein separating the amplification products is performed by electrophoresis (e.g., capillary electrophoresis).

330. The method of any one of embodiments 309 to 329, wherein the amplification products are denatured by application of heat during separation, or prior to and during separation.

331. The method of any one of embodiments 309 to 330, wherein the amplification products are separated in a separation channel (e.g., a capillary) that is part of the cartridge.

332. The method of any one of embodiments 309 to 330, wherein the amplification products are separated in a separation channel (e.g., a capillary) that is not part of the cartridge.

333. The method of any one of embodiments 329 to 332, further comprising preparing the amplification products for introduction (e.g., injection) into a separation channel by field-amplified stacking (FAS), wherein FAS is performed by positioning in an electrophoresis sample channel a diluted mixture comprising the amplification products of lower salt concentration or lower ionic strength between areas comprising an electrophoresis buffer of higher salt concentration or higher ionic strength.

334. The method of any one of embodiments 309 to 333, wherein one or more, or all, of the fluidic channels are microfluidic channels.

335. The method of any one of embodiments 309 to 334, which is performed using the cartridge of any one of embodiments 159 to 210 or the cartridge of any one of embodiments 211 to 253.

336. The method of any one of embodiments 309 to 335, further comprising determining a likelihood of a match between the source of the nucleic acid and an individual whose genetic profile is stored in a database (e.g., CODIS).

337. The method of any one of embodiments 309 to 336, further comprising determining a likelihood of a genetic relationship (e.g., kinship) between the source of the nucleic acid and another individual.

338. The method of any one of embodiments 309 to 337, further comprising transferring results of the genetic analysis (e.g., raw data, parsed data, a genetic profile of the source of the nucleic acid, a likelihood of a match between the source of the nucleic acid and an individual, or a likelihood of a genetic relationship between the source of the nucleic acid and another individual, or any combination thereof) to an internal database and/or an external database (e.g., a database used by law enforcement).

339. The method of any one of embodiments 309 to 338, which is completed within about 1.5 hours or about 1 hour.

340. The method of any one of embodiments 309 to 339, which is performed with a coefficient of variation of no more than about 10%, 5% or 1%, and/or with an accuracy of at least about 90%, 95% or 99%.

341. The method of any one of embodiments 309 to 340, which is performed using the integrated and automated system of any one of embodiments 272 to 308.

342. A method of positioning a sample/analyte for injection into a separation channel, comprising:
   (i) providing an electrophoresis assembly comprising:
      (a) a fluidic conduit (e.g., a sample/analyte channel) having a channel inlet and a channel outlet;
      (b) a separation channel (e.g., an electrophoresis capillary) having a separation channel inlet and a separation channel outlet,
         wherein the separation channel comprises an electrically conductive separation medium (e.g., polymer or gel), and
         wherein the separation channel inlet is in fluidic communication and electrical communication with the fluidic conduit at a point of connection;
      (c) an anode and a cathode defining an electrical path and configured to apply a voltage across the separation channel inlet and the separation channel outlet,
         wherein the anode or the cathode (e.g., the cathode when the sample/analyte is a nucleic acid) is in or adjacent to the fluidic conduit at or adjacent to the point of connection;
      (d) a meter configured to measure current through the separation channel or voltage across the separation channel;
   (ii) positioning a bolus of a material (e.g., air) downstream of a sample/analyte in the fluidic conduit, wherein the material has an electrical conductivity that differs from the electrical conductivity of an electrophoresis buffer or the sample/analyte;
   (iii) moving the bolus of material and the sample/analyte in the fluidic conduit in the direction of the separation channel while measuring current or voltage with the meter;
   (iv) detecting with the meter a change in current or voltage that corresponds to movement of the bolus of material into the electrical path; and
   (v) based on the detecting, moving the sample/analyte into the electrical path.

343. The method of embodiment 342, further comprising:
   (vi) applying a sufficient amount of voltage (e.g., about 3 kV to about 5 kV, or about 4 kV) to inject the sample/analyte into the separation channel.

344. The method of embodiment 342 or 343, wherein the cathode is a forked cathode comprising two or more (e.g., three) forks.

345. A system for detecting an article, comprising:
a cartridge engaged with a cartridge module, wherein the cartridge comprises a sample receptacle configured to receive an article that optionally comprises a sample; and
a detection assembly configured to detect the presence or absence of an article in the sample receptacle.

346. The system of embodiment 345, wherein the detection assembly comprises a sensor configured to detect a signal (e.g., light or an electrical signal) produced in response to the presence or absence of an article in the sample receptacle.

347. The system of embodiment 345 or 346, wherein the detection assembly comprises a light source and a light detector configured so that light emitted by the light source travels an optical path that traverses the sample receptacle, and wherein the amount or quality of light detected by the light detector when no article is present in the sample receptacle differs from the amount or quality of light detected by the light detector when an article is present in the sample receptacle.

348. The system of embodiment 347, wherein the amount of light detected by the light detector is less, or no light is detected by the light detector, when an article is present in the sample receptacle compared to the amount of light detected by the light detector when no article is present in the sample receptacle.

349. The system of embodiment 347 or 348, wherein the light source is a light-emitting diode (LED) or a laser.

350. The system of any one of embodiments 346 to 349, wherein the detection or lack of detection of a signal, or the amount or quality of detected signal (e.g., light), is communicated to a software of the system or to a user display.

351. The system of any one of embodiments 345 to 350, wherein the cartridge is the cartridge of any one of embodiments 159 to 210 or the cartridge of any one of embodiments 211 to 253.

352. A system for controlling custody of a sample, comprising:
(a) a cartridge comprising a sample receptacle configured to receive an article (e.g., a swab) that optionally comprises a sample;
(b) a cartridge module having a cartridge receptacle configured to receive the cartridge;
(c) a housing that encloses the cartridge module and the cartridge, wherein the housing comprises a closable door;
(d) at least one sensor that produces a signal indicating:
(1) insertion or removal of an article into or from the sample receptacle;
(2) whether the cartridge is inserted into the cartridge receptacle; or
(3) whether the door is open or closed; and
(e) a computer programmed to record a signal from the at least one sensor for a recording period of time and to display a signal history to a user.

353. The system of embodiment 352, which further comprises the detection assembly of any one of embodiments 345 to 351.

354. The system of embodiment 352 or 353, wherein the at least one sensor comprises a signal output terminal operably connected to the computer.

355. The system of any one of embodiments 352 to 354, wherein the computer comprises logic that determines from the signal history:
(1) whether or when an article has been inserted into or has been removed from the sample receptacle;
(2) whether or when the cartridge has been inserted into or has been removed from the cartridge receptacle; or
(3) whether or when the door has been opened or has been closed.

356. The system of any one of embodiments 352 to 355, wherein the cartridge module further comprises a memory device (e.g., EEPROM) reader.

357. The system of any one of embodiments 352 to 356, wherein the cartridge further comprises a readable and/or writable memory device (e.g., an EEPROM memory chip) configured to store, receive and/or transmit information relating to the cartridge (e.g., information relating to the history, a recommended use-by date, the current use (e.g., whether the cartridge is operably engaged with the cartridge module, information input from a user, and/or information generated by the system/instrument employing the cartridge in operation), the configurations, the conditions, the physical features and/or the chemical features of the cartridge).

358. The system of any one of embodiments 352 to 357, wherein the cartridge is the cartridge of any one of embodiments 159 to 210 or the cartridge of any one of embodiments 211 to 253.

359. The system of any one of embodiments 352 to 358, wherein a radio frequency identification (RFID) tag or a 2-D bar code is affixed (e.g., permanently affixed) to a portion of the article.

360. The system of embodiment 359, wherein an RFID tag or a 2-D bar code is affixed (e.g., permanently affixed) to a portion of the article (e.g., an end of a swab) that would not contact a reagent or a liquid in the sample receptacle.

361. A kit comprising:
at least one first container configured to receive at least one sample comprising an analyte for analysis; and
at least one second container comprising at least one consumable reagent for use in analysis of the analyte.

362. The kit of embodiment 361, wherein the analyte is a biomolecular analyte (e.g., a polynucleotide comprising DNA and/or RNA nucleotides, a polypeptide or a polysaccharide, or any combination thereof).

363. The kit of embodiment 361 or 362, which comprises a plurality of second containers.

364. The kit of any one of embodiments 361 to 363, wherein at least one of the at least one first container, or at least one of the at least one second container, is disposable.

365. The kit of any one of embodiments 361 to 364, wherein all of the at least one first container or all of the at least one second container, or all of the at least one first container and all of the at least one second container, are disposable.

366. The kit of any one of embodiments 361 to 365, wherein the at least one consumable reagent comprises one or more reagents for performing a chemical or biochemical reaction (e.g., nucleic acid amplification) on the analyte.

367. The kit of any one of embodiments 361 to 366, wherein the at least one first container comprises at least one consumable reagent for use in analysis of the analyte.

368. The kit of any one of embodiments 361 to 367, wherein the at least one consumable reagent is selected from the group consisting of solutions and buffers (e.g., wash solutions and buffers, reaction solutions and buffers, solutions and buffers for extracting analytes from samples, solutions and buffers for isolating analytes (e.g., for capturing analytes to magnetically responsive particles), dilution solutions and buffers, and electrophoresis solutions and buffers), enzymes for performing chemical and biochemical reactions (e.g., enzymes that mediate nucleic acid reactions, such as DNA polymerases, RNA polymerases and reverse transcriptases), chemical reagents (e.g., amplification primers, reverse transcription primers, labeling reagents (e.g., fluorescent dyes), deoxyribonucleotide triphosphates, ribonucleotide triphosphates, lysis reagents, anti-foaming reagents, and metal salts (e.g., magnesium chloride)), and separation media (e.g., polymers and gels for electrophoresis).

369. The kit of any one of embodiments 361 to 368, which comprises:
(a) a plurality of the first containers, wherein each of the first containers is configured for use in a single analysis run; and
(b) (i) one second container, wherein the second container comprises at least one consumable reagent in a quantity sufficient for a number of analysis runs equal to the number of first containers; or
(ii) a plurality of the second containers, wherein each of the second containers comprises at least one consumable reagent in a quantity sufficient for a number of analysis runs equal to the number of first containers.

370. The kit of any one of embodiments 361 to 369, wherein each of the at least one first container:
is configured to receive a different sample in each of a plurality of sample receptacles; and
comprises a plurality of reaction chambers, one reaction chamber for each sample receptacle, wherein each reaction chamber is configured to perform a chemical or biochemical reaction (e.g., nucleic acid amplification) on a biomolecular analyte comprised in each of a plurality of different samples.

371. The kit of any one of embodiments 361 to 370, wherein each of the at least one first container is configured for use in a single analysis run using a system or instrument configured to perform the analysis on the analyte.

372. The kit of any one of embodiments 361 to 371, wherein each of the at least one second container is configured for use in a plurality of analysis runs using a system or instrument configured to perform the analysis on the analyte.

373. The kit of any one of embodiments 361 to 372, which comprises all consumable reagents necessary for performing the analysis on the analyte.

374. The kit of any one of embodiments 361 to 373, wherein:
the analysis comprises short tandem repeat (STR) analysis; and
the at least one consumable reagent comprises:
(i) reagents for extracting DNA from the at least one sample, isolating the extracted DNA and purifying the isolated DNA (e.g., lysis reagents, capture particles, and wash solutions or buffers), reagents for performing amplification (e.g., by PCR) of one or more selected STR loci (e.g., one or more pairs of forward and reverse primers optionally labeled with a dye (e.g., a fluorescent dye), a DNA polymerase (e.g., a Taq polymerase), deoxyribonucleotide triphosphates, and optionally a metal salt (e.g., magnesium chloride)), and reagents for performing electrophoresis (e.g., an electrophoresis buffer and a separation medium (e.g., a polymer or gel)); and
(ii) optionally a reagent for diluting nucleic acid amplification products prior to their separation by electrophoresis (e.g., water or a buffer) and optionally controls for analyzing separated amplification products (e.g., a size standard, an allelic ladder, and a positive control).

375. The kit of embodiment 374, which comprises consumable reagents sufficient to isolate DNA from the at least one sample, to amplify one or more selected STR loci of the isolated DNA, and to analyze (including separate) amplification products.

376. The kit of any one of embodiments 361 to 375, wherein each of the at least one first container separately is comprised in a first cartridge configured to engage an assembly of a system or instrument that performs part or all of the analysis of the analyte.

377. The kit of embodiment 376, wherein the first cartridge is the cartridge of any one of embodiments 159 to 210 or the cartridge of any one of embodiments 211 to 253.

378. The kit of embodiment 376 or 377, wherein:
the one second container is comprised, or each of the plurality of second containers separately is comprised, in a second cartridge configured to engage an assembly of the system or instrument; or
two or more of the plurality of second containers separately are comprised in different kinds of cartridges, wherein each of the different kinds of cartridges is configured to engage an assembly of the system or instrument.

379. The kit of embodiment 378, which comprises:
(a) a first cartridge comprising at least one sample receptacle, reagents for extracting, isolating and purifying DNA from a sample, and reagents for amplifying one or more selected nucleotide sequences (e.g., by PCR);
(b) a second cartridge comprising a separation medium (e.g., a polymer or gel) for electrophoresis and an electrophoresis buffer; and
(c) a third cartridge comprising the same or a different electrophoresis buffer, and optionally a solution (e.g., water) for cathode preparation and clean-up.

380. A cartridge comprising:
a) a fluidic device comprising one or a plurality of fluidic channels arranged substantially in a first plane; and
b) a sample container comprising one or a plurality of sample receptacles, each receptacle having an elongate shape defined by an axis in a long dimension of the shape, wherein each elongate axis is arranged substantially in a second plane; wherein:
the fluidic channels and the sample receptacles are fluidically connected to one another; and
the first and second planes are substantially parallel to each other.

381. The cartridge of embodiment 380 further comprising:
c) a reagent container comprising one or a plurality of reagent chambers, each reagent chamber having an elongate shape defined by an axis in a long dimension of the shape, wherein each elongate axis is arranged substantially in a third plane; and
d) a reaction container comprising one or a plurality of reaction chambers, each reaction chamber having an elongate shape defined by an axis in a long dimension of the shape, wherein each elongate axis is arranged substantially in a fourth plane;
wherein:
the fluidic channels, the sample receptacles, the reagent chambers and the reaction chambers are fluidically connected to one another; and
the first, second, third and fourth planes are substantially parallel to each other.

382. A sample cartridge comprising:
a) a fluidic device comprising one or a plurality of fluidic channels arranged substantially in a first plane;
b) a sample container comprising one or a plurality of sample receptacles, wherein the fluidic channels and the sample receptacles are fluidically connected to one another;
wherein the sample cartridge is configured to be loaded with sample into sample receptacles and move analyte from the sample into the fluidic channels when the sample cartridge is engaged with a cartridge module configured to receive the sample cartridge, and the first plane is oriented at least 10°, at least 20°, at least 30°, at least 40°, at least 50°, at least 60°, at least 70°, at least 80°, or at least 90° off horizontal.

EXAMPLE 1

FIGS. 34A-D show examples of a cartridge for processing a sample. FIG. 34A shows a cartridge 3400 having a container 3401 with reagent and processing chambers, as described herein. The cartridge 3400 is configured for use with systems of the invention. The cartridge includes a sample chamber for accepting a sample, such as with the aid of a Q-tip or cotton swab. A thermal conductor 3406 is disposed over a thermocycling chamber (see below) of the cartridge 3400. The thermal conductor 3406 is configured to distribute (or spread) heat from a heating element (e.g., Peltier) to the chambers 3407 of the thermocycler assembly 3405. The thermal conductor can be formed of graphite, graphene, copper, tantalum or aluminum. In some cases, the thermal conductor is formed of a layer of a thermally conductive material. In other cases, the thermal conductor is formed of a plurality of layers, such as a layer of a thermally conductive material (e.g., graphite) adapted to come in thermal communication with a heating element, and a layer of a polymeric material (e.g., polypropylene) adjacent to the layer of the thermally conductive material that is adapted to come in contact with a sample in each chamber 3407 of the thermocycler assembly 3405. For instance, the thermal conductor can include a layer of graphite laminated to a layer of polypropylene. The layer of polypropylene can be adapted to come in contact with a sample in the chamber 3407 during sample processing.

Figure 34B:
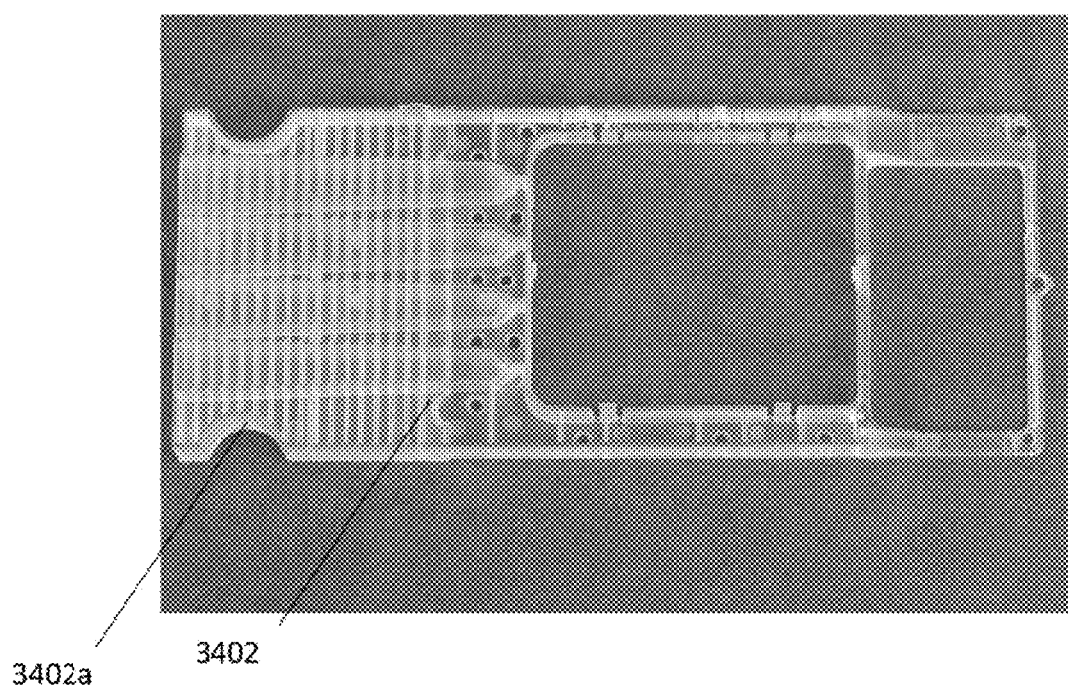
Figure 34C:
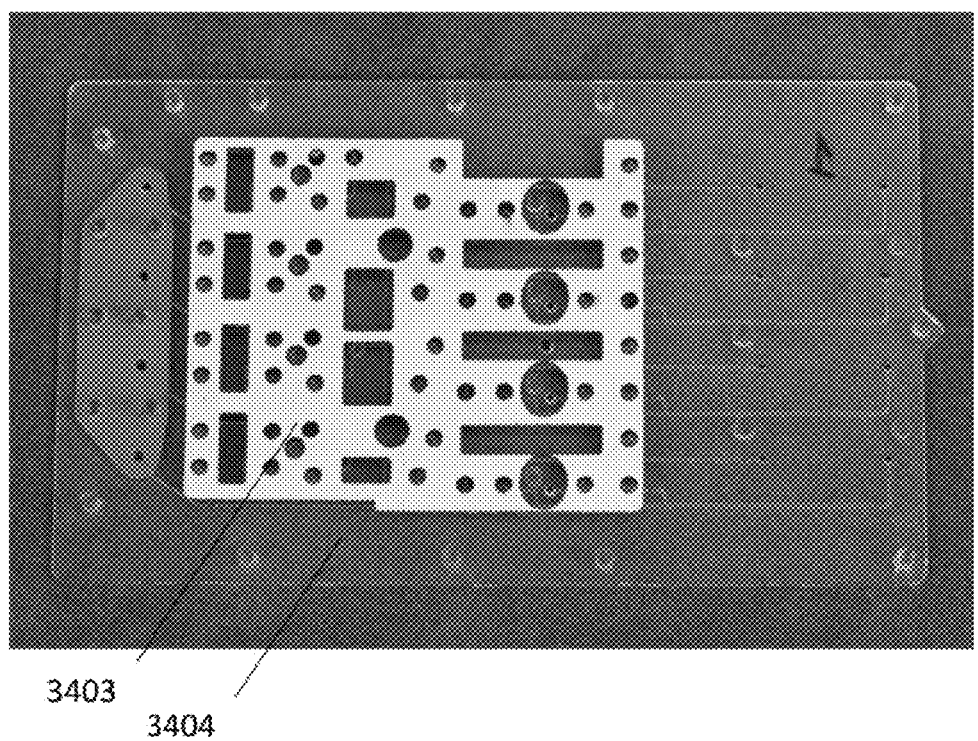
Figure 34D:
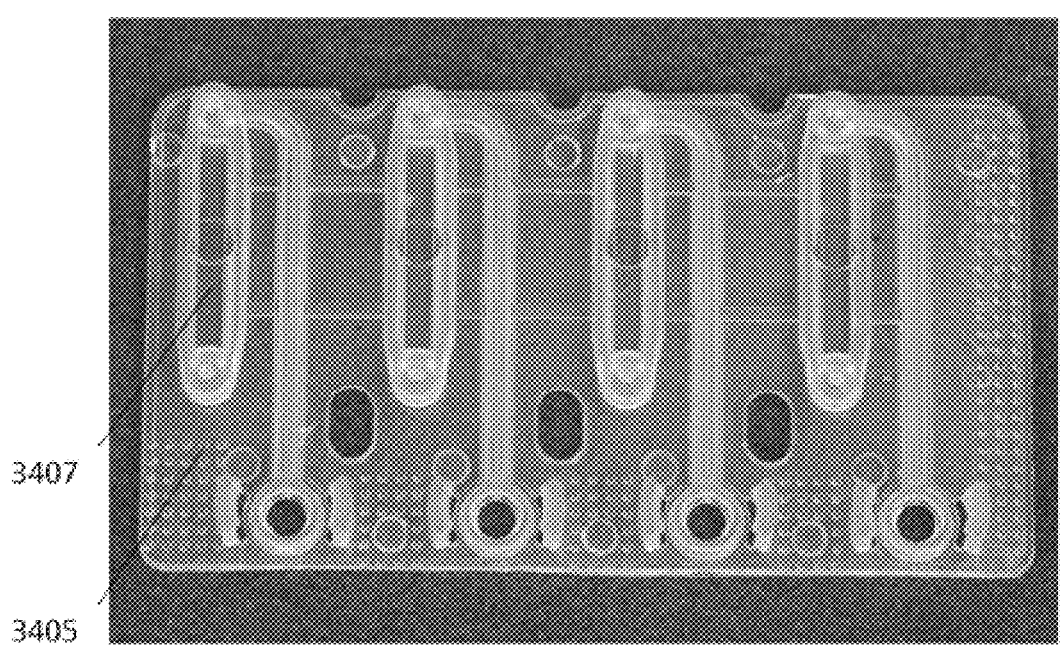

With reference to FIG. 34B, the cartridge 3400 includes a holder or frame 3402 for holding the container 3401. The holder 3402 includes a holding member 3402a for enabling a user to carry the cartridge 3400, such as to insert the cartridge 3400 into a system for processing a sample. With reference to FIG. 34C, the cartridge 3400 includes a layer of deformable material 3403 configured to rest adjacent to the container 3401, and a microfluidic device 3404 having microfluidic channels for transporting samples and reagents to and from chambers of the container 3401, and pneumatic actuation channels for actuating valves of the microfluidic channels of the cartridge 3400. FIG. 34D shows a thermocycler assembly 3405 for performing temperature-regulated processing of a sample, such as PCR. The thermocycler assembly 3405 is configured to be mounted on the microfluidic device 3404, which is configured to be integrated with other components of the cartridge 3400 with the aid of the holder 3402.

Figure 44:
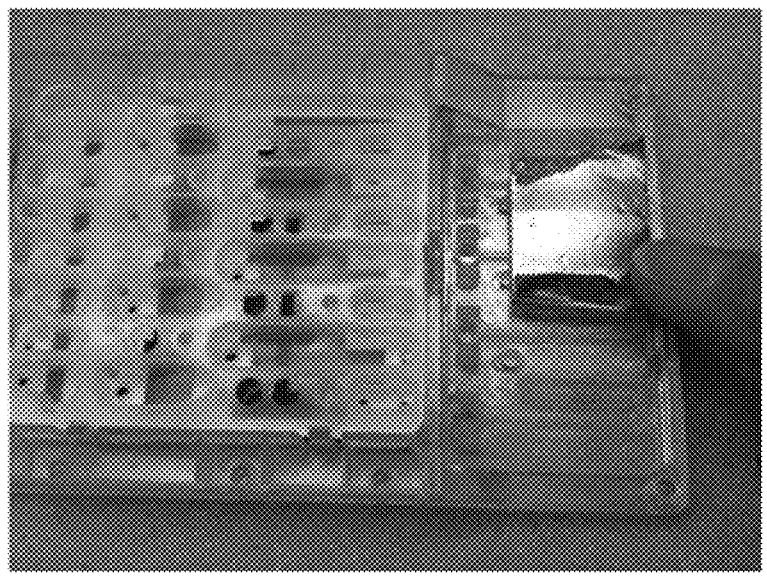
FIG. 44 shows a portion of a cartridge having a thermocycler assembly comprising four reaction chambers and a thermal conductor that has been peeled away to show the four reaction chambers configured to perform amplification (e.g., by PCR) with thermal cycling, in accordance with an embodiment of the invention.

The thermocycler assembly 3405 is a plastic piece that is bolted to an external surface of the microfluidic device 3404. The thermocycler assembly 3405 includes four chambers 3407, with each chamber 3407 having an elongate shape that can have an opening running most of the length of the chamber 3407—i.e., the chamber 3407 can be trough-like. In some cases, the chamber 3407 has a depth of about 0.02 inch (or about 508 microns) and a volume of about 20 microliters. With reference to FIG. 44, the chamber 3407 is covered with the layer of the thermal conductor 3406 that is configured to come in contact with a heating and cooling element (not shown) during sample processing. The heating and cooling element can be external to the cartridge 3400 (see, e.g., thermal cycling heating and cooling device 4200 in FIG. 42). In some cases, a surface of the layer of the thermal conductor is adapted to come in contact with a sample in each chamber of the thermocycler assembly 3405 during sample processing through an opening running most of the length of each chamber.

During sample processing, magnetic-field attractable beads (also "magnetic beads" herein) are directed from the container 3401 and into a reaction chamber 3407 of the thermocycler assembly 3405, where they are immobilized with the aid of a magnetic field provided by a magnetic field source (e.g., magnet, induction coil) adjacent to the chamber 3407. The magnetic field source can be provided in the cartridge, such as, for example, disposed in a compartment between the thermocycler assembly 3405 and the microfluidic device 3404. The compartment can be formed in the thermocycler assembly 3405, and the magnetic field source can be provided in the compartment prior to attaching the thermocycler assembly 3405 to the microfluidic device 3404 (see FIG. 45). An amplification premix is provided to the chamber 3407 and with the beads immobilized in the chamber 3407 the sample is amplified. Following amplification, the amplified sample is directed out of the chamber 3407 and to the container 3401. The beads remain in the chamber 3407 of the thermocycler assembly 3405.

Systems and methods provided herein, including the components of such systems and various routines of such methods, may be combined with or modified by other systems and methods. In some situations, the system 100 described above in the context of FIGS. 1-7, including various components of the system, may be combined or modified by the systems described in U.S. Patent Publication No. 2011/0005932 to Jovanovich et al. ("UNIVERSAL SAMPLE PREPARATION SYSTEM AND USE IN AN INTEGRATED ANALYSIS SYSTEM") ("Jovanovich"), which is entirely incorporated herein by reference. For examples, various features of the electrophoresis capillaries of FIG. 5 and the anode cartridge and interface module of FIG. 6 can be combined with, modified by, or elaborated by the teachings of Jovanovich.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of embodiments of the invention herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A system comprising:
   (a) a cartridge module comprising a receptacle for receiving a cartridge;
   (b) a cartridge received in the receptacle, the cartridge comprising:
      (i) a container comprising a plurality of closed and fluidically isolated chambers, wherein each of the plurality of chambers comprises a first and second opening, each opening closed by a friable seal; and
      (ii) a fluidic device comprising a fluidic chip that comprises a fluidics layer comprising a plurality of fluidic channels, an actuation layer comprising actuation channels and an elastomer layer sandwiched between them, and a plurality of puncturing elements, wherein each fluidic channel communicates with a first port and a second port in the fluidic device, and wherein said puncturing elements each include one of said ports communicating with one of said fluidic channels;

(c) wherein the cartridge module further comprises a pressure application member for engaging the fluidic device with the container, wherein, upon engaging the fluidic device with the container, said puncturing elements puncture the friable seal that closes each opening of each of the plurality of chambers, putting each opening in communication with one of the ports, thereby (1) creating a flow path between two chambers through a fluidic channel on the fluidic device; and (2) creating a flow path between two fluidic channels on the fluidic device through a single chamber.

2. The system of claim 1 wherein the fluidic device comprises one or more pneumatically actuated valves for regulating fluid flow to said plurality of chambers; and wherein the cartridge module further comprises:

(1) a first assembly having a first pressure manifold that engages a first side of said cartridge and brings said one or more chambers in fluidic communication with a first pressure source;

(2) a second assembly having a second pressure manifold that engages a second side of said cartridge and brings said one or more valves in fluidic communication with a pressure source for pneumatic actuation; and (3) an elongation or moving member that moves one or both of said first pressure manifold and said second pressure manifold towards said cartridge.

3. The system of claim 2 wherein the first assembly further comprises:

a plurality of tubes, wherein each of the plurality of tubes is independently pressure-driven and is configured to sealingly engage with one of a plurality of the ports communicating with the fluidic channels of the cartridge, and wherein engagement of an end of a tube with a port creates a fluidic communication between the port and the first pressure source.

4. The system of claim 3 wherein the second assembly further comprises:

a plurality of tubes, wherein each of the plurality of tubes is independently pressure-driven and is configured to sealingly engage with one of a plurality of pneumatic ports communicating with pneumatic channels communicating with said values of the cartridge, and wherein engagement of an end of a tube with a pneumatic port creates a fluidic communication between the pneumatic port and the pressure source for pneumatic activation.

5. The system of claim 1, wherein said plurality of closed and fluidically isolated chambers comprise:

a chamber holding one or more lysis reagents;
a chamber having capture particles; and
a chamber having a wash solution;
wherein the system further comprises an amplification reagent container comprising PCR amplification reagents, wherein the amplification reagent container is fluidically isolated from the thermal cycling chamber and is configured to deliver the PCR amplification reagents to the thermal cycler chamber upon actuation,
wherein the system is configured to receive a sample comprising a nucleic acid; and to perform PCR amplification on the nucleic acid, thereby producing an amplification product.

6. The system of claim 5 further comprising:

(d) a separation and detection module configured to separate and detect the amplification products; and (e) an analysis module configured to analyze the detected amplification products, wherein the analysis module comprises memory and a processor that executes code which identifies an allele of one amplified nucleotide sequence, or alleles of at least one or all of a plurality of amplified nucleotide sequences.

7. The system of claim 6, wherein the system processes, or processes and analyzes, a biological sample in about two hours or less.

8. The system of claim 6, wherein the system processes and/or analyzes a biological sample at an accuracy of at least about 95%.

9. The system of claim 1 wherein the pressure application member comprises a cam for applying pressure against the cartridge.

10. The system of claim 1 wherein the cartridge receptacle is configured as a slot.

11. The system of claim 1 which comprises a plurality of cartridge receptacles configured to receive and hold a plurality of cartridges.

12. The system of claim 2 wherein said elongation or moving member is coupled to one or both of said first assembly and said second assembly through a cable.

13. The system of claim 12, wherein said cable is Bowden cable.

14. The system of claim 12, wherein said elongation or moving member moves one or both of said first pressure manifold and said second pressure manifold away from said cartridge.

15. The system of claim 2, wherein said elongation or moving member comprises an air-driven piston, the movement of which moves one or both of said first pressure manifold and said second pressure manifold towards said cartridge.

16. The system of claim 3 wherein two or more of the plurality of tubes are independently spring-biased.

17. The system of claim 3 wherein the plurality of tubes are configured to transmit fluid into and/or out of channels in the cartridge which are in fluidic communication with the plurality of ports.

18. The system of claim 1 wherein the fluidic device comprises one or more selectably closable channels.

19. The system of claim 1 wherein the fluidic channel is in fluid communication with one or more valves.

20. The system of claim 19, wherein the one or more valves are pneumatically actuated diaphragm valves.

21. The system of claim 1 wherein said plurality of closed and fluidically isolated chambers comprise macrofluidic chambers.

22. The system of claim 1, further comprising a thermal cycler assembly configured for polymerase chain reaction (PCR).

23. The system of claim 22, wherein said thermal cycler assembly comprises a thermal cycling chamber in the cartridge.

24. The system of claim 23, further comprising a magnetic field application member adjacent to said thermal cycling chamber.

25. The system of claim 1, further comprising a sample receptacle comprising a sample chamber adapted to receive a sample, and in fluidic communication with one of the fluidic channels.

26. The system of claim 25, wherein said sample chamber is adapted to hold a cotton swab.

27. The system of claim 5, further comprising is a waste chamber.

28. The system of claim 1, further comprising a layer of deformable material between said container and said fluidic device.

29. The system of claim 1 wherein said friable seal is formed of a metallic material.

30. The system of claim 1 wherein said fluidic channel is a microfluidic channel.

* * * * *